(12) United States Patent
Cho et al.

(10) Patent No.: US 7,785,720 B2
(45) Date of Patent: *Aug. 31, 2010

(54) COMPOUND AND ORGANIC LIGHT EMITTING DEVICE USING THE SAME

(75) Inventors: Wook Dong Cho, Daejeon Metropolitan (KR); Ji Eun Kim, Daejeon Metropolitan (KR); Byung Sun Jeon, Seoul (KR); Dong Seob Jeong, Seoul (KR); Seok Hee Yoon, Daejeon Metropolitan (KR); Jae Min Moon, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 782 days.

This patent is subject to a terminal disclaimer.

(21) Appl. No.: 11/660,903

(22) PCT Filed: Sep. 23, 2005

(86) PCT No.: PCT/KR2005/003179

§ 371 (c)(1),
(2), (4) Date: Feb. 23, 2007

(87) PCT Pub. No.: WO2006/080646

PCT Pub. Date: Aug. 3, 2006

(65) Prior Publication Data

US 2008/0093983 A1    Apr. 24, 2008

(30) Foreign Application Priority Data

Sep. 24, 2004    (KR) .................... 10-2004-0077214

(51) Int. Cl.
*H01L 51/54* (2006.01)
*C09K 11/00* (2006.01)

(52) U.S. Cl. .................. 428/690; 428/917; 313/504; 313/506; 252/301.16; 257/40; 257/E51.032; 546/15; 546/18; 556/407

(58) Field of Classification Search ................ 556/408, 556/407
See application file for complete search history.

(56) References Cited

U.S. PATENT DOCUMENTS

| | | | |
|---|---|---|---|
| 5,763,636 A * | 6/1998 | Kreuder et al. ................ 558/46 |
| 6,329,082 B1 * | 12/2001 | Kreuder et al. .............. 428/690 |
| 6,605,373 B2 | 8/2003 | Woo et al. |
| 6,613,454 B2 | 9/2003 | Ara et al. |
| 6,630,254 B2 | 10/2003 | Leclerc et al. |
| 2003/0168970 A1 * | 9/2003 | Tominaga et al. ........... 313/504 |
| 2004/0219386 A1 | 11/2004 | Thoms |

FOREIGN PATENT DOCUMENTS

| | | |
|---|---|---|
| EP | 1 310 539 B1 | 3/2005 |
| JP | 2008-510801 | 4/2008 |
| JP | 2008-511155 | 4/2008 |
| JP | 2008-511156 | 4/2008 |
| JP | 2008-511161 | 4/2008 |
| WO | WO 93/09074 A2 | 5/1993 |
| WO | WO 2004/020371 A1 | 3/2004 |
| WO | WO 2006/003564 | 3/2006 |
| WO | WO 2006/080637 | 8/2006 |
| WO | WO 2006/080638 | 8/2006 |
| WO | WO 2006/080645 | 8/2006 |
| WO | WO 2006/080646 | 8/2006 |

* cited by examiner

*Primary Examiner*—D. Lawrence Tarazano
*Assistant Examiner*—Michael Wilson
(74) *Attorney, Agent, or Firm*—McKenna Long & Aldridge LLP

(57) ABSTRACT

Disclosed is an organic light emitting device. The organic light emitting device comprises a first electrode, organic material layer(s) comprising a light emitting layer, and a second electrode. The first electrode, the organic material layer(s), and the second electrode form layered structure and at least one layer of the organic material layer(s) include the compound of Formula 1 or the compound of Formula 1 into which a thermosetting or photo-crosslinkable functional group is introduced.

8 Claims, 1 Drawing Sheet

[Fig. 1]
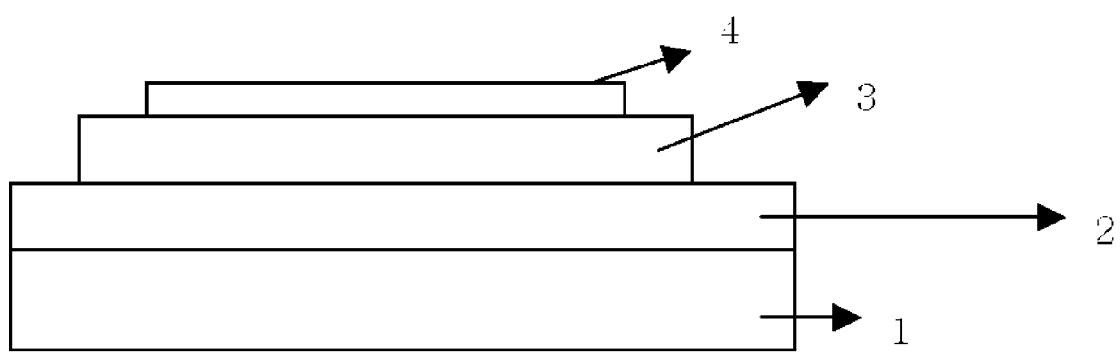
[Fig. 2]
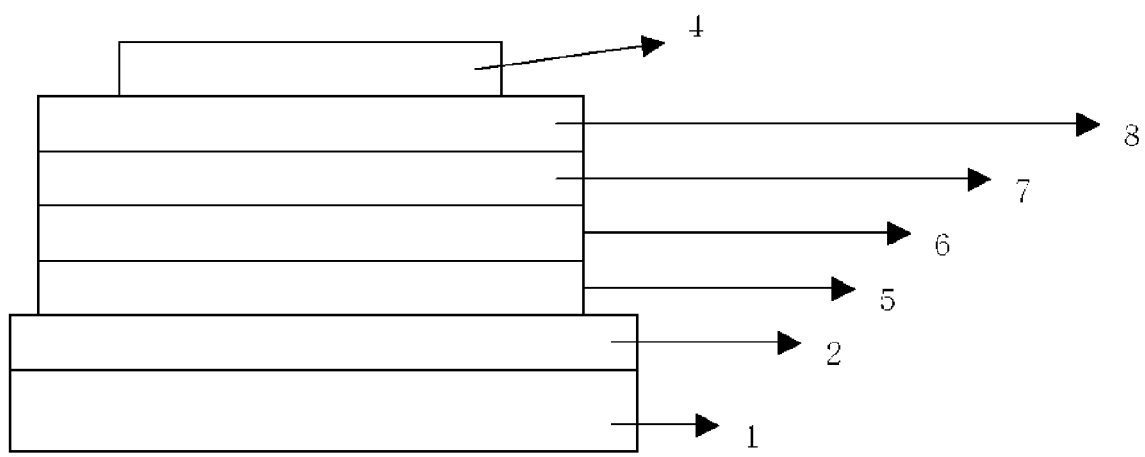

COMPOUND AND ORGANIC LIGHT EMITTING DEVICE USING THE SAME

This application claims priority to International application No. PCT/KR2005/003179 filed on Sep. 23, 2005, and Korean Application No. 10-2004-0077214 filed on Sep. 24, 2004, both of which are incorporated by reference, as if fully set forth herein.

TECHNICAL FIELD

The present invention relates to an organic light emitting device which comprises a fluorene derivative capable of significantly improving a lifespan, efficiency, and electrochemical and thermal stabilities thereof.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic light emitting device including an organic material having the above-mentioned requirements in the art.

DISCLOSURE OF INVENTION

Technical Problem

Therefore, the object of the present inventions is to provide an organic light emitting device which is capable of satisfying conditions required of a material usable for an organic light emitting device, for example, a proper energy level, electrochemical stability, and thermal stability, and which includes a fluorene derivative having a chemical structure capable of playing various roles required in the organic light emitting device, depending on a substituent group.

Technical Solution

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

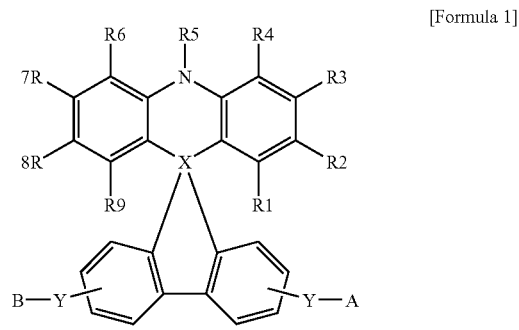

[Formula 1]

wherein X is C or Si;

A is

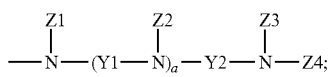

B is

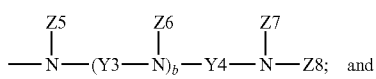 and a and b are zero or positive integer;

Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Y1 to Y4 are each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Z1 to Z8 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophene group which is substituted with hydrocarbons having a carbon number of 1-20 or aromatic hydrocarbons having a carbon number of 6-20; or a boron group which is substituted with aromatic hydrocarbons.

R1 to R4 and R6 to R9 are each independently selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, and an ester group. They may form aliphatic or hetero condensation rings along with adjacent groups.

R5 is selected from the group consisting of hydrogen, a substituted or unsubstituted alkyl group, a substituted or unsubstituted cycloalkyl group, a substituted or unsubstituted alkenyl group, a substituted or unsubstituted aryl group, and a substituted or unsubstituted heterocyclic group.

Carbon at an ortho-position of the aryl or heterocyclic group and R4 or R6 may form a condensation ring along with a group selected from the group consisting of O, S, NR, PR, C=O, CRR', and SiRR', with the proviso that R5 is the aryl group or the heterocyclic group, wherein R and R' are each independently selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, and an ester group, and R and R' may form a condensation ring to form a spiro compound.

A detailed description will be given of the substituent groups of Formula 1.

In Z1 to Z8 as the substituent groups of Formula 1, the aromatic compounds are exemplified by monocyclic aromatic rings, such as phenyl, biphenyl, and terphenyl, and multicyclic aromatic rings, such as naphthyl, anthracenyl, pyrenyl, and perylenyl. The hetero aromatic compounds are exemplified by thiophene, furan, pyrrole, imidazole, thiazole, oxazole, oxadiazole, thiadiazole, triazole, pyridyl, pyridazyl, pyrazine, quinoline, and isoquinoline.

Examples of aliphatic hydrocarbons having a carbon number of 1-20 include straight chain aliphatic hydrocarbons, branched chain aliphatic hydrocarbons, saturated aliphatic hydrocarbons, and unsaturated aliphatic hydrocarbons. They are exemplified by an alkyl group, such as a methyl group, an ethyl group, an n-propyl group, an isopropyl group, an n-butyl group, a sec-butyl group, an iso-butyl group, a ter-butyl group, a pentyl group, and a hexyl group; an alkenyl group having a double bond, such as styryl; and an alkynyl group having a triple bond, such as an acetylene group.

The carbon number of the alkyl, alkoxy, and alkenyl groups of R1 to R9 of Formula 1 is not limited, but is preferably 1-20.

The length of the alkyl group contained in the compound does not affect the conjugate length of the compound, but may affect the method of applying the compound to the organic light emitting device, for example, a vacuum deposition method or a solution coating method.

Illustrative, but non-limiting, examples of the aryl group of R1 to R9 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R9 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

Illustrative, but non-limiting, examples of the heterocyclic group of R1 to R9 of Formula 1 include a thiophene group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

In addition, illustrative, but non-limiting, examples of the alkenyl, aryl, arylamine, and heterocyclic groups of R1 to R9 of Formula 1 include compounds shown in the following Formulae.

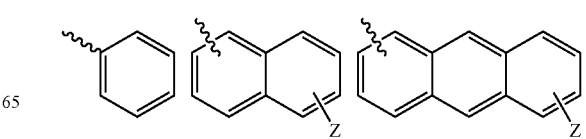

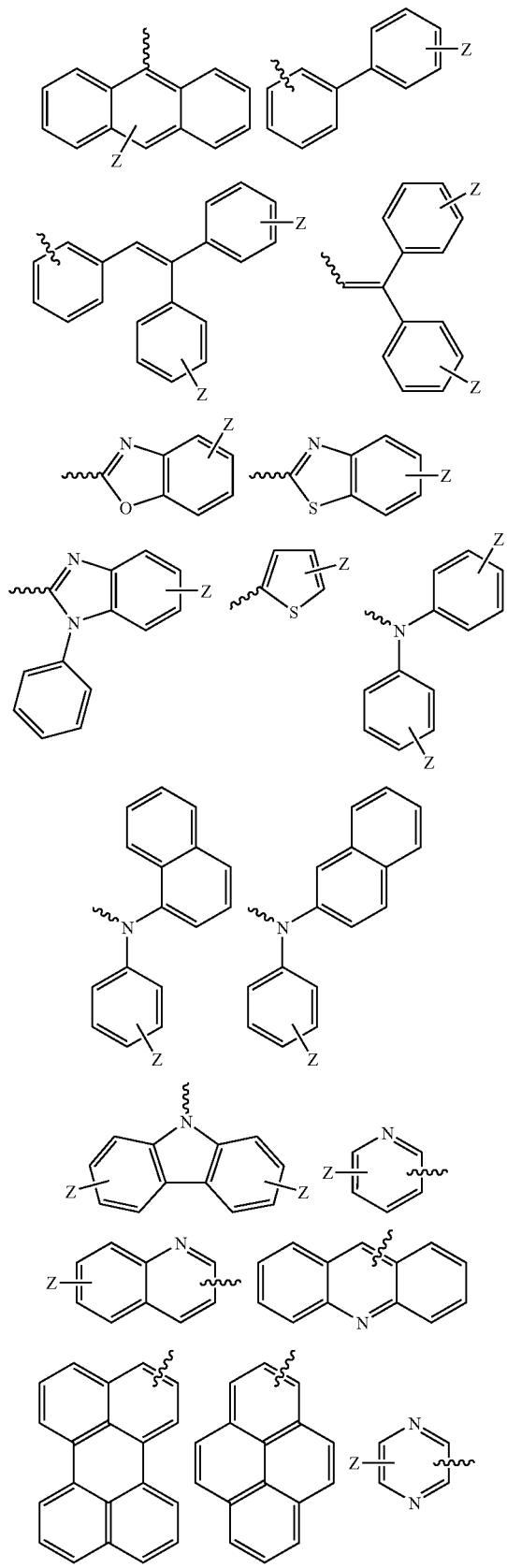

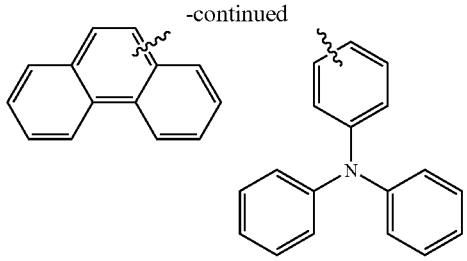

In the above Formulae, Z is a group selected from the group consisting of hydrogen, aliphatic hydrocarbons having a carbon number of 1-20, an alkoxy group, an arylamine group, an aryl group, a heterocyclic group, a nitrile group, and an acetylene group. Examples of the arylamine, aryl, and heterocyclic groups of Z are as shown in the above-mentioned substituent groups of R1 to R9.

According to a preferred embodiment of the present invention, R5 of Formula 1 is an aryl or an heterocyclic group.

According to another preferred embodiment of the present invention, R5 of Formula 1 is an aryl or an heterocyclic group, and carbon at an ortho-position of the aryl or heterocyclic group and R4 or R6 form a condensation ring along with a group selected from the group consisting of O, S, NR, PR, C=O, CRR', and SiRR' (R and R' are as defined in Formula 1).

According to still another preferred embodiment of the present invention, R5 of Formula 1 is an aryl or an heterocyclic group, and carbon at the ortho-position of the aryl or heterocyclic group and R4, and carbon at the ortho-position of the aryl or heterocyclic group and R6 form the condensation ring along with a group selected from the group consisting of O, S, NR, PR, C=O, CRR', and SiRR' (R and R' are as defined in Formula 1).

According to the preferred embodiment of the present invention, illustrative, but non-limiting, examples of the compound of Formula 1 include compounds of the following Formulae 2 to 119. [Formulae 2 to 119]

2

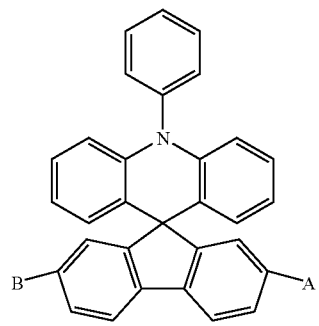

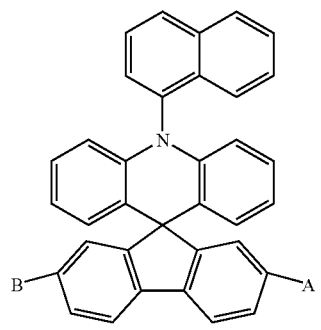
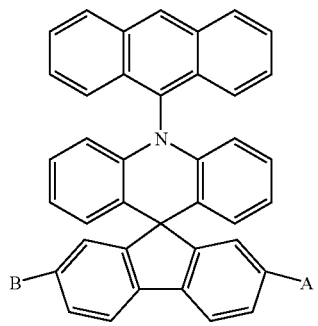
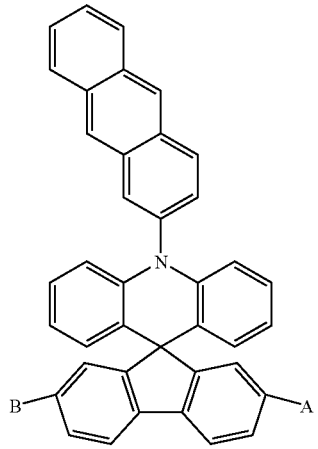
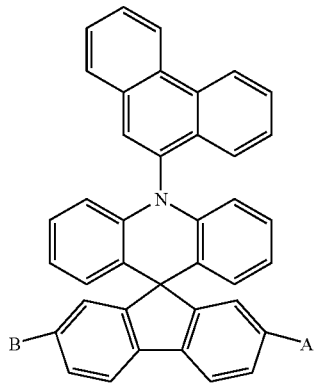
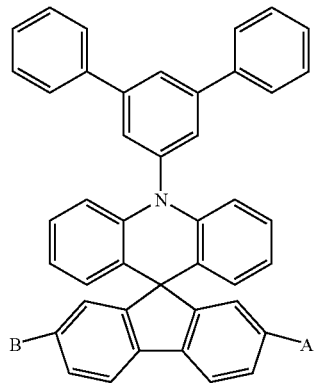

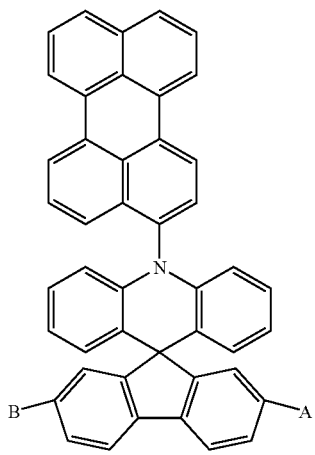
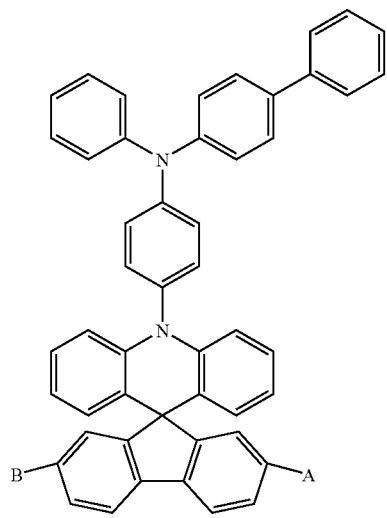
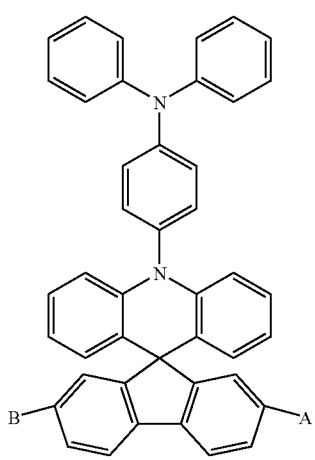
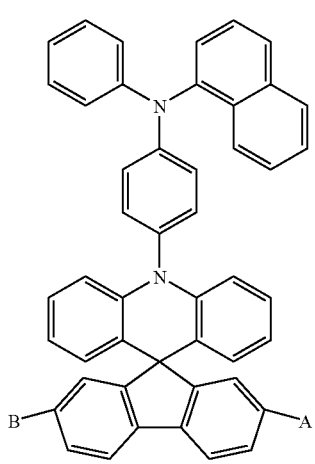

13
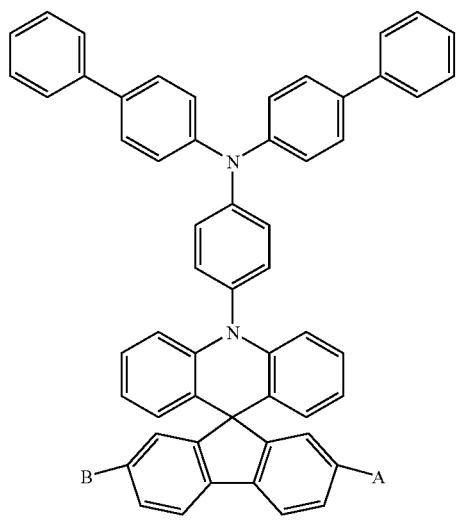
14
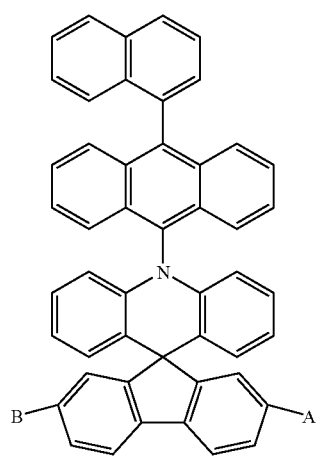
15
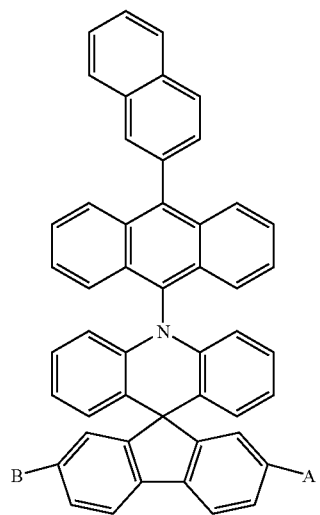
16
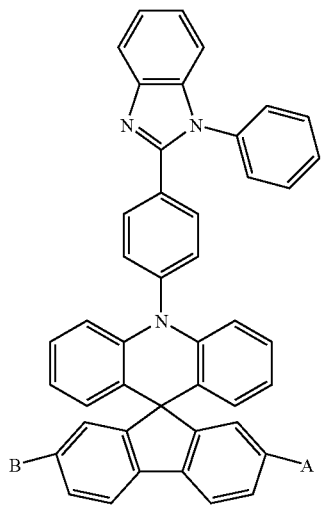
17
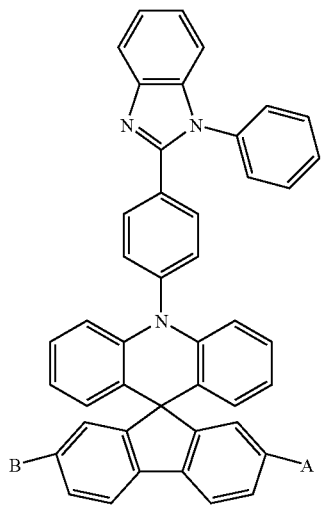
18
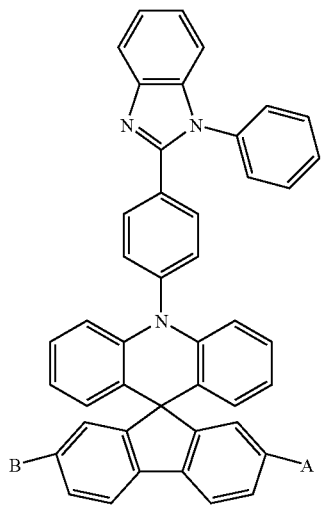

-continued
19
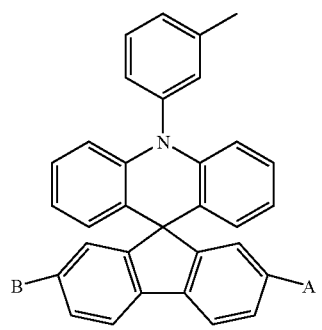
20
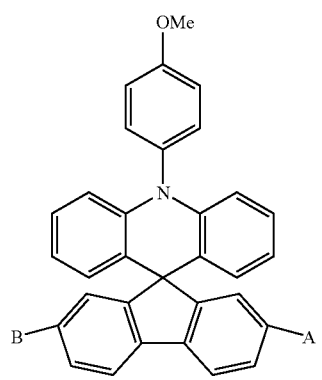
21
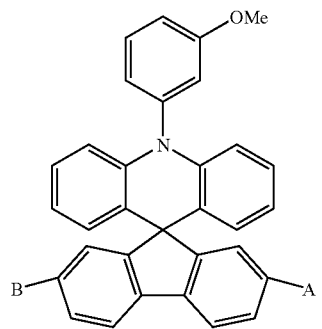
22
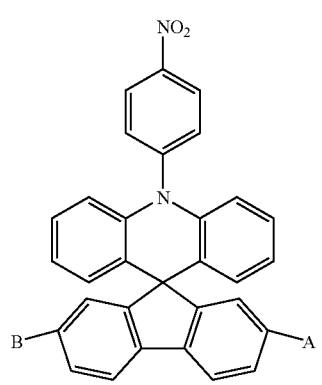
-continued
23
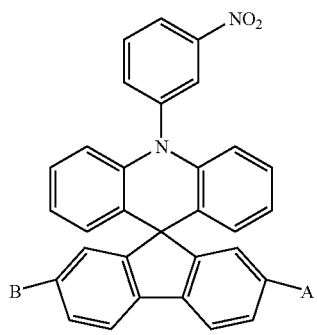
24
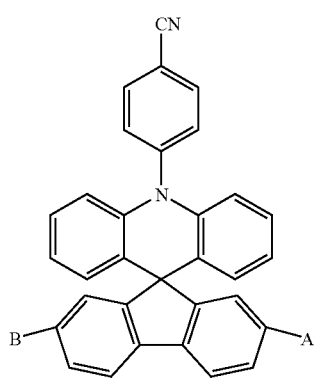
25
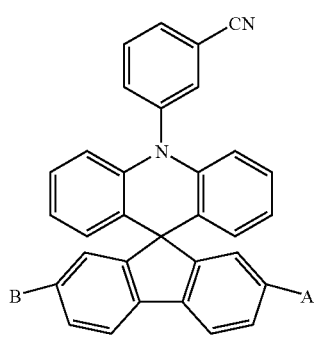
26
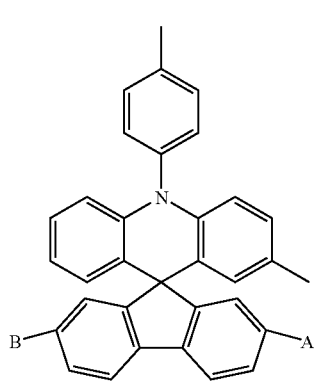

-continued
27
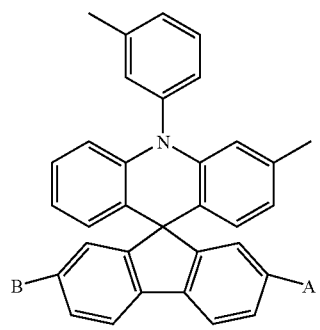
28
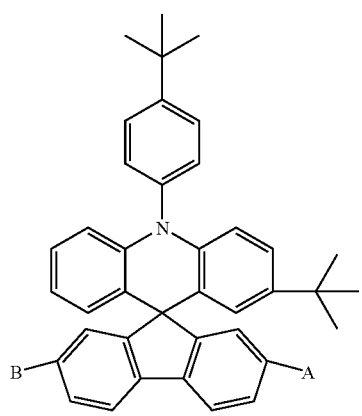
29
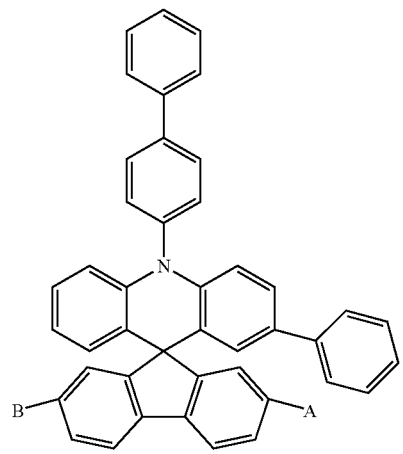
30
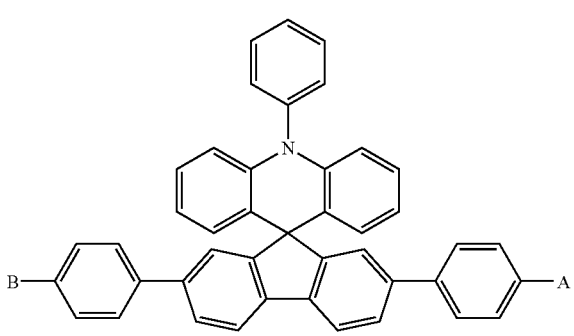
-continued
31
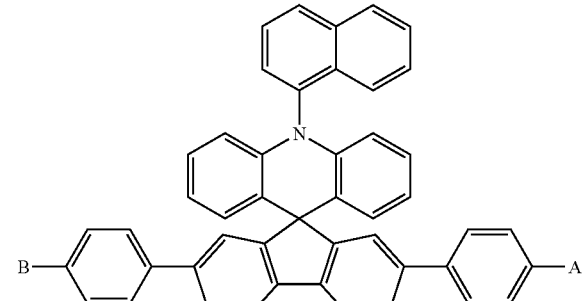
32
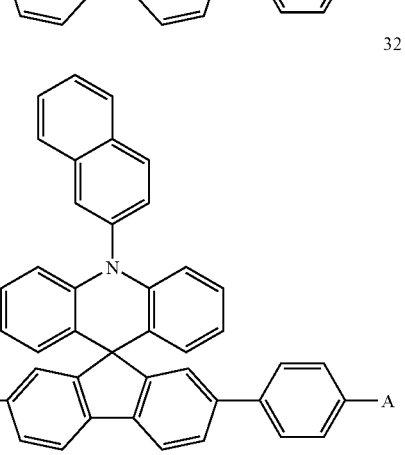
33
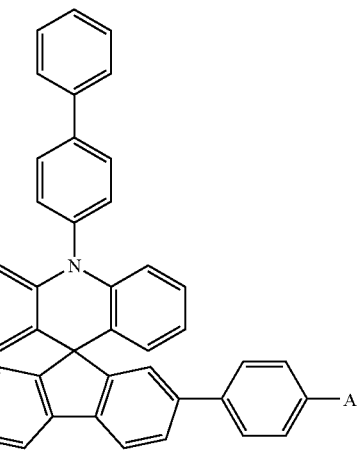
34
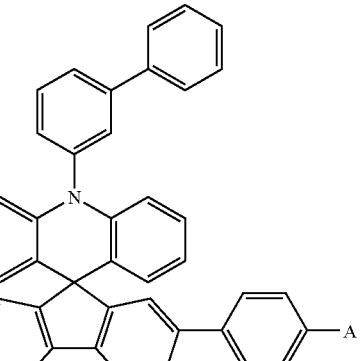

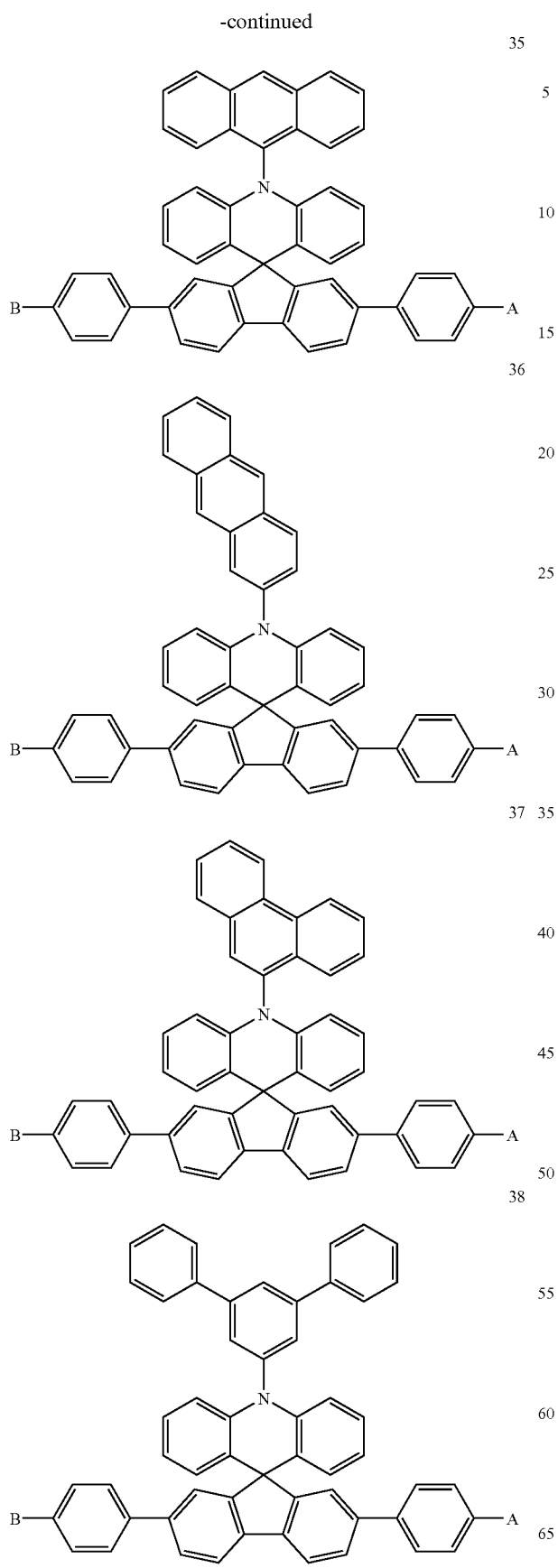
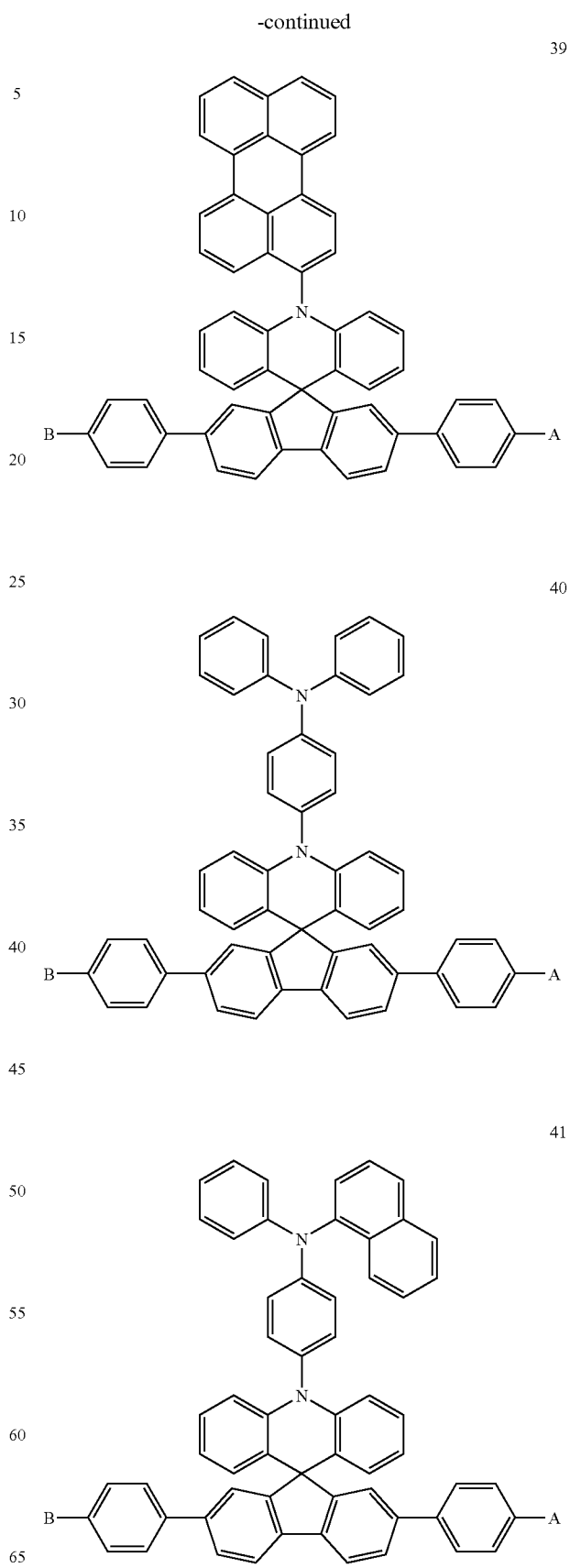

42
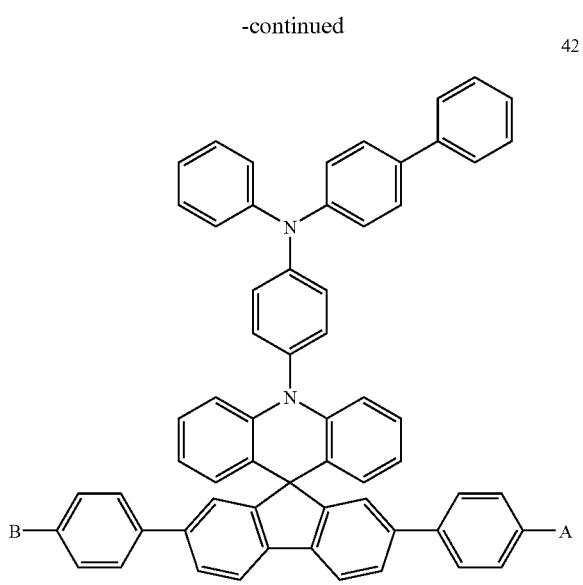
43
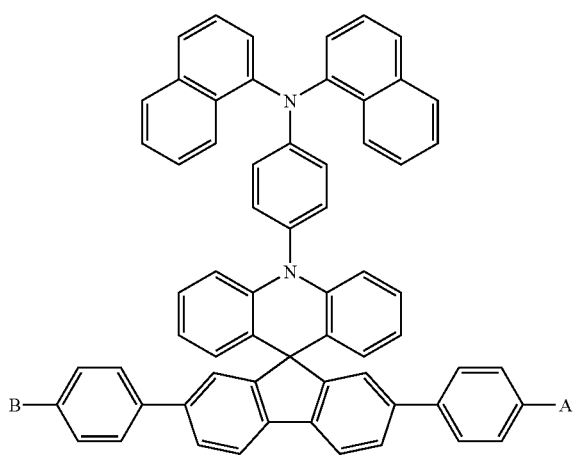
44
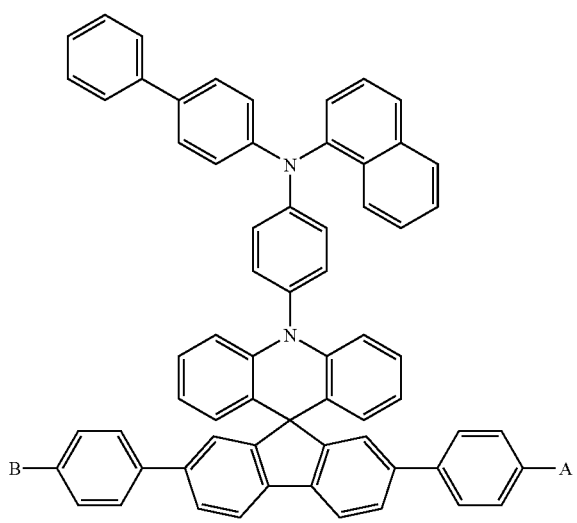
45
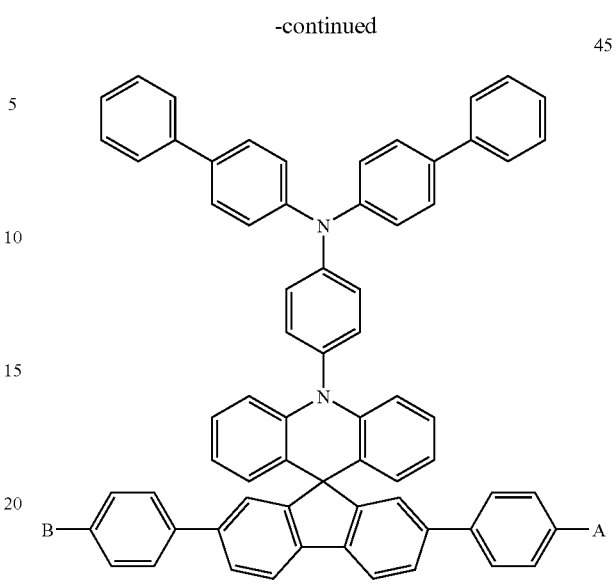
46
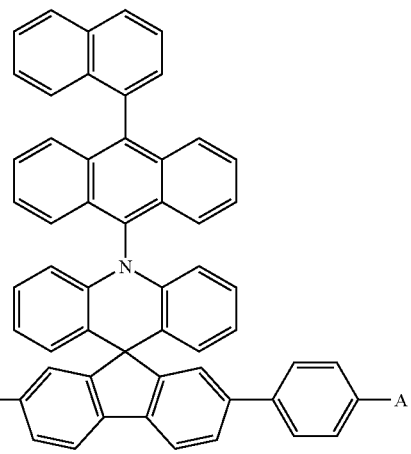
47
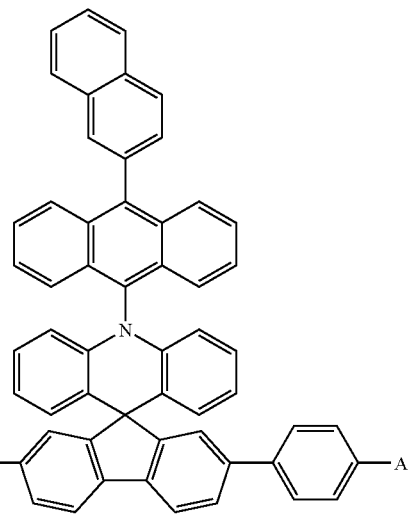

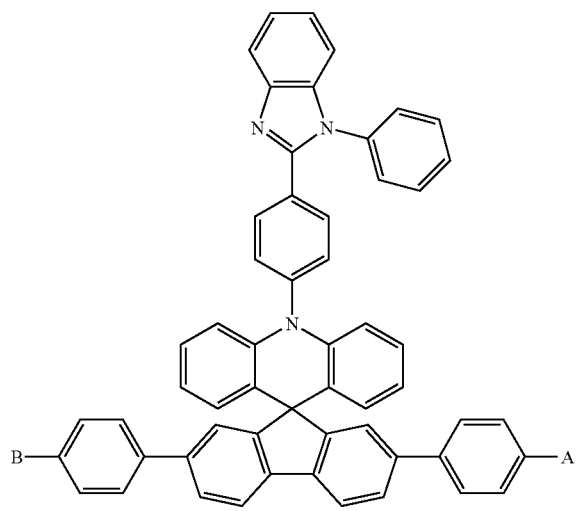
48
49
50
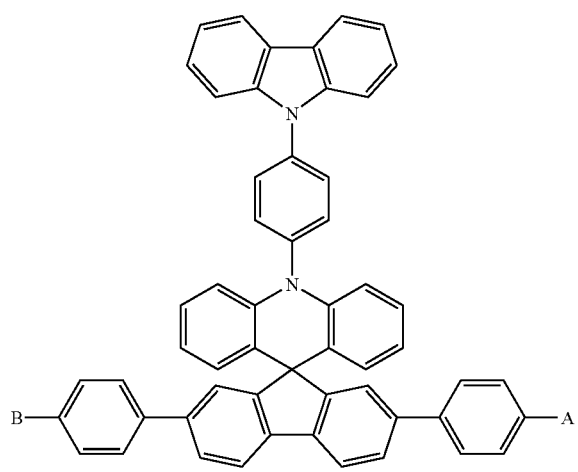
51
52
53
54

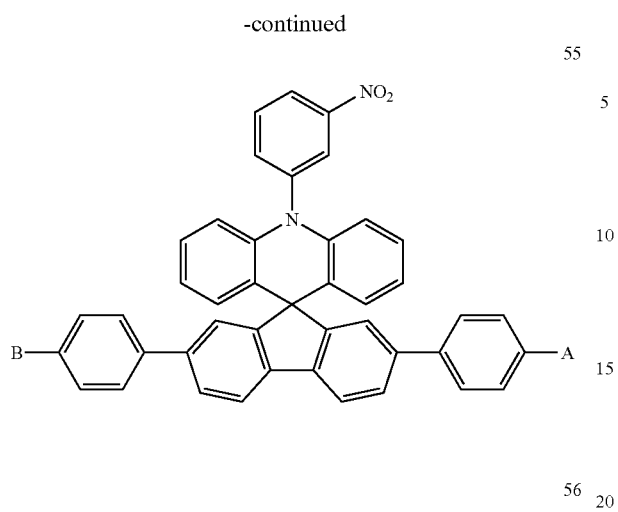
55
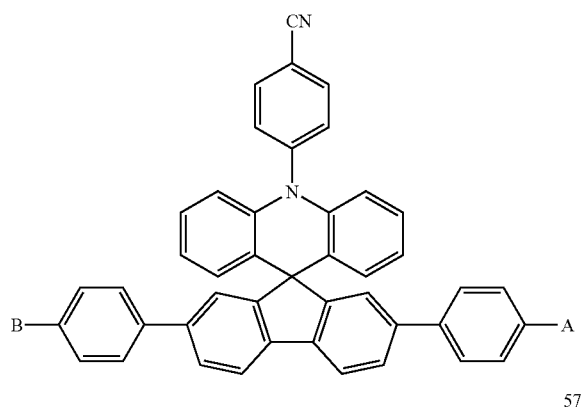
56
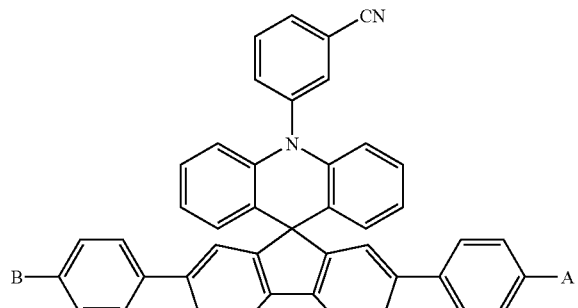
57
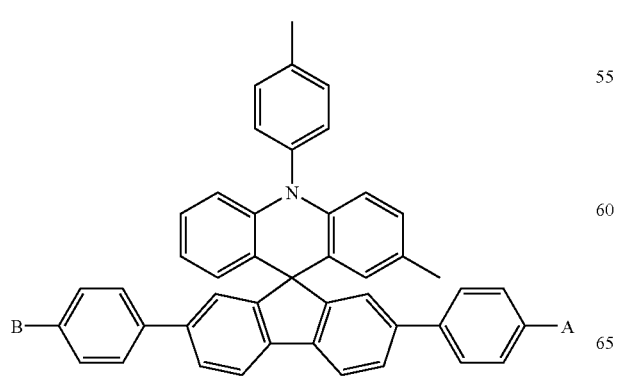
58
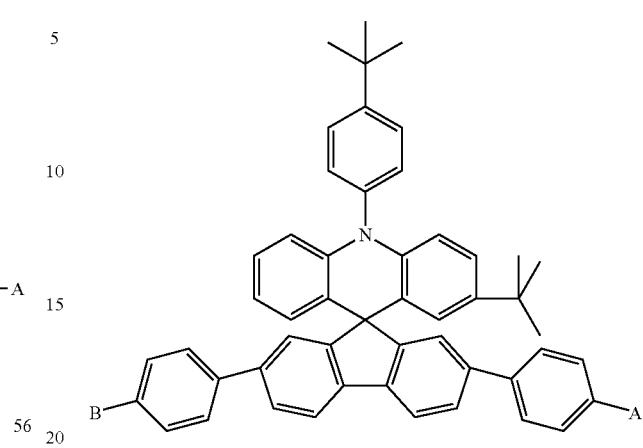
59
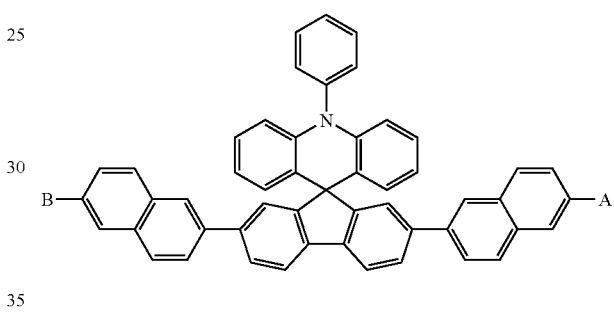
60
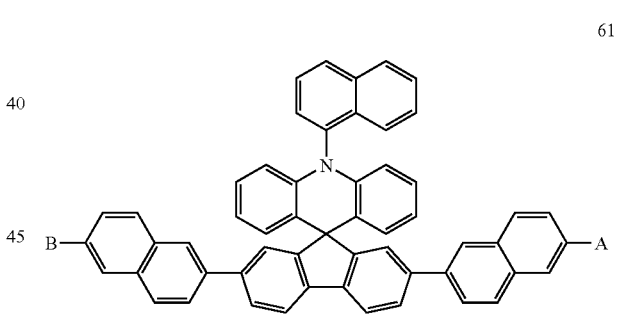
61
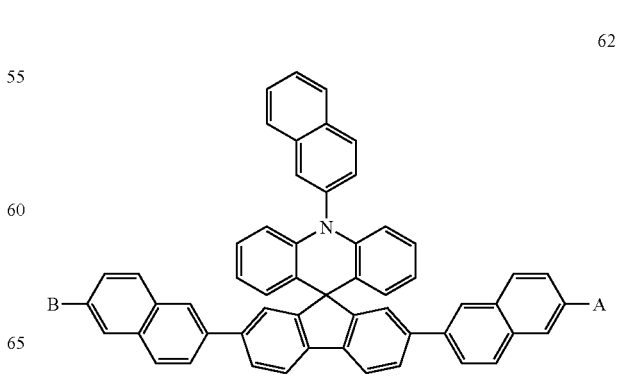
62

63
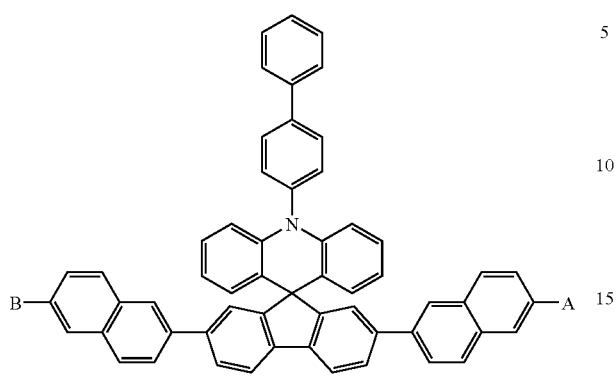
64
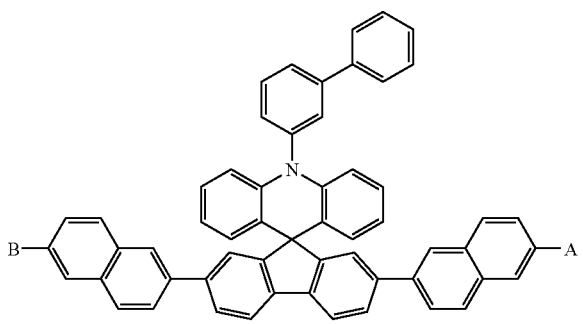
65
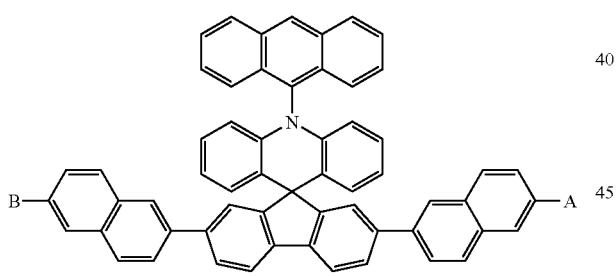
66
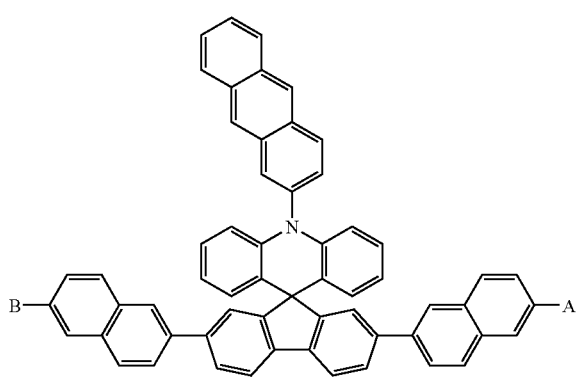
67
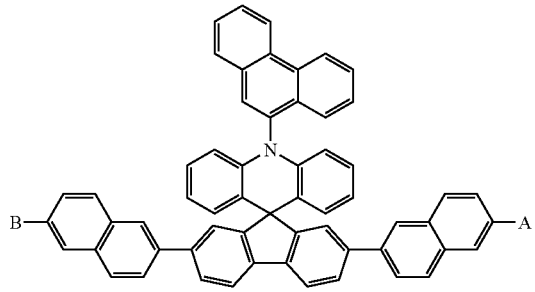
68
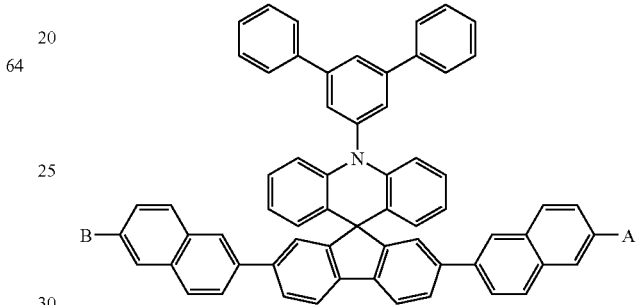
69
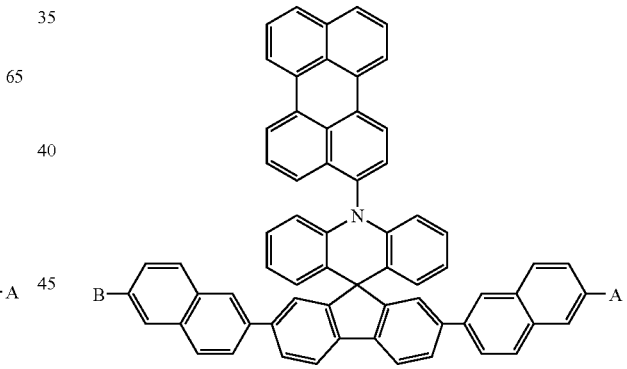
70
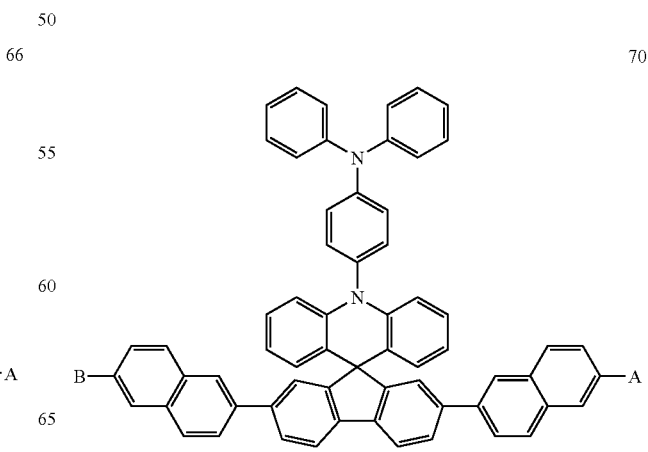

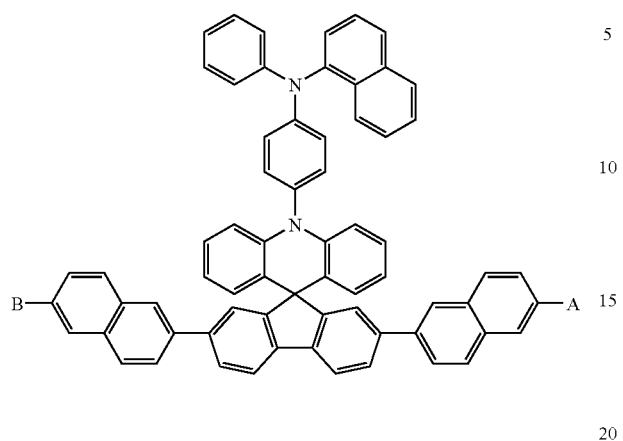
71
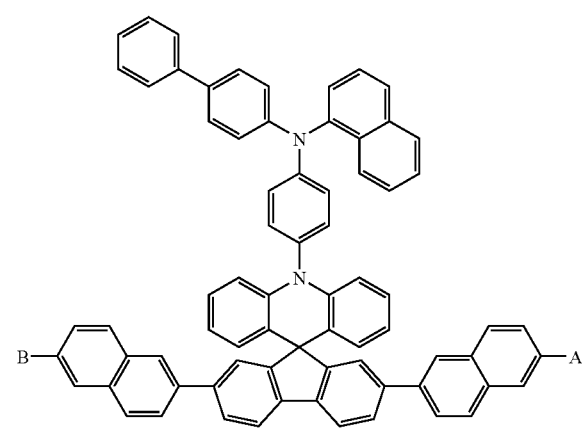
74
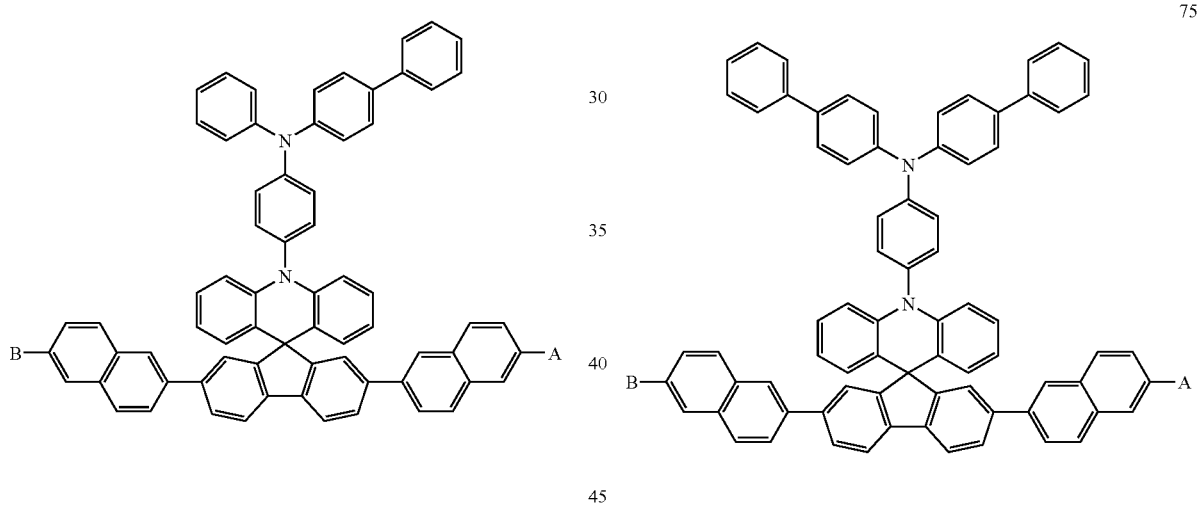
72
75
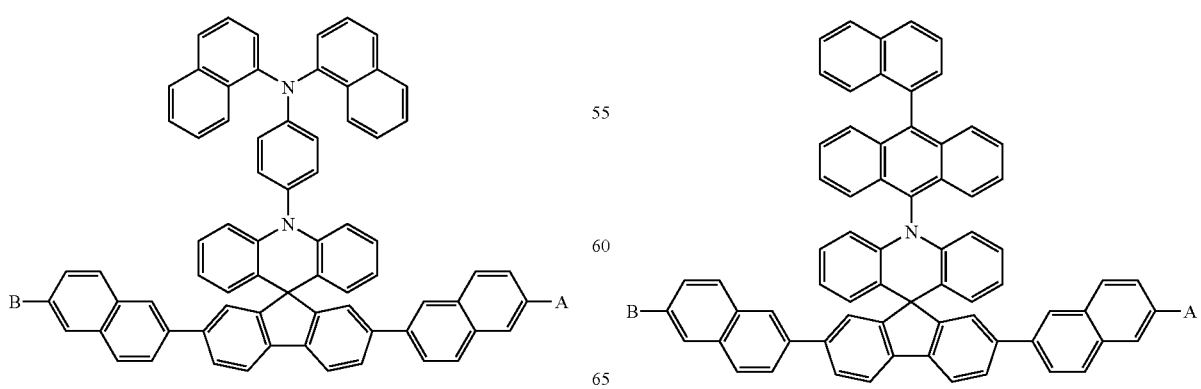
73
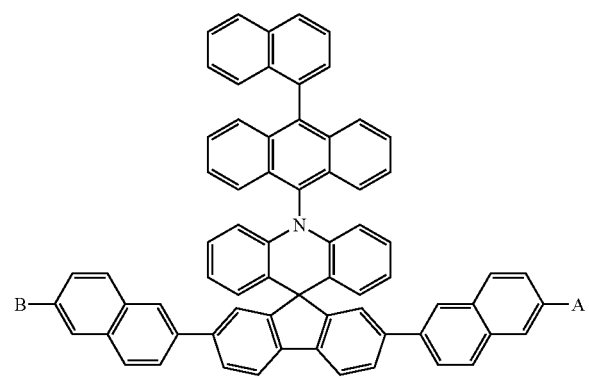
76

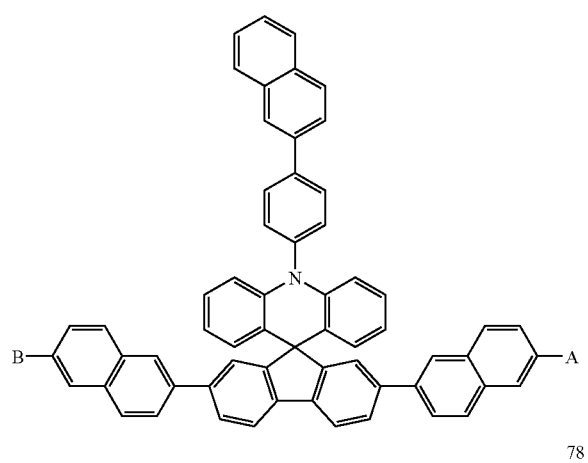
77
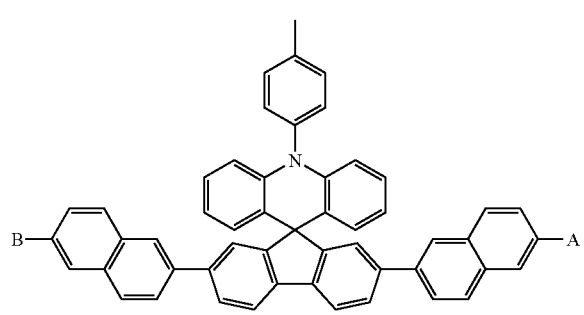
78
79
80
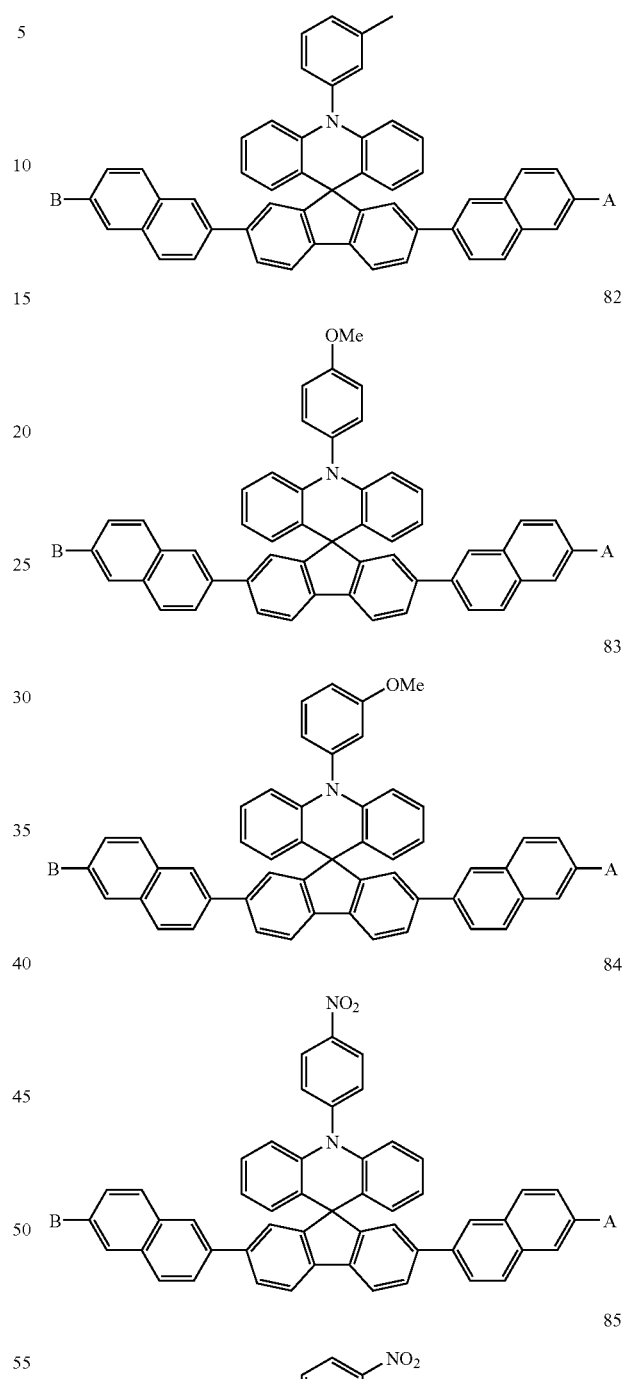
81
82
83
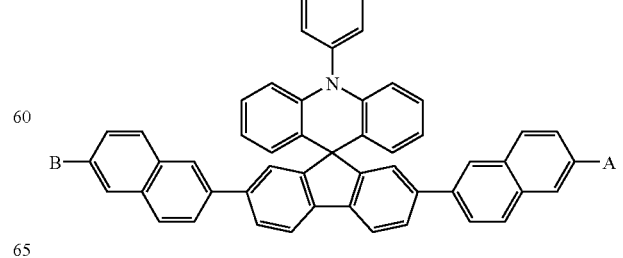
84
85

-continued
86
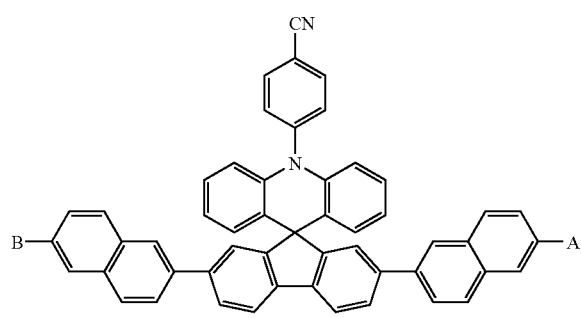
87
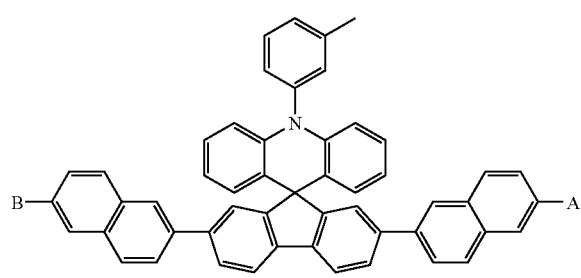
88
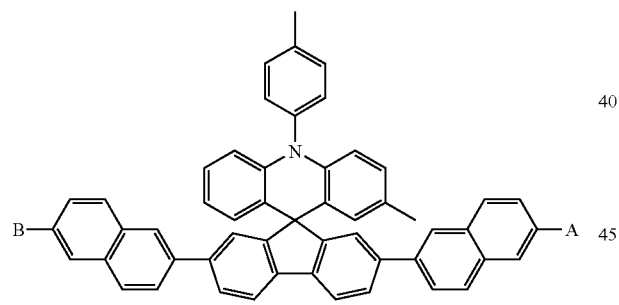
89
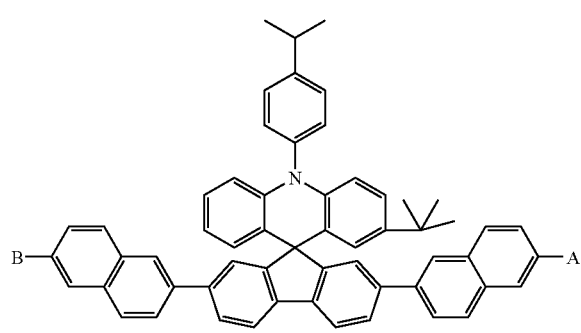
-continued
90
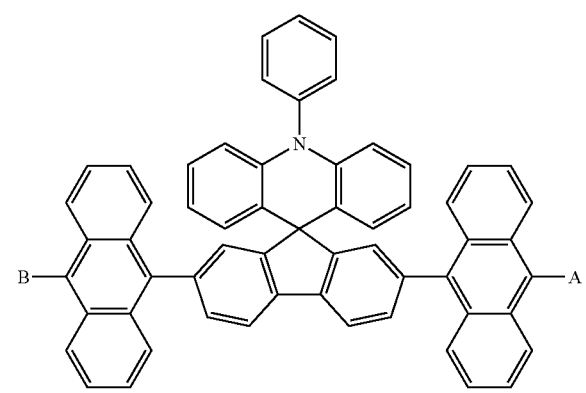
91
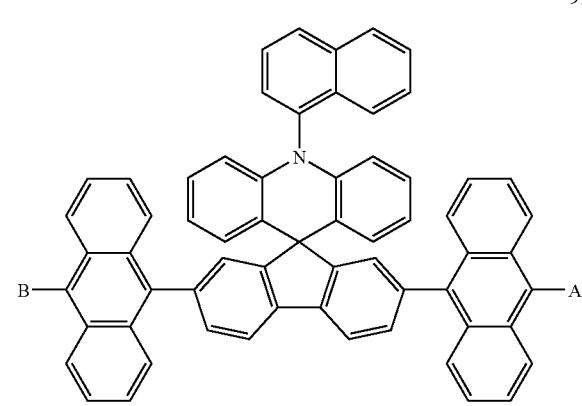
92
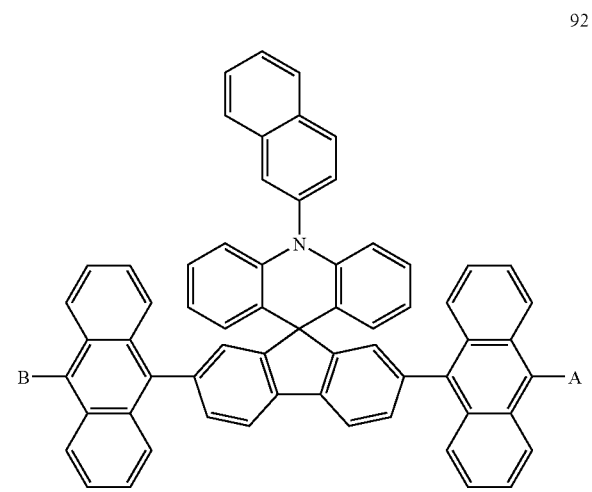

-continued
93
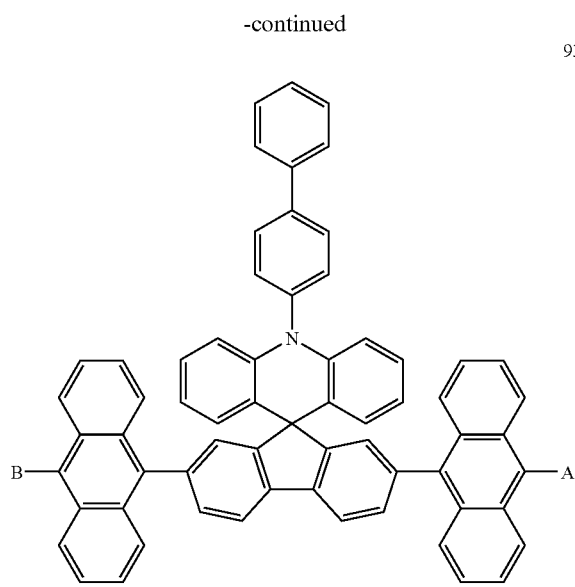
94
96
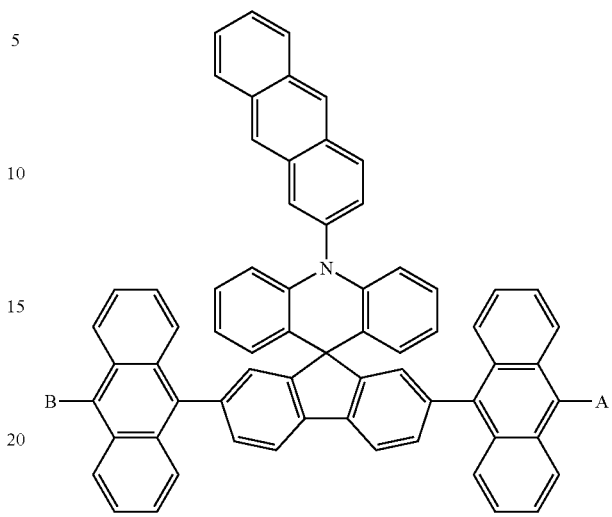
97
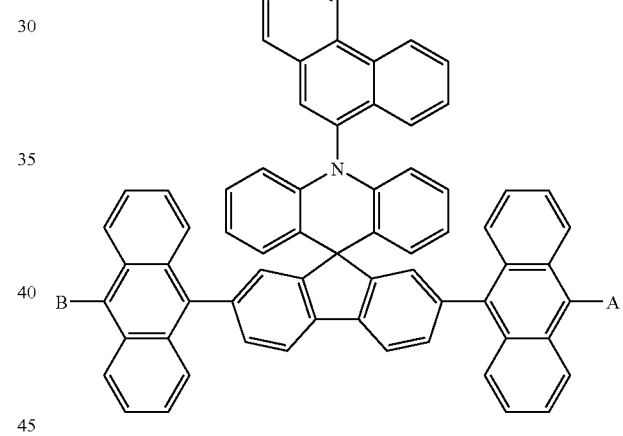
95
98
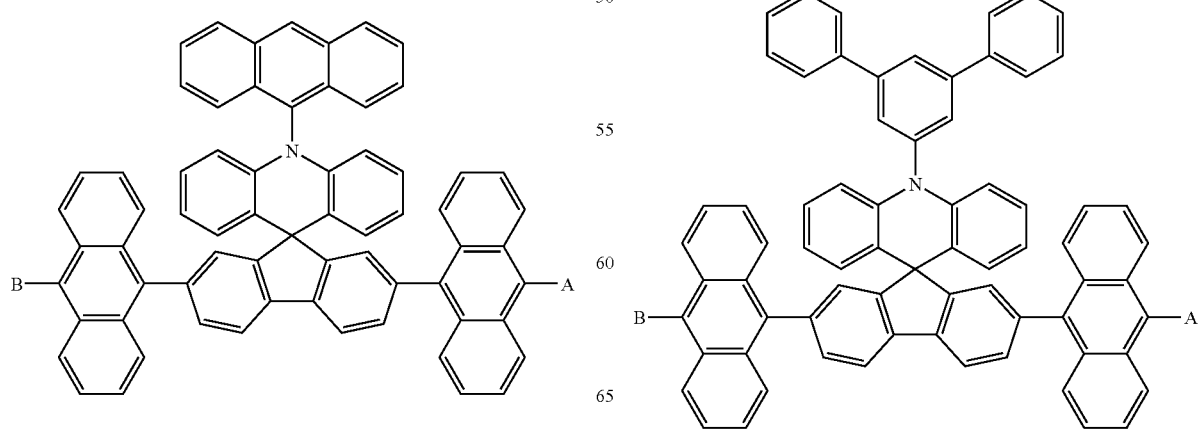

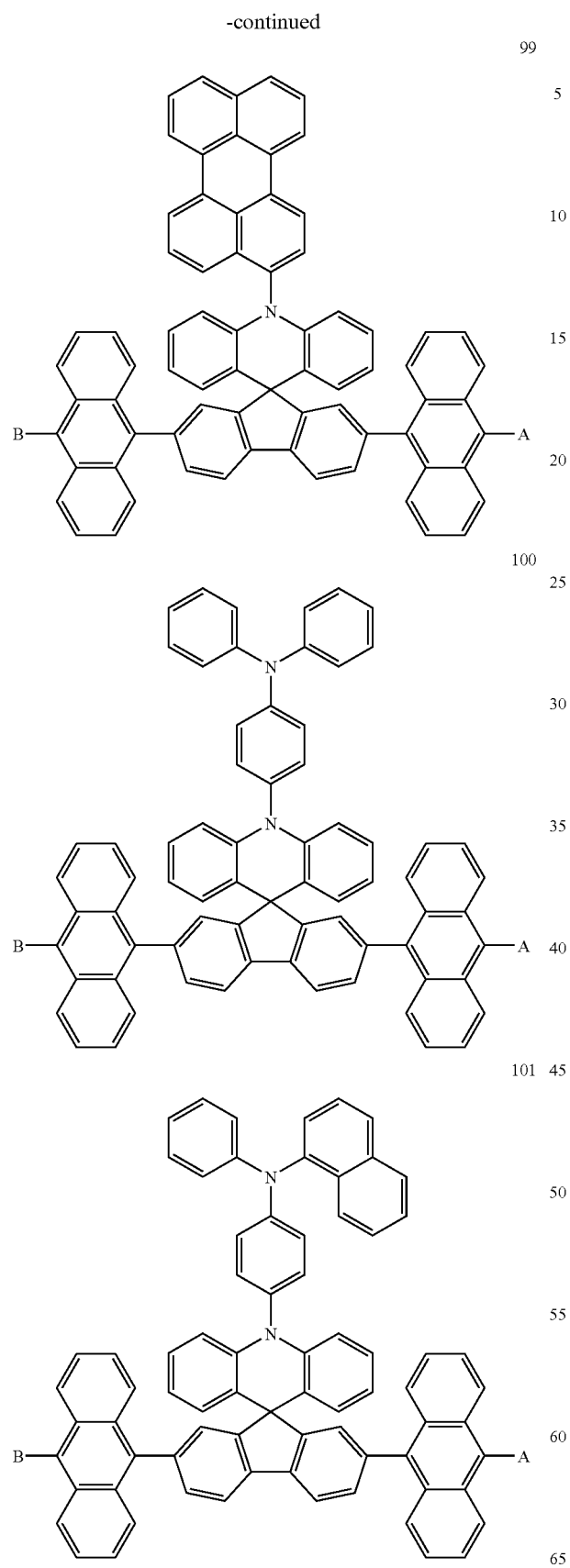
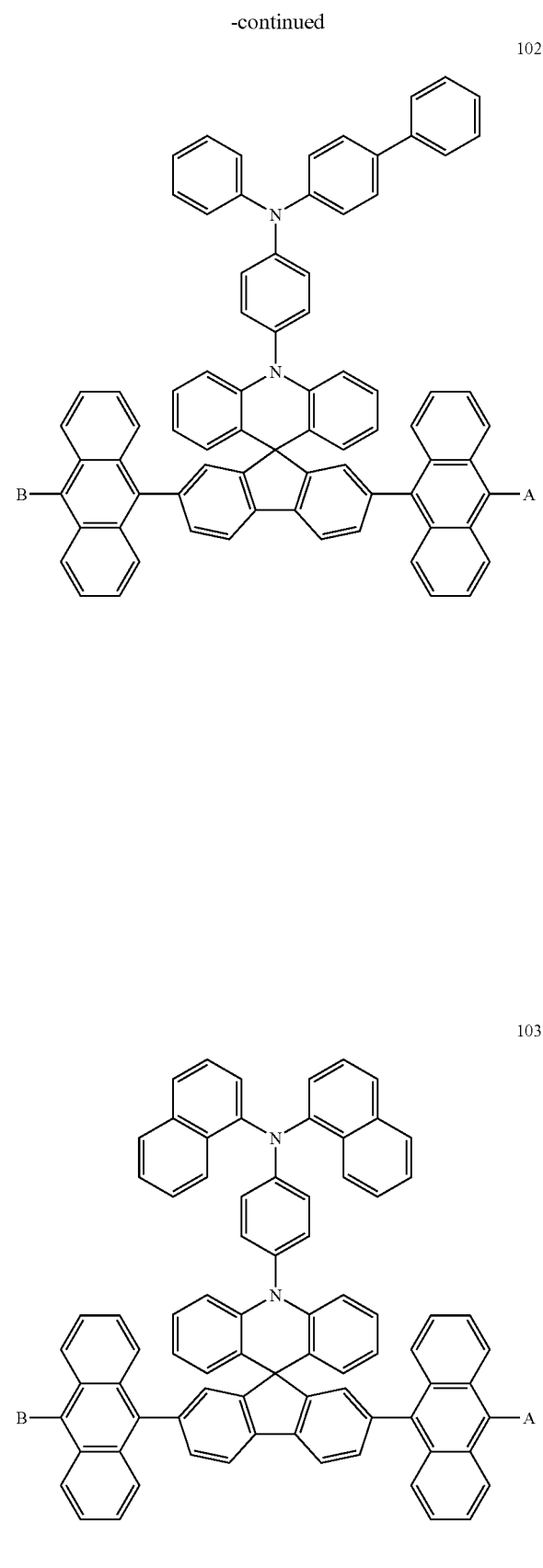

104
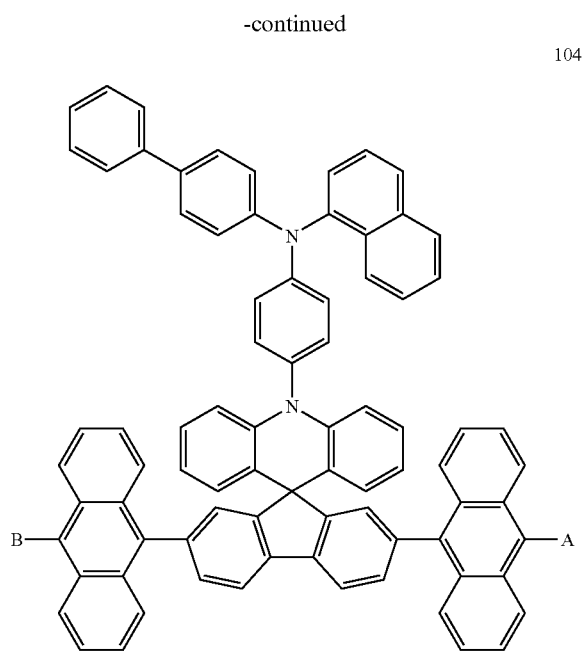
106
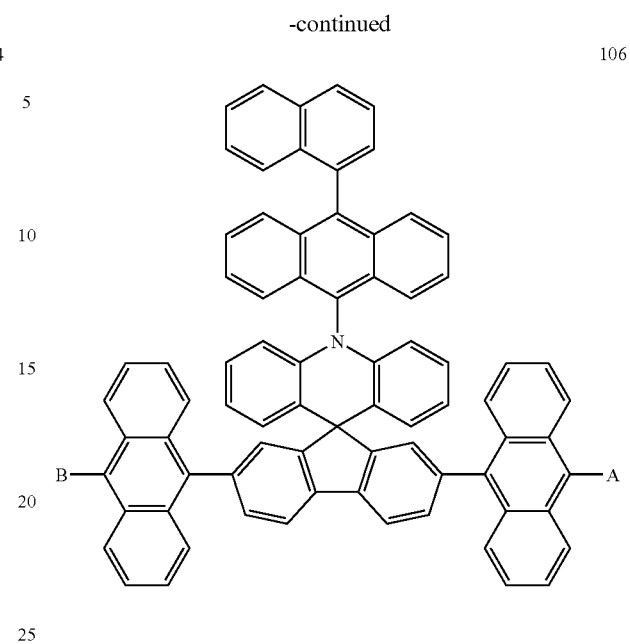
105
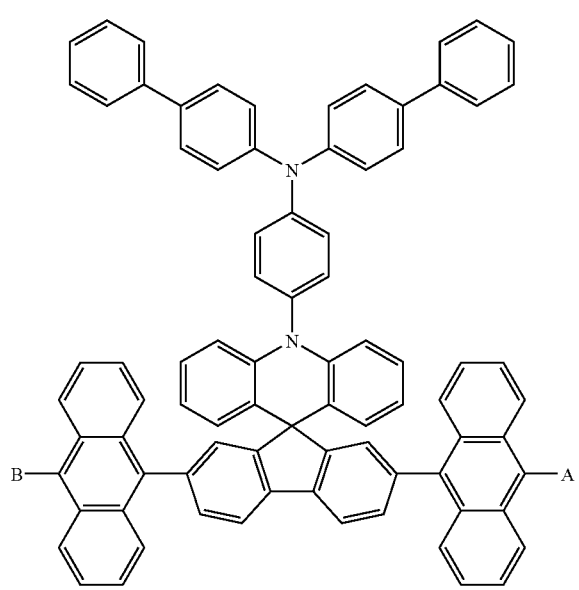
107
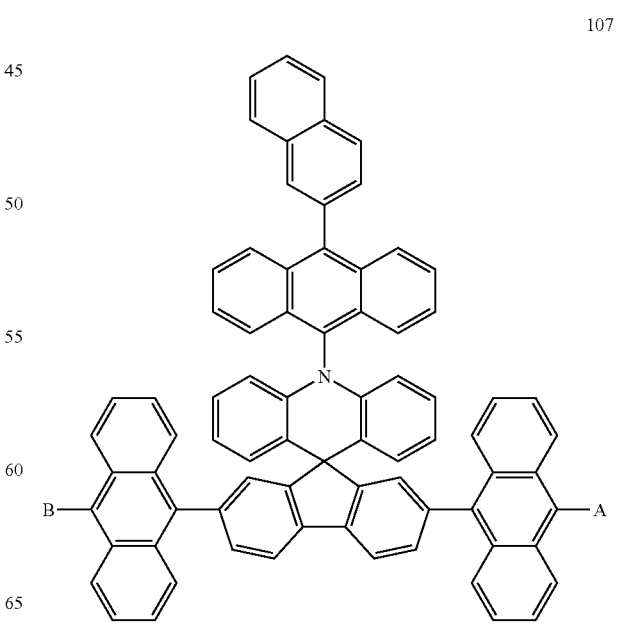

-continued
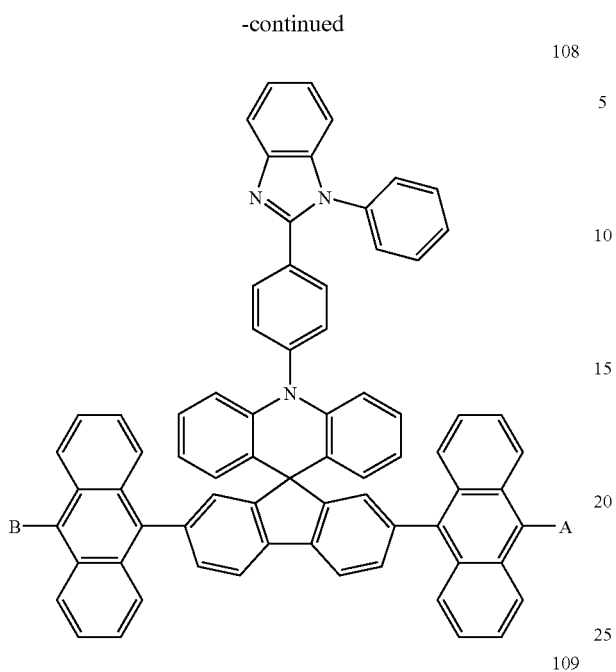
108
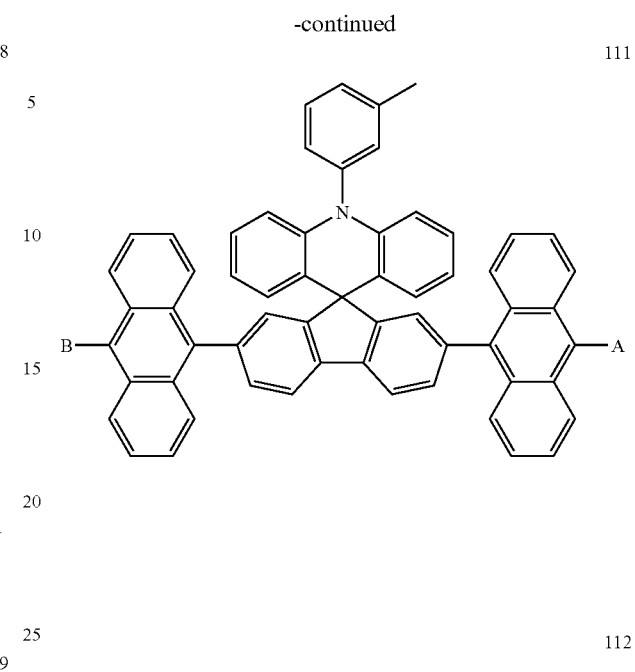
111
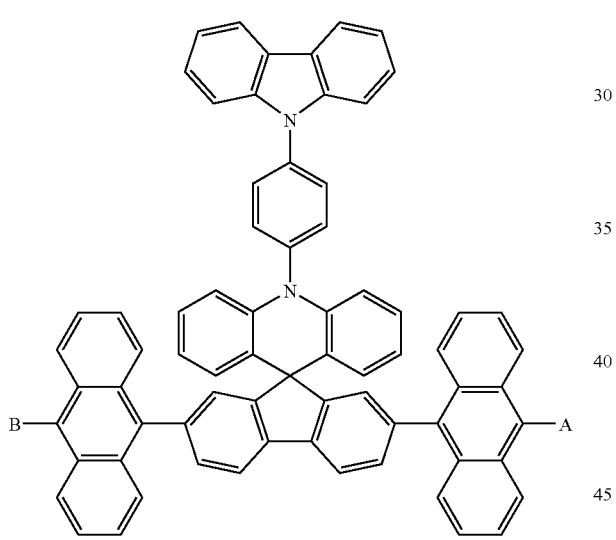
109
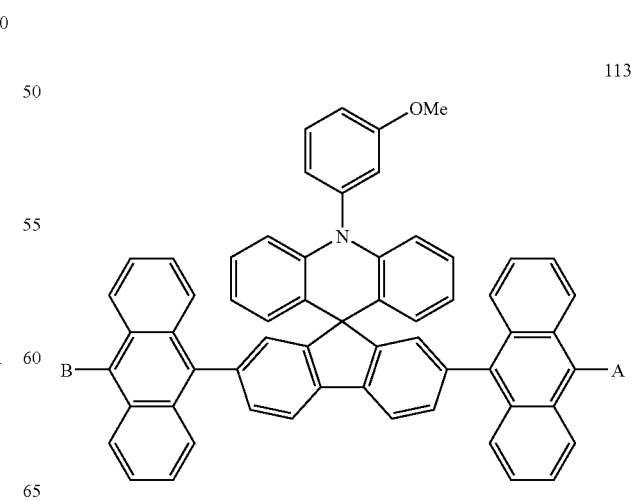
112
110
113

-continued

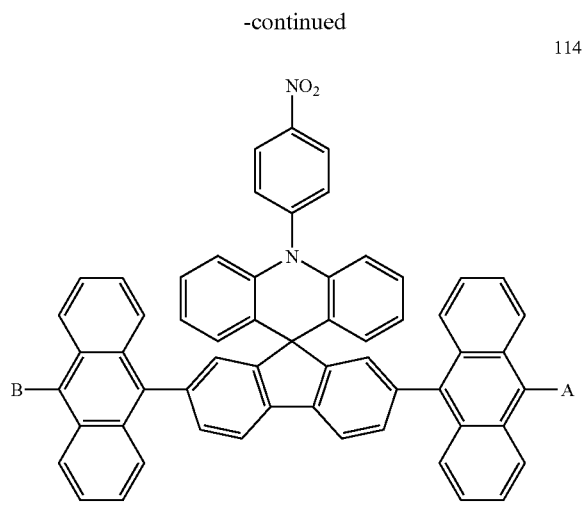
114

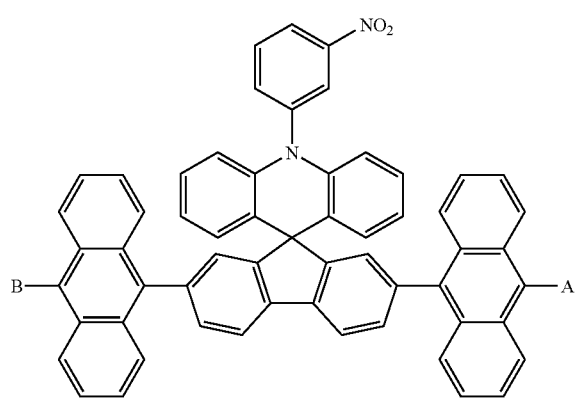
115

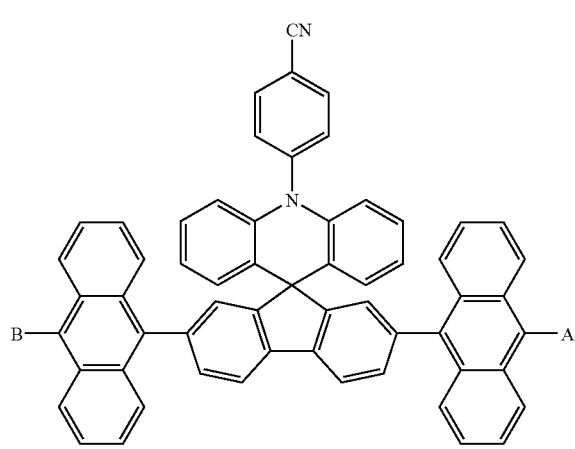
116

-continued

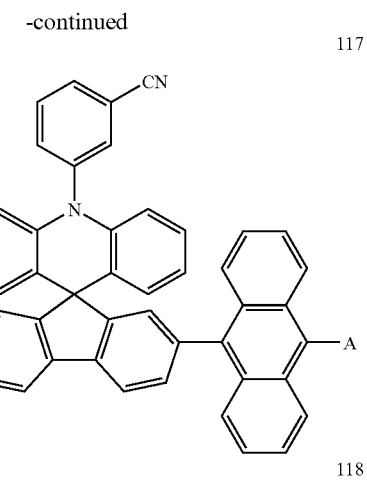
117

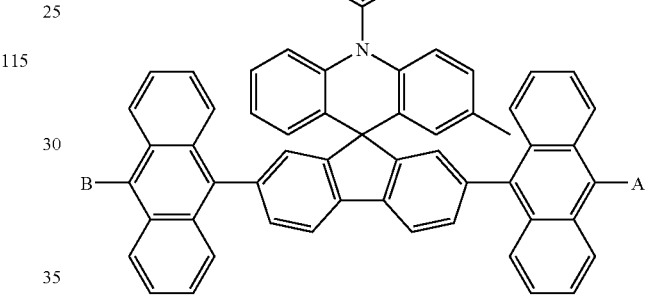
118

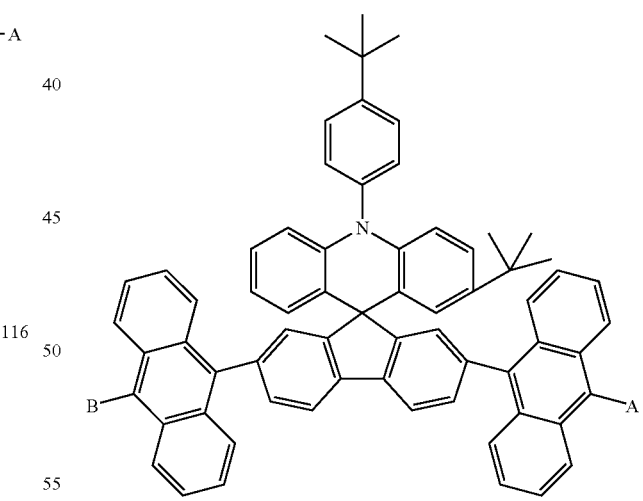
119

In the above, Formulae, A and B are as defined in Formula 1.

Illustrative, but non-limiting, examples of A and B are as follows. Combination of the compounds of Formulae 2 to 119 and the following substituent groups A and B can form various derivative compounds. For example, if the compound of Formula 2 is combined with the substituent group 1, the resulting product will be designated by the compound of Formula 2-1.

[A and B]
1
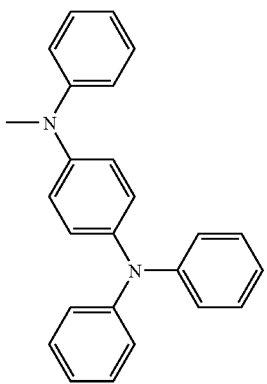
2
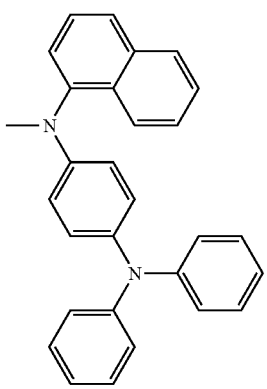
3
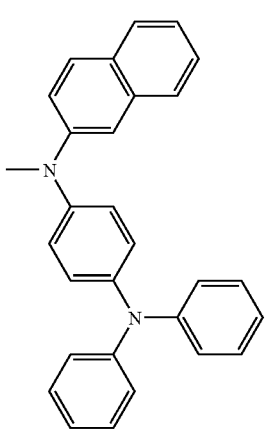
-continued
4
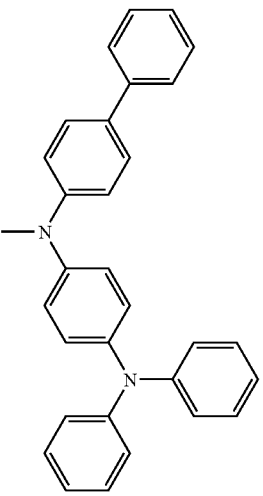
5
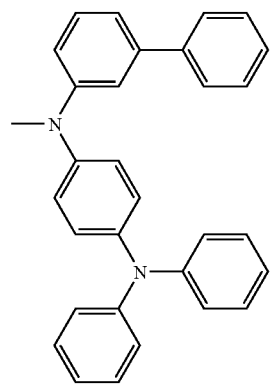
6
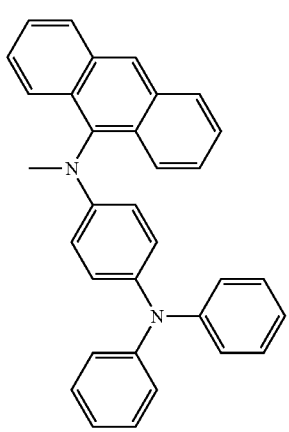

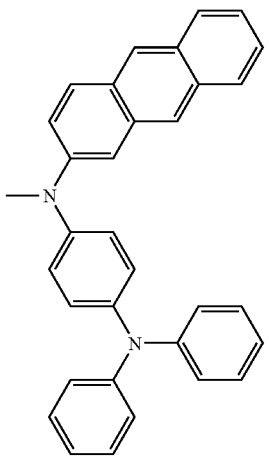
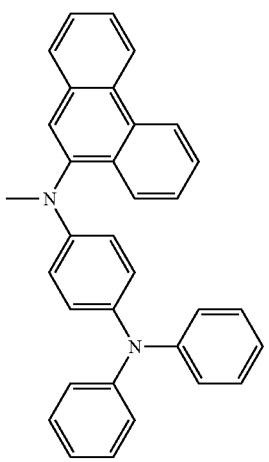
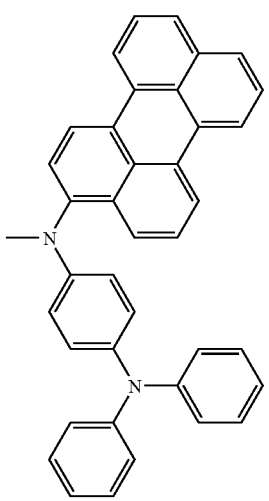
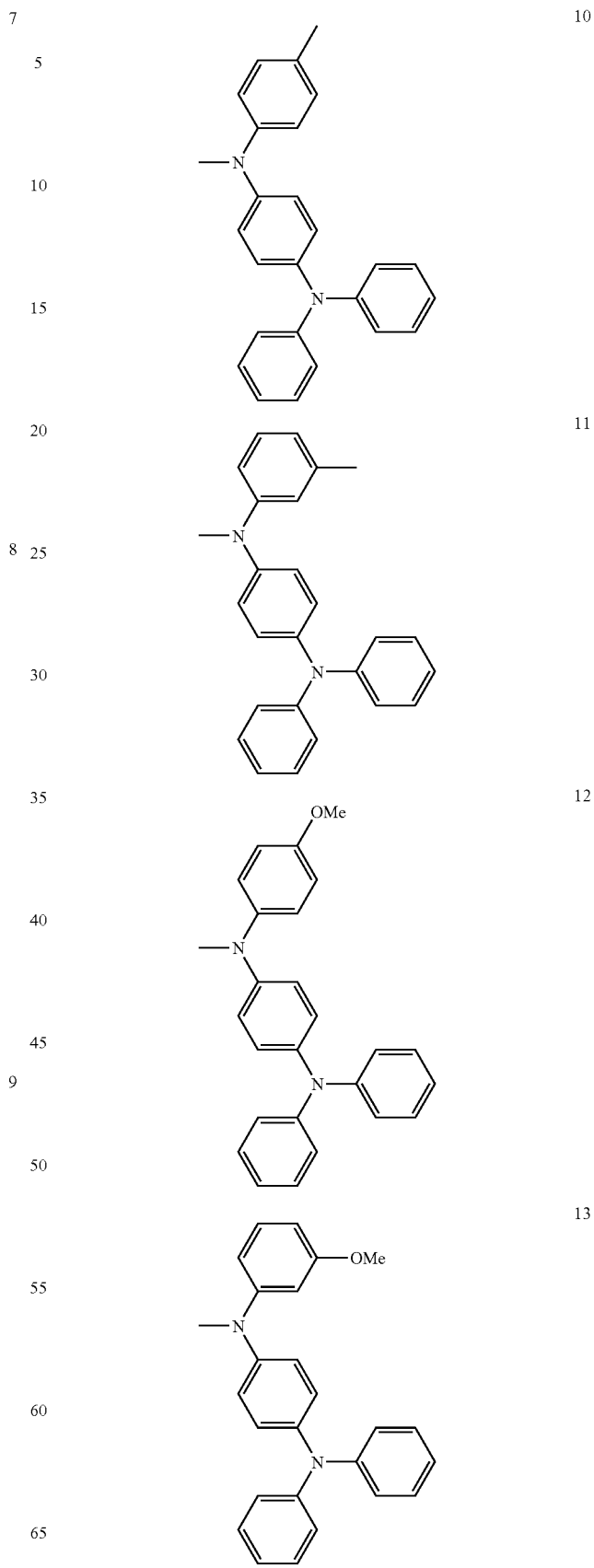

14
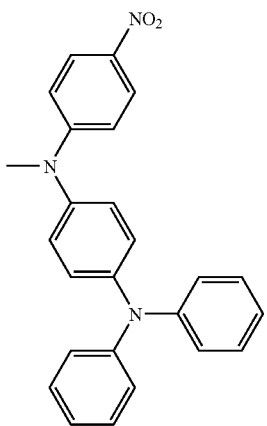
15
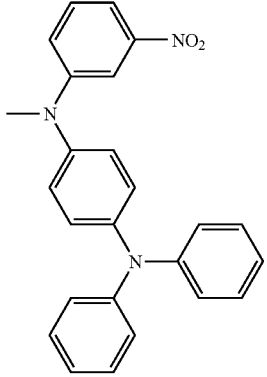
16
17
18
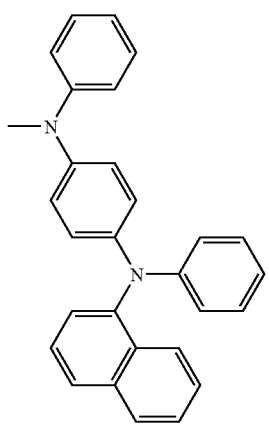
19
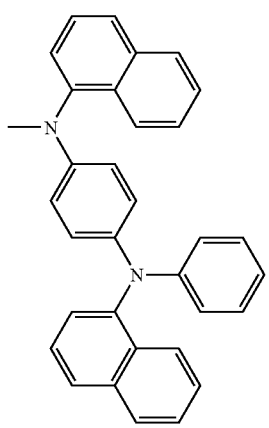
20
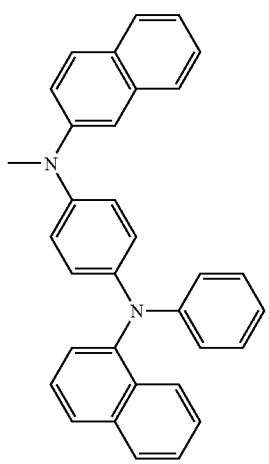

21
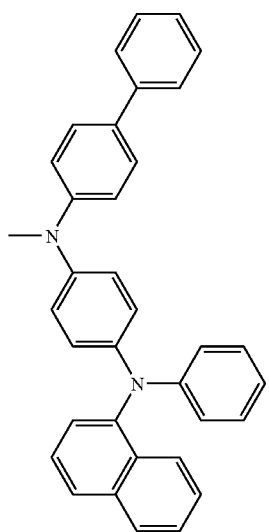
22
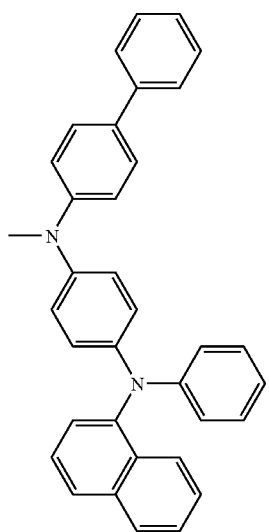
23
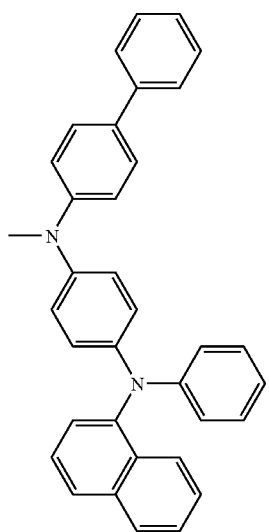
24
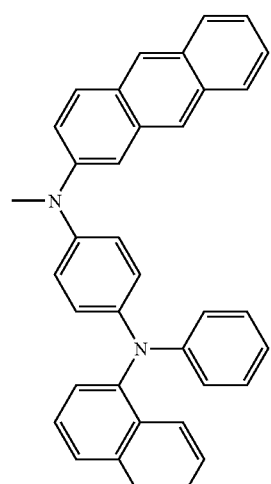
25
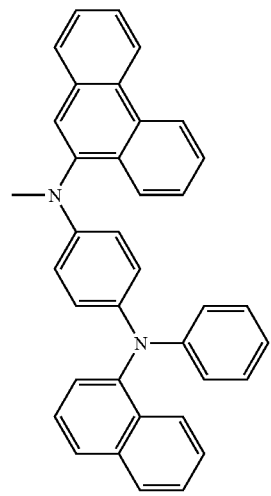
26
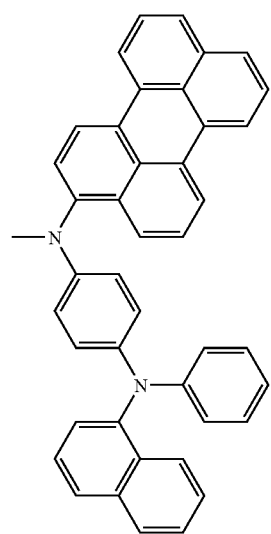

27
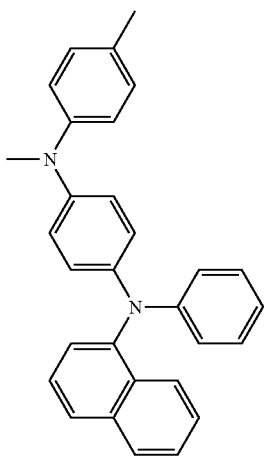
28
29
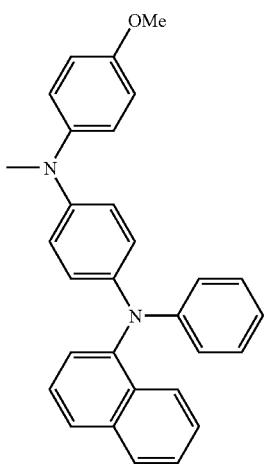
30
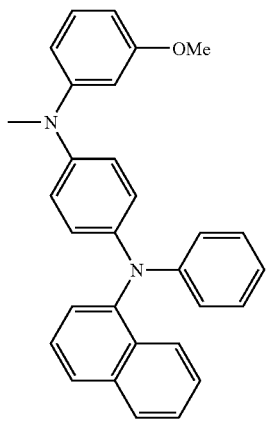
31
32

-continued
33
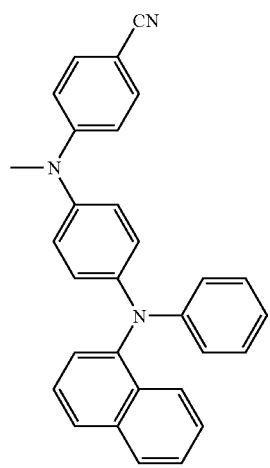
34
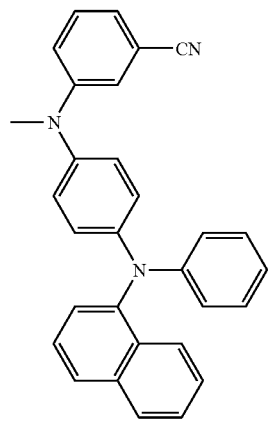
35
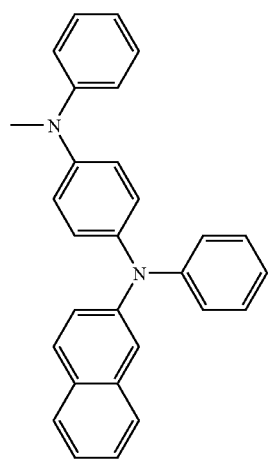
-continued
36
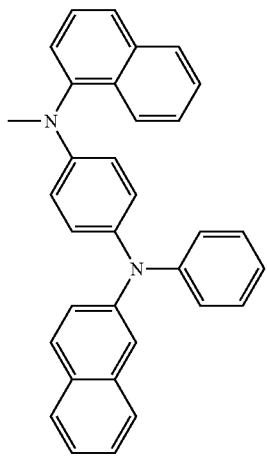
37
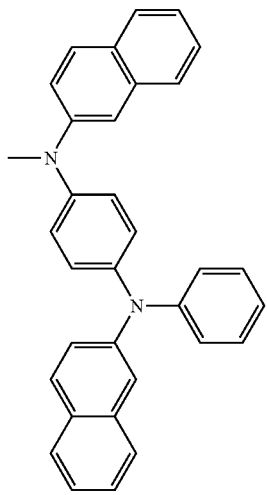
38
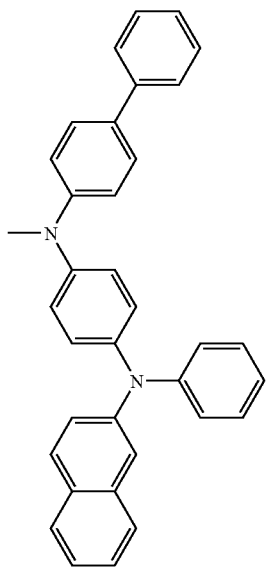

-continued
39
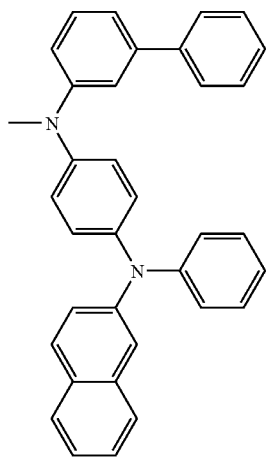
40
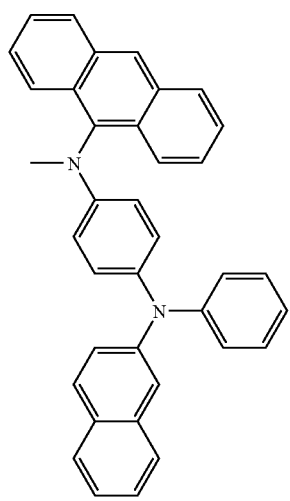
41
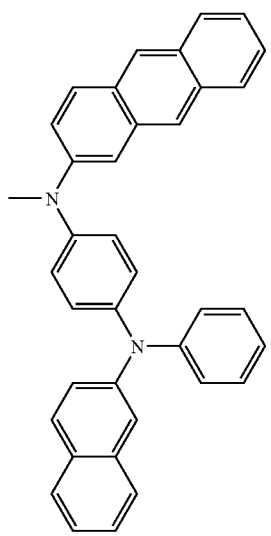
-continued
42
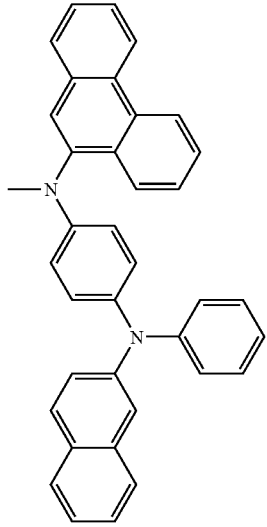
43
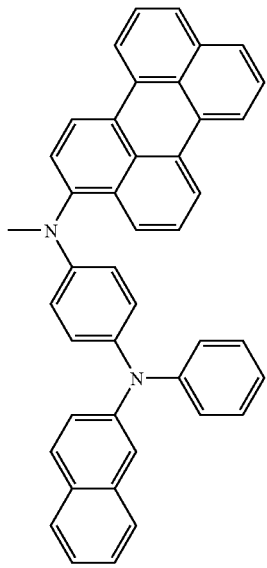
44
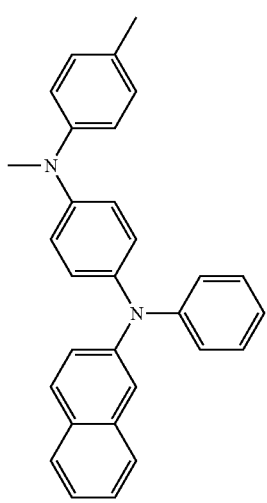

45
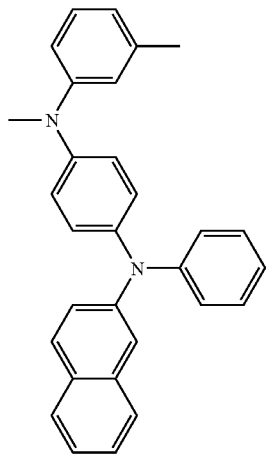
46
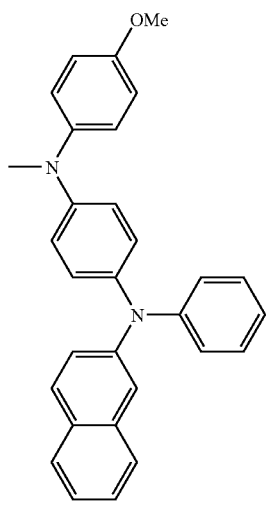
47
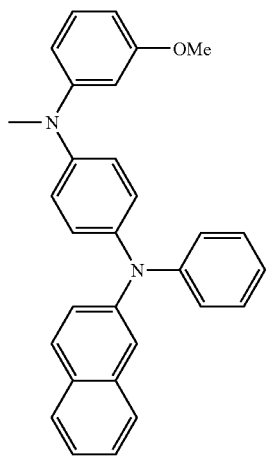
48
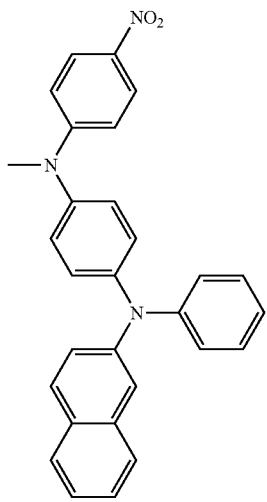
49
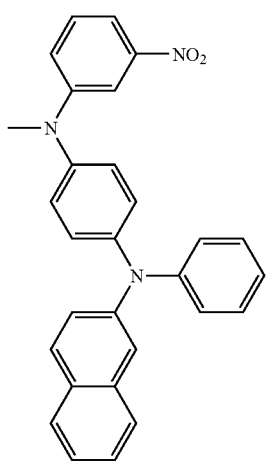
50
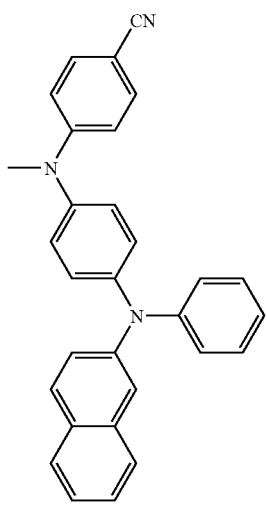

-continued
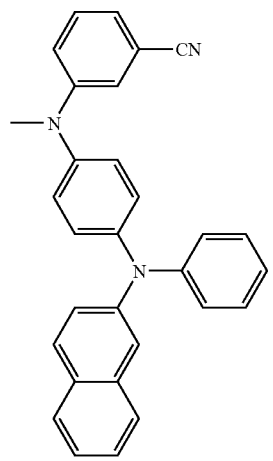
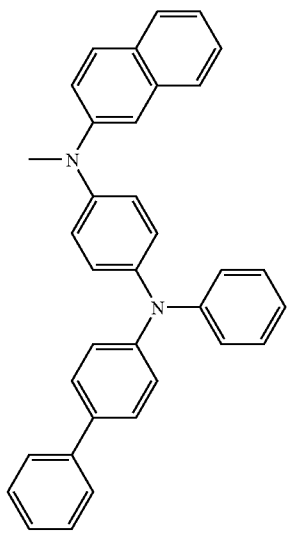

-continued
57
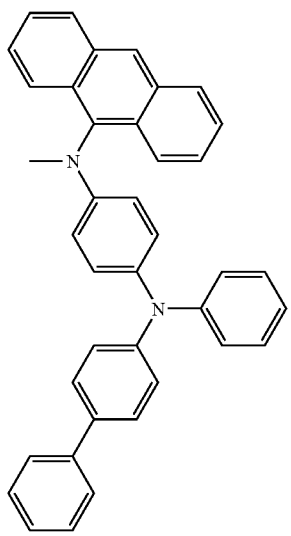
58
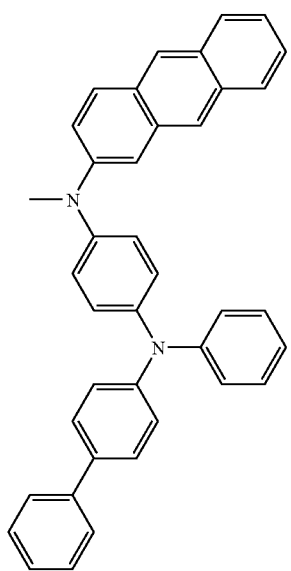
59
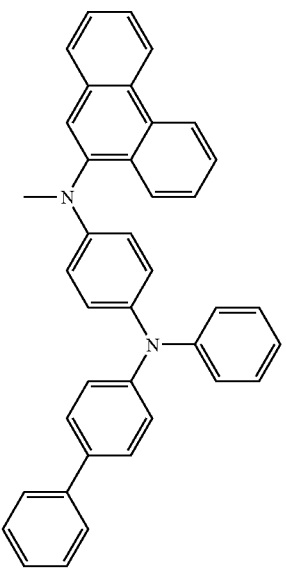
60
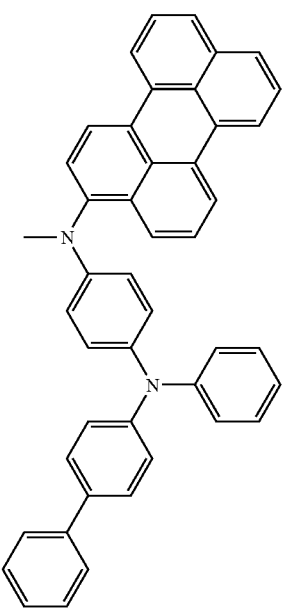

61
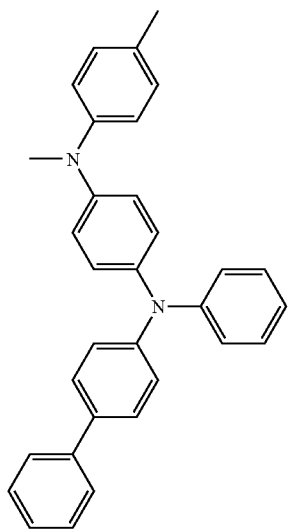
62
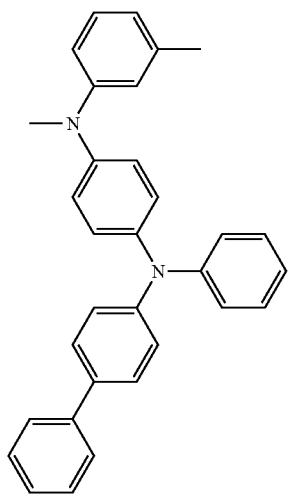
63
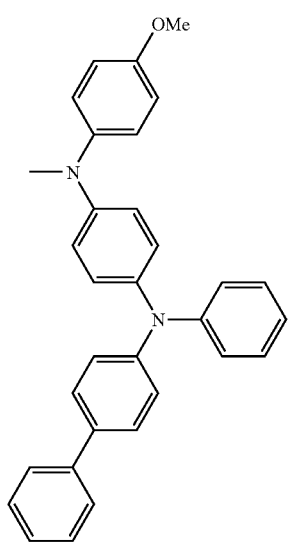
64
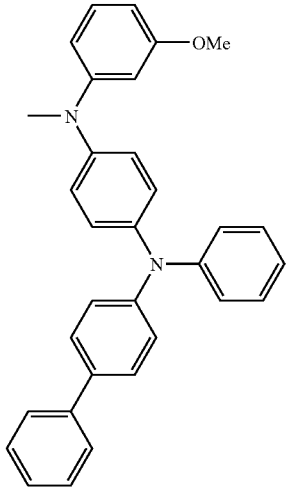
65
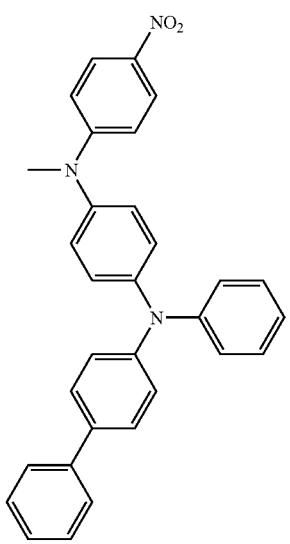
66
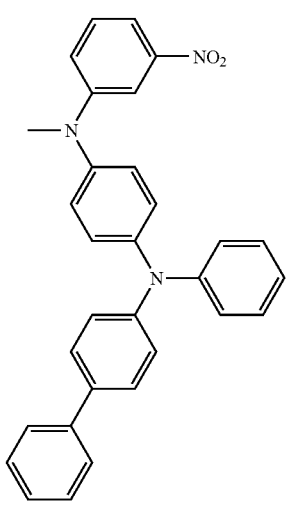

-continued
67
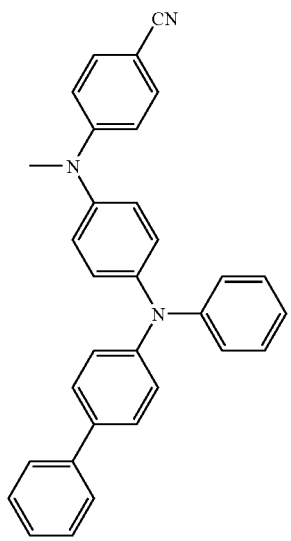
68
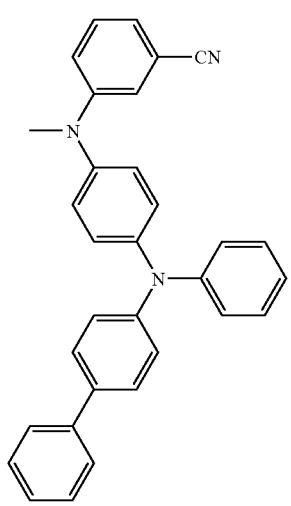
69
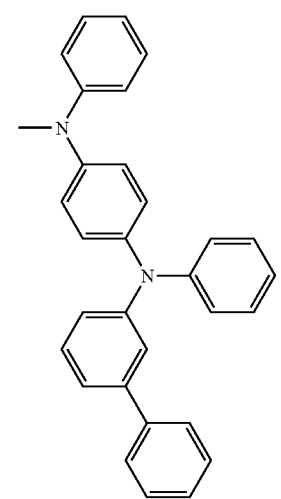
-continued
70
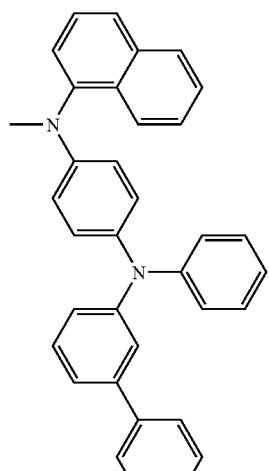
71
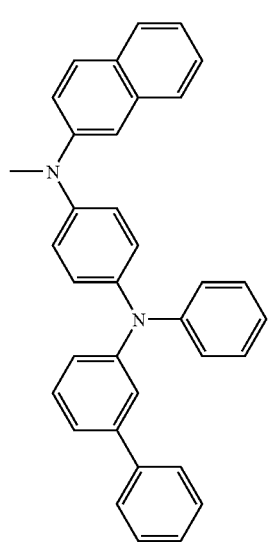
72
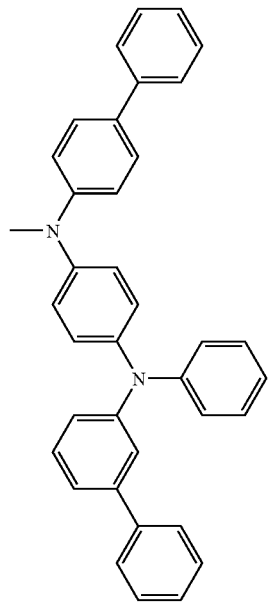

-continued
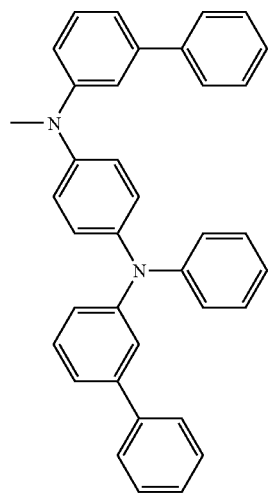
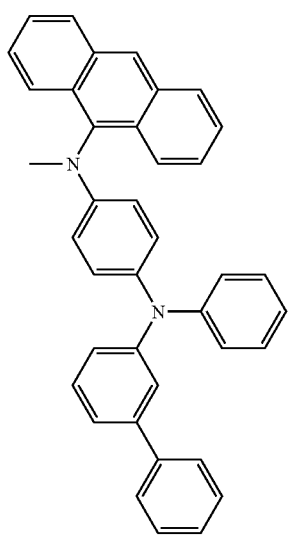
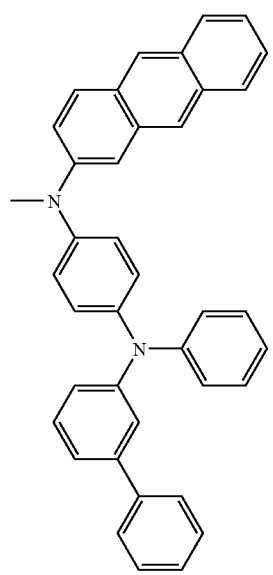
-continued
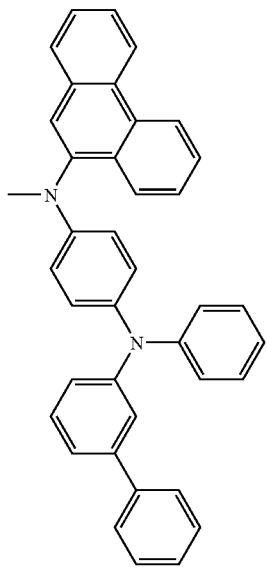
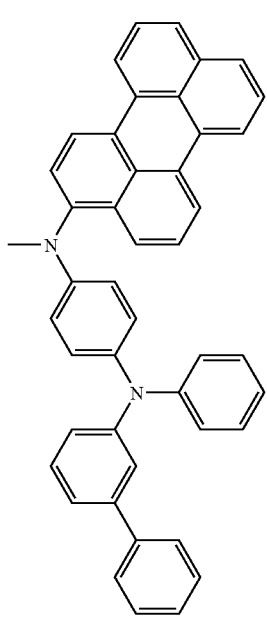

-continued
78
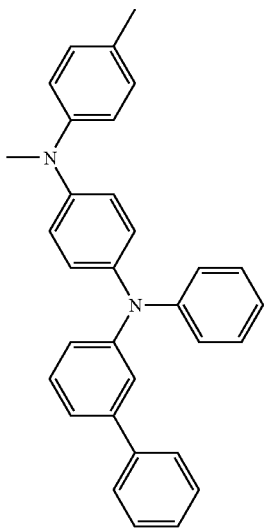
79
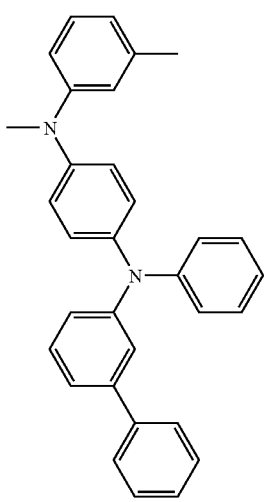
80
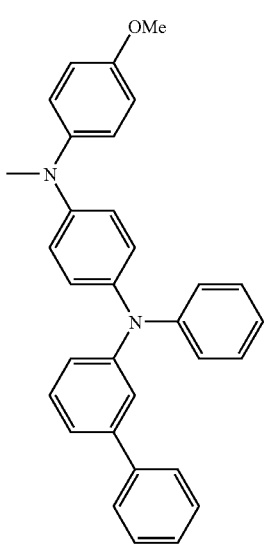
-continued
81
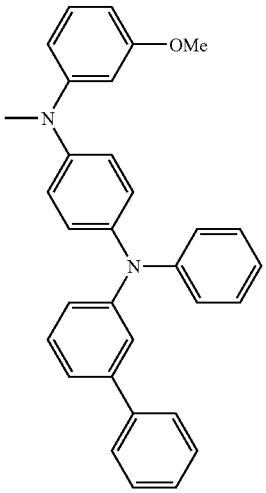
82
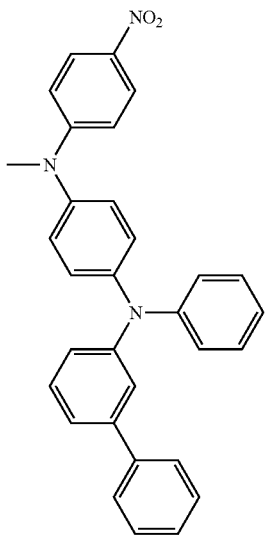
83
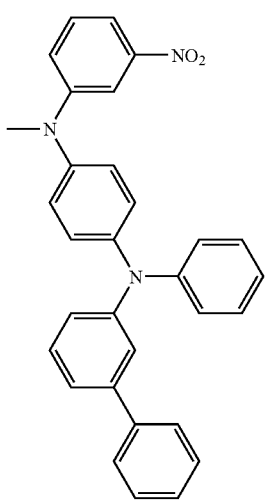

-continued
84
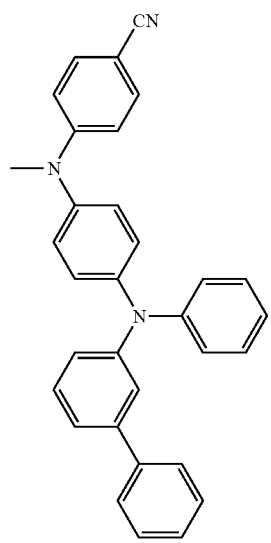
85
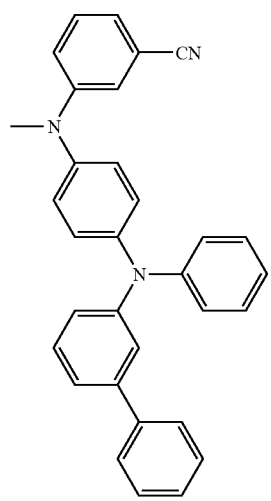
86
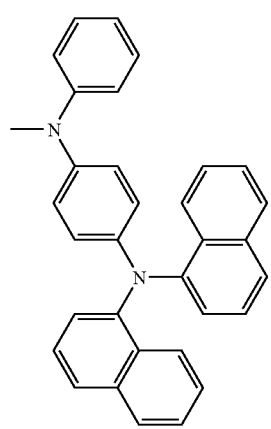
-continued
87
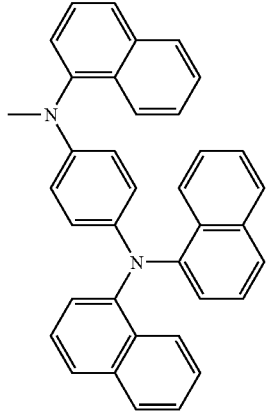
88
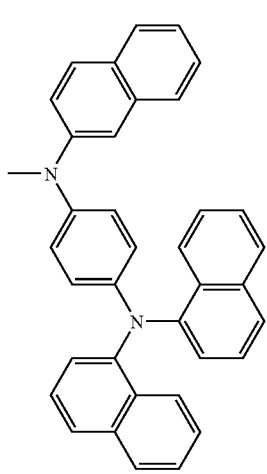
89
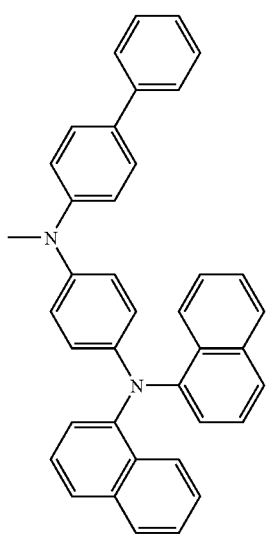

90
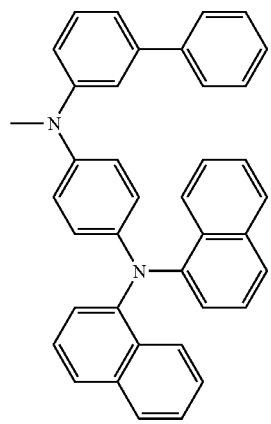
91
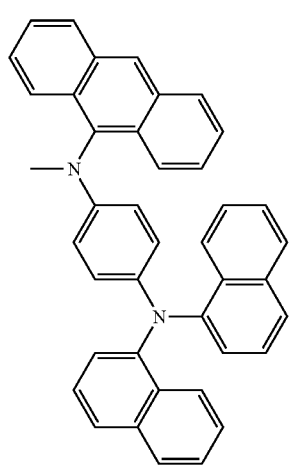
92
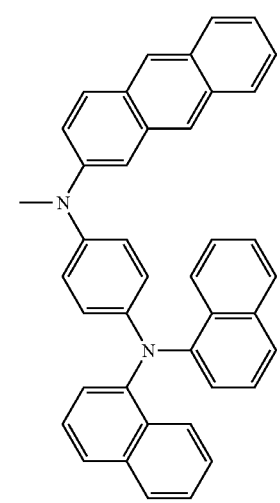
93
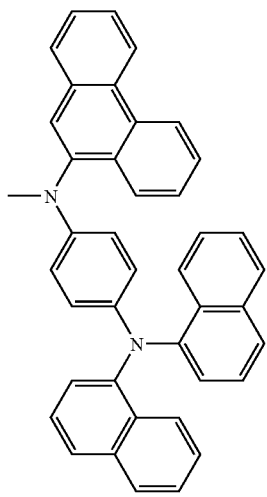
94
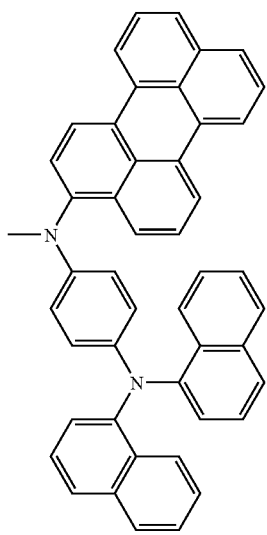
95
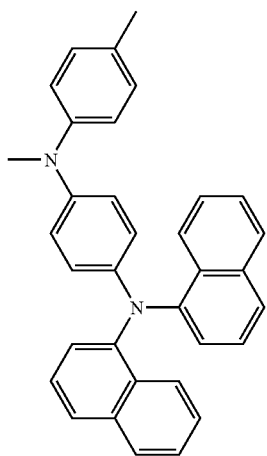

-continued
96
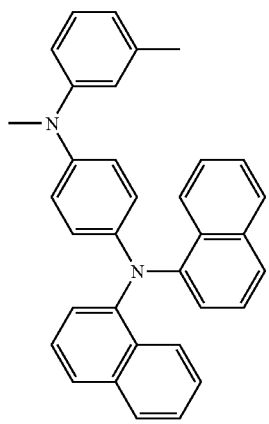
97
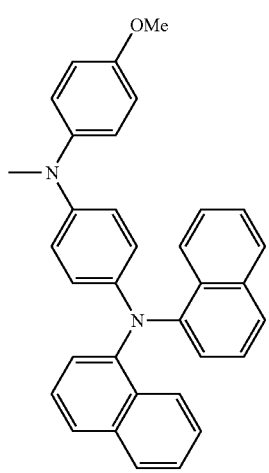
98
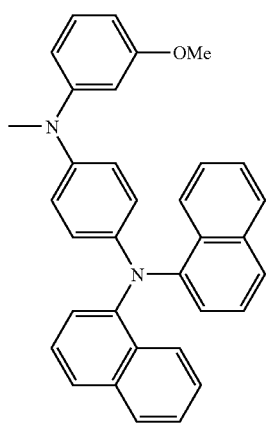
-continued
99
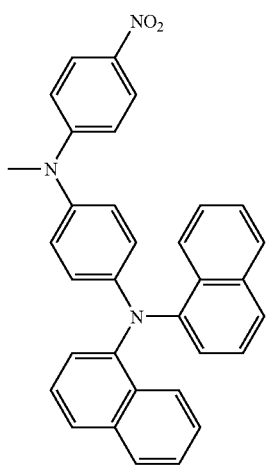
100
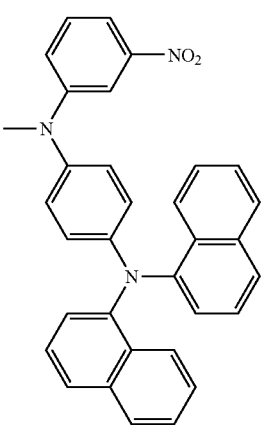
101
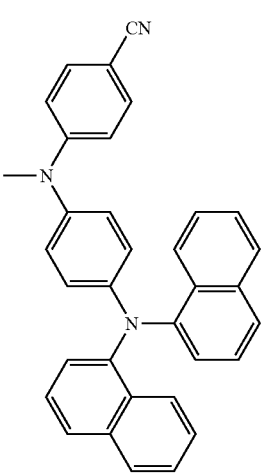

-continued
102
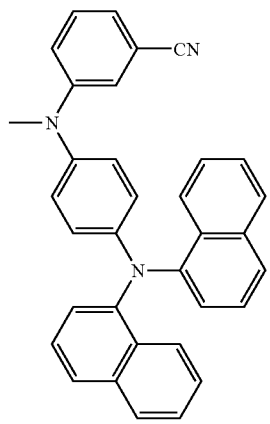
103
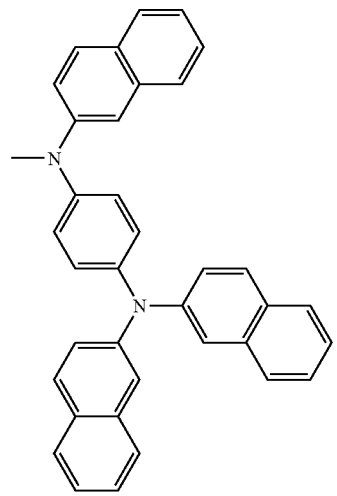
104
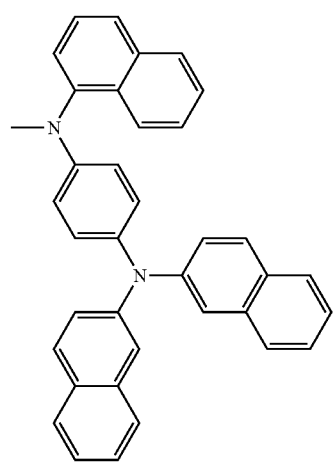
-continued
105
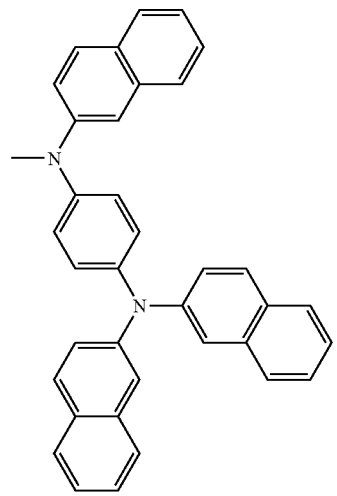
106
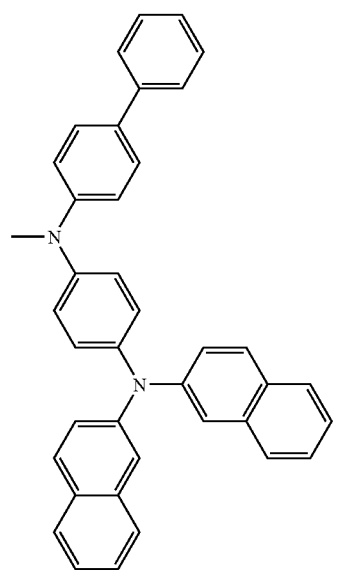
107
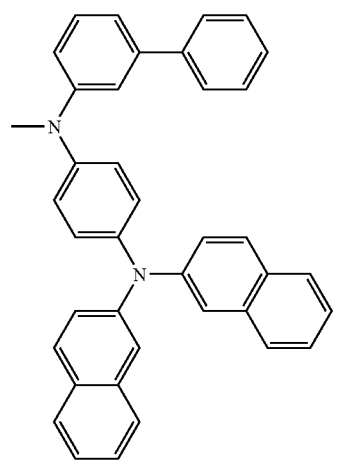

-continued
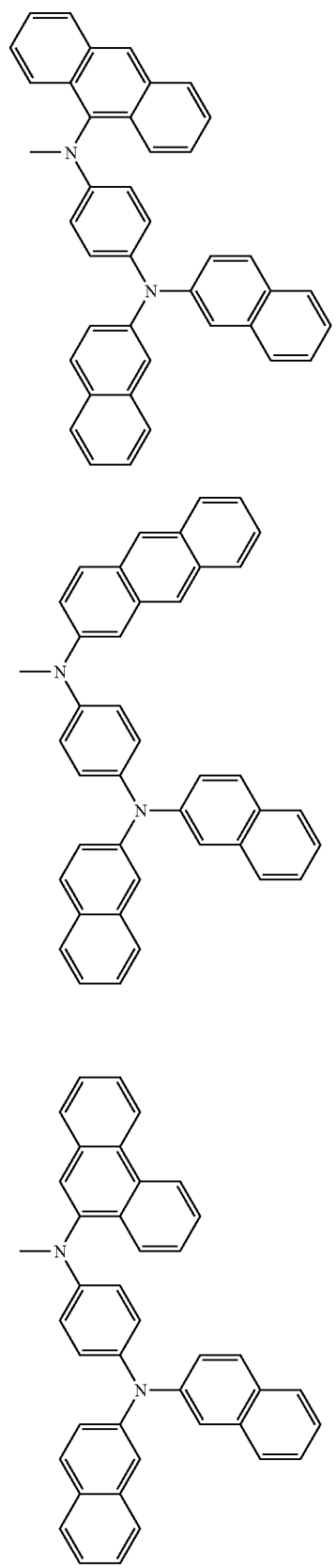
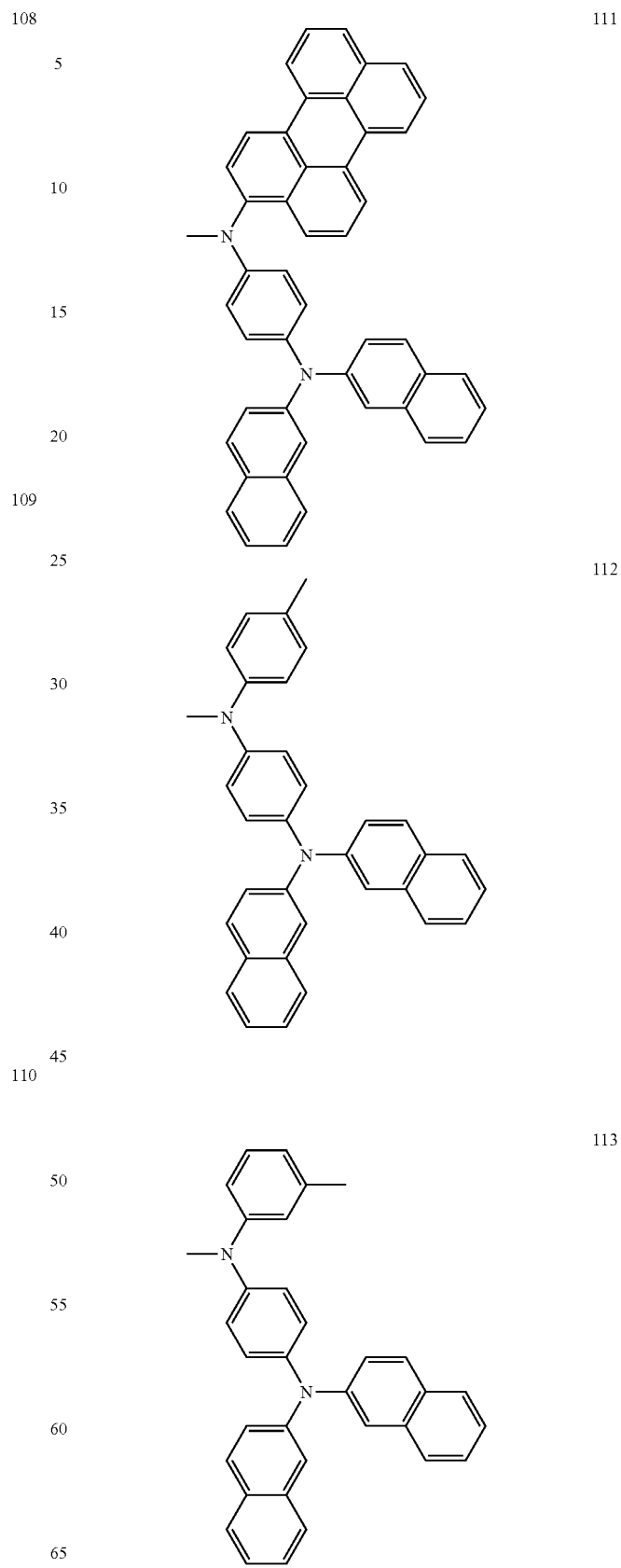

114 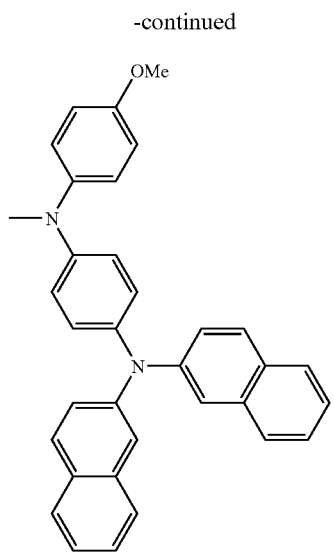
115 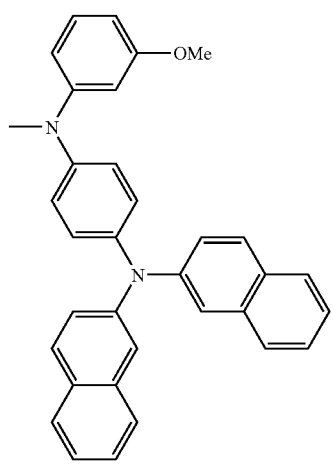
116 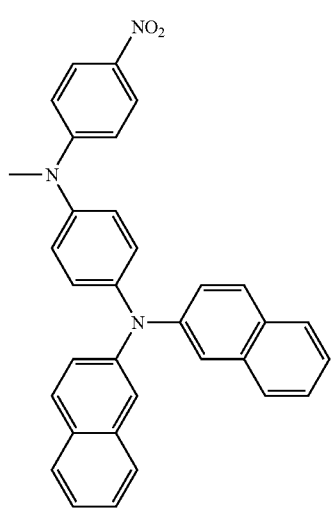
117 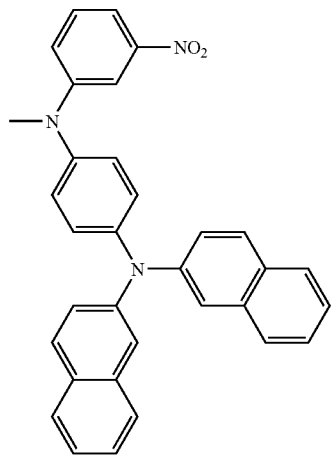
118 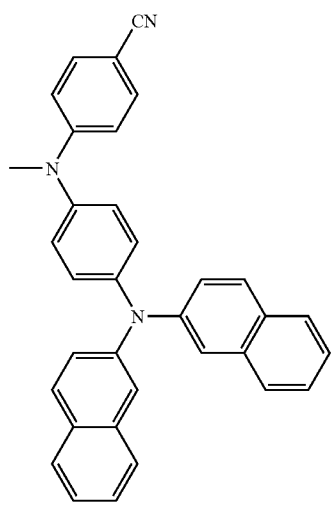
119 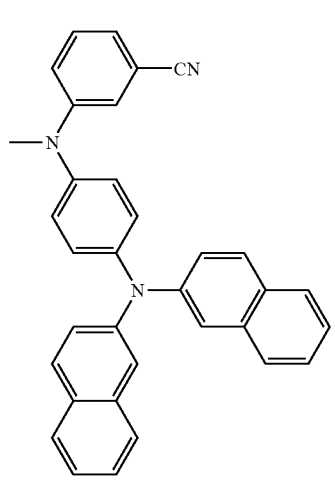

-continued
120
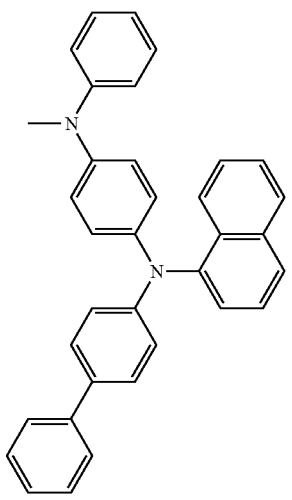
121
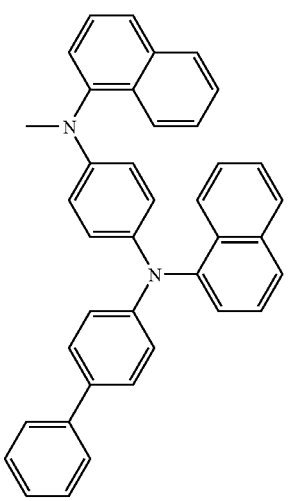
122
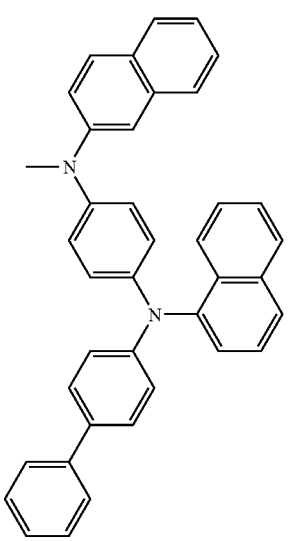
-continued
123
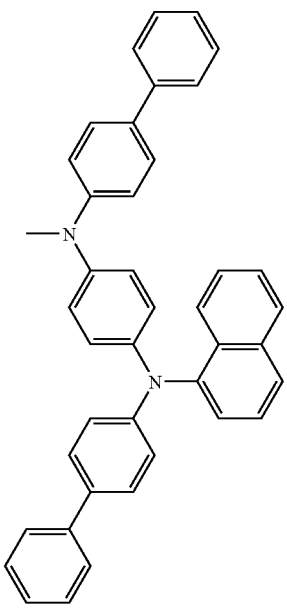
124
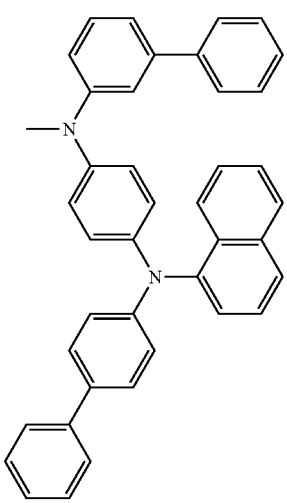
125
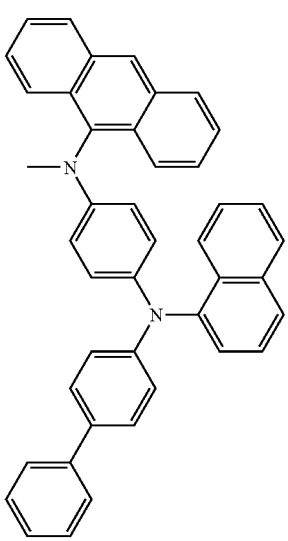

126
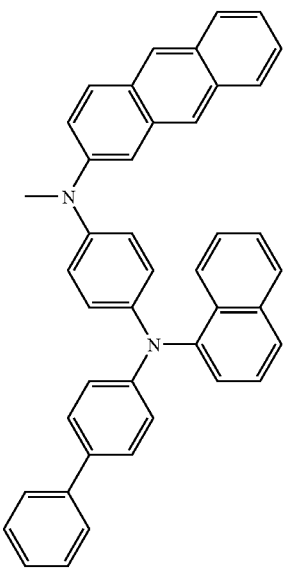
127
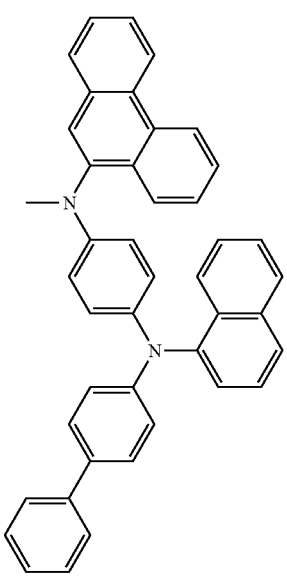
128
129
130
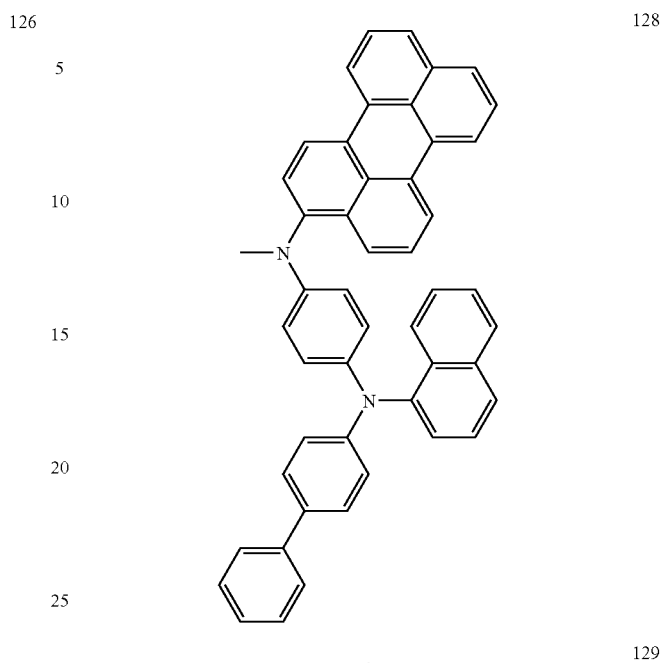
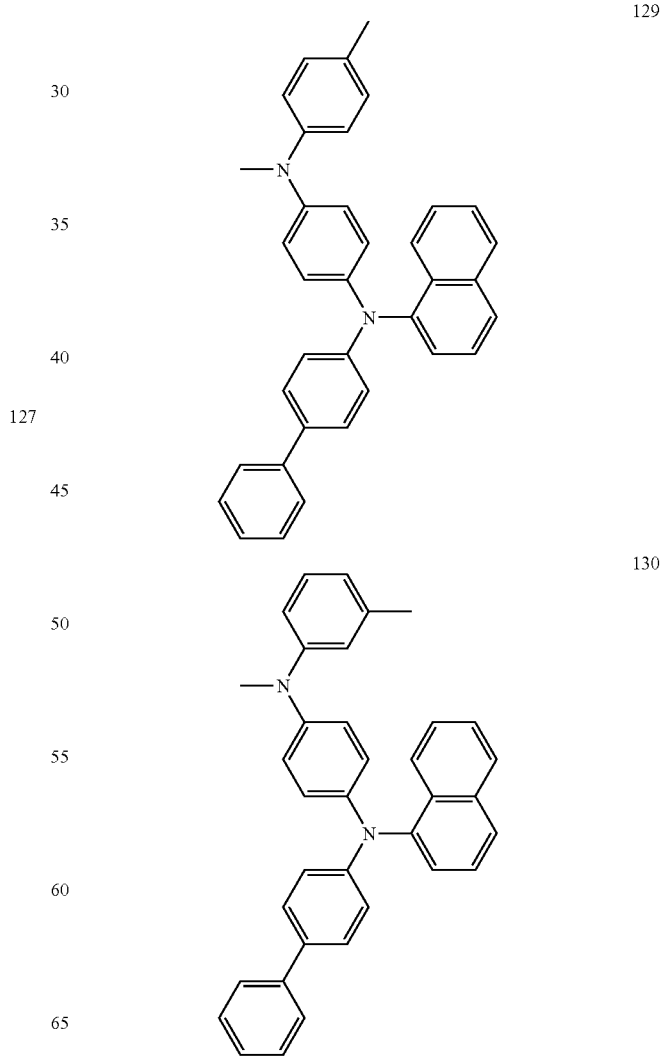

-continued
131
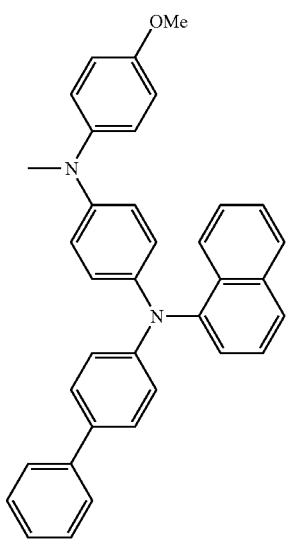
132
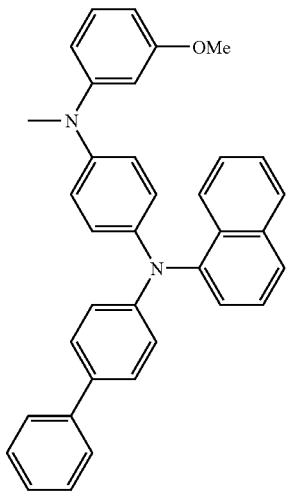
133
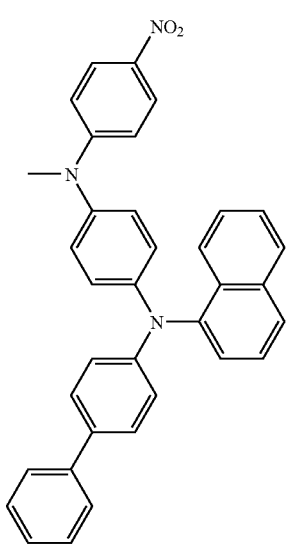
-continued
134
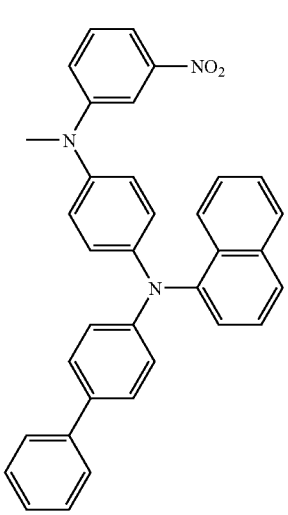
135
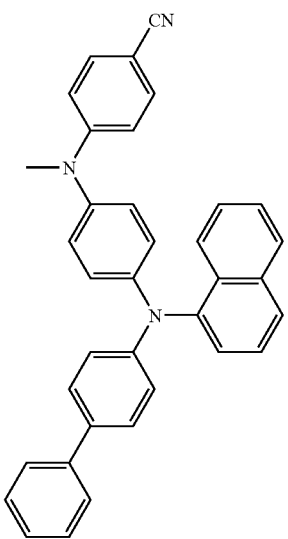
136
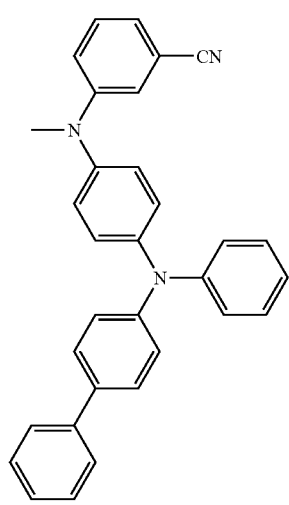

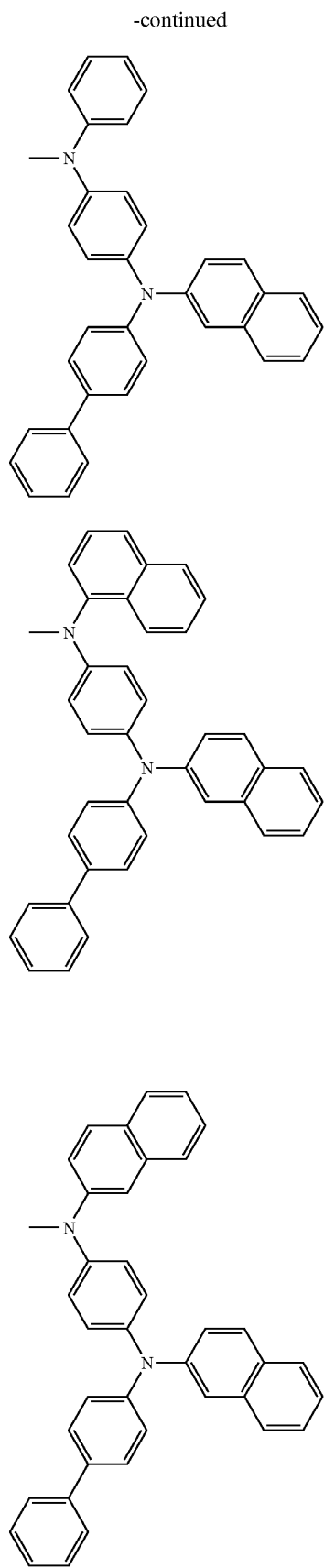
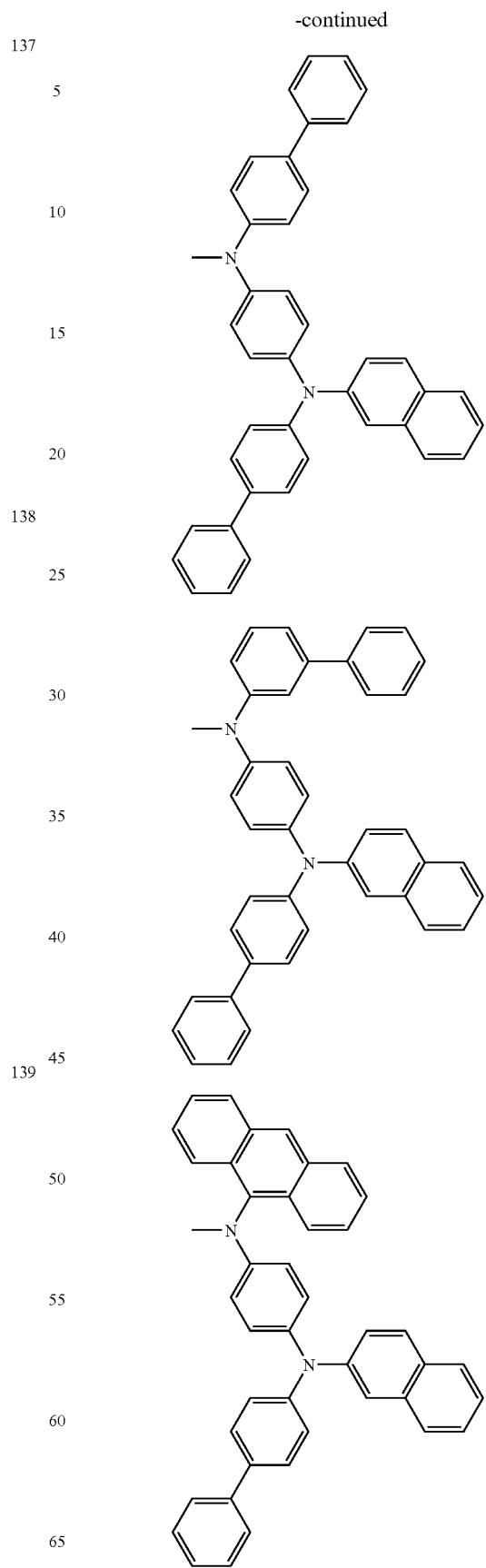

-continued
143
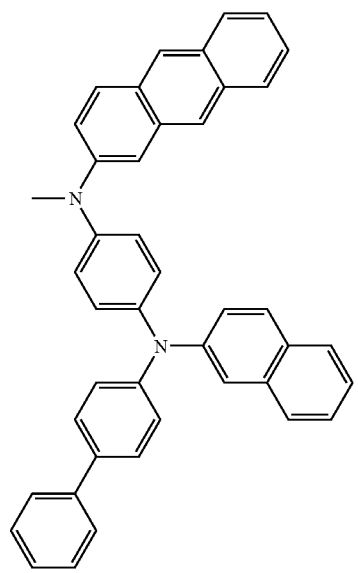
144
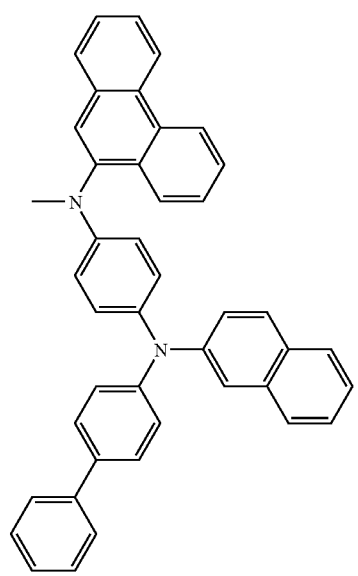
145
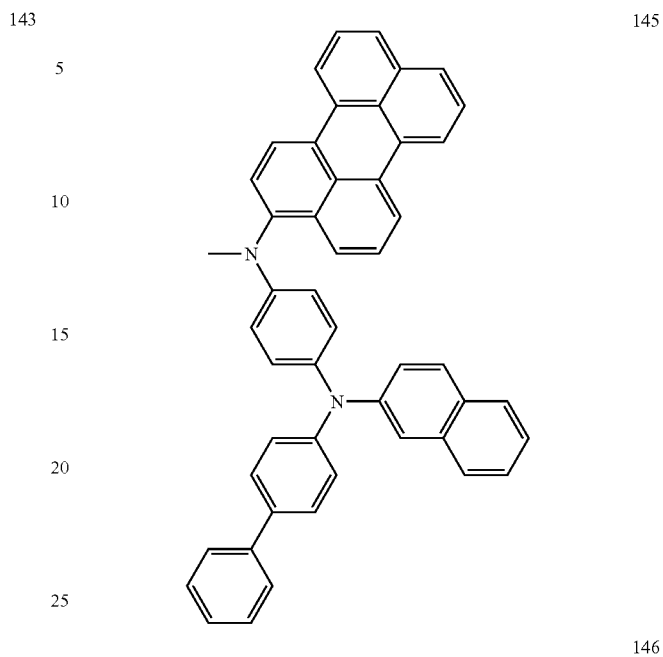
146
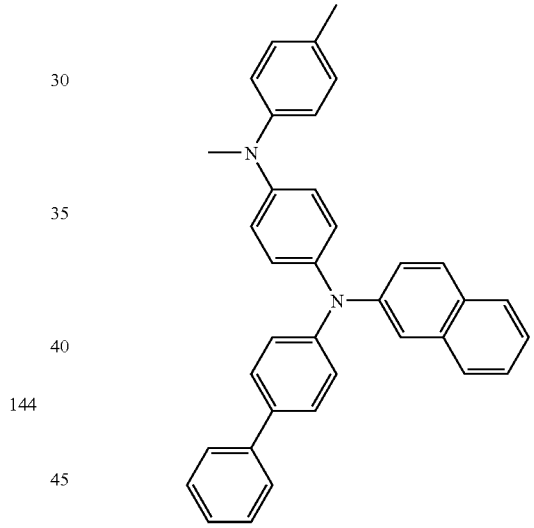
147
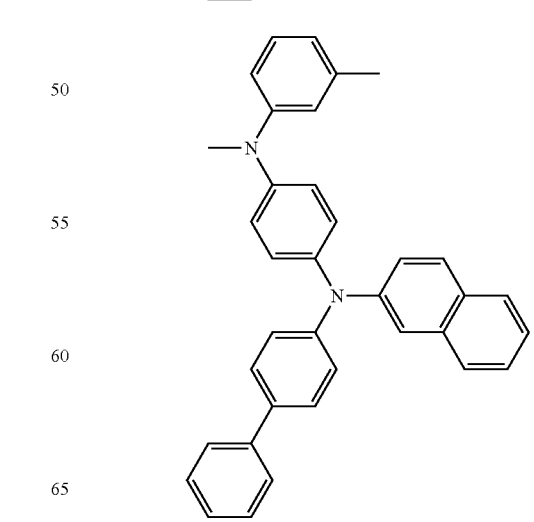

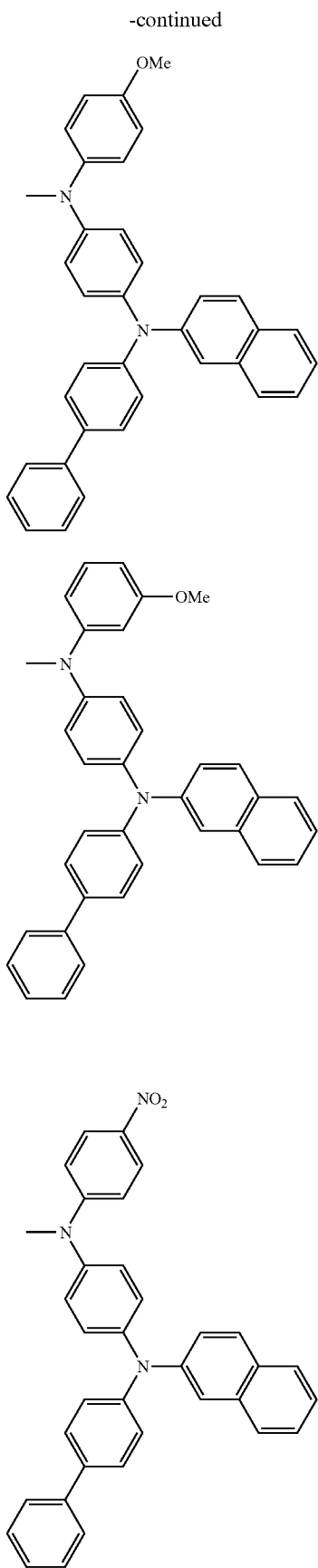
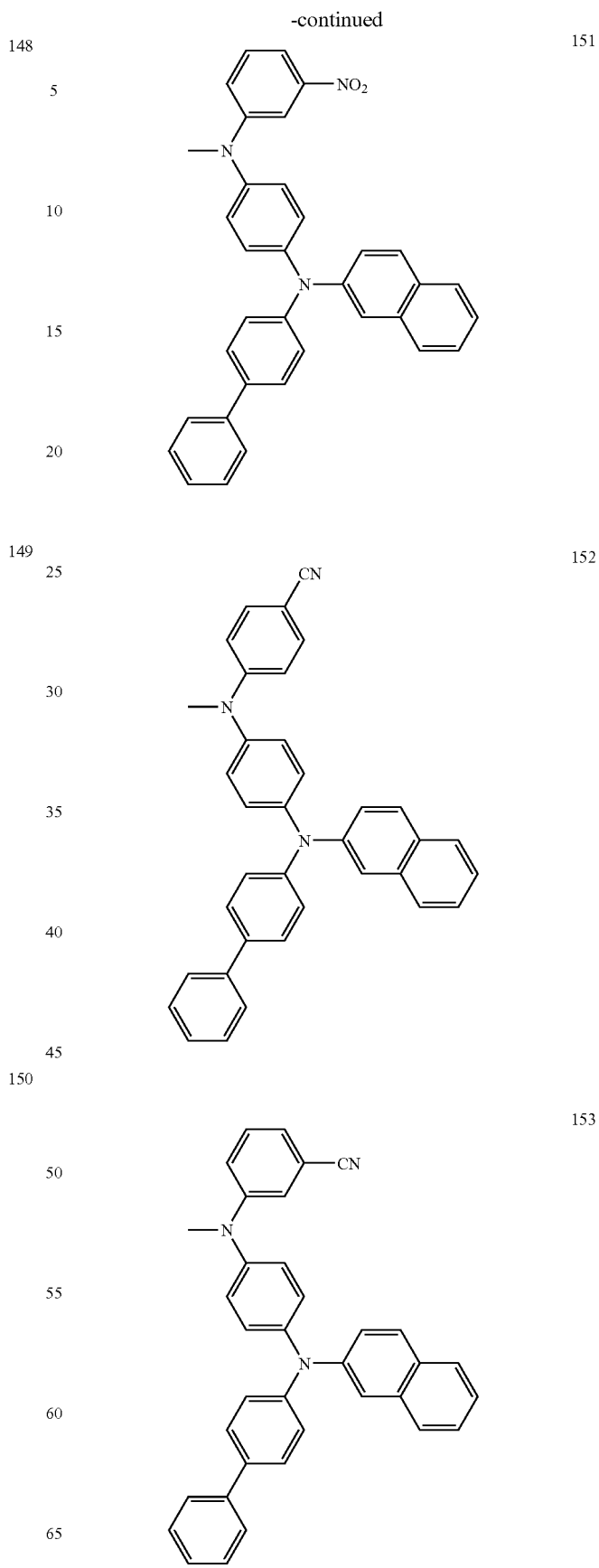

-continued
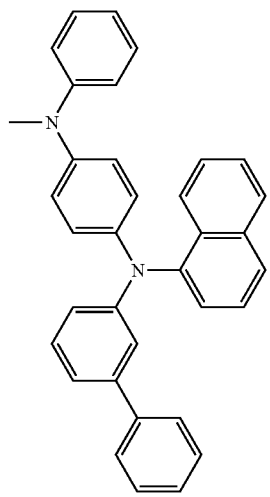
154
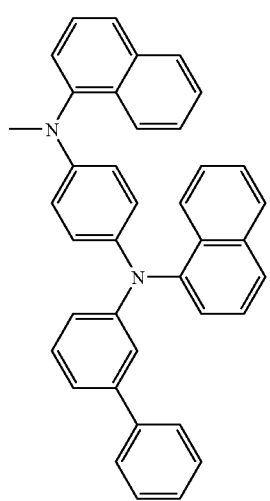
155
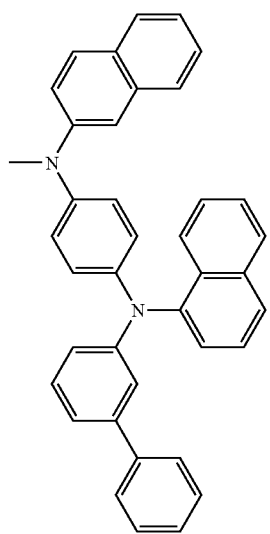
156
-continued
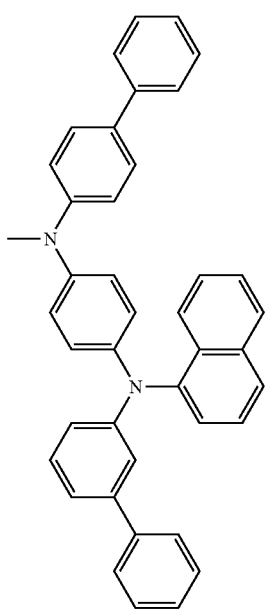
157
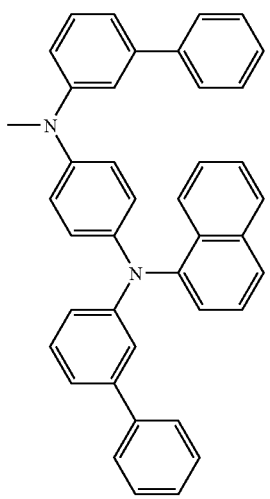
158
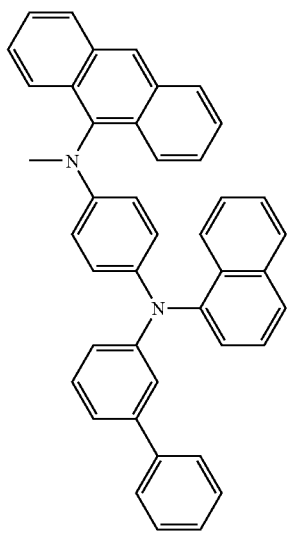
159

-continued
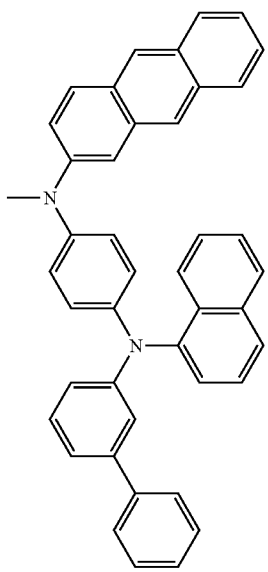
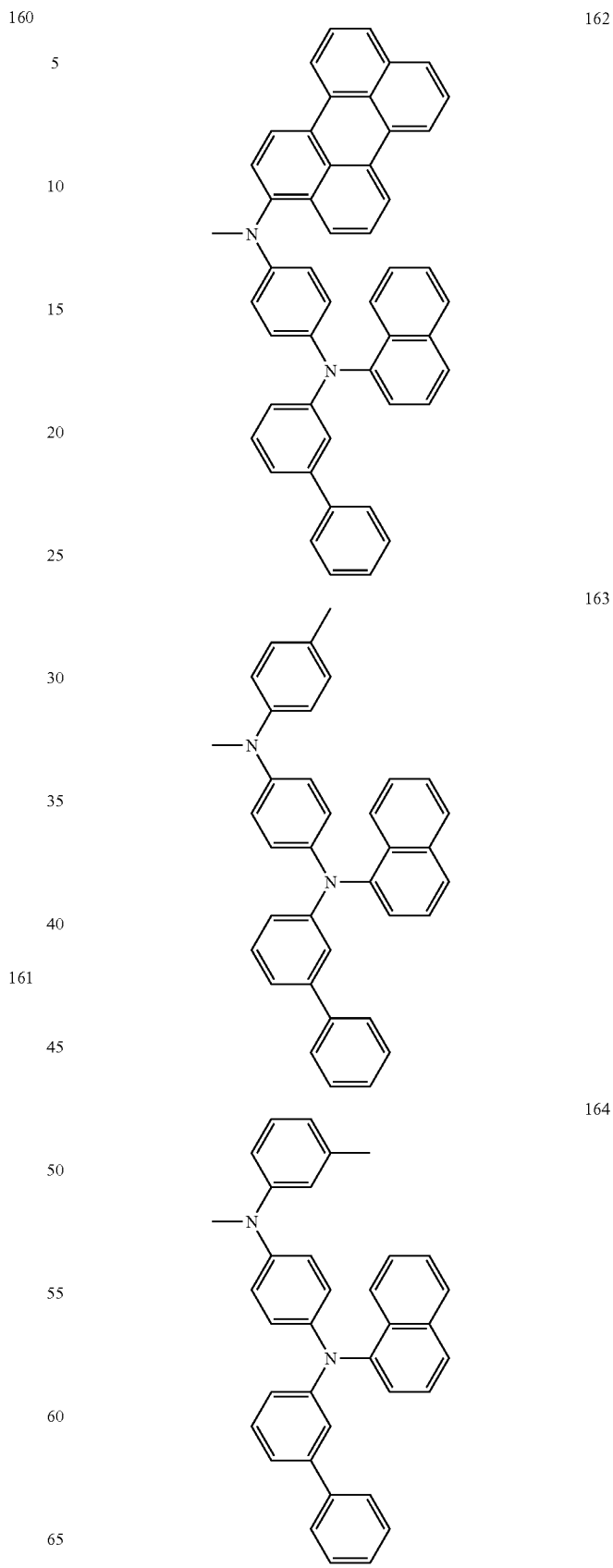

165
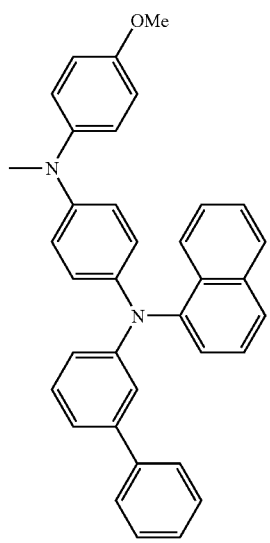
166
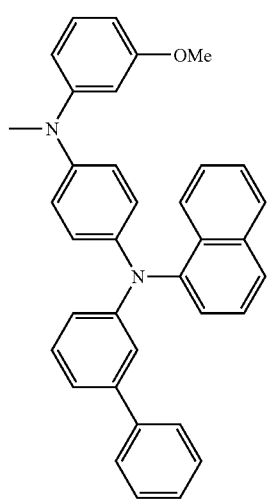
167
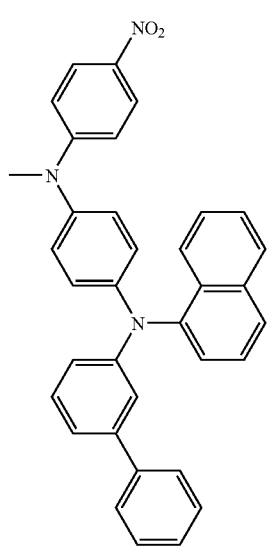
168
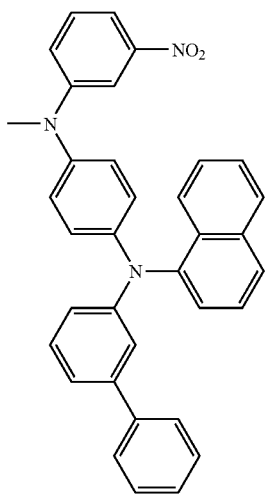
169
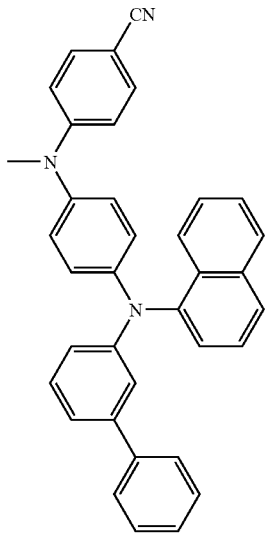
170
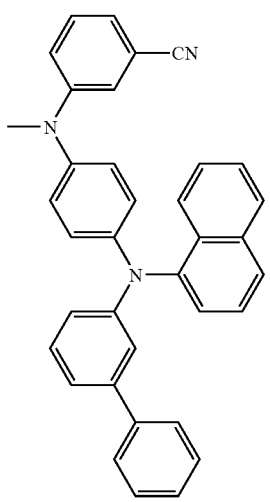

-continued
171
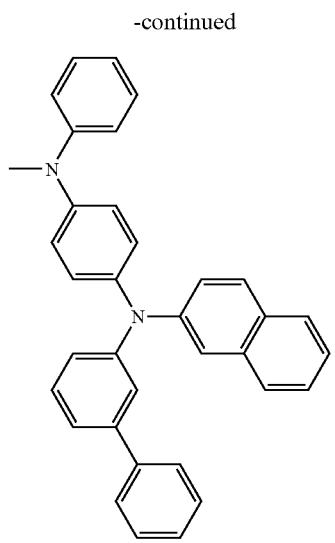
172
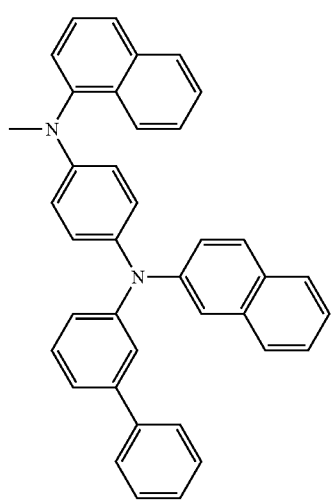
173
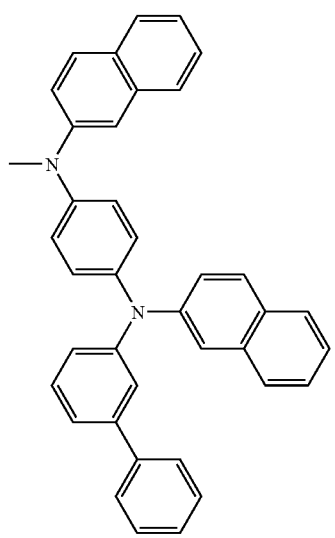
-continued
174
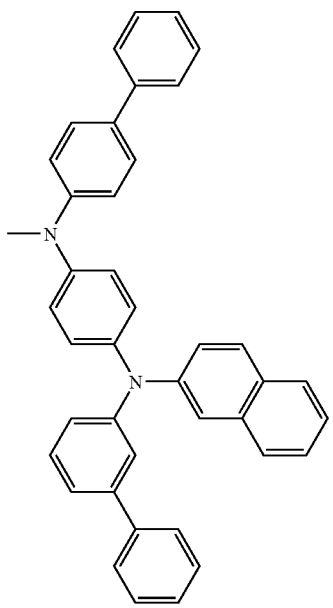
175
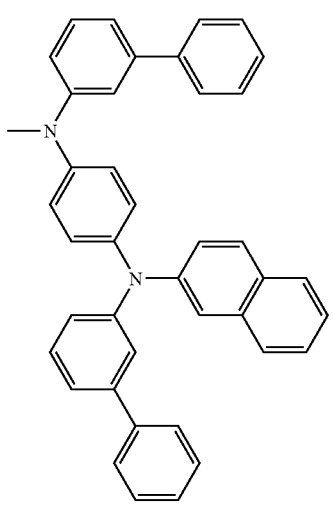
176
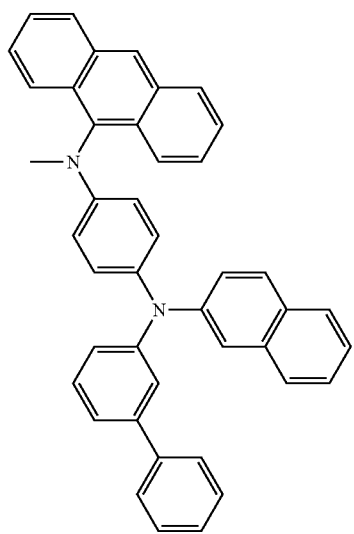

103
-continued
177
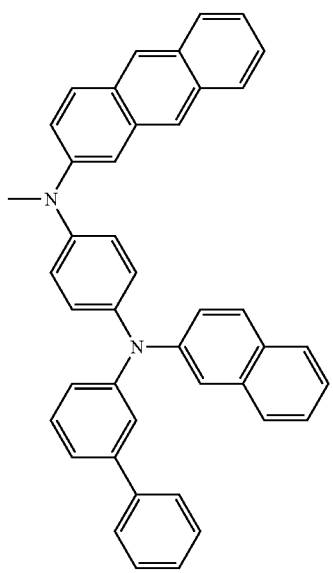
178
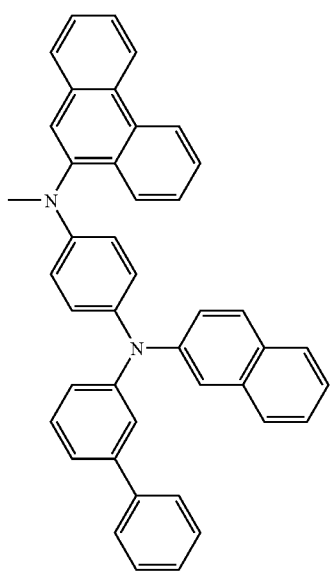
104
-continued
179
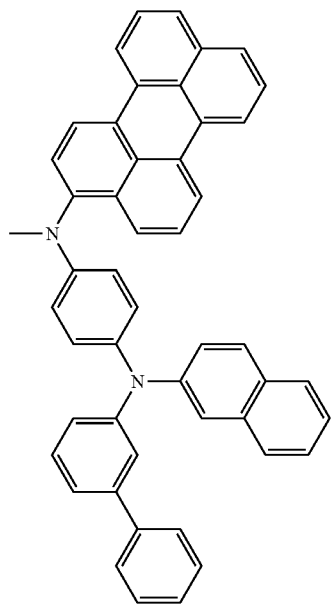
180
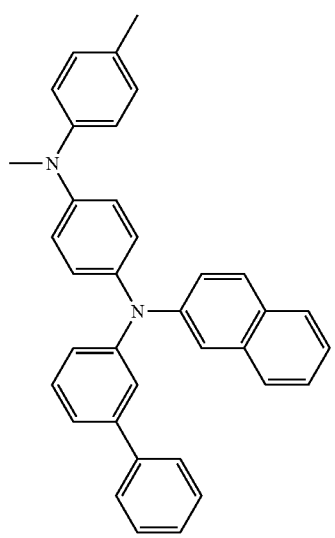
181
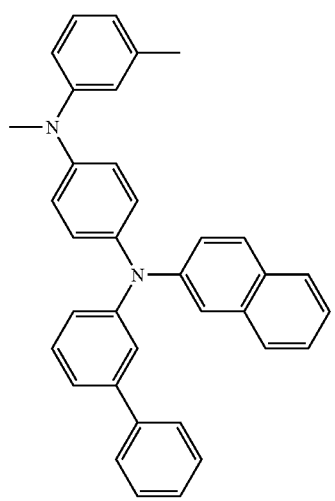

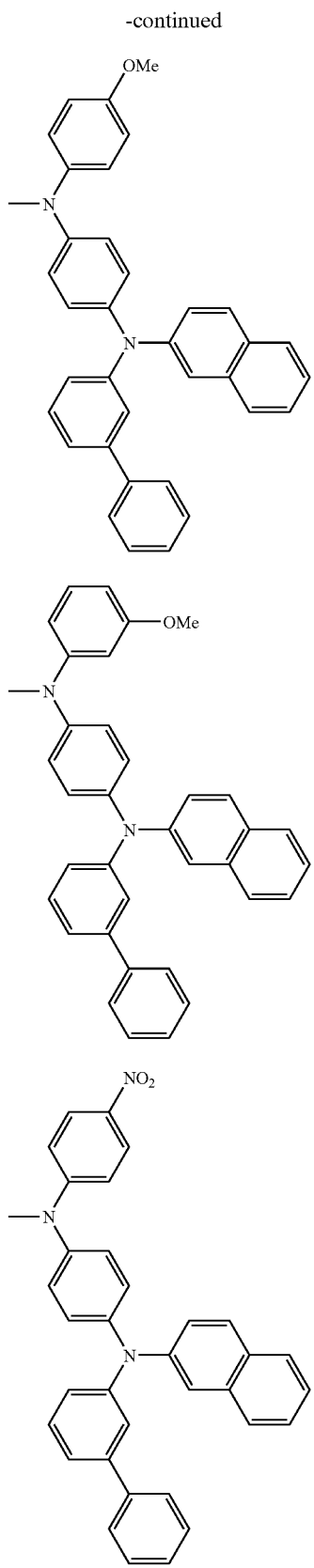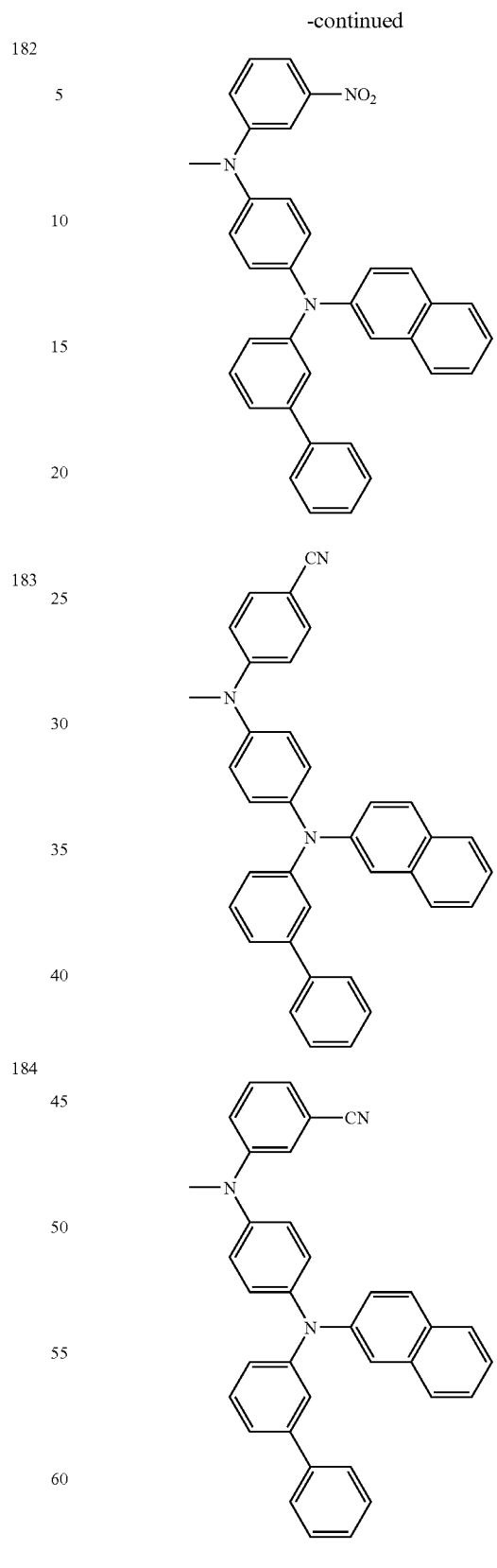

188
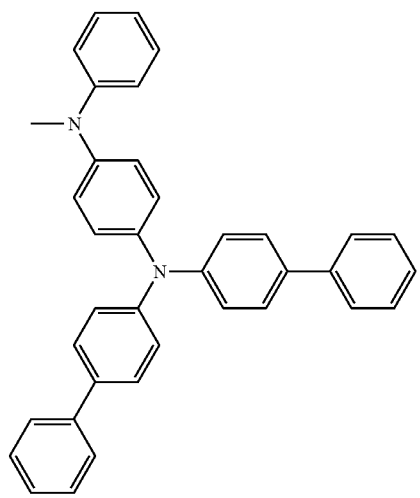
189
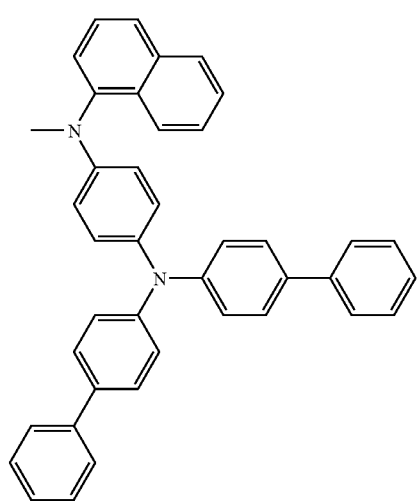
190
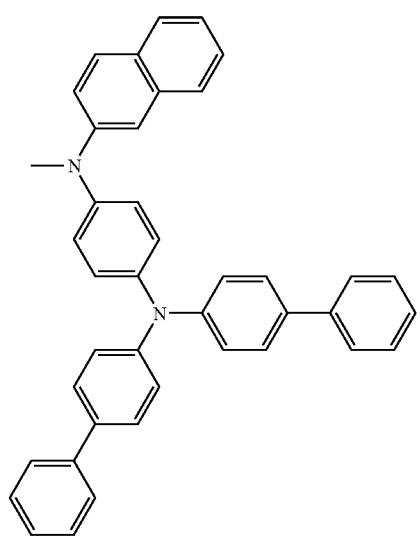
191
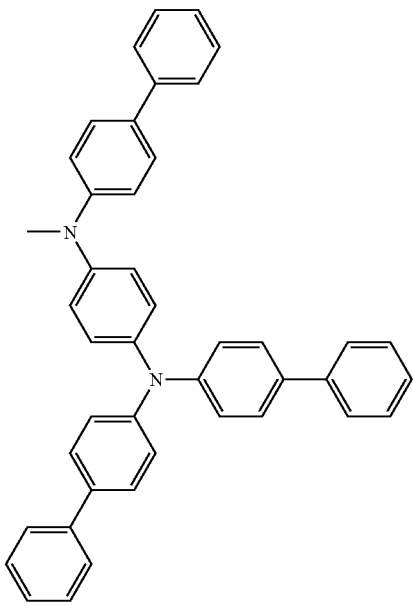
192
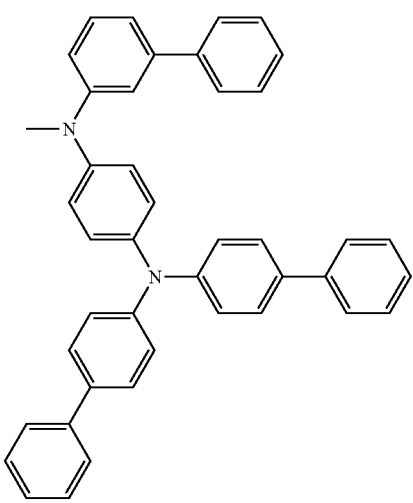
193
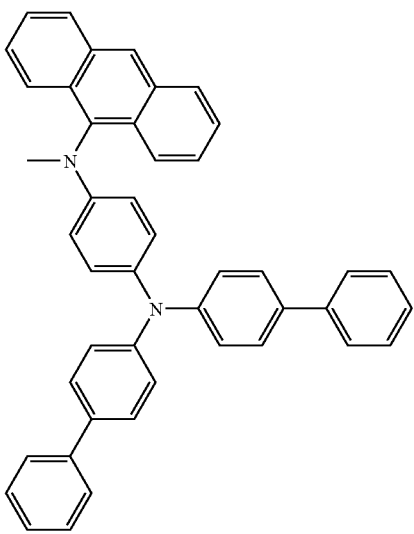

-continued
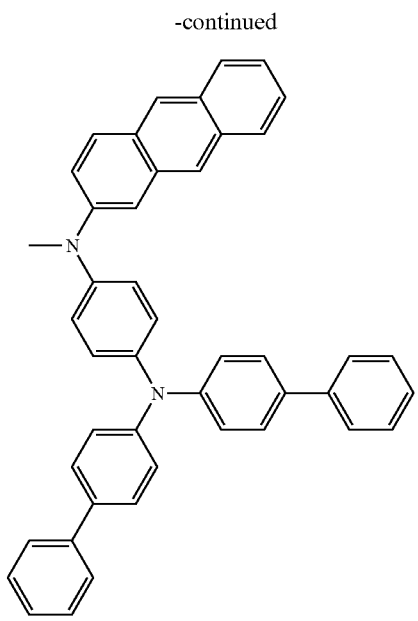
194
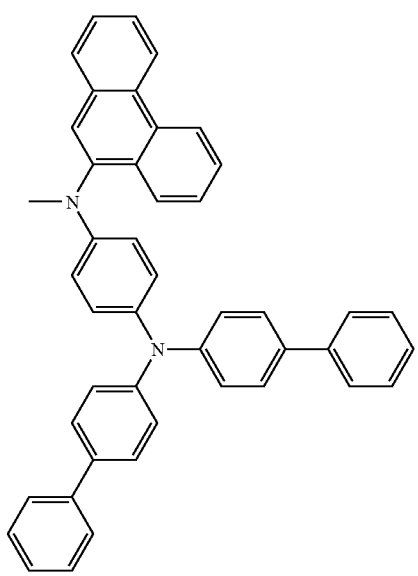
195
-continued
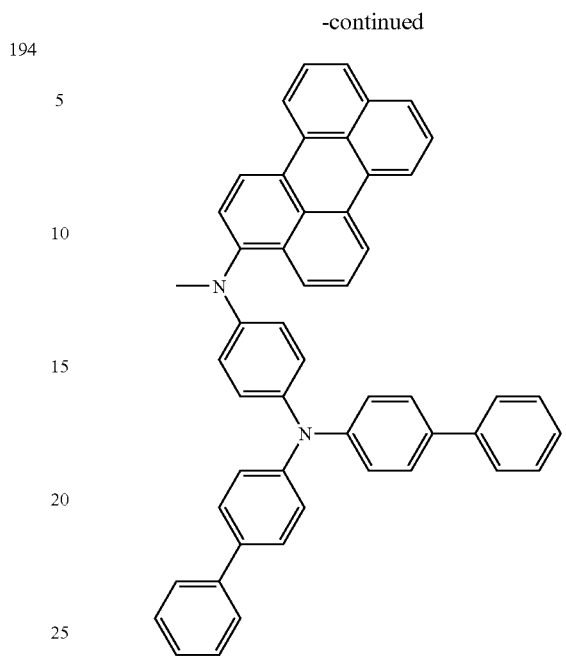
196
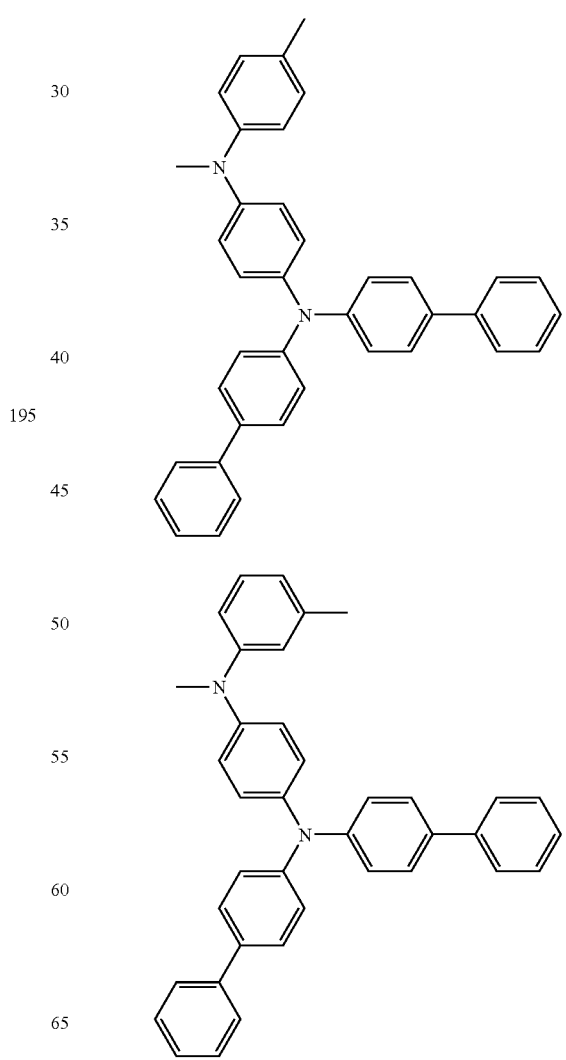
197
198

-continued
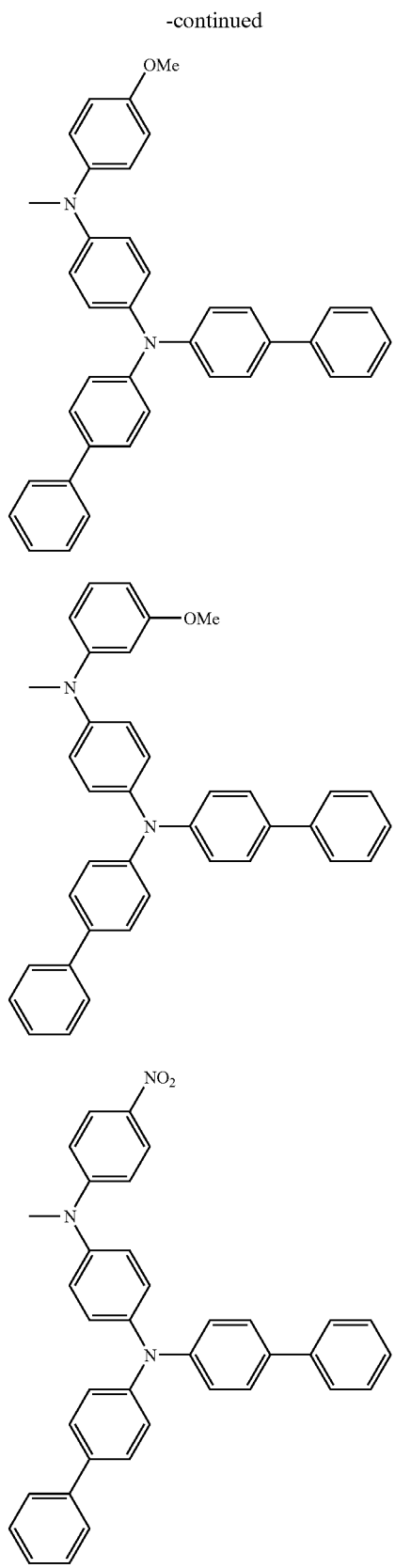
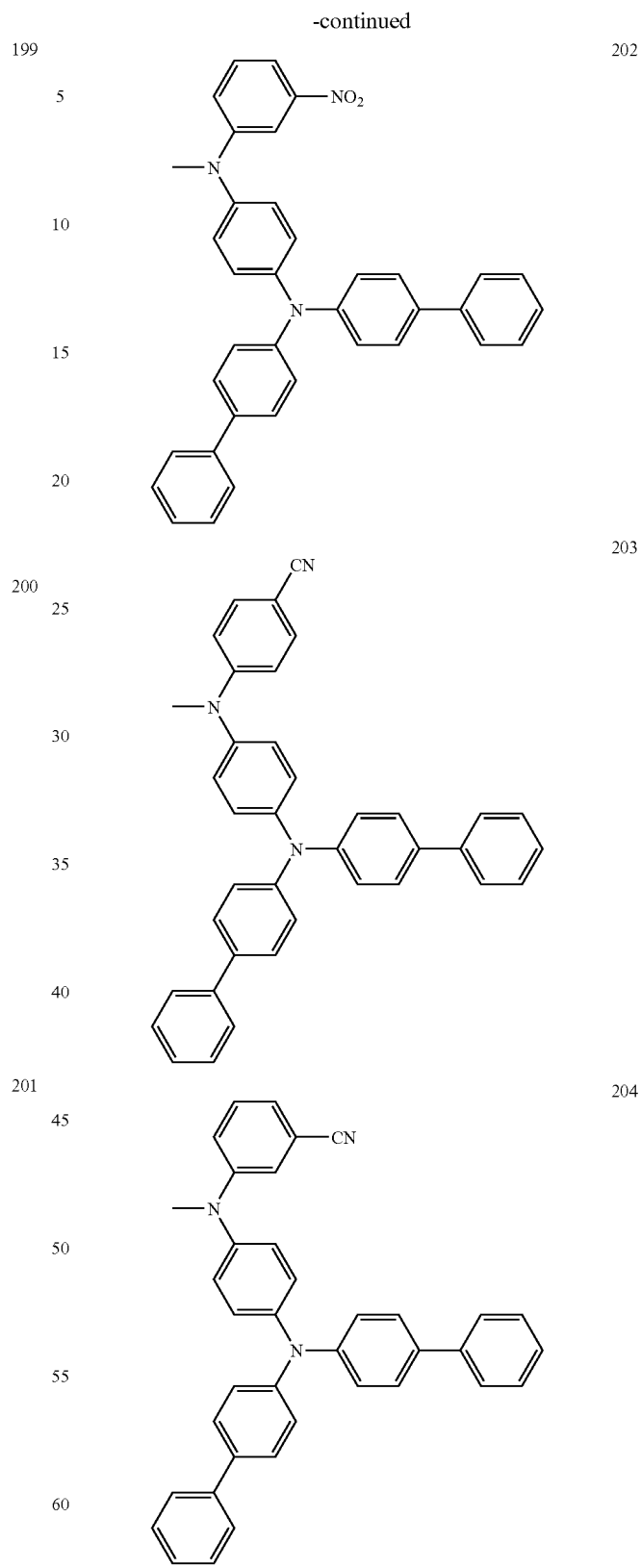

-continued
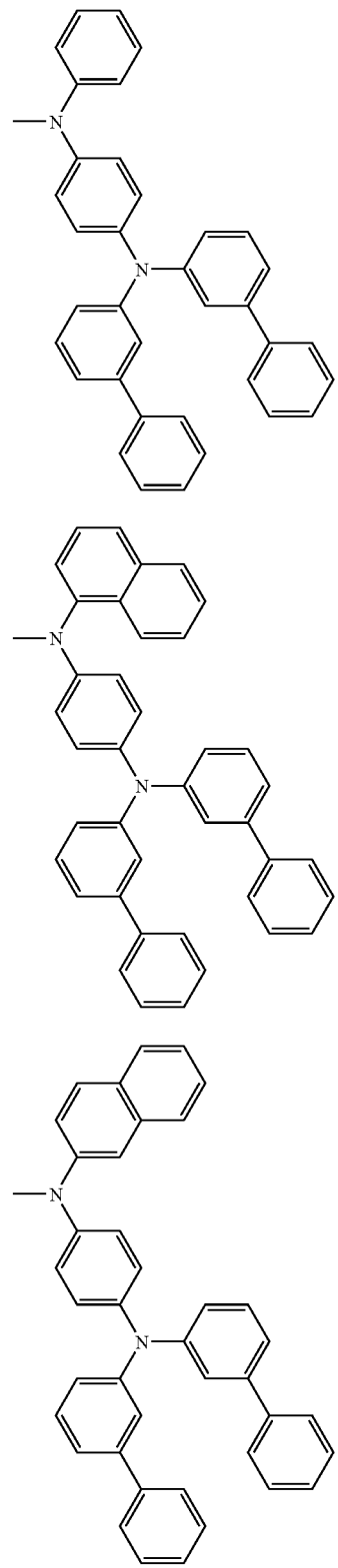
205
206
207
-continued
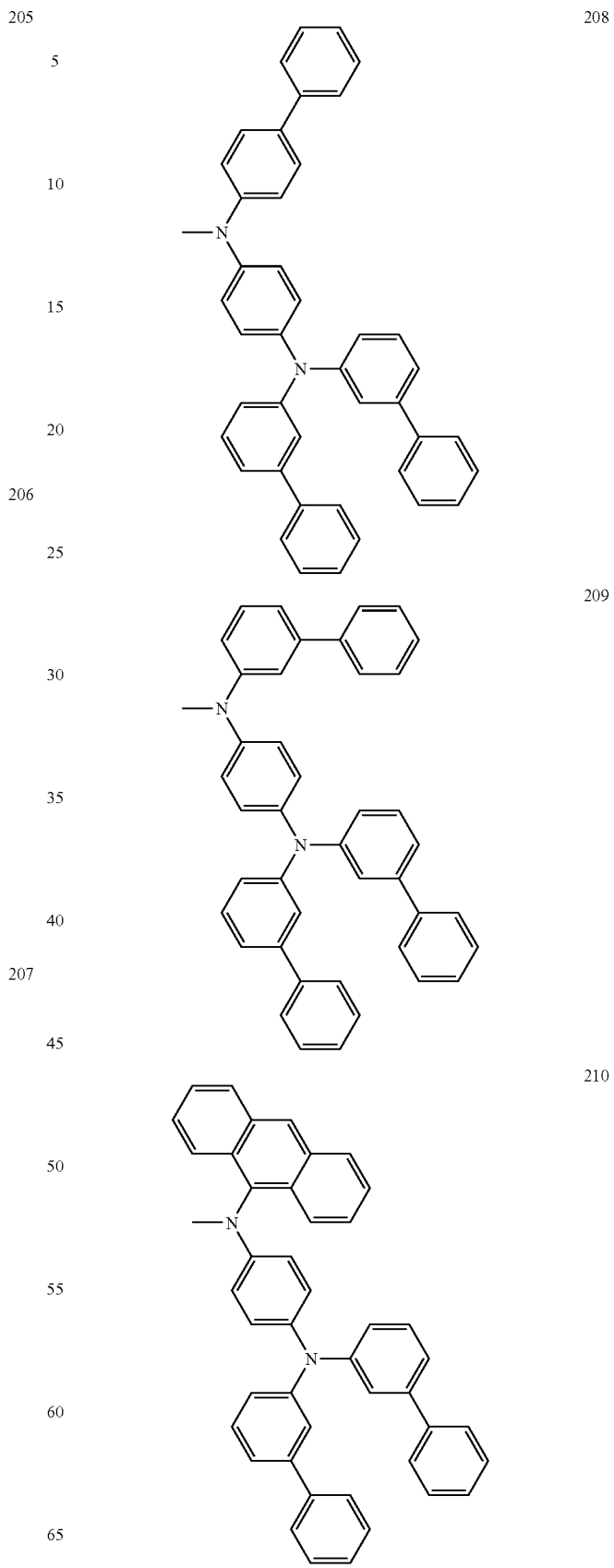
208
209
210

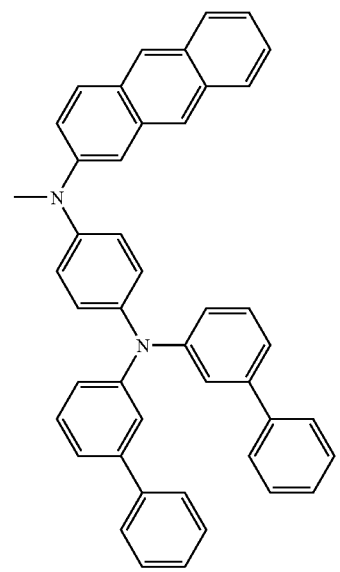
211
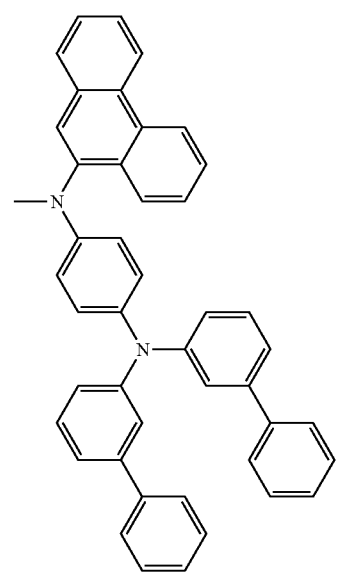
212
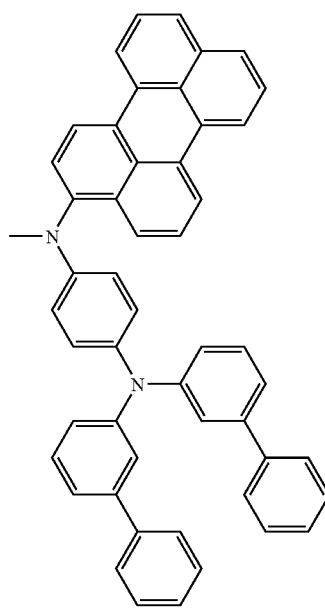
213
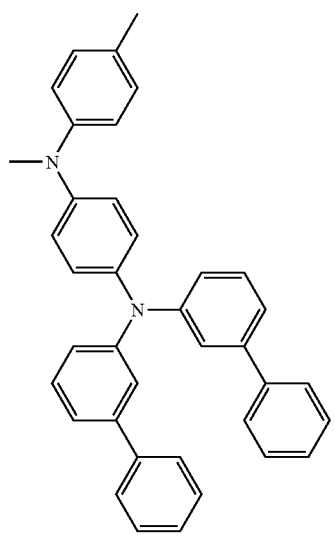
214
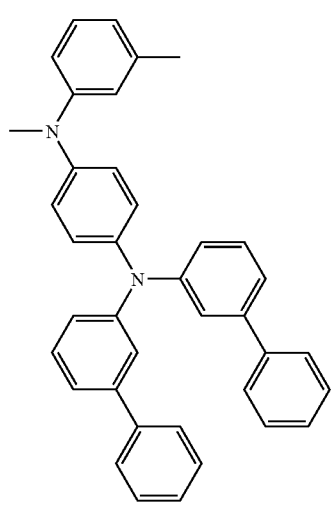
215

-continued
216
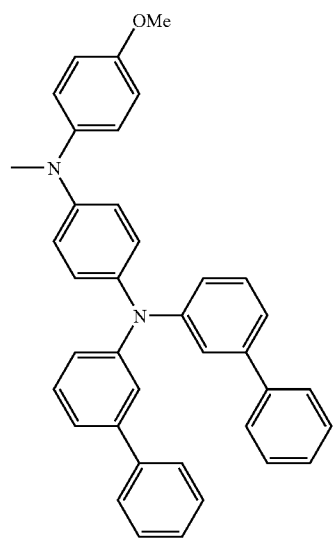
217
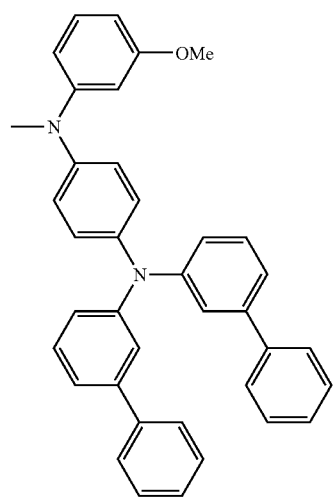
218
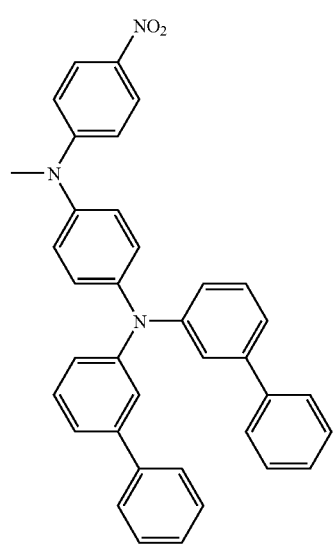
-continued
219
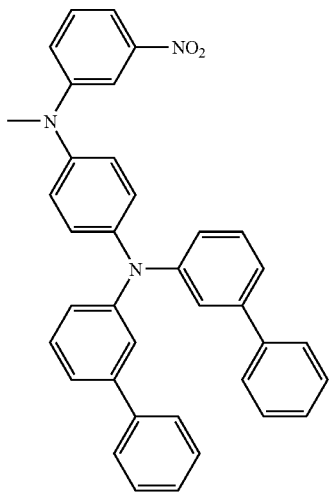
220
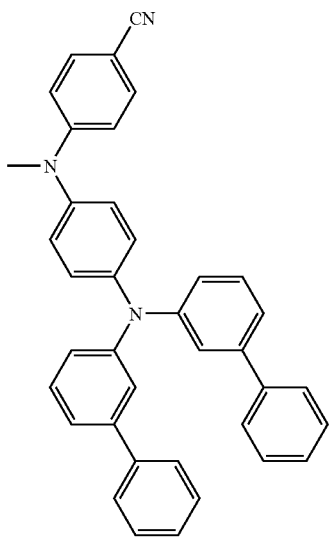
221
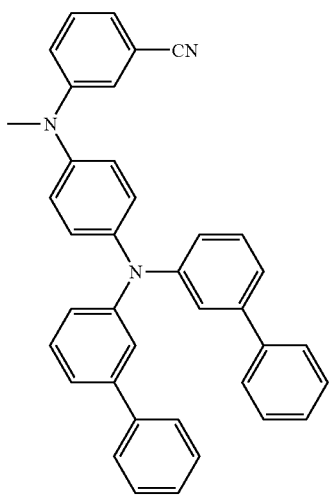

-continued
222 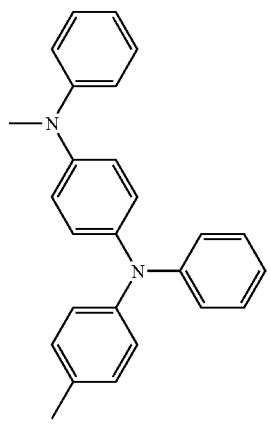
223 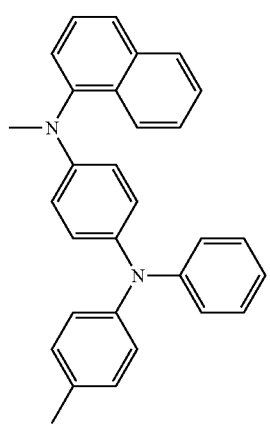
224 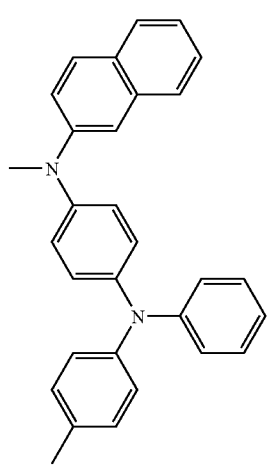
-continued
225 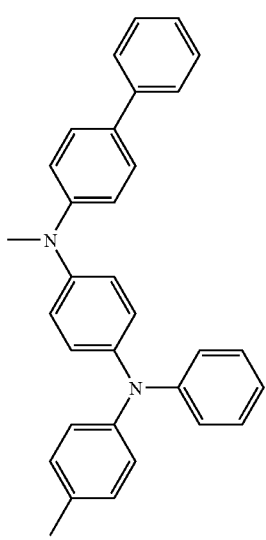
226 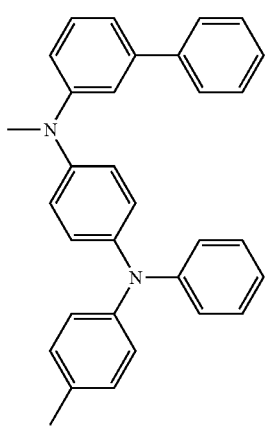
227 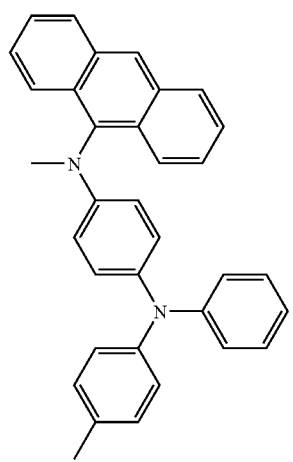

-continued
228
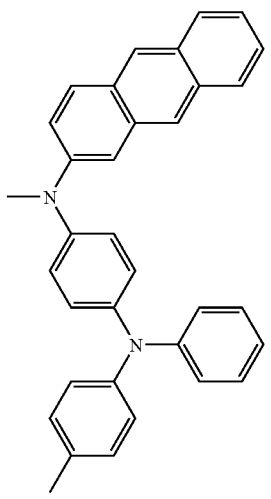
229
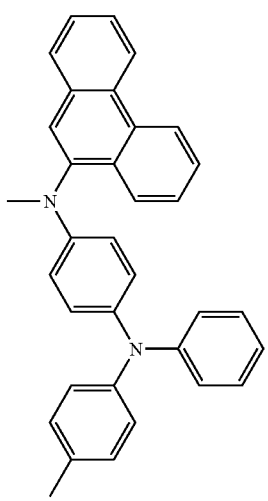
230
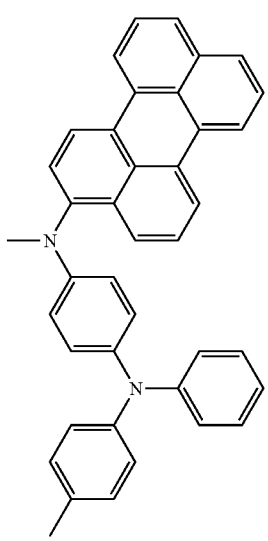
-continued
231
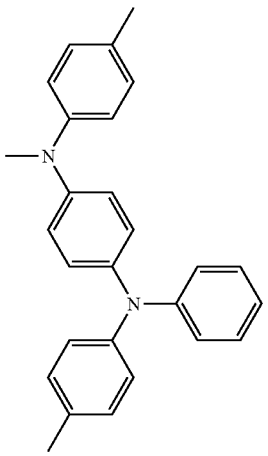
232
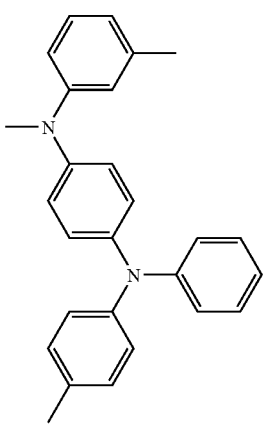
233
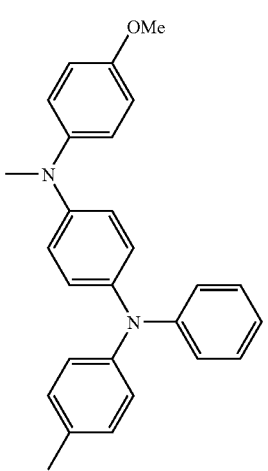

-continued
234
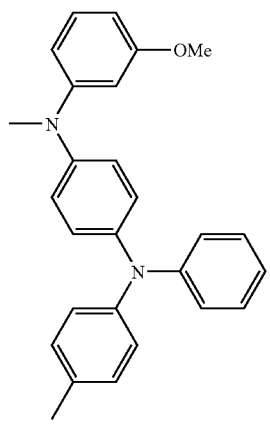
235
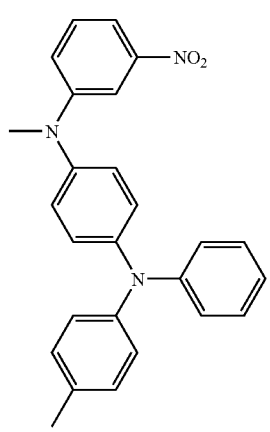
236
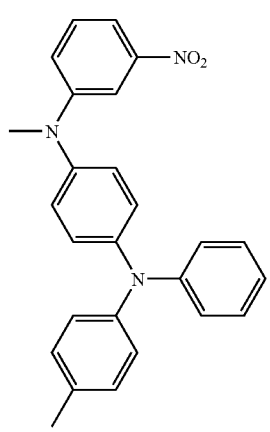
-continued
237
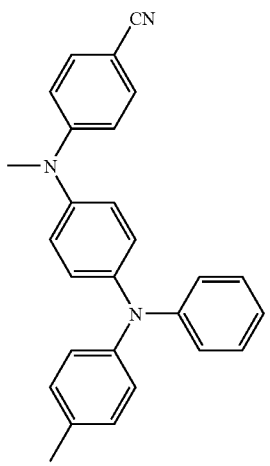
238
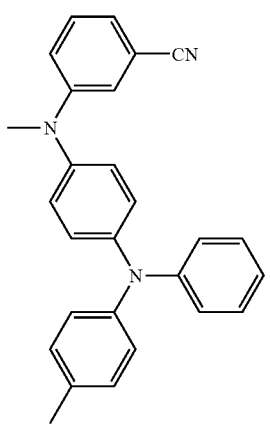
239
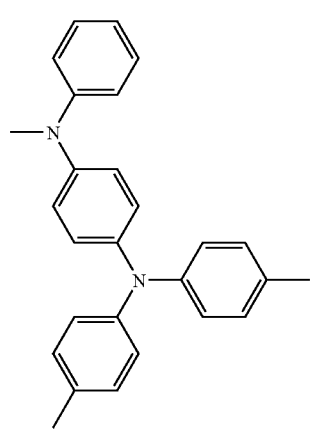

-continued
240
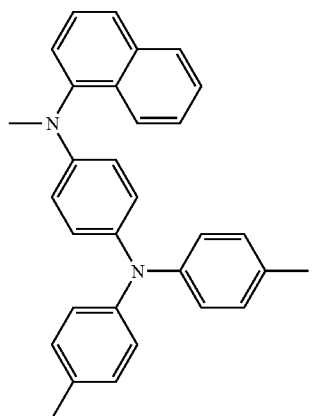
241
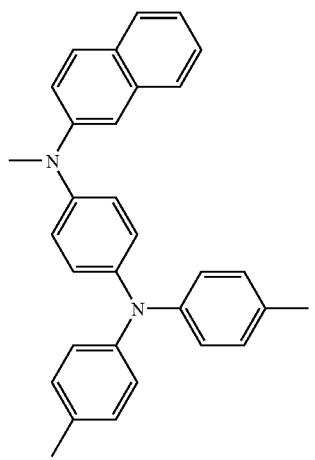
242
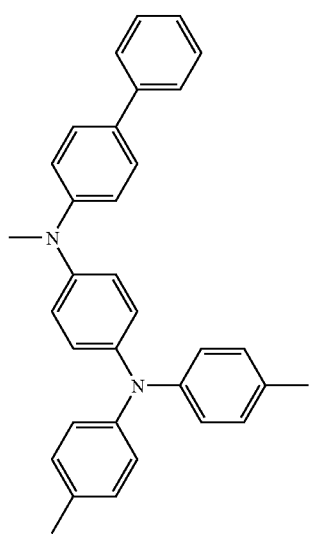
-continued
243
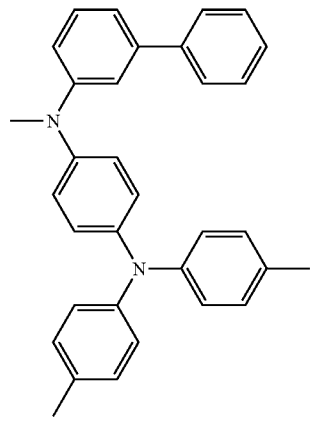
244
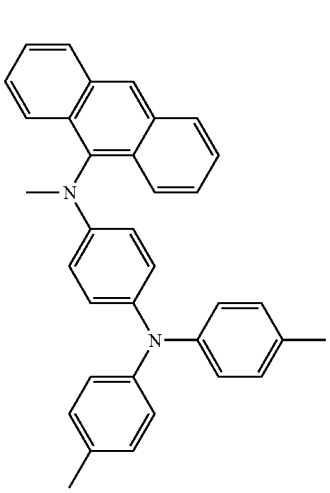
245
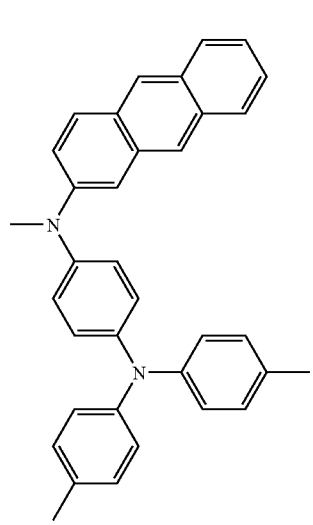

-continued
246
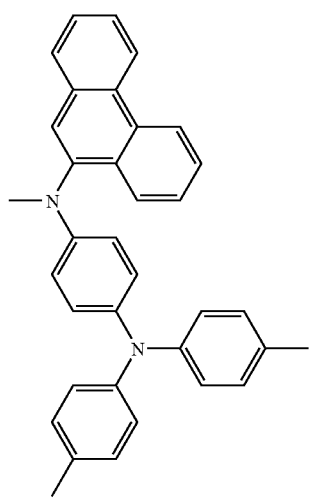
247
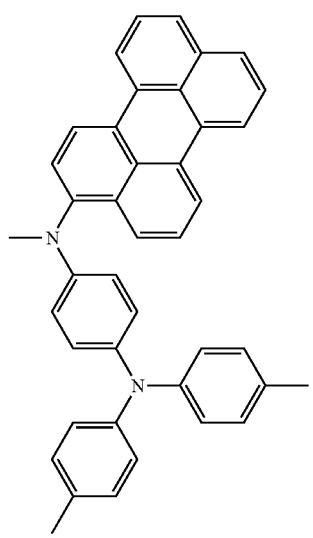
248
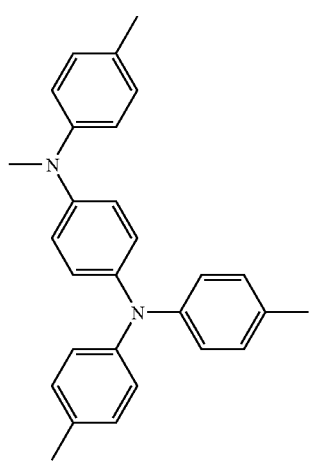
-continued
249
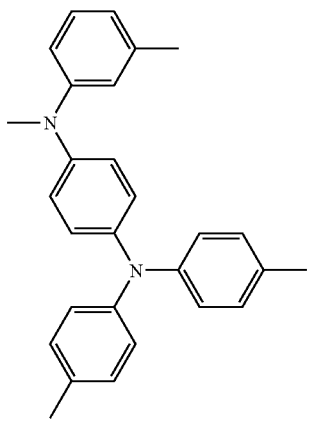
250
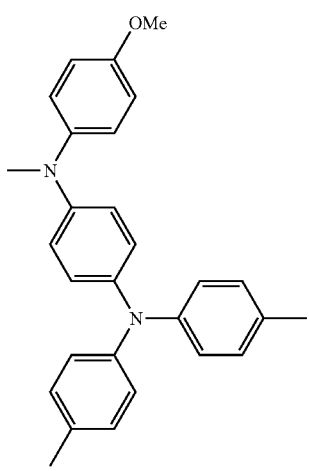
251
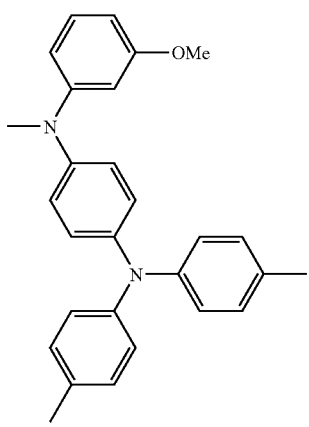

252
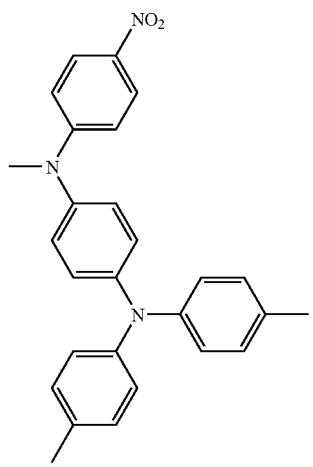
255
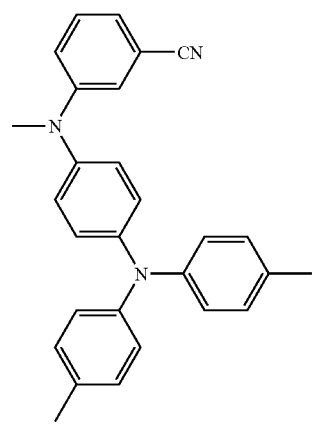
253
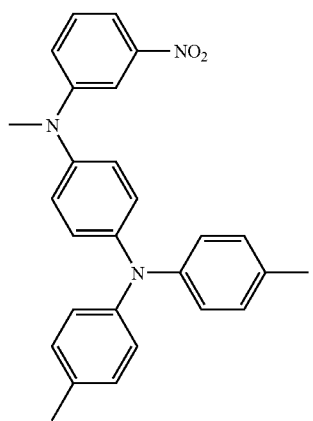
256
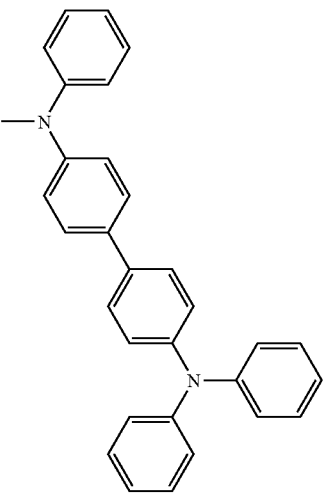
254
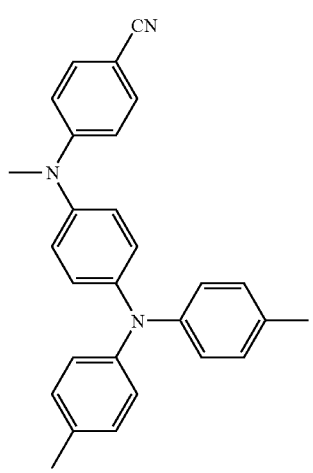
257
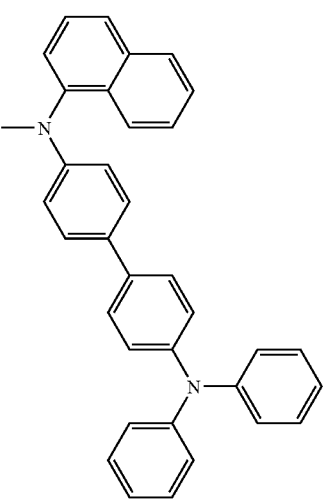

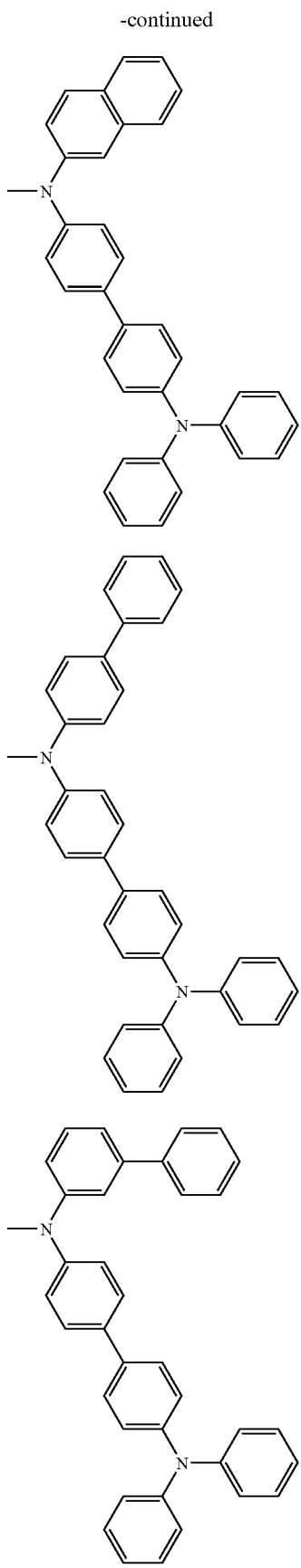
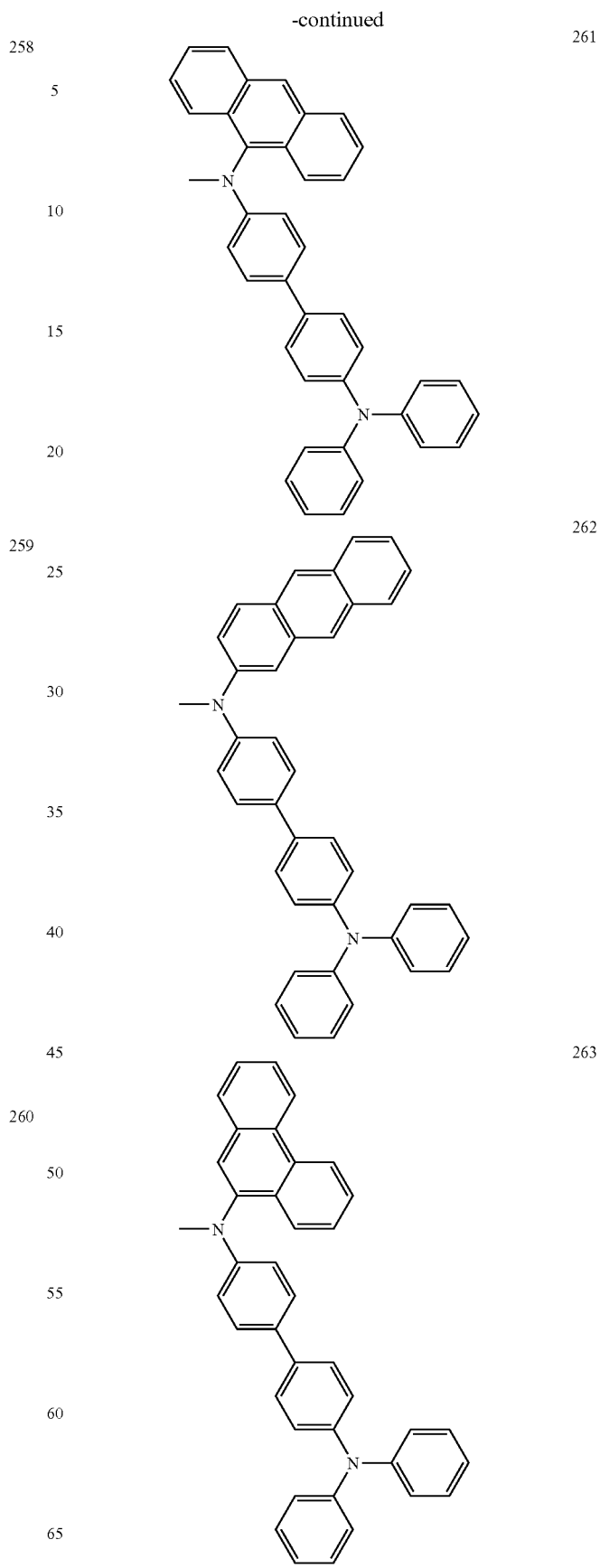

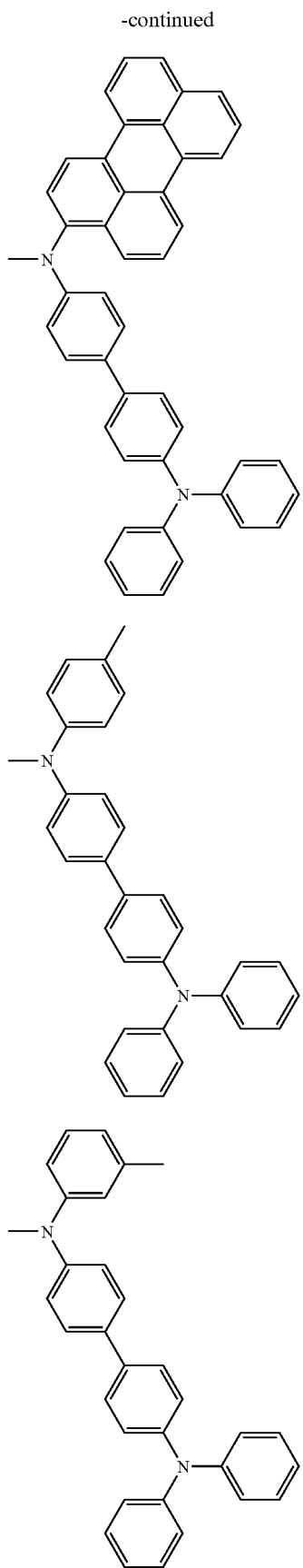
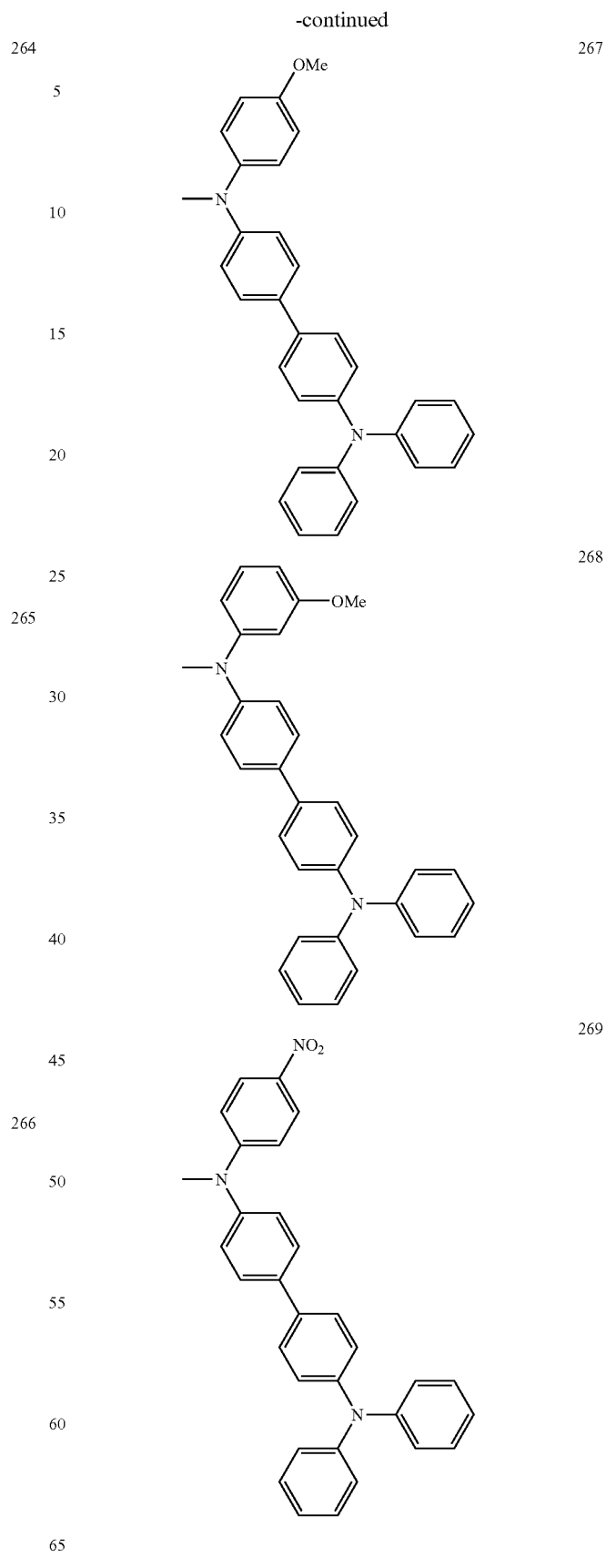

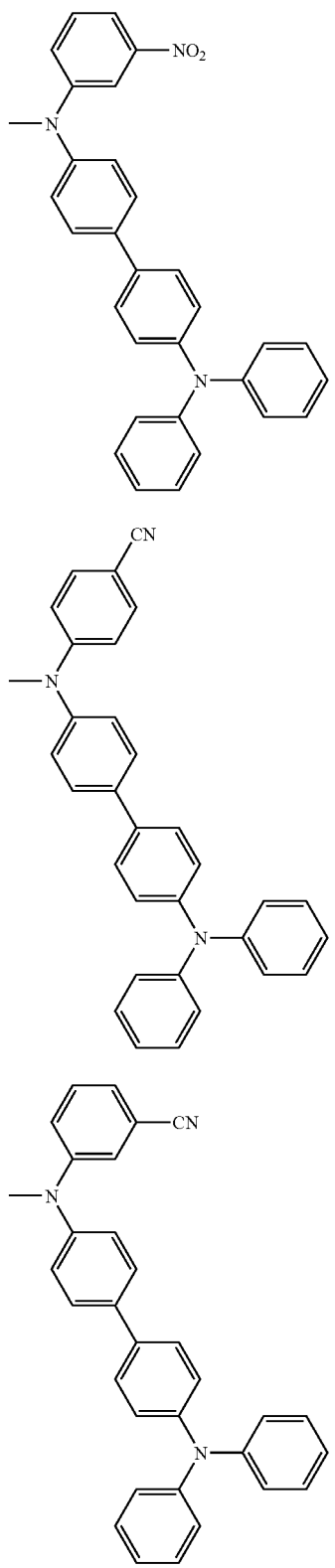
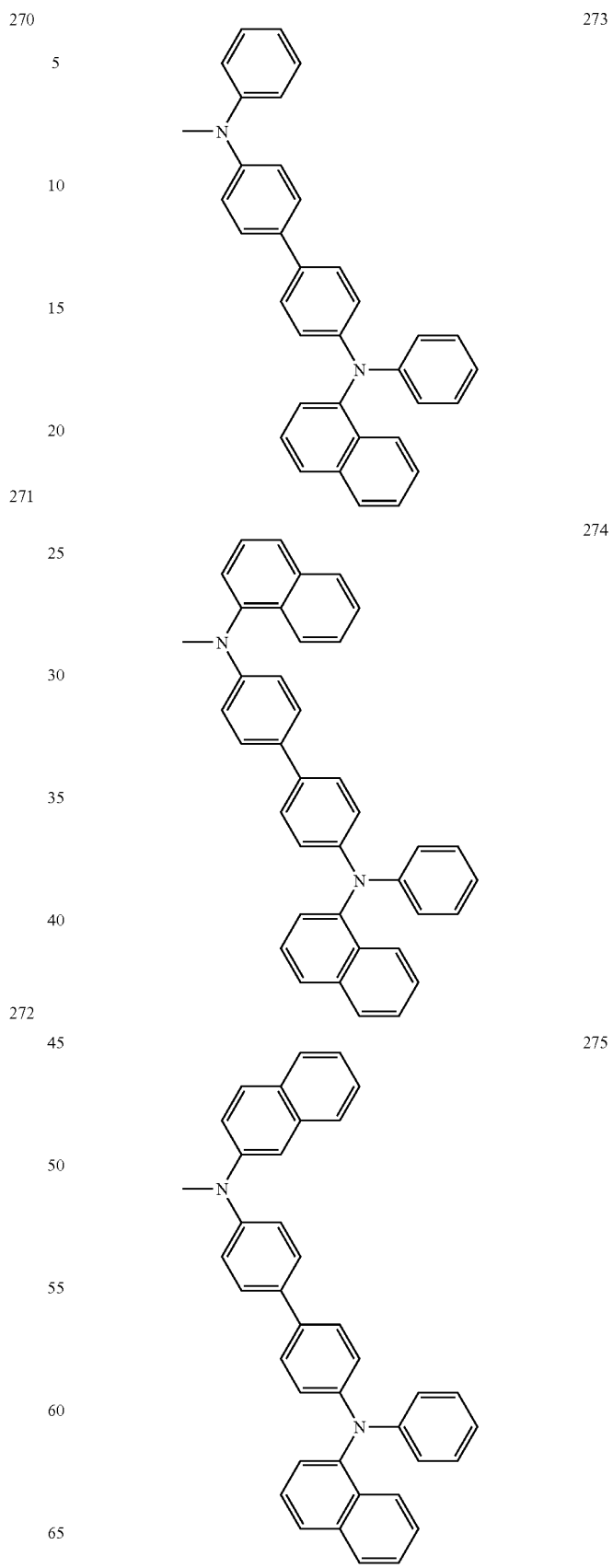

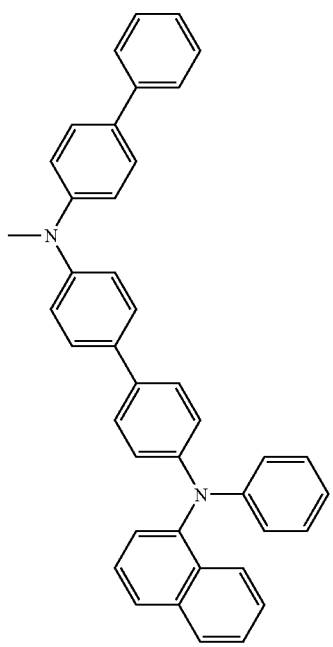
276
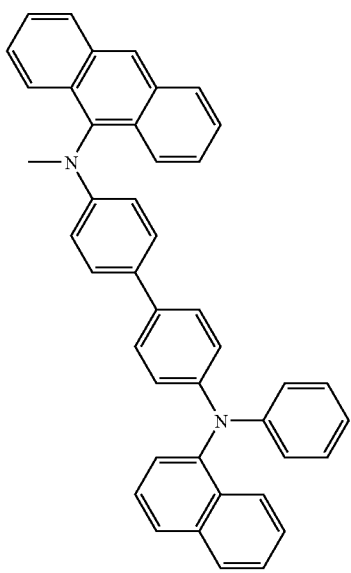
278
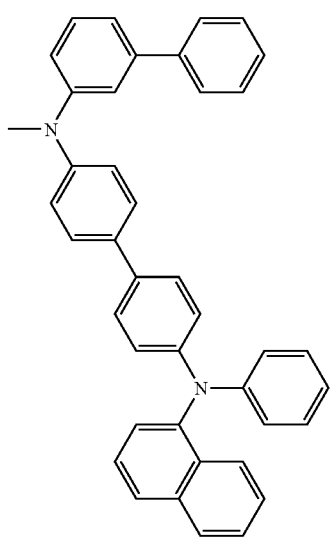
277
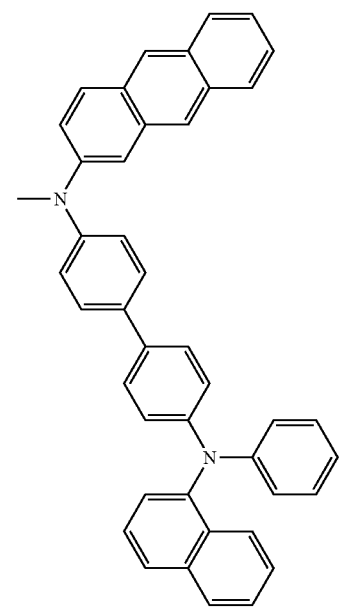
279

-continued
280
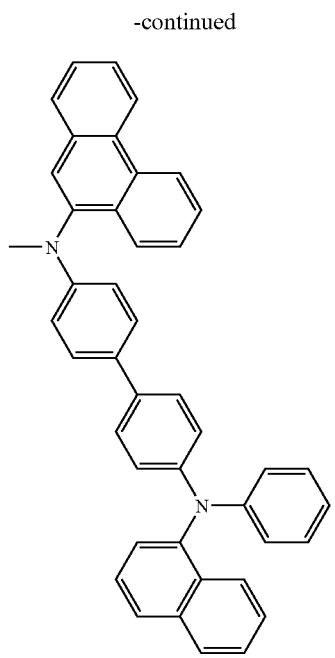
281
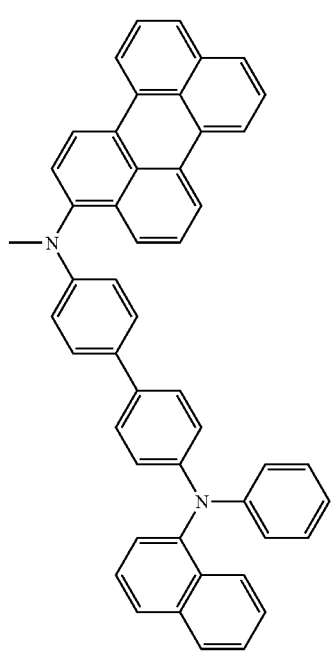
-continued
282
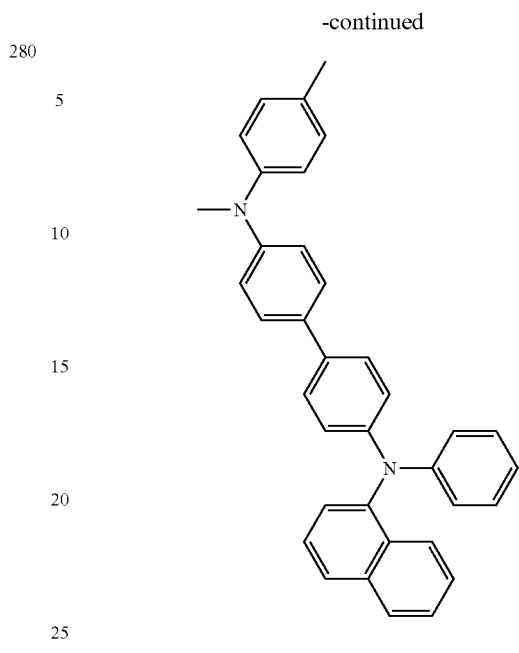
283
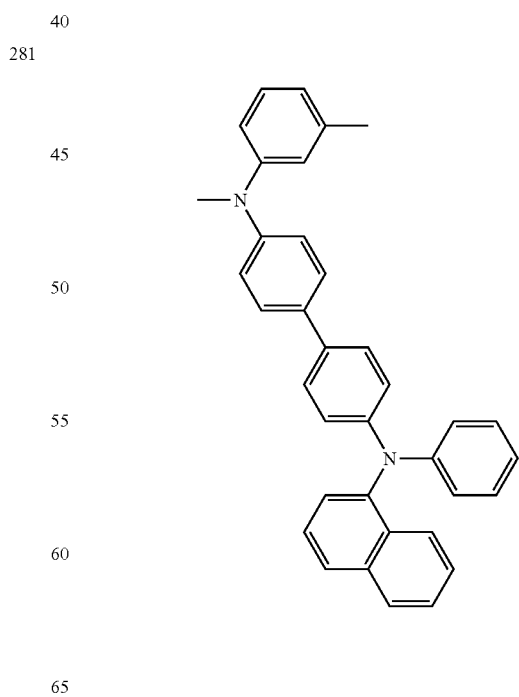

284
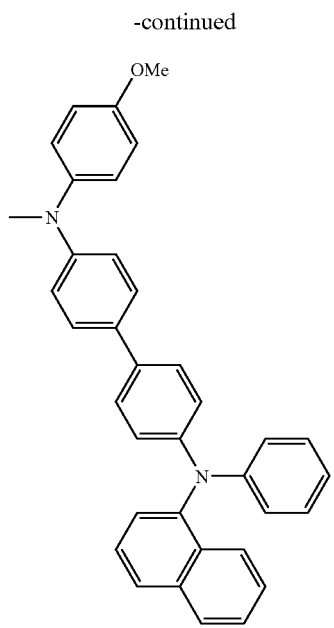
286
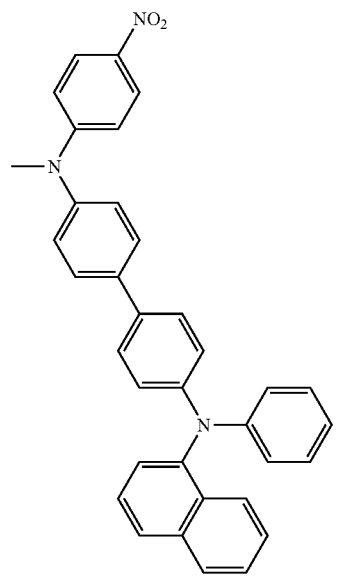
285
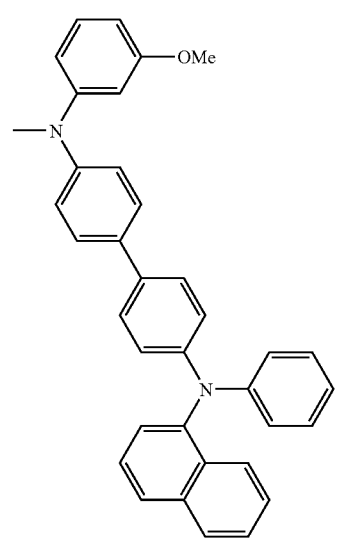
287
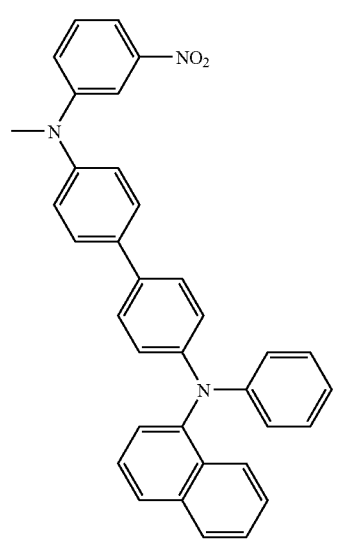

288
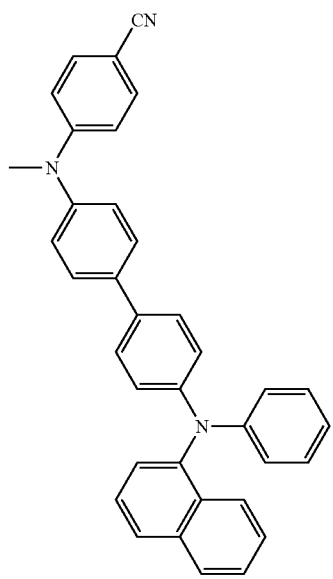
289
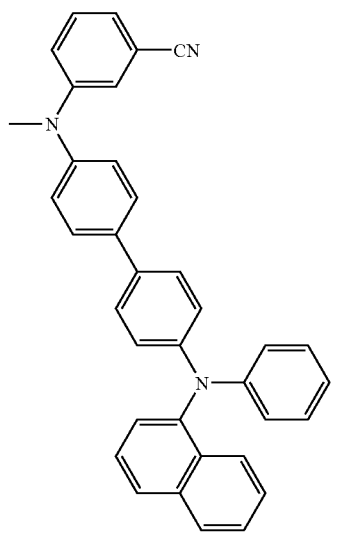
290
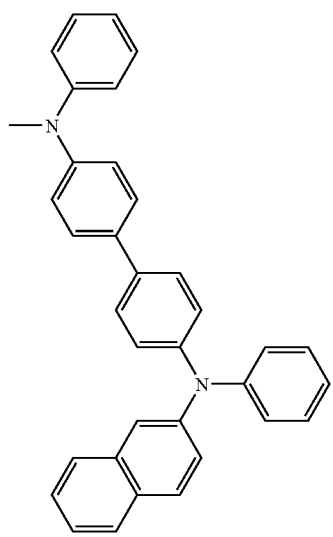
291
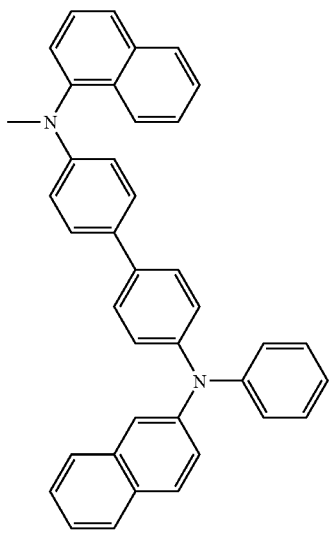
292
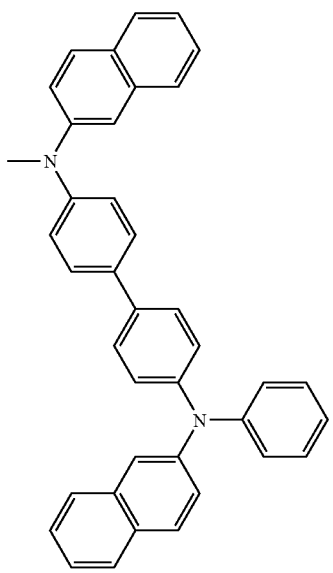

-continued
293
294
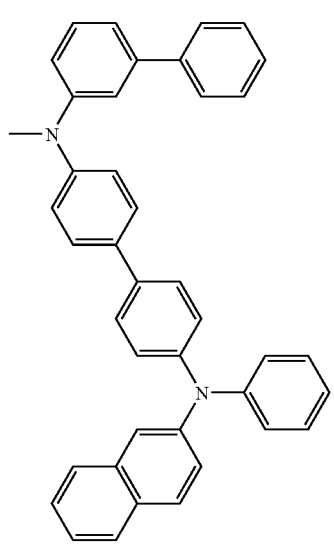
-continued
295
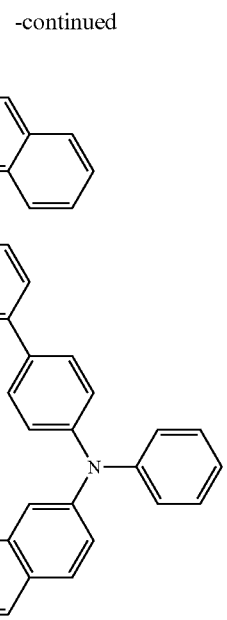
296
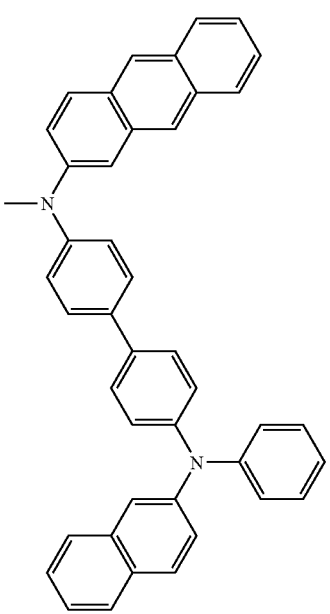

-continued
297
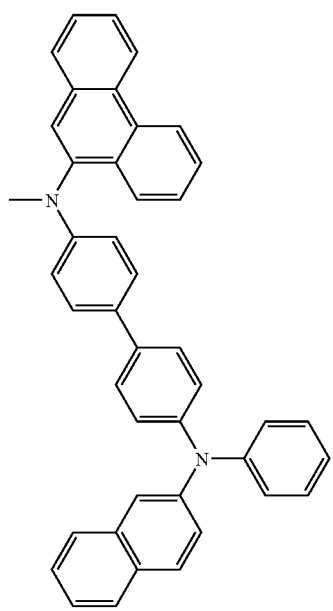
298
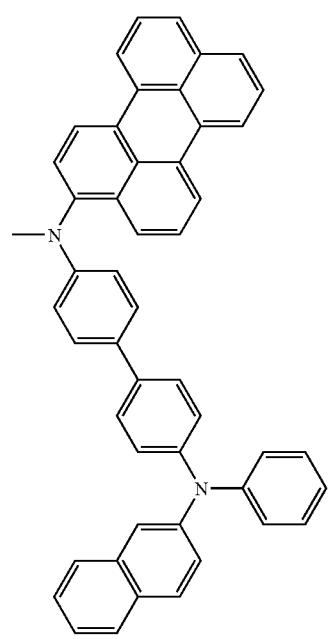
-continued
299
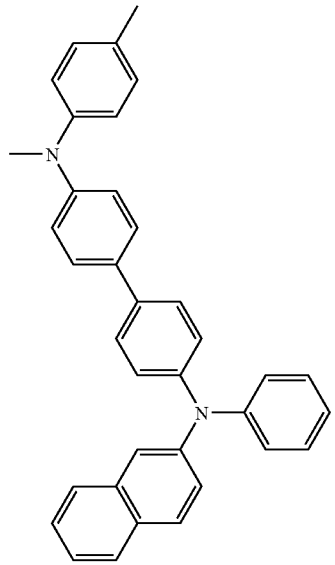
300
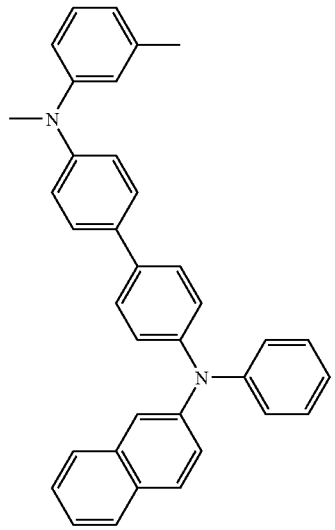

-continued
301
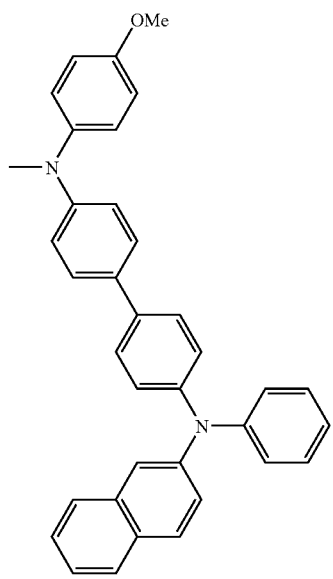
302
303
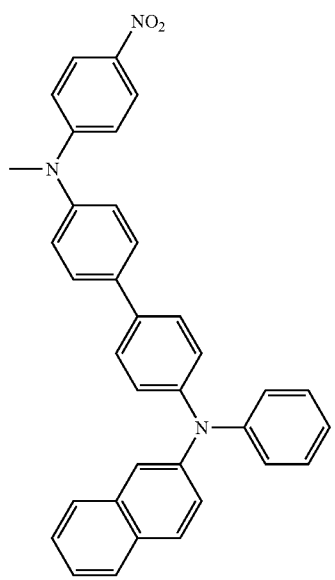
304

-continued
305
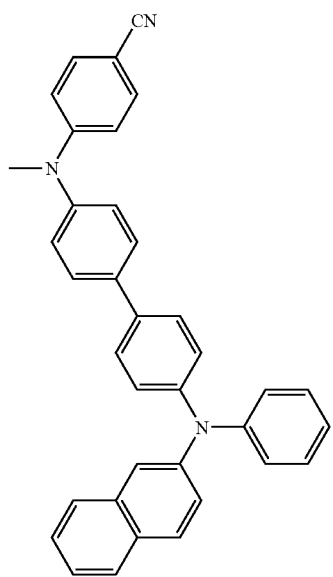
306
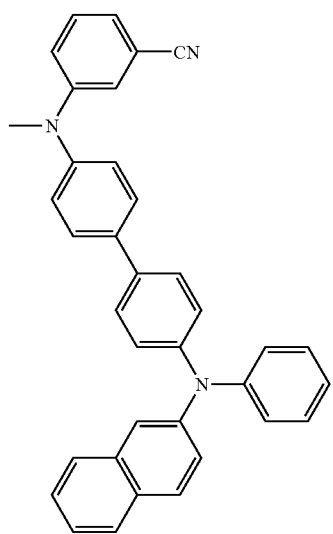
-continued
307
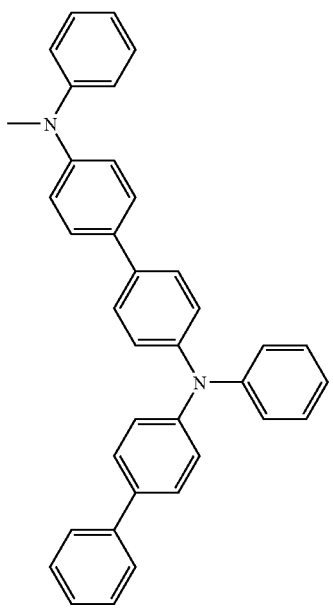
308
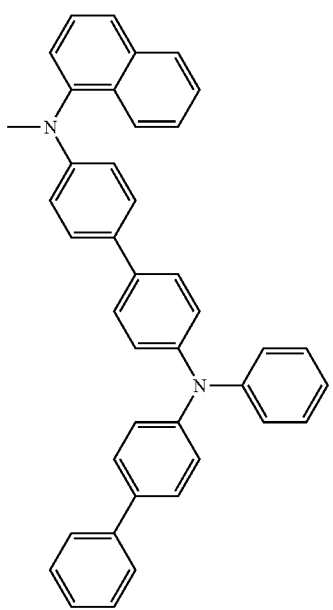

-continued
309
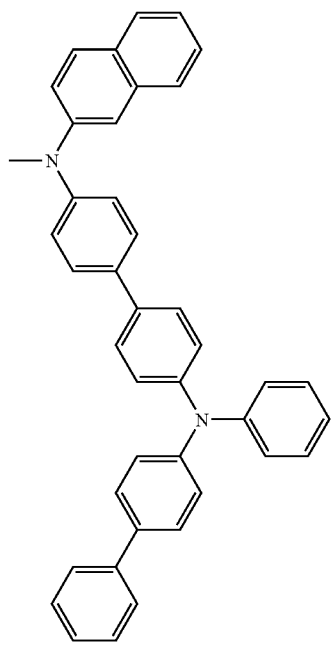
310
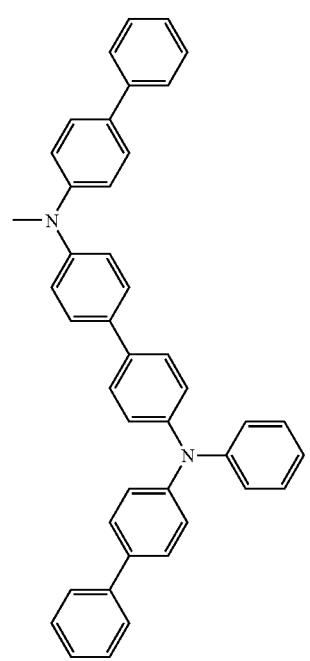
311
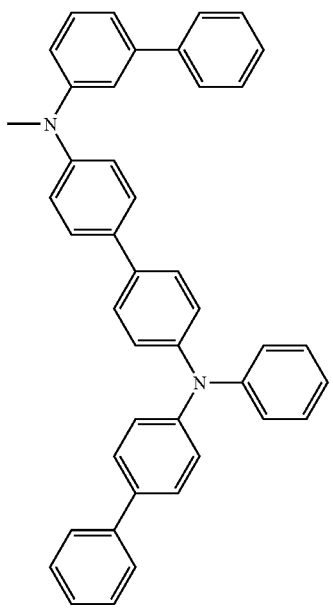
312
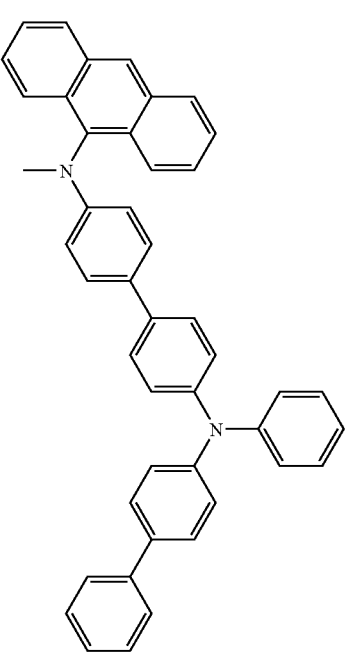

-continued
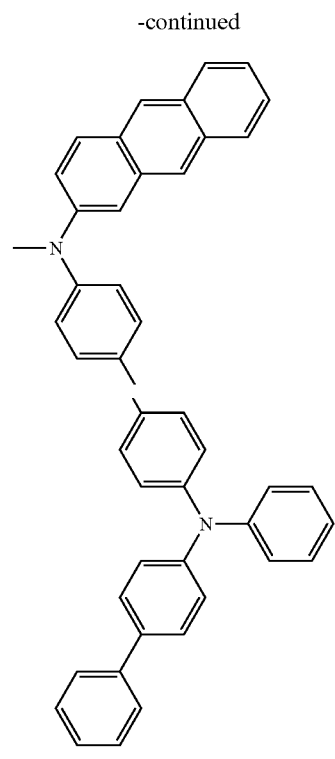
313
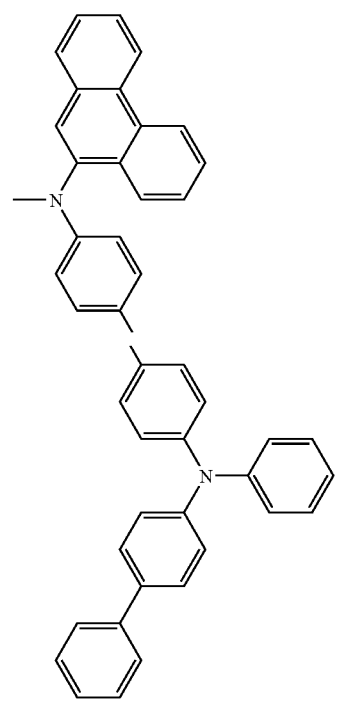
314
-continued
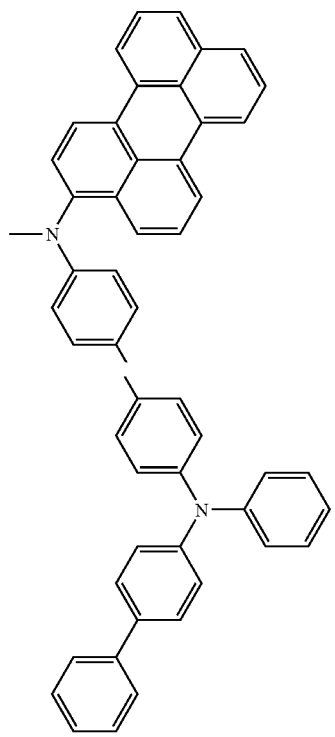
315
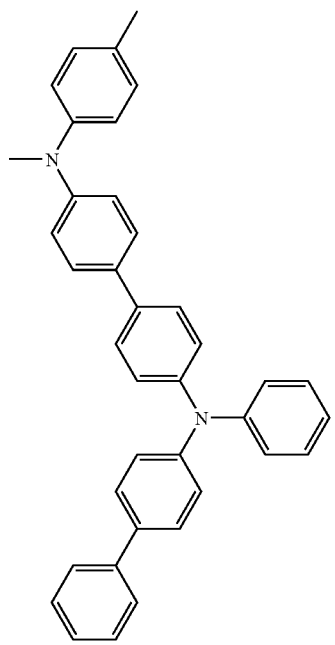
316

-continued
317
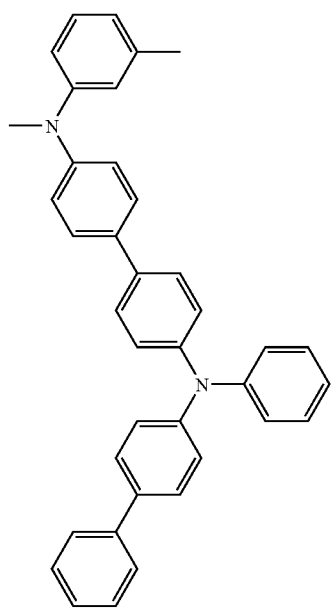
318
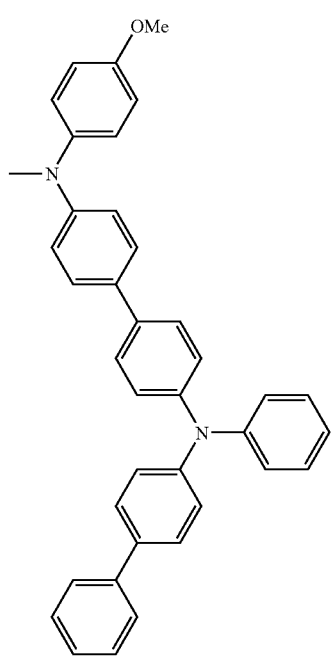
319
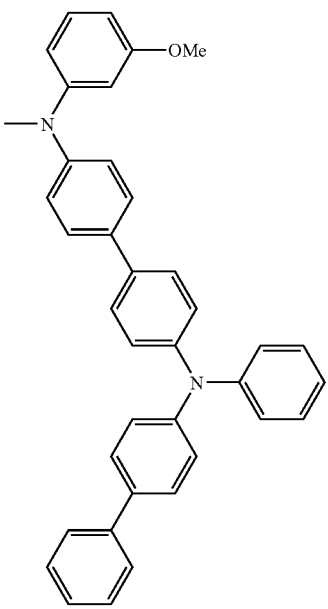
320
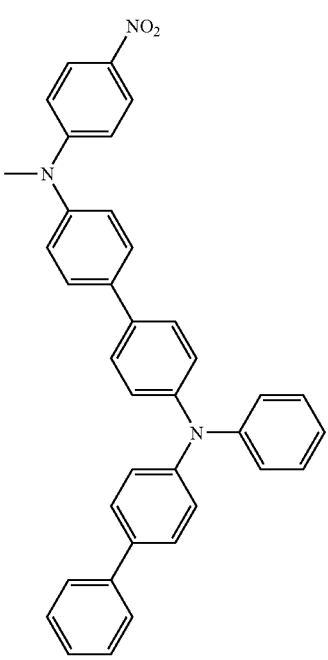

-continued
321
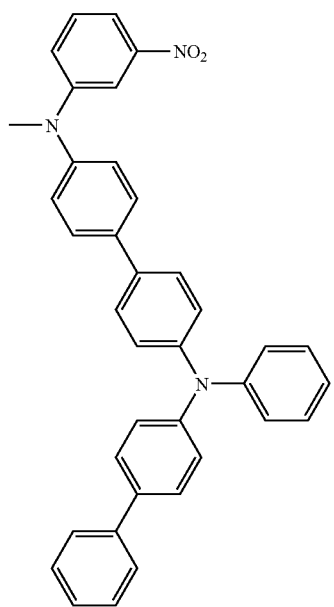
322
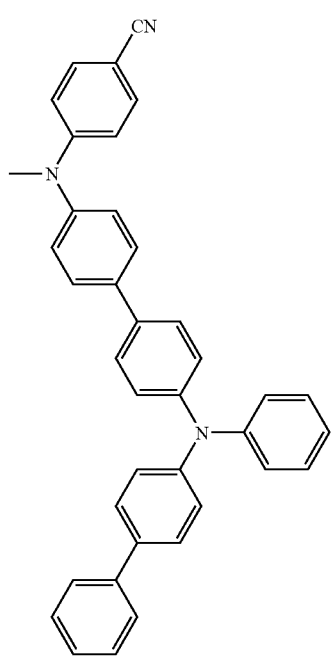
-continued
323
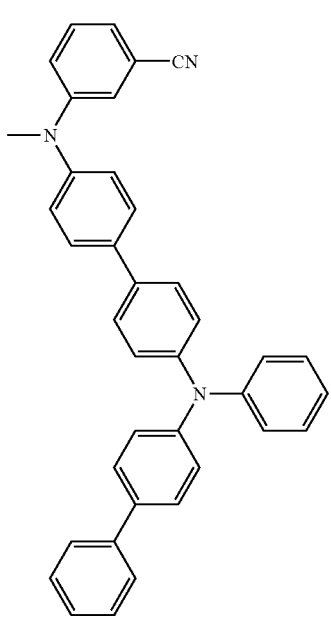
324
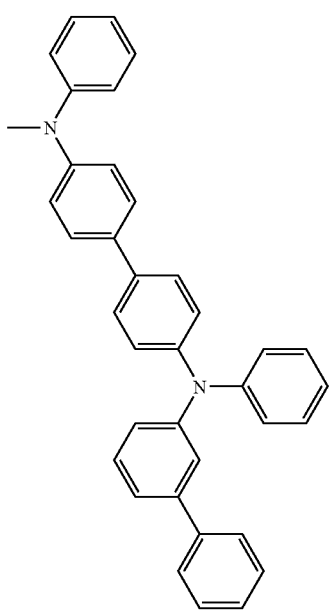

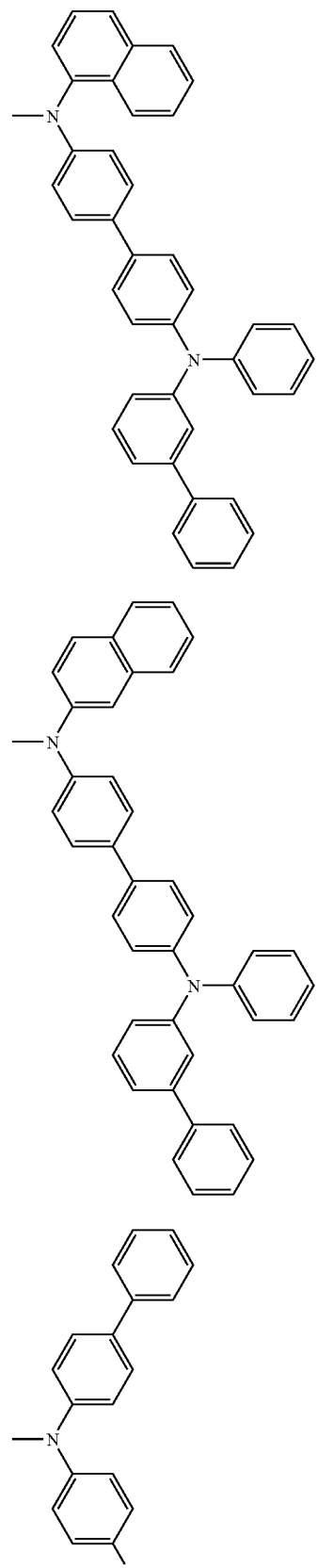
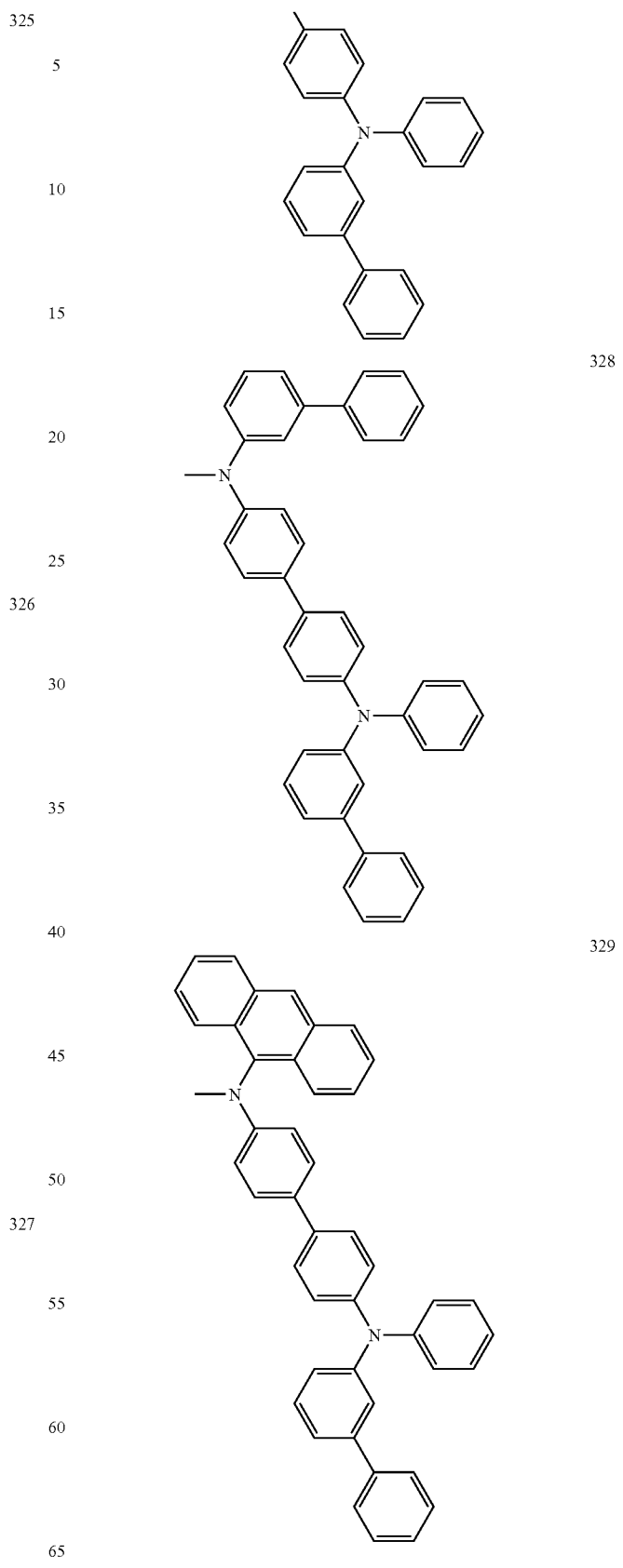

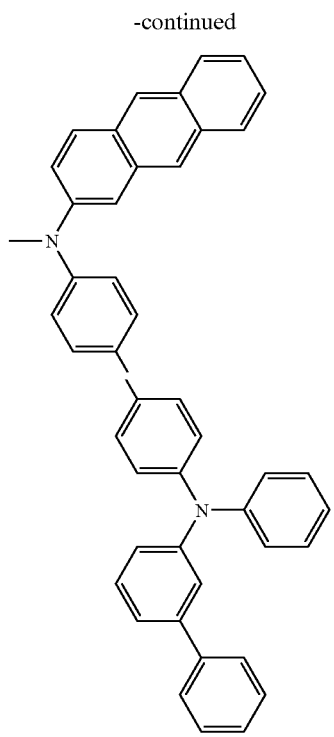
330
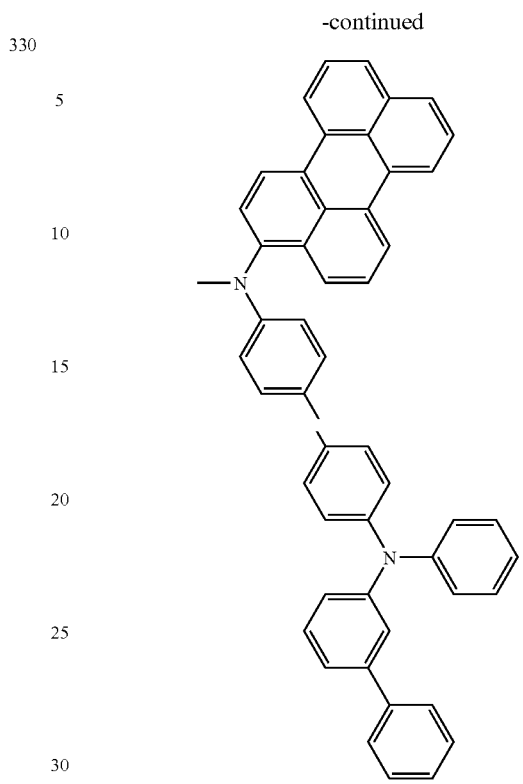
332
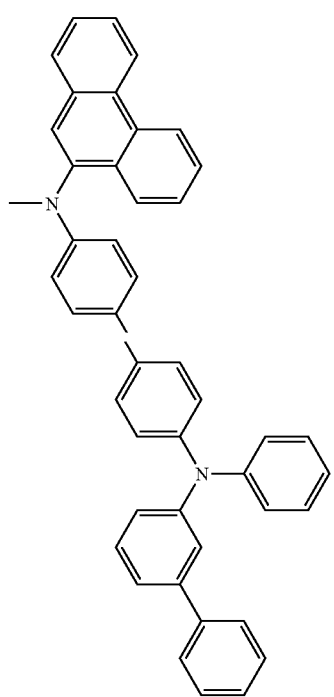
331
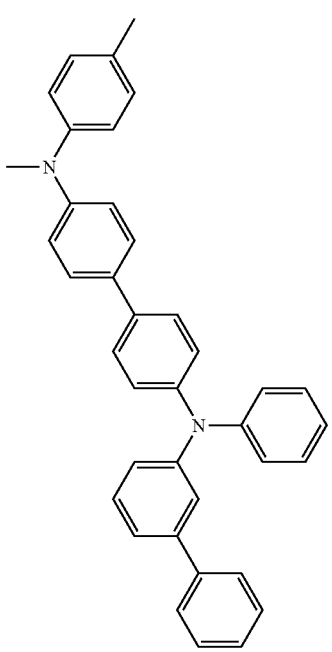
333

334
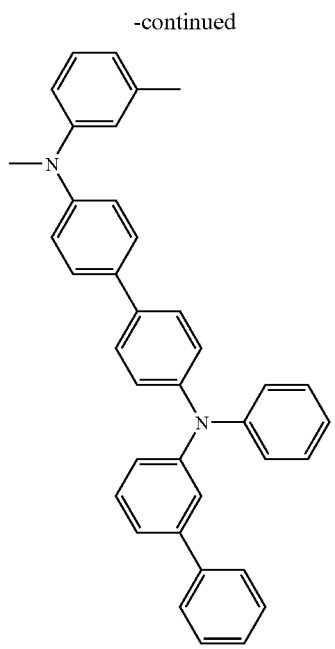
335
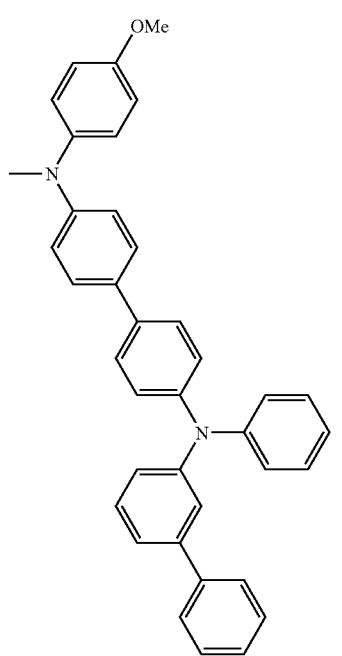
336
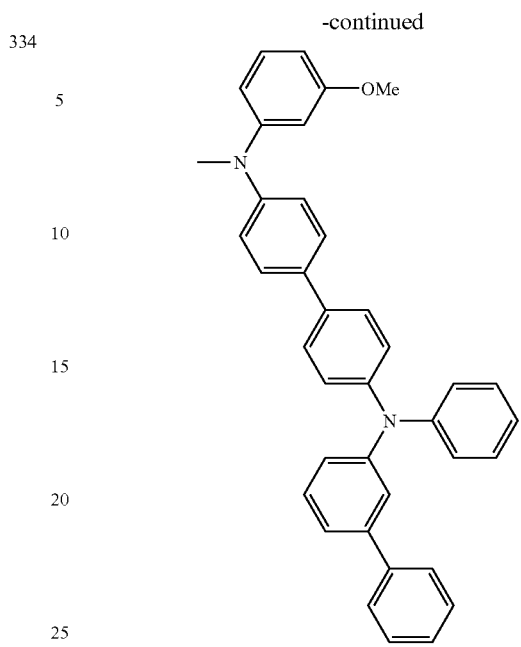
337
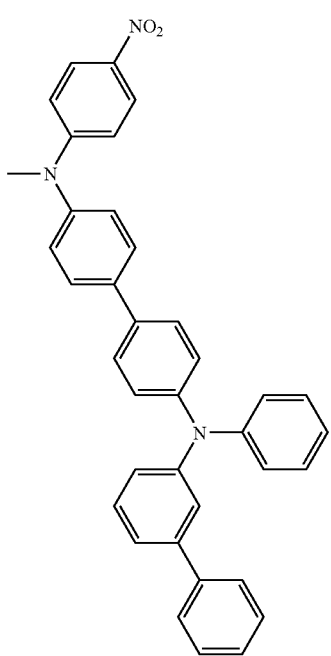

338
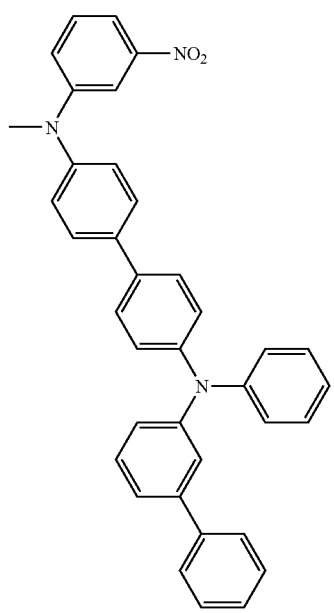
339
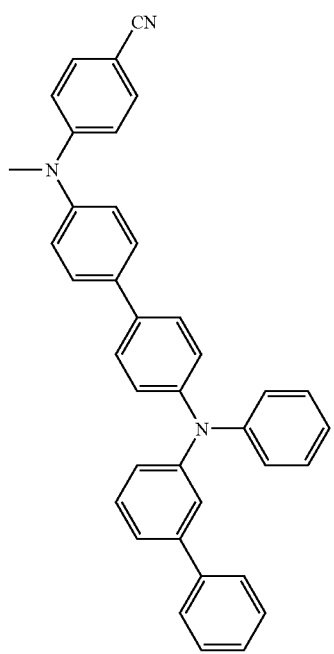
340
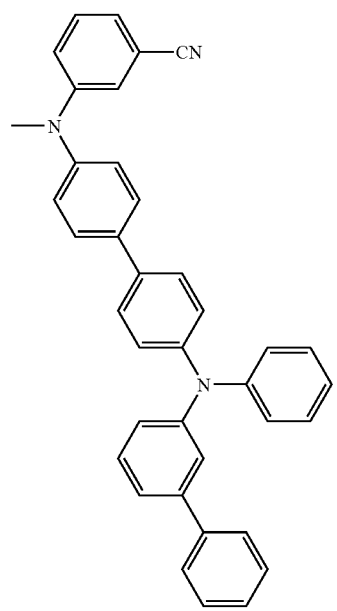
341
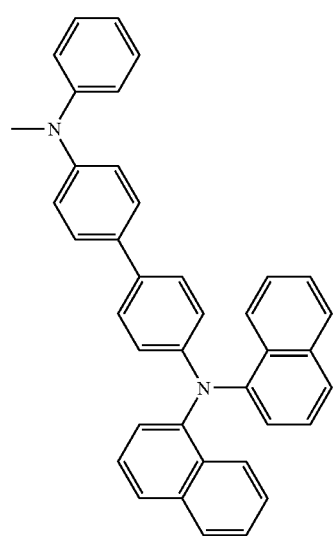
342

-continued
343
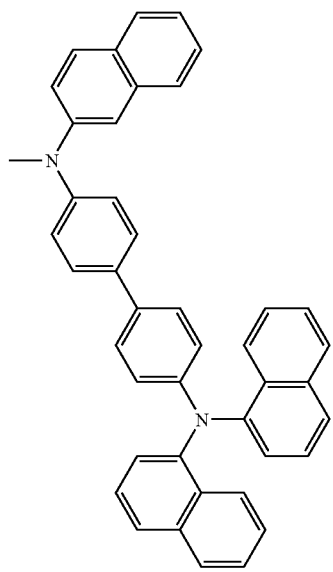
345
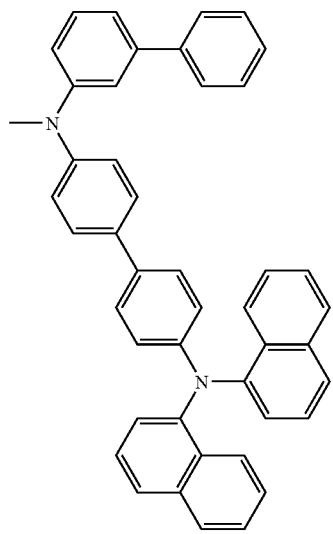
344
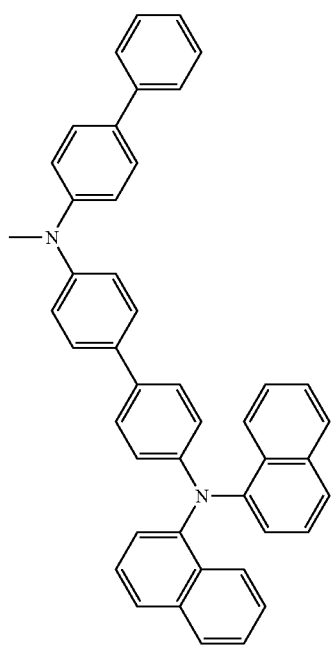
346
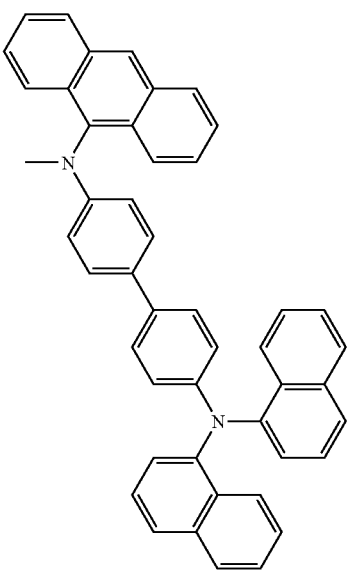

-continued
347
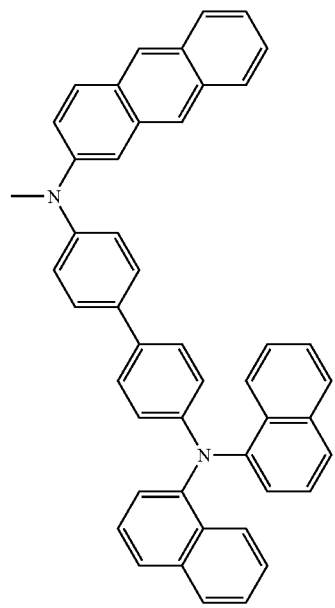
348
349
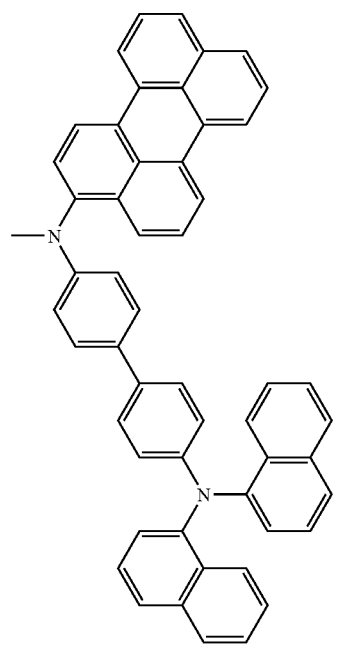
350

-continued
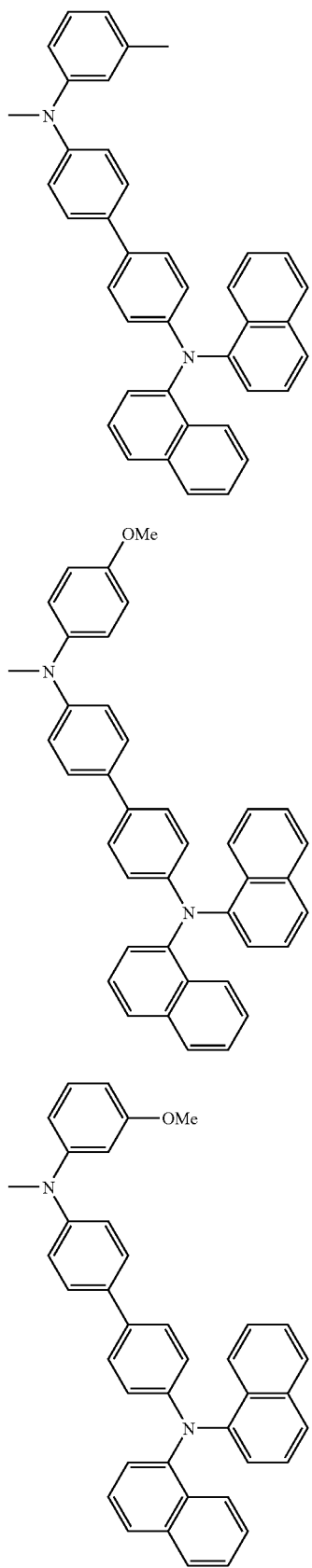
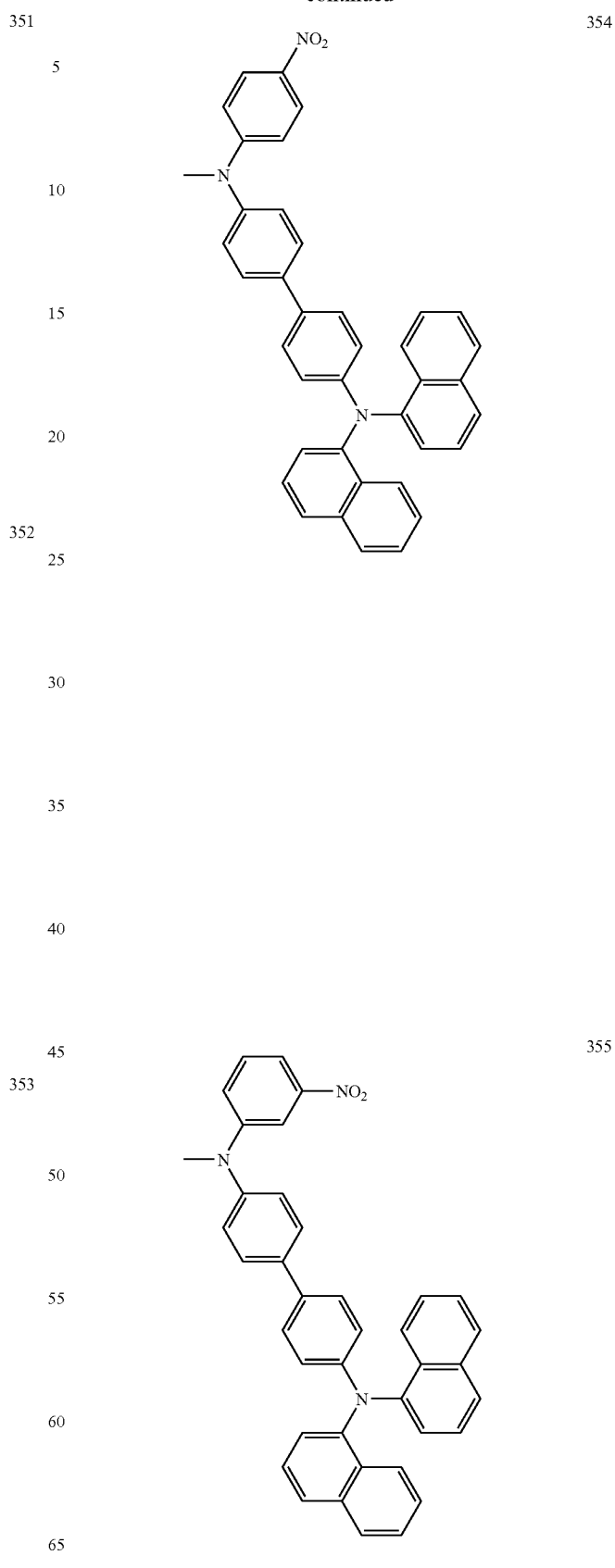

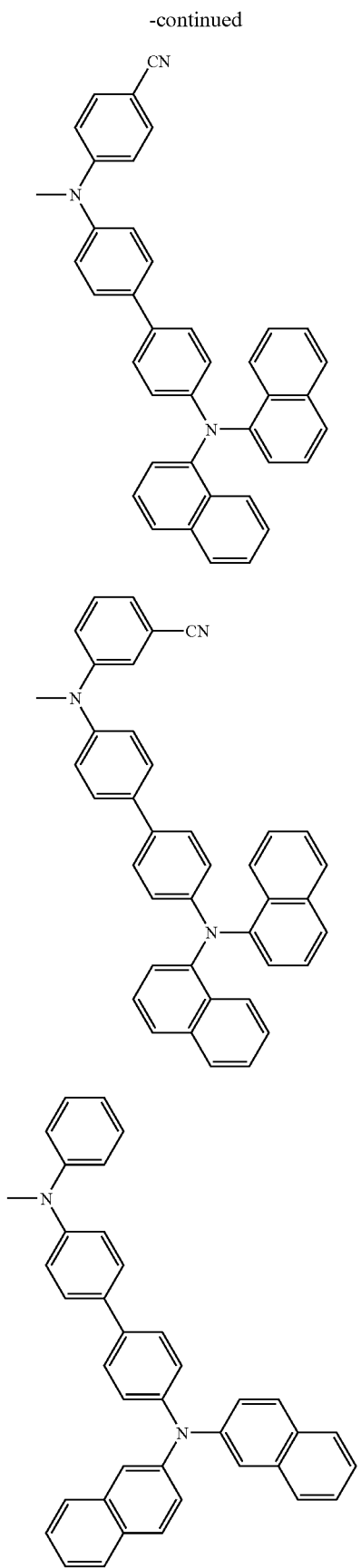

-continued
361
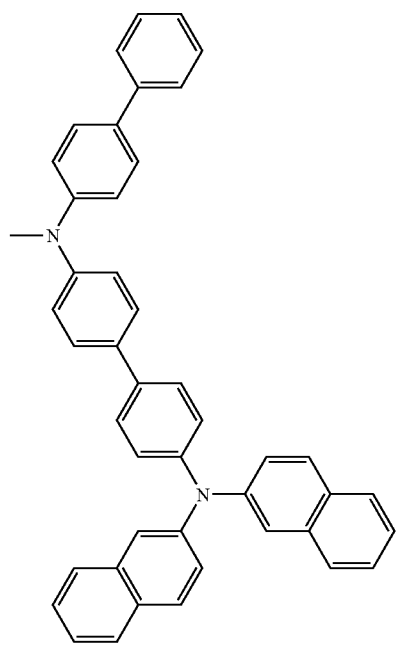
362
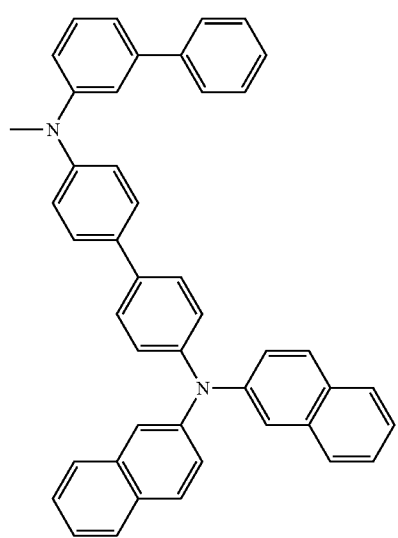
-continued
363
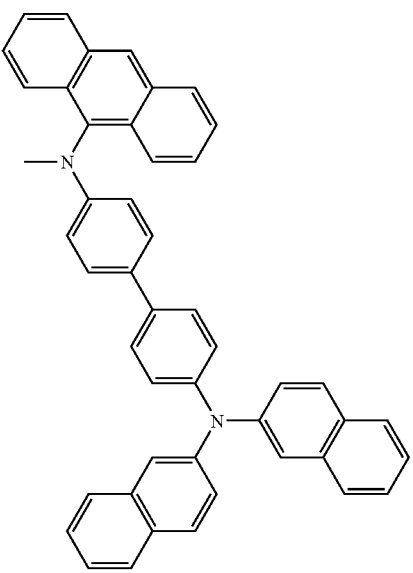
364
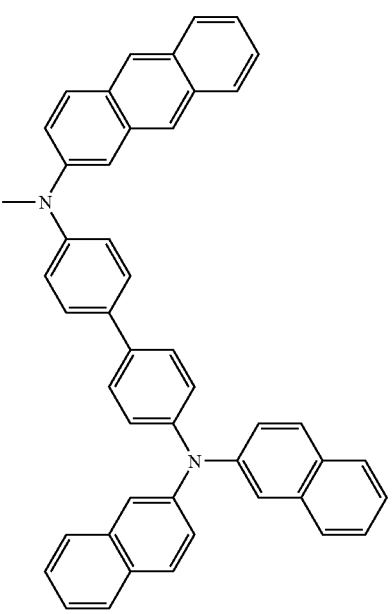

-continued
365
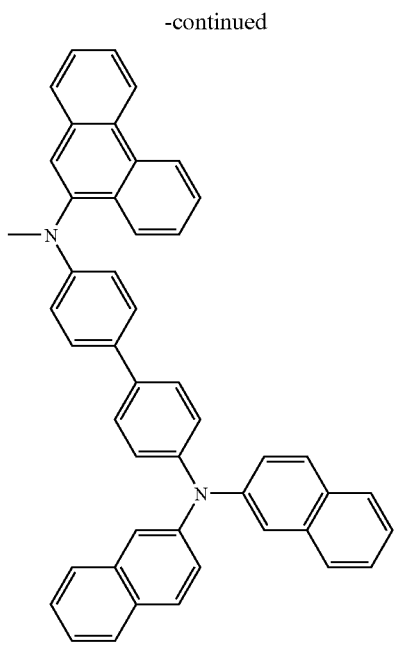
366
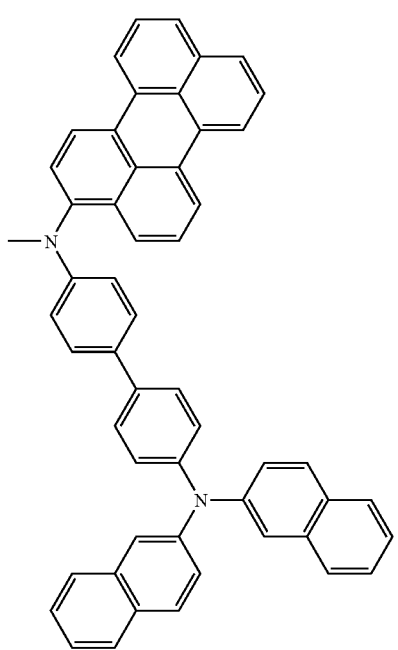
-continued
367
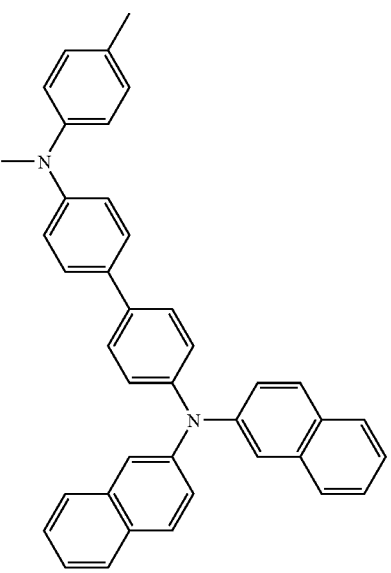
368
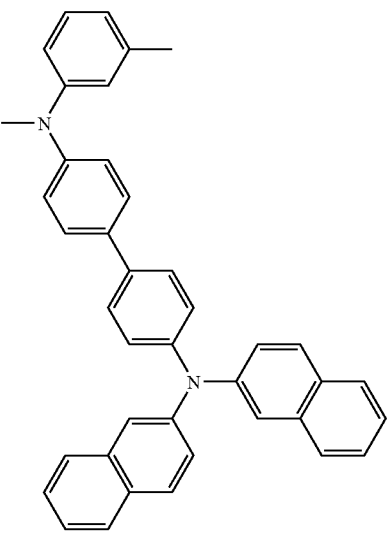

-continued
369
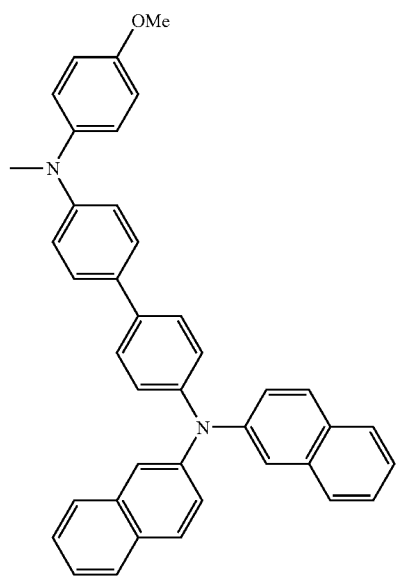
370
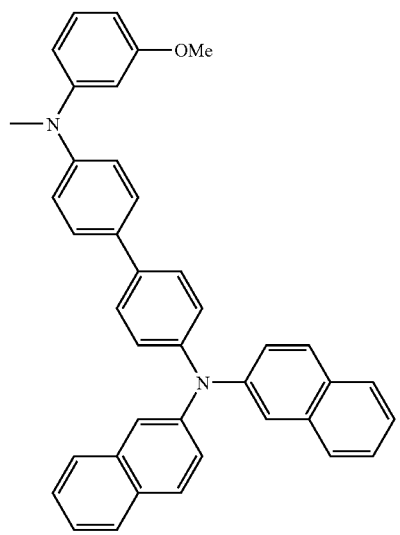
-continued
371
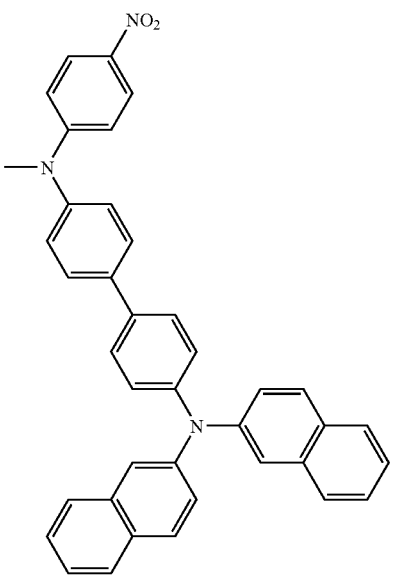
372
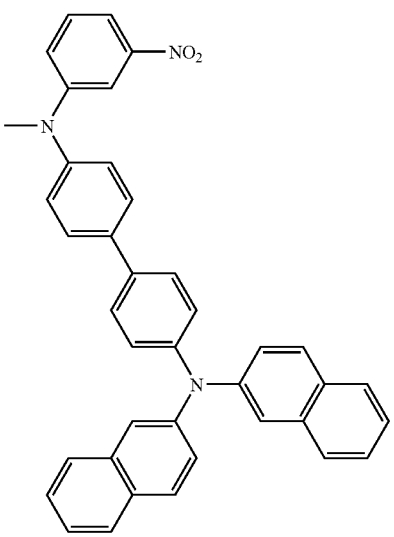

-continued
373
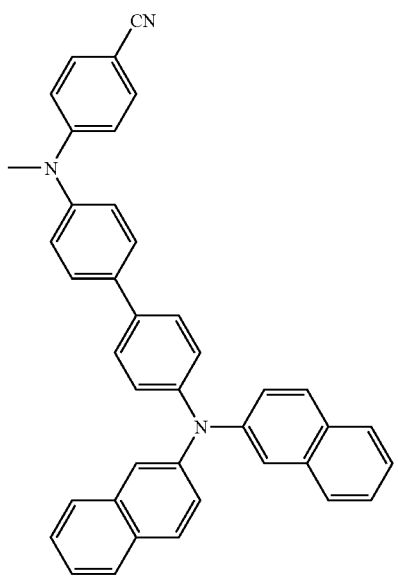
374
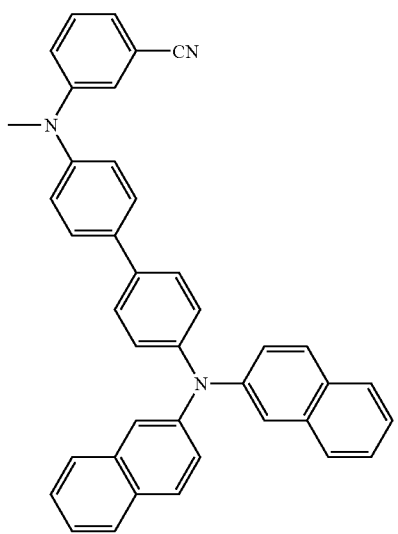
375
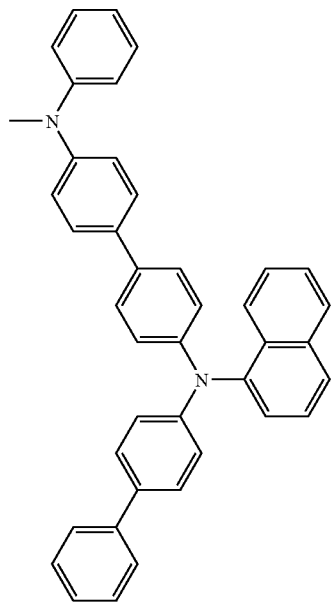
376
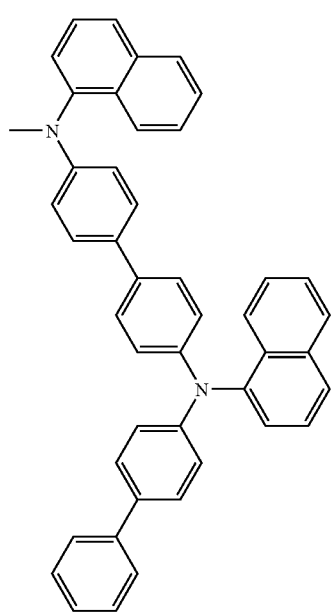

377
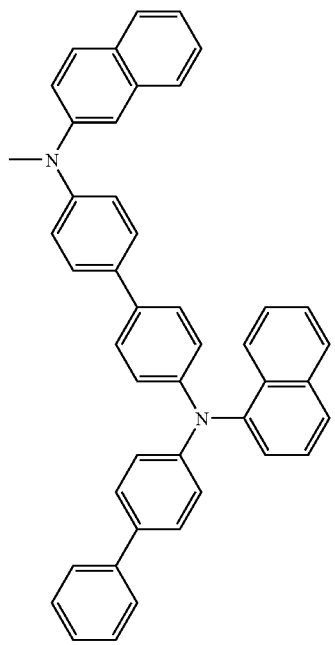
378
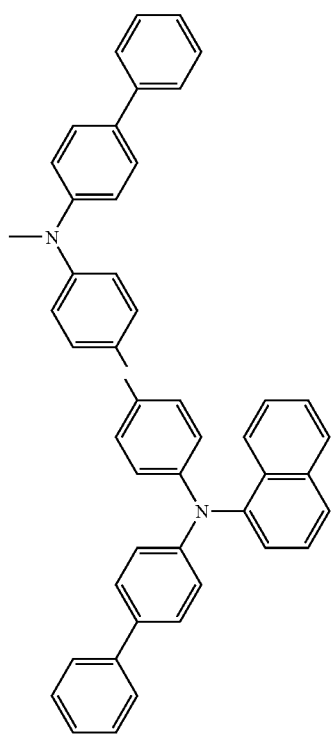
379
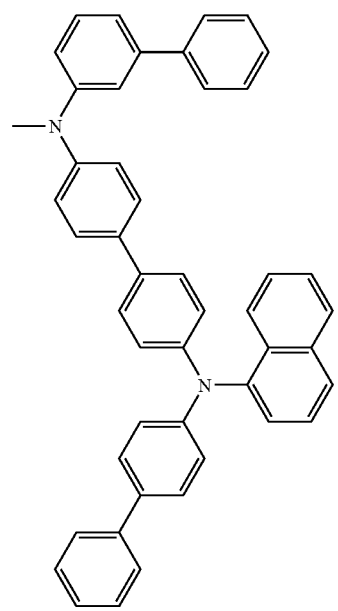
380
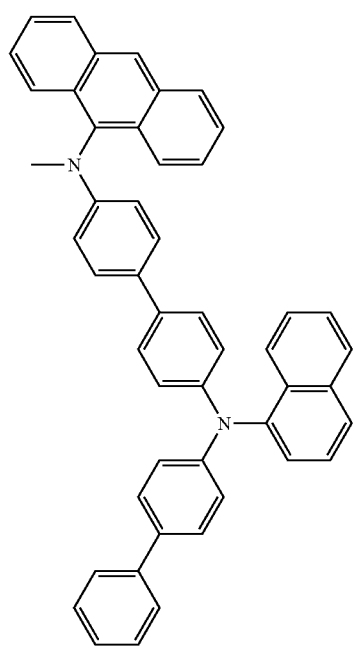
381
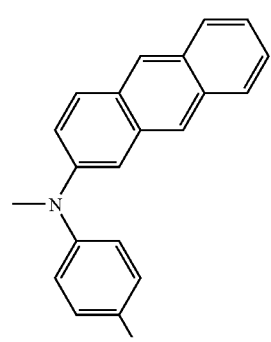

-continued
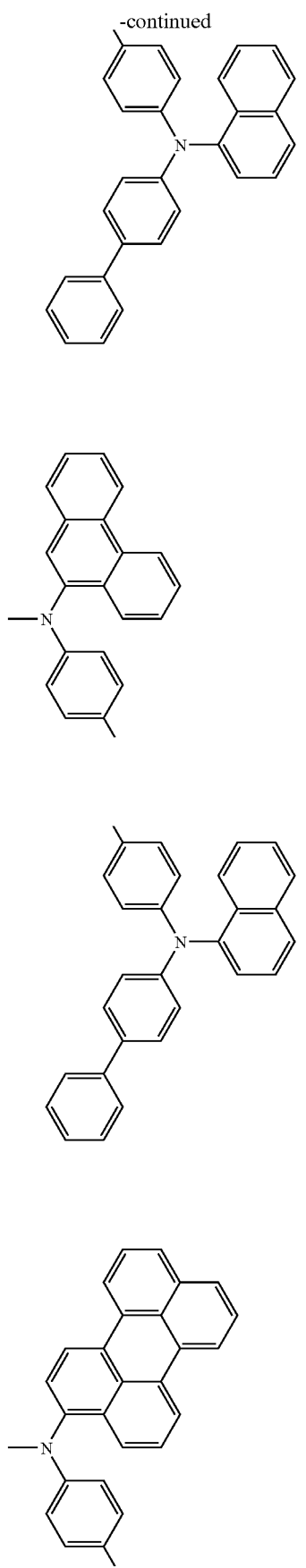
382
383
-continued
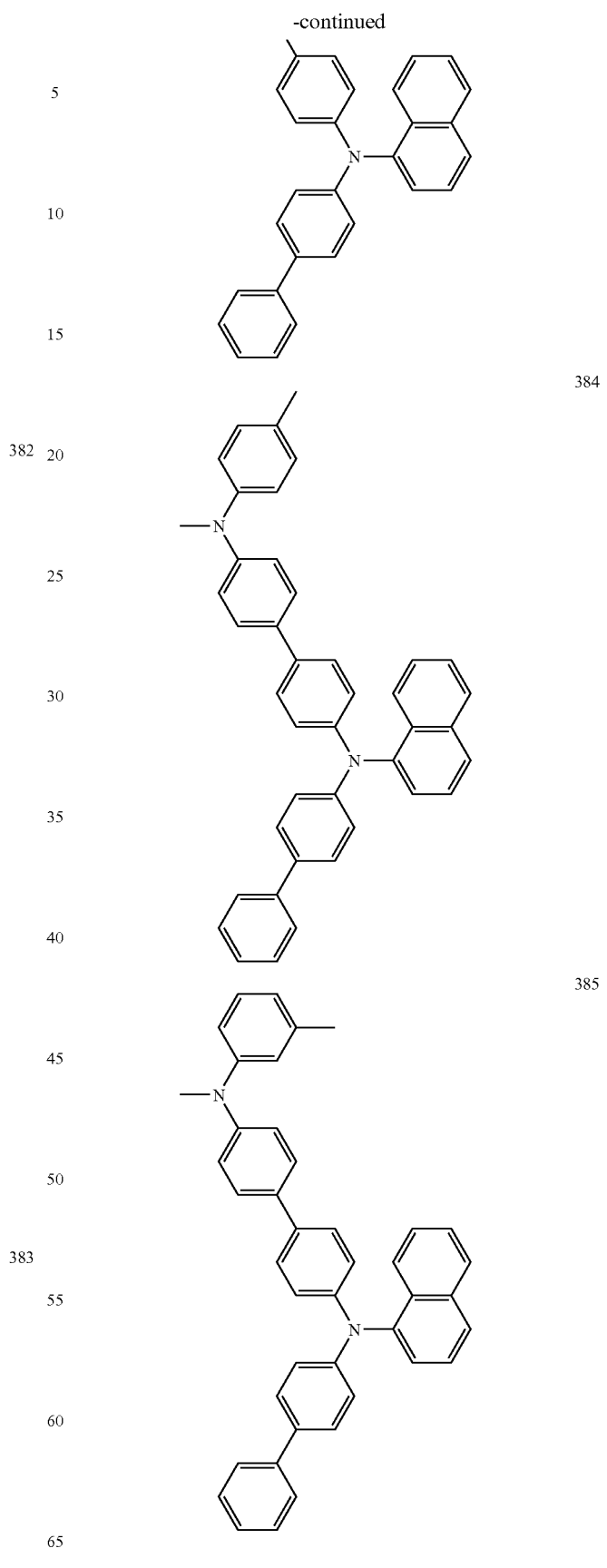
384
385

386
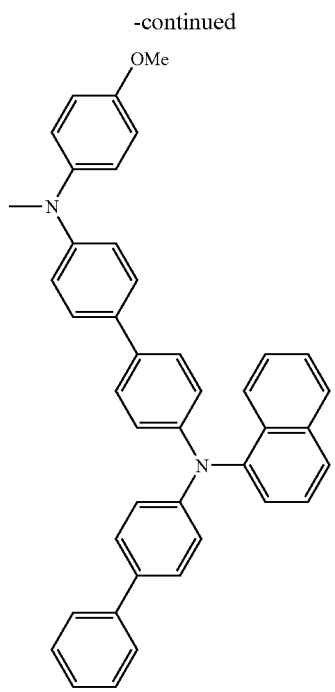
387
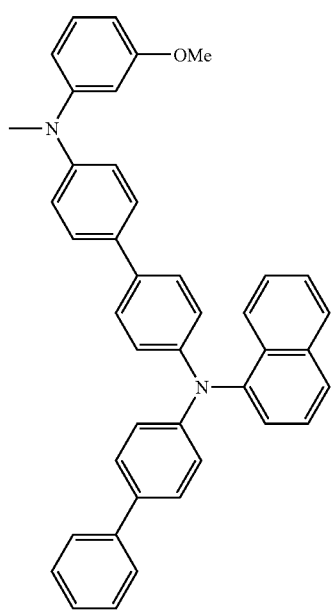
388
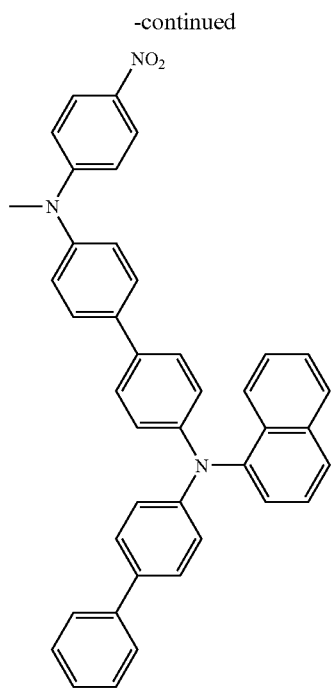
389
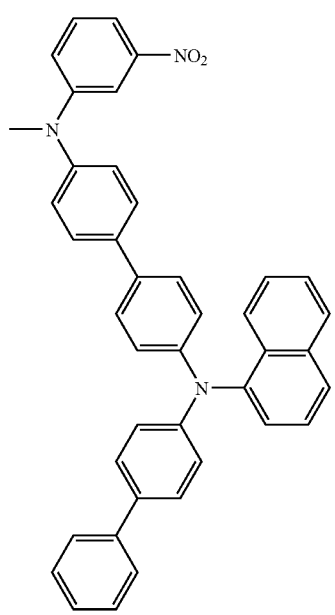

191
192
-continued
390
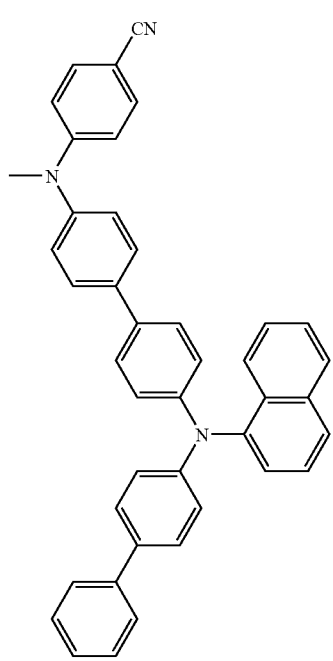
-continued
392
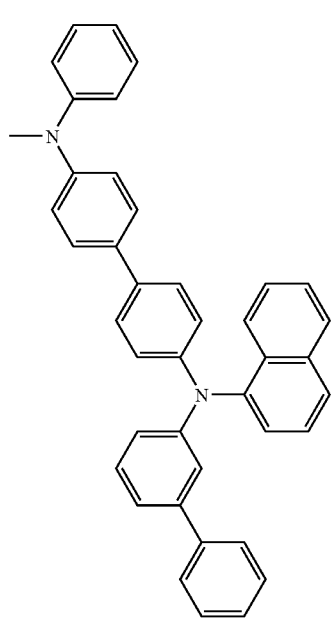
391
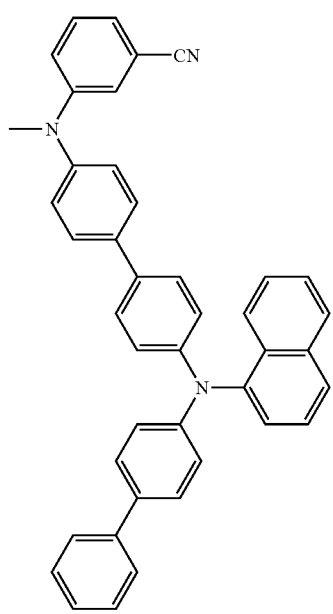
393
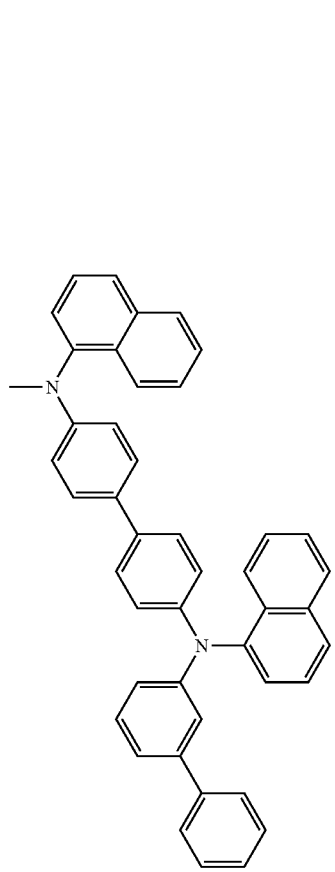

-continued
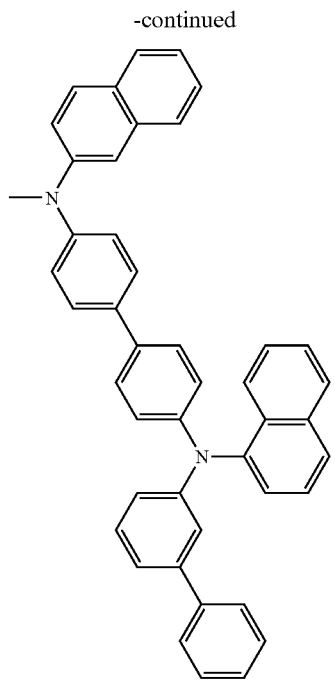
394
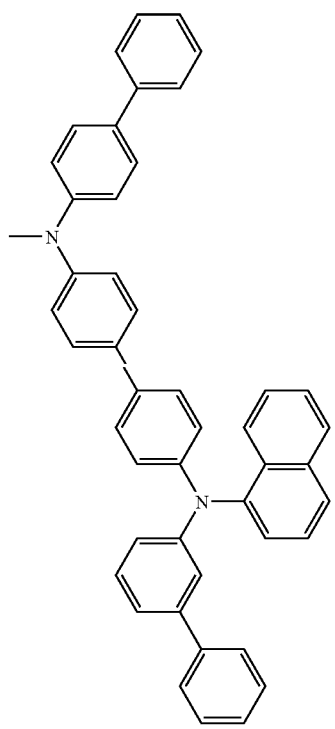
395
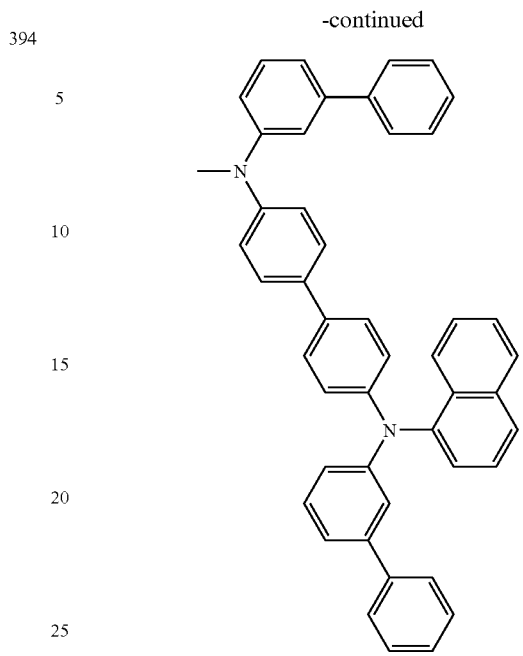
396
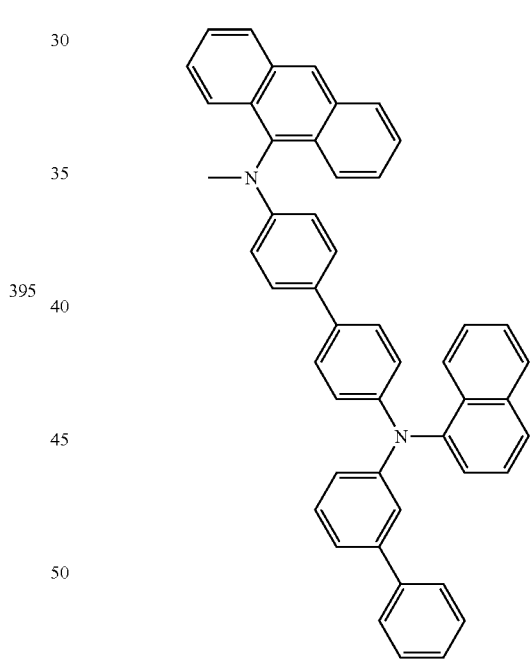
397
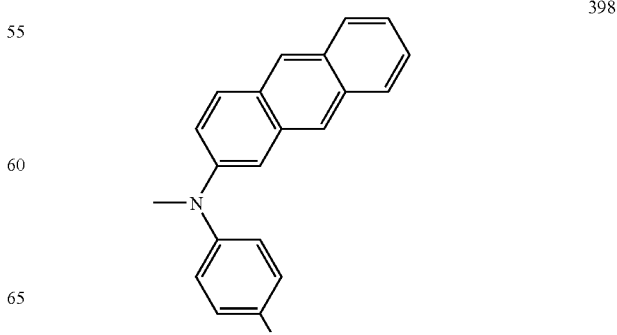
398

195 196
-continued -continued
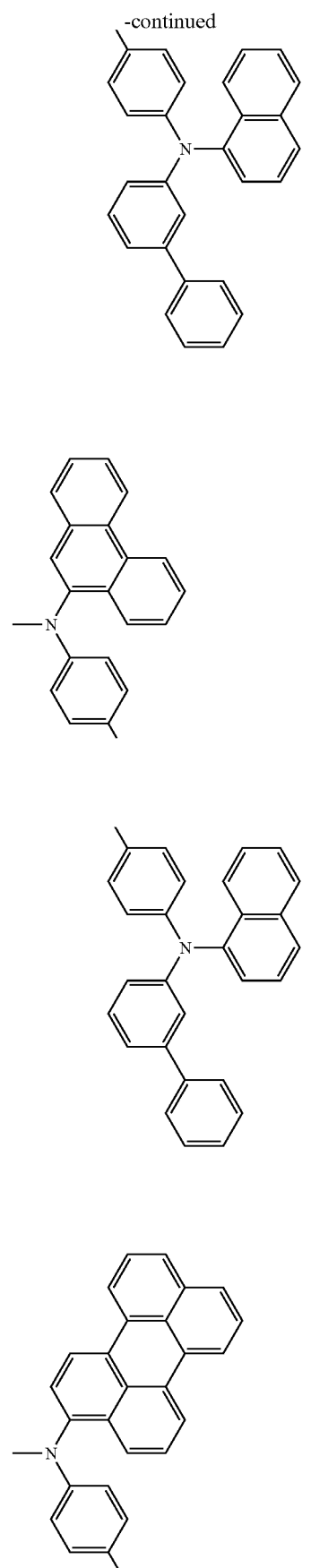
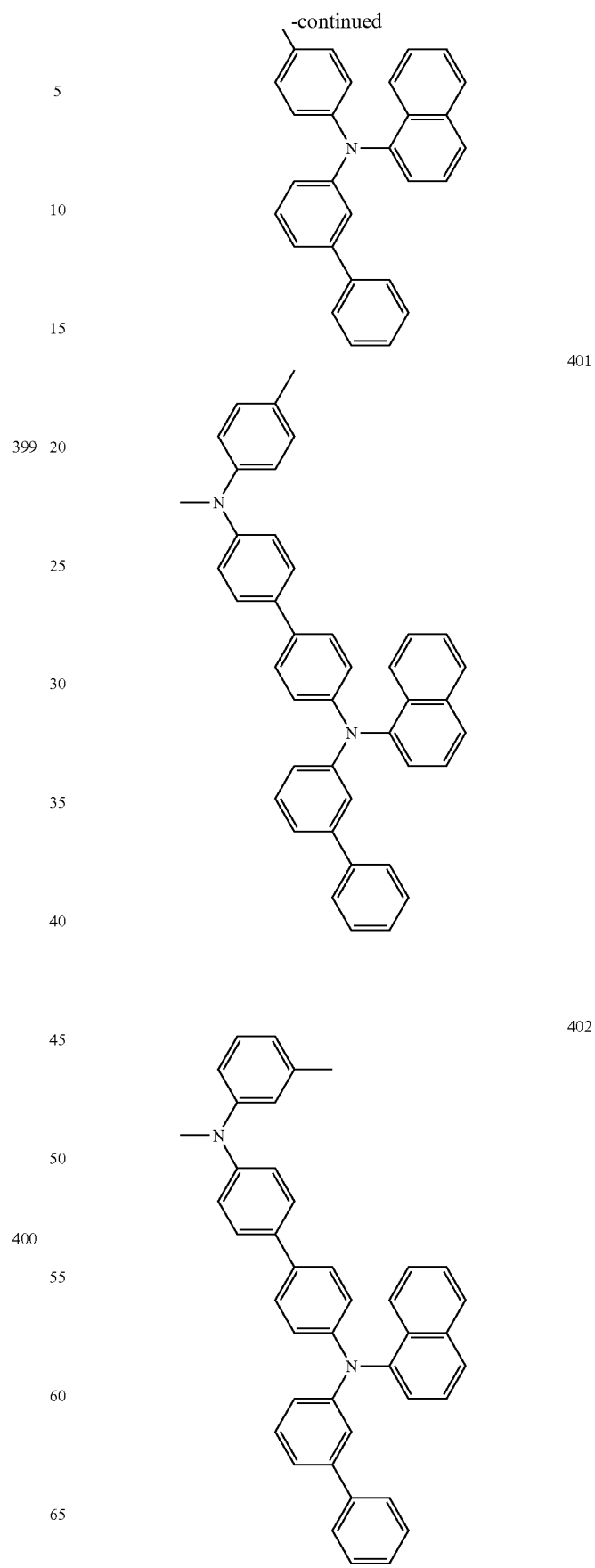

-continued
403
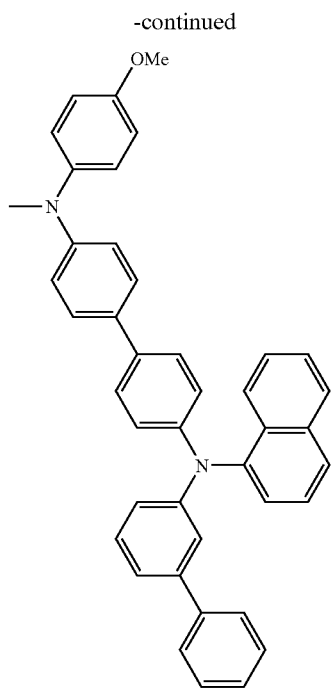
405
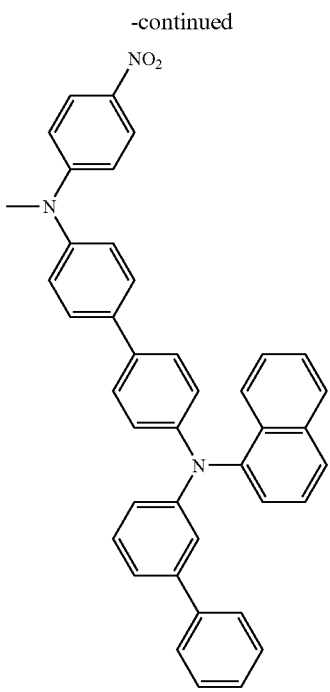
404
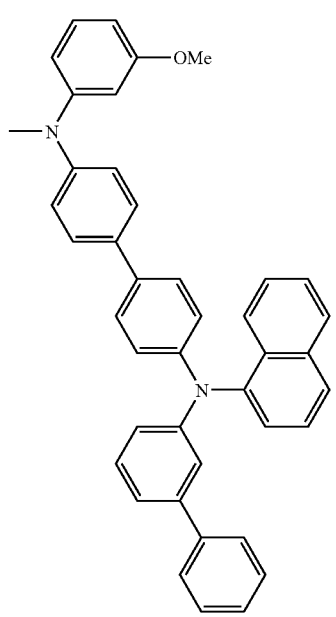
406
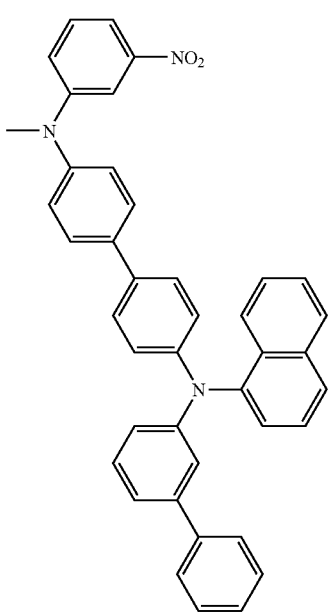

-continued
407
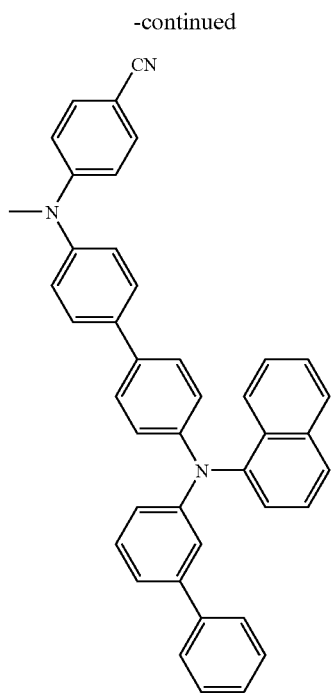
408
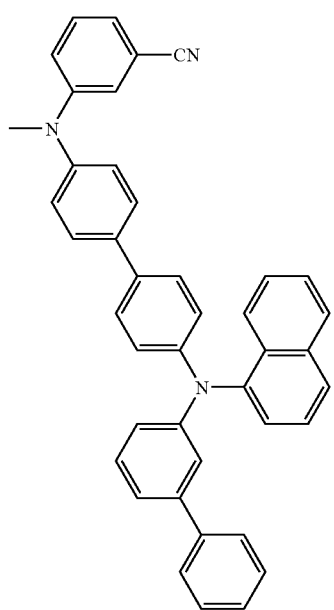
-continued
409
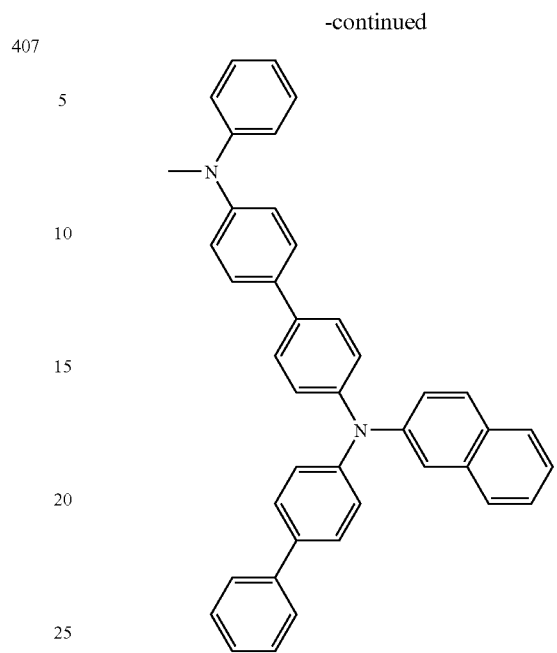
410

-continued
411
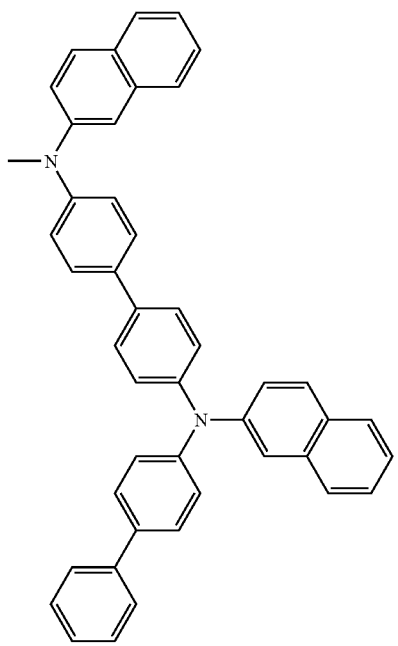
412
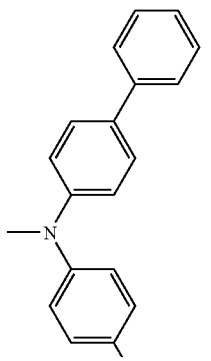
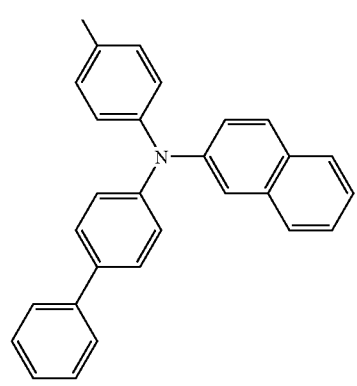
-continued
413
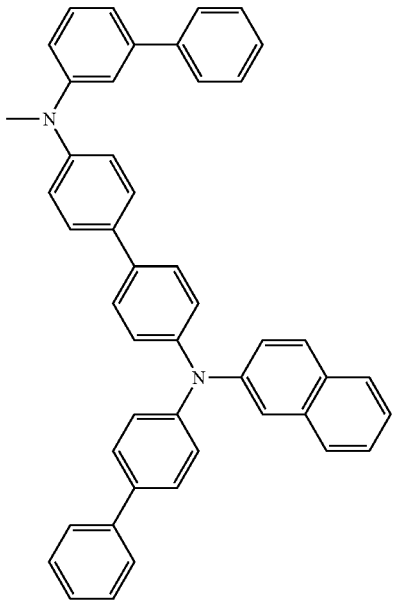
414
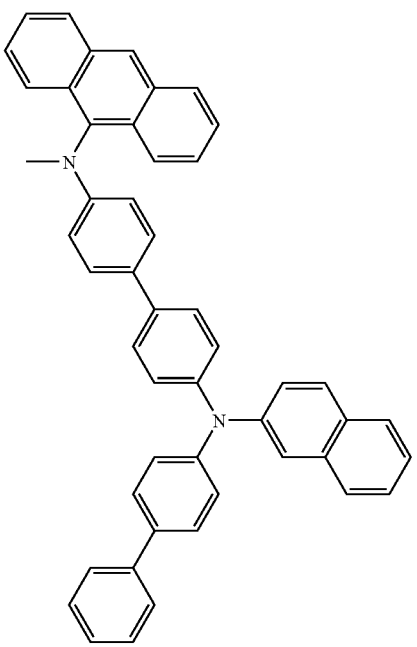
415

-continued
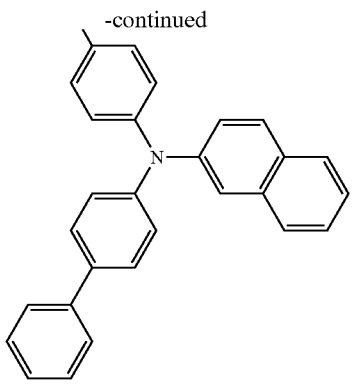
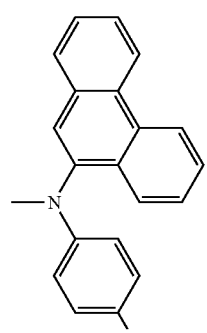
416
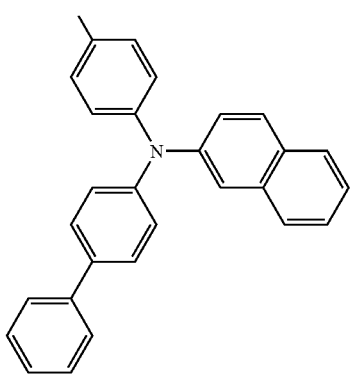
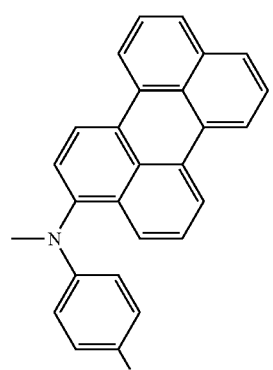
417
-continued
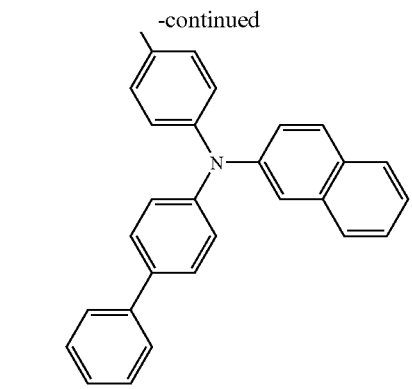
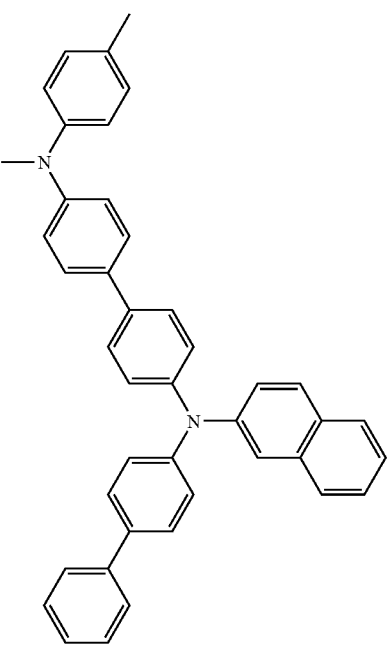
418
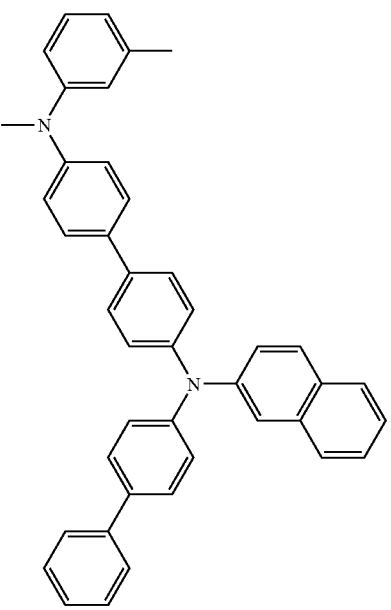
419

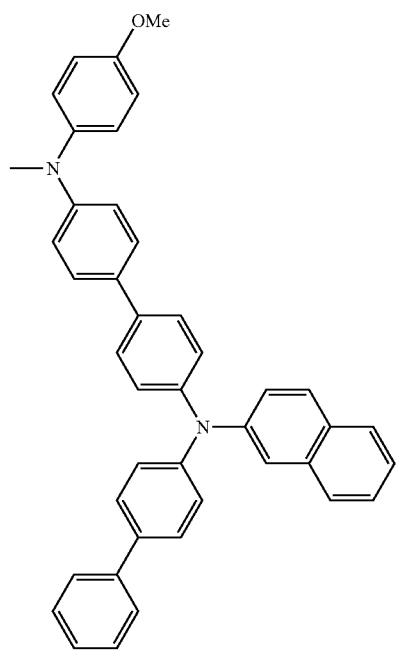
420
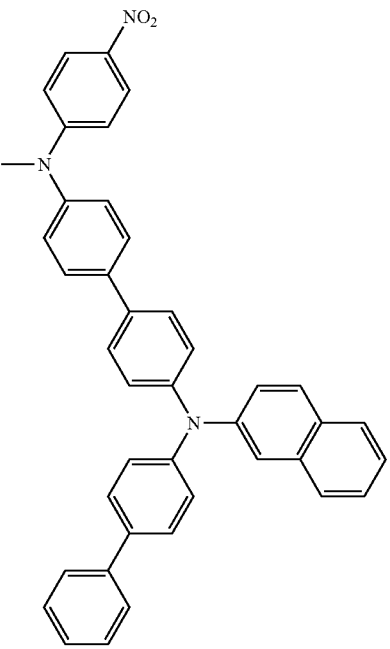
422
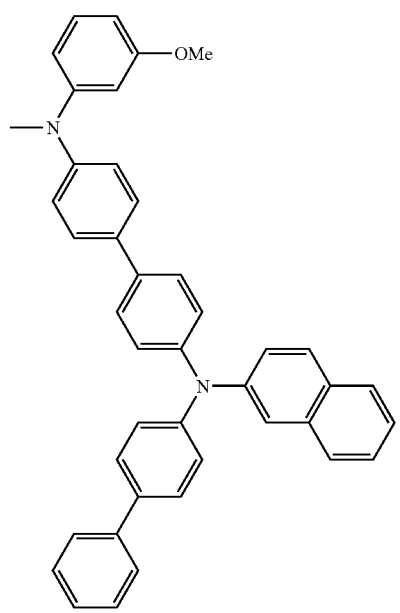
421
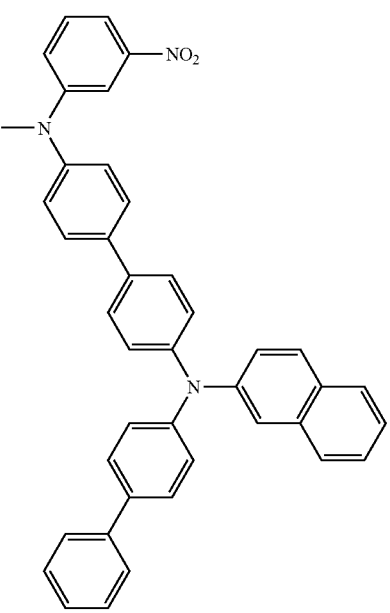
423

424
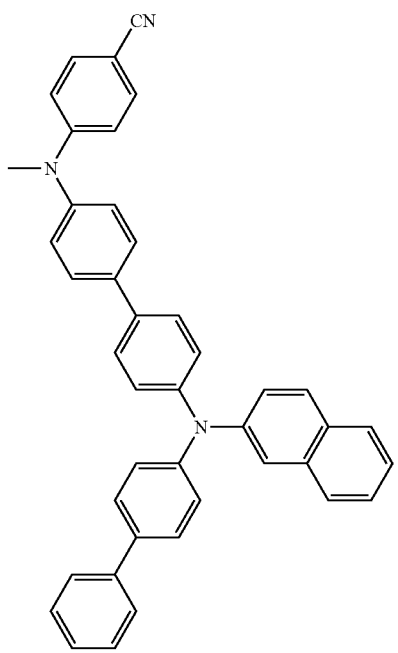
425
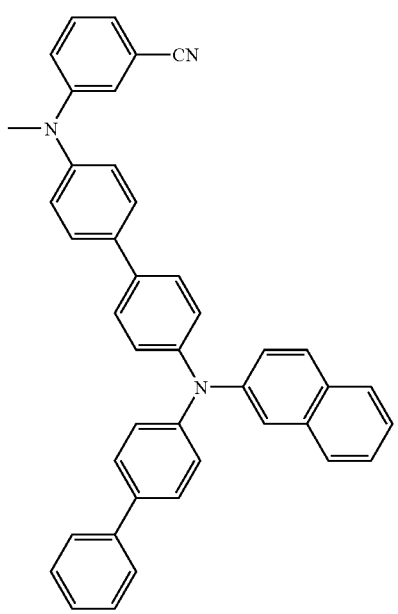
426
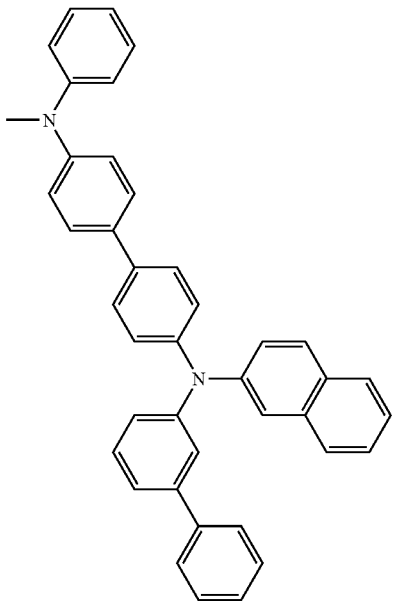
427
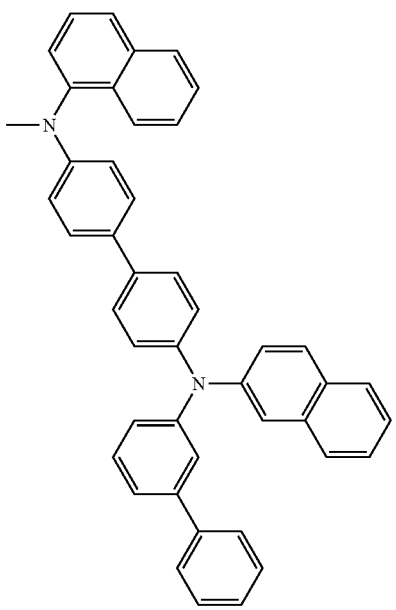

-continued
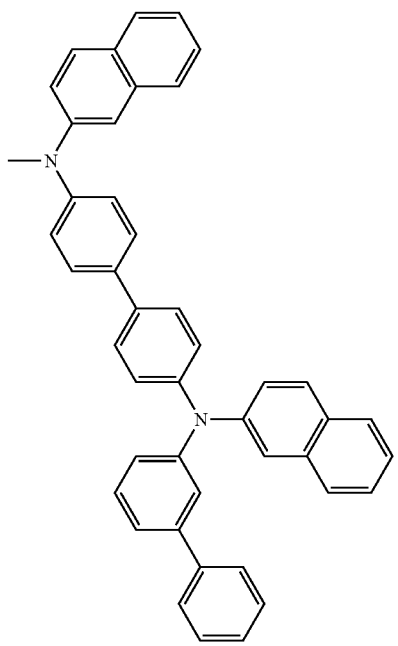
428
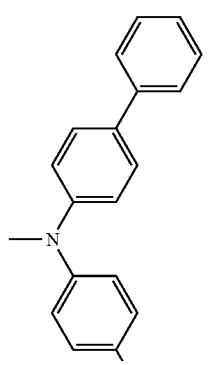
429
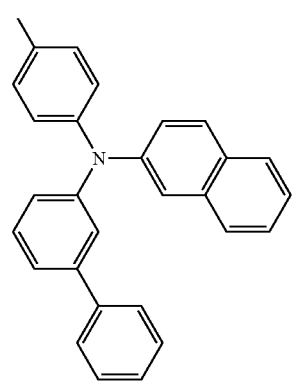
-continued
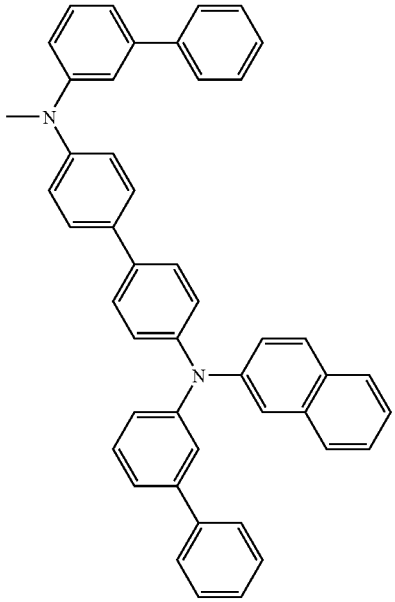
430
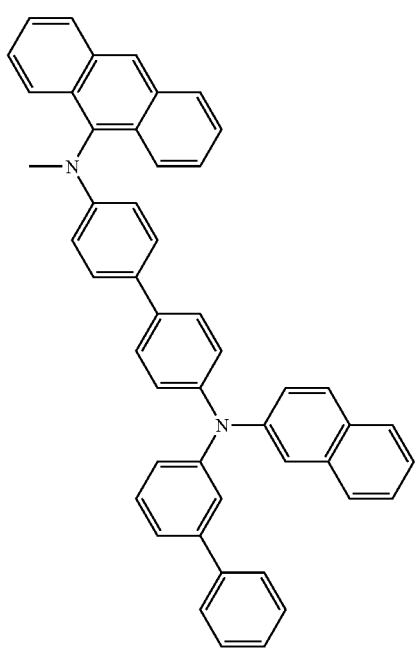
431
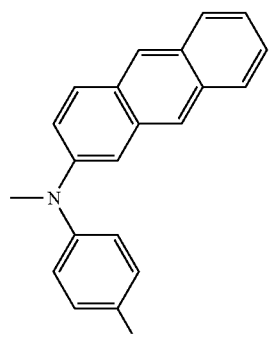
432

211
-continued
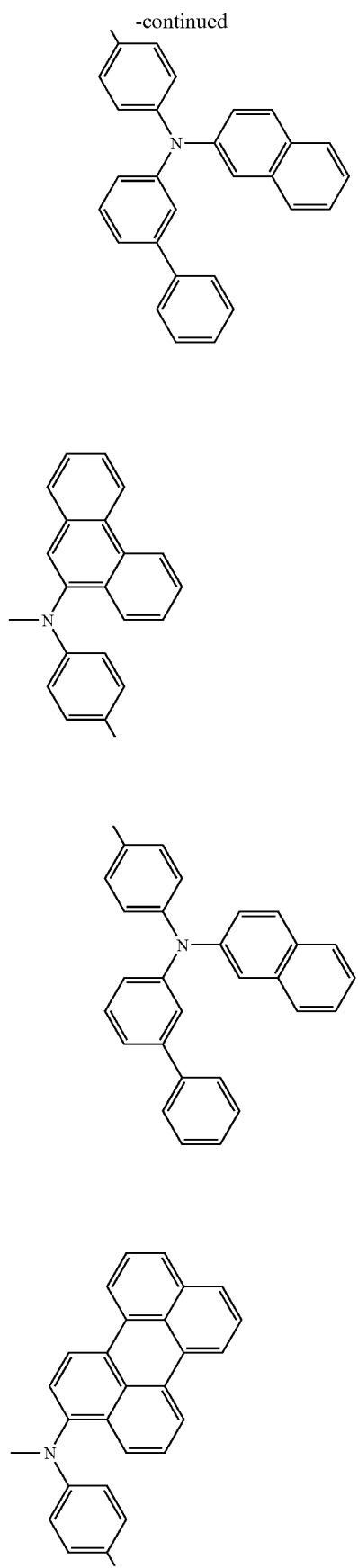
433
434
212
-continued
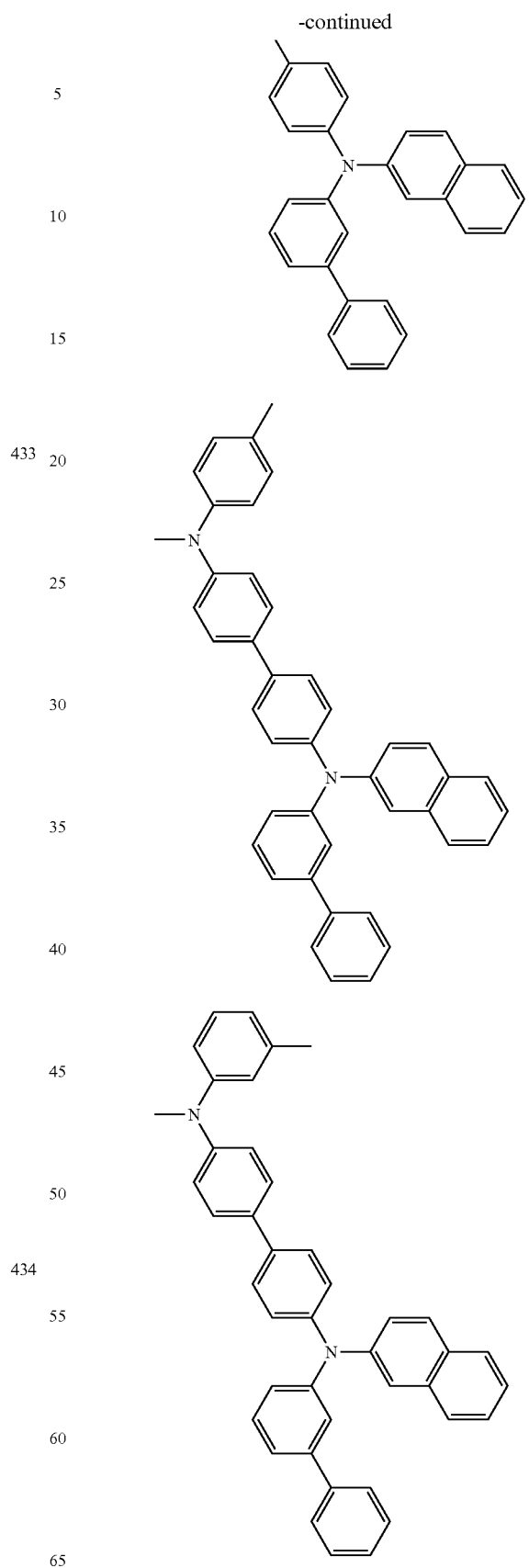
435
436

437
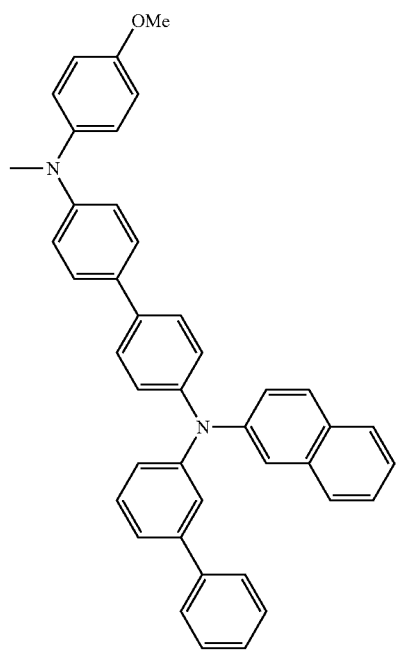
438
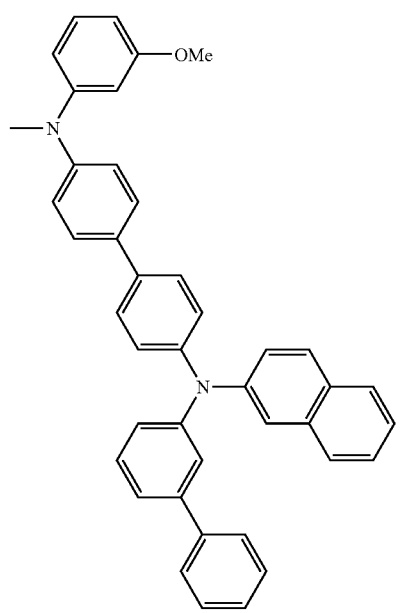
439
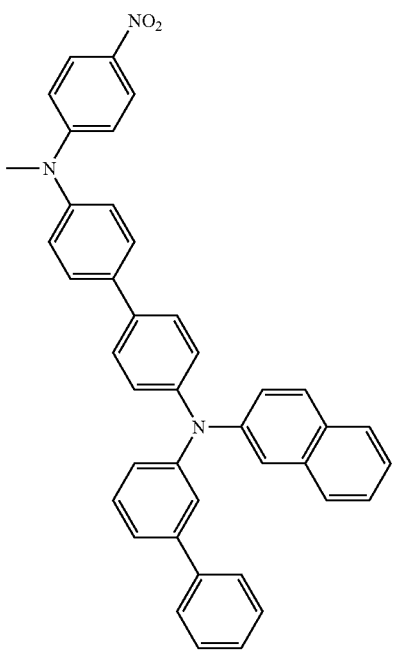
440
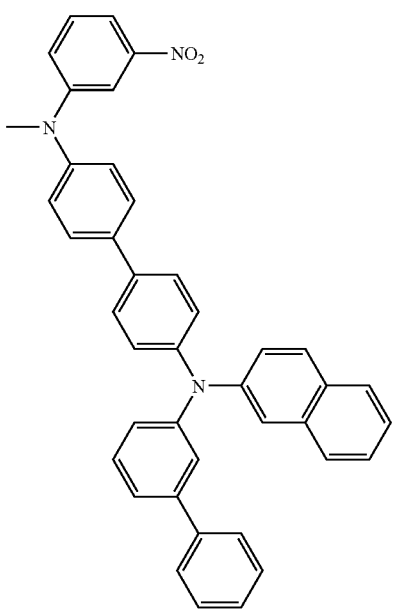

441
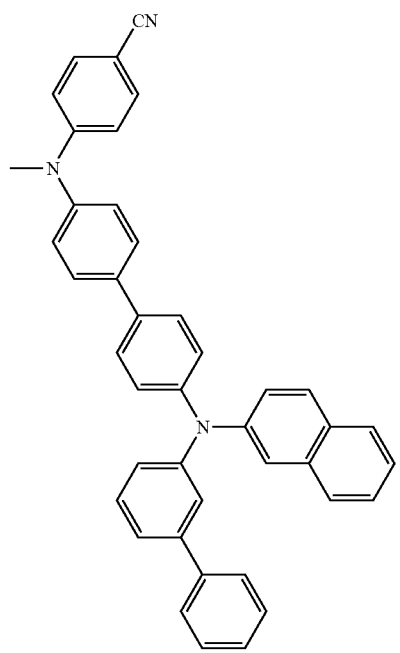
442
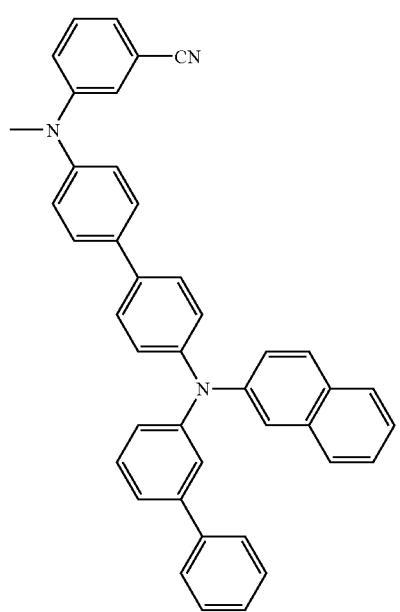
443
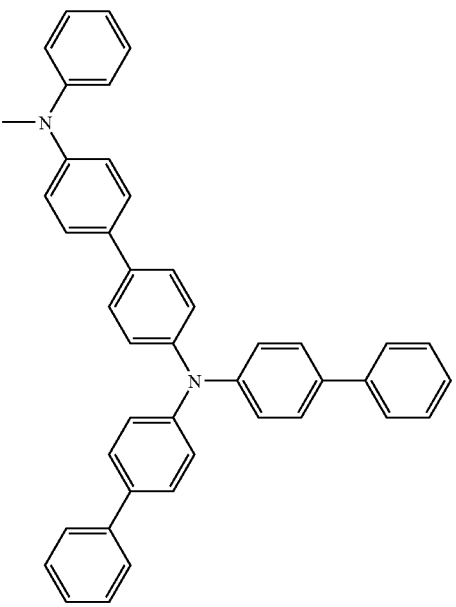
444
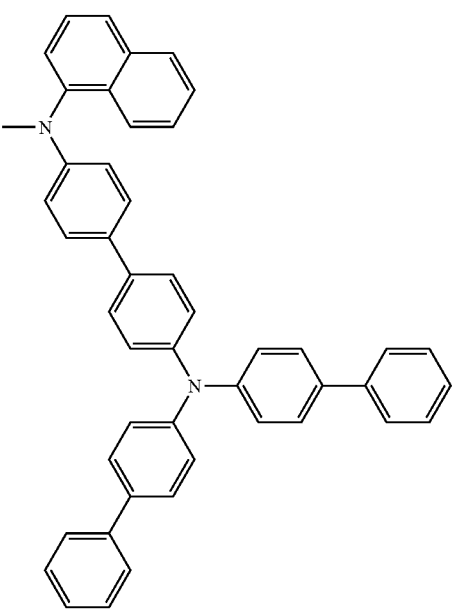

-continued
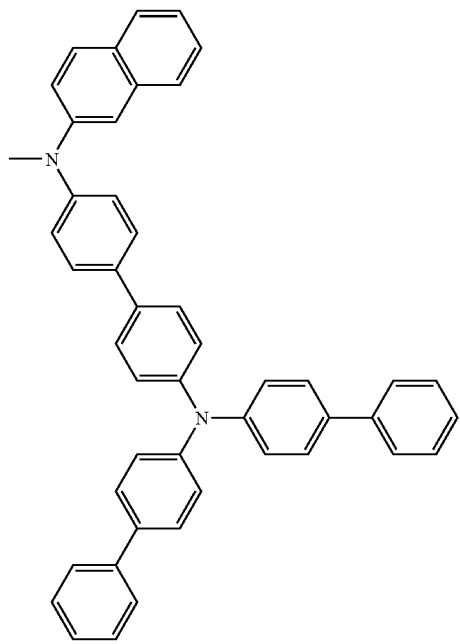
445
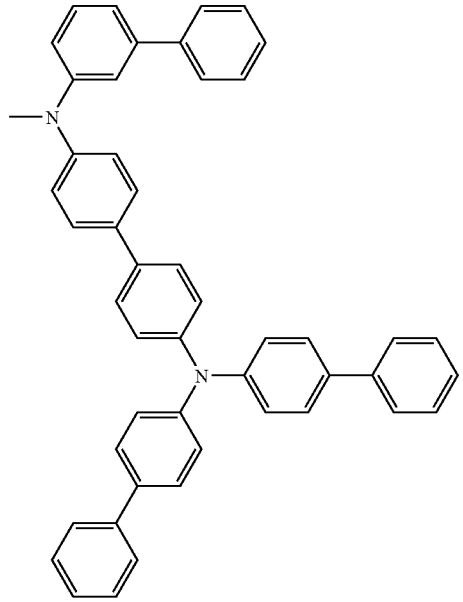
447
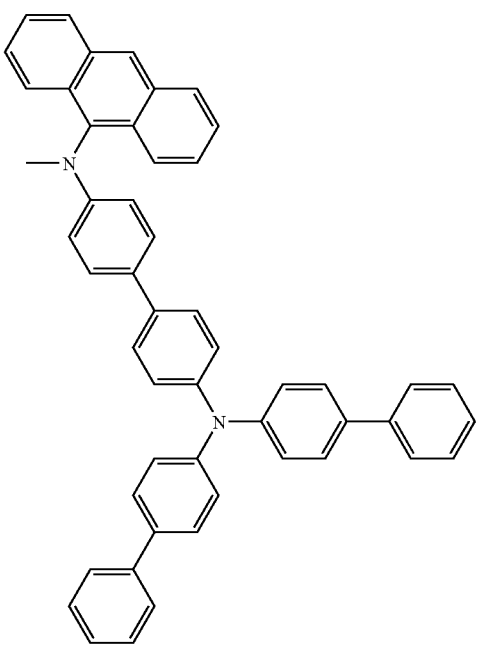
448
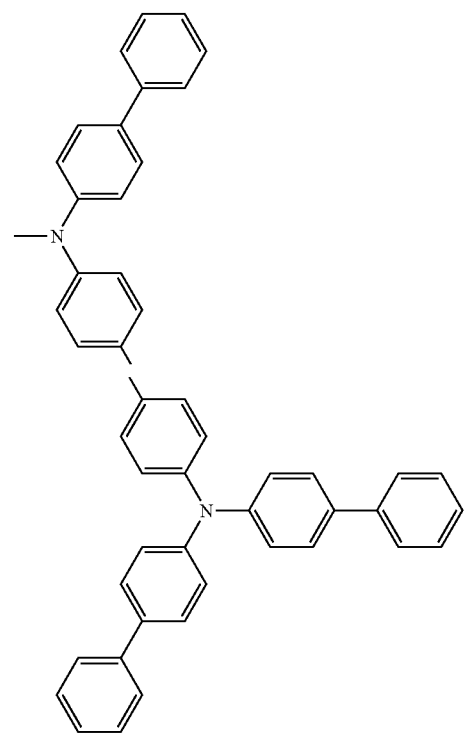
446
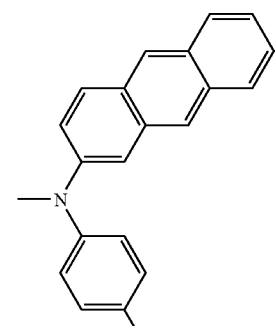
449

219
-continued
220
-continued
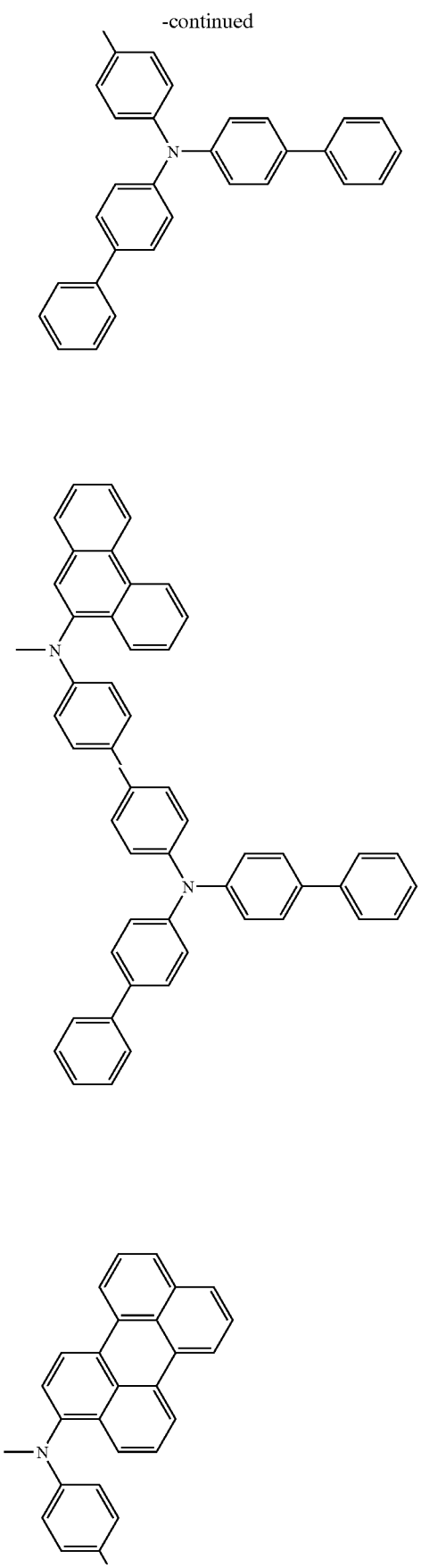
450
451
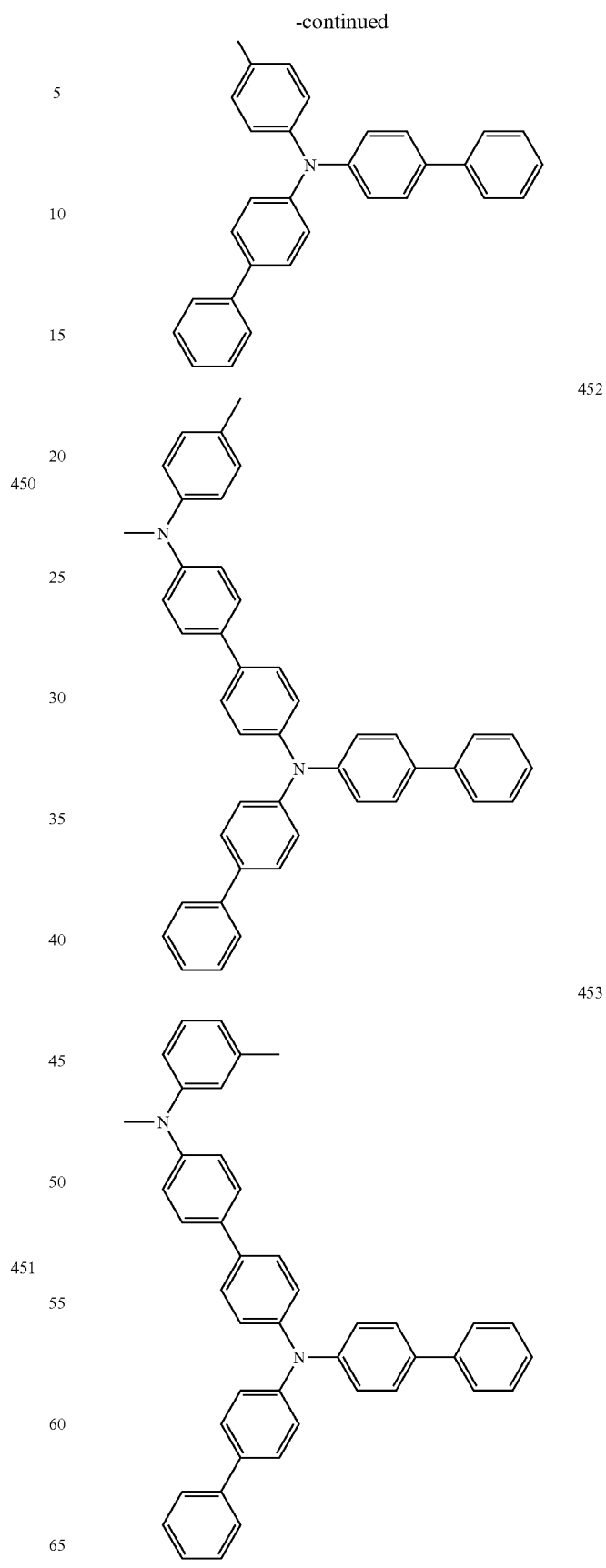
452
453

454
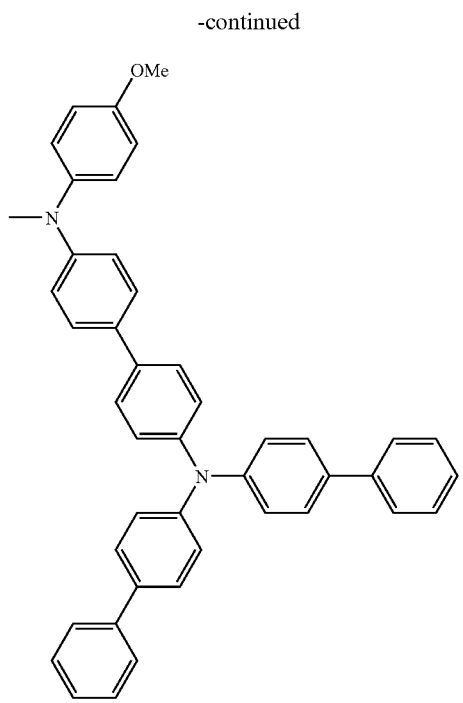
455
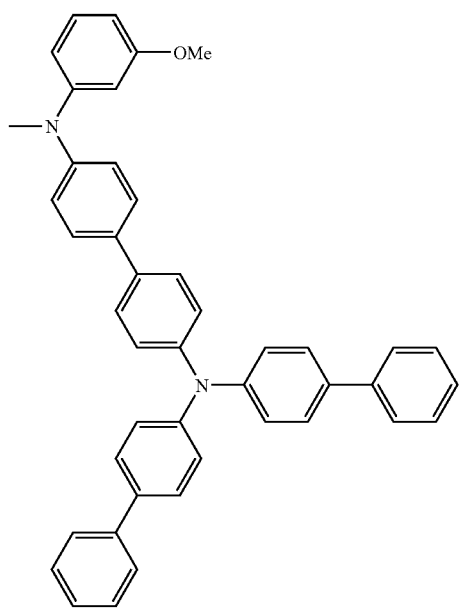
456
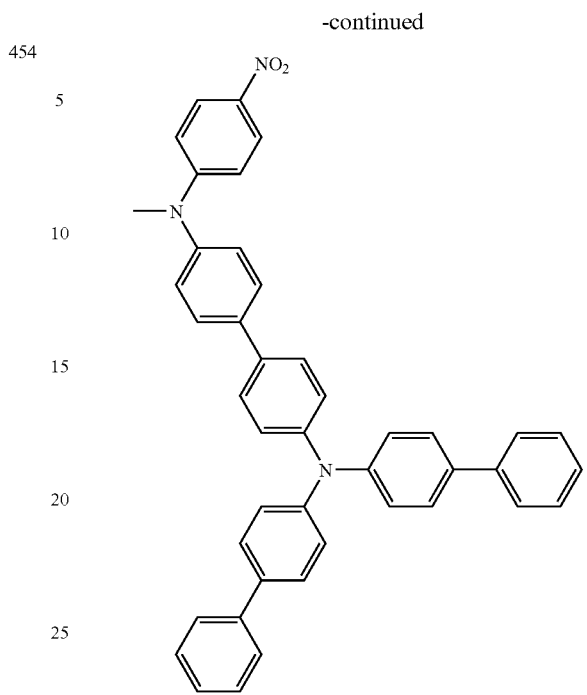
457
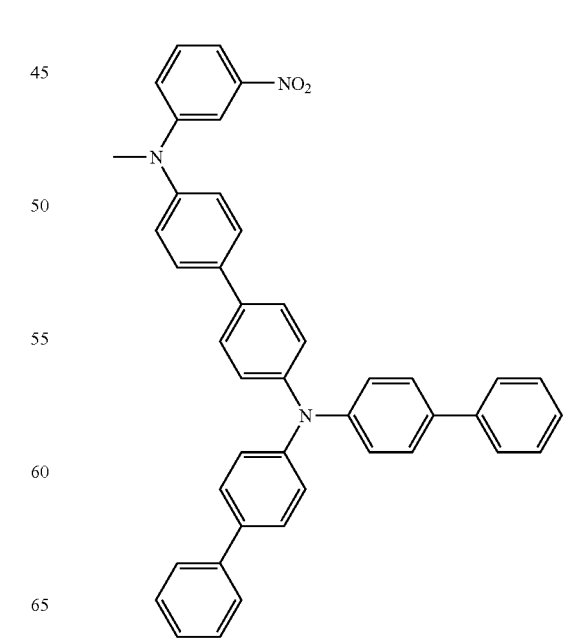

458
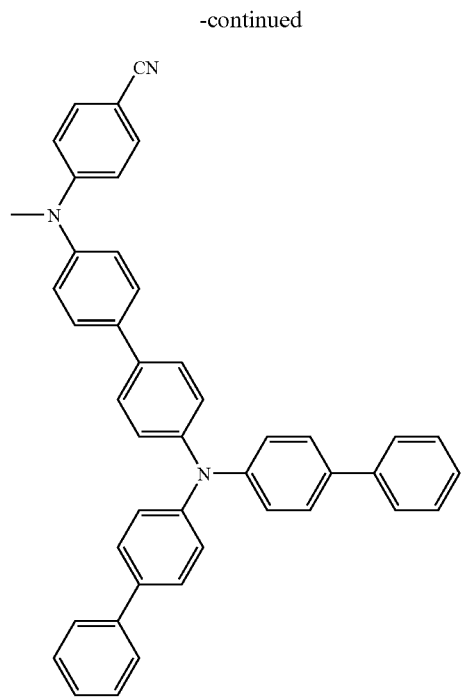
459
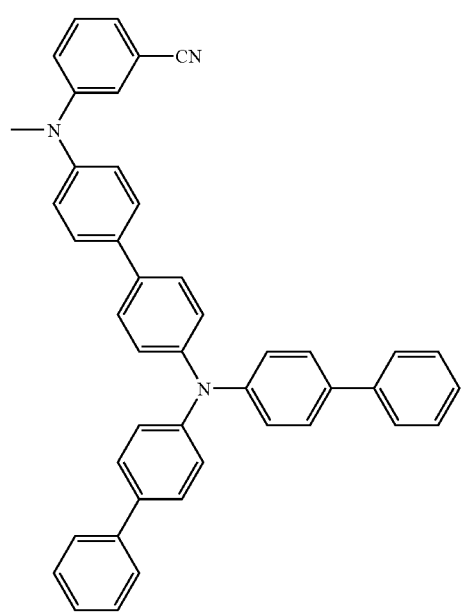
460
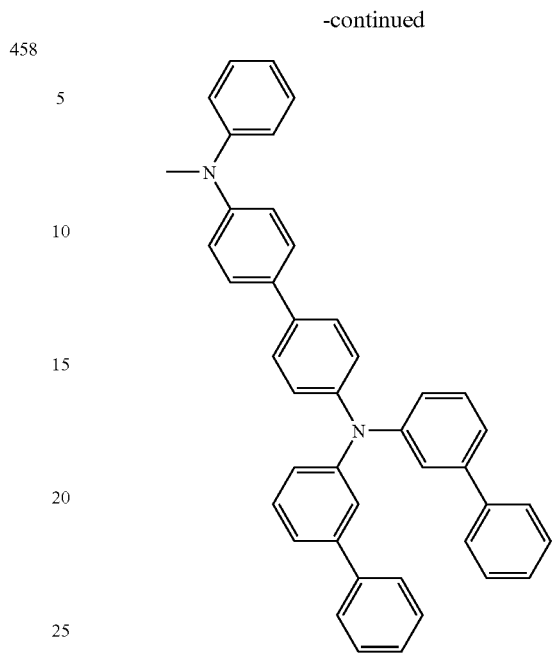
461
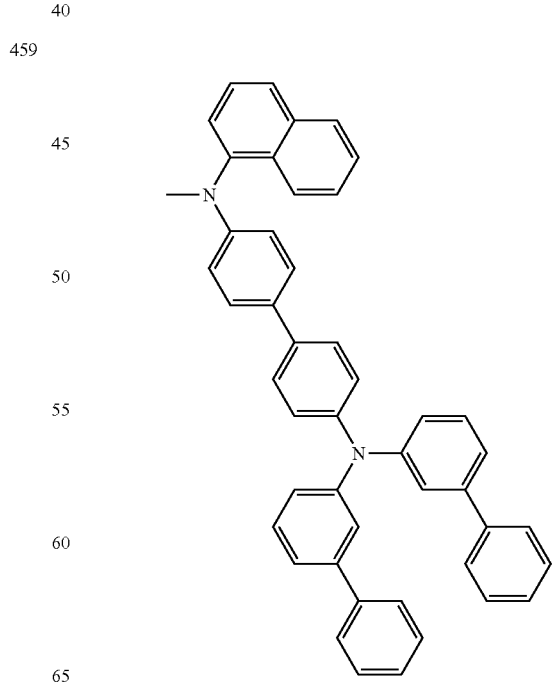

225
-continued
462
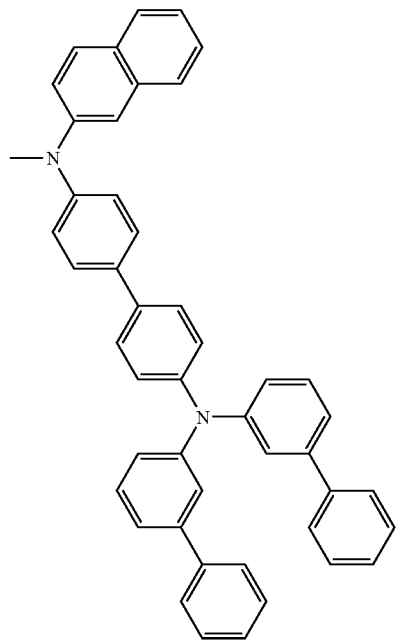
463
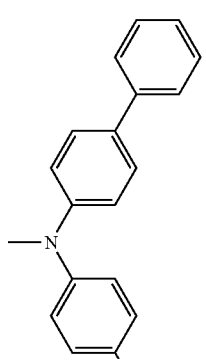
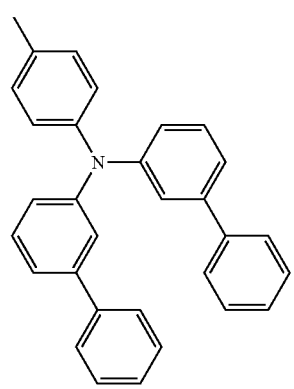
226
-continued
464
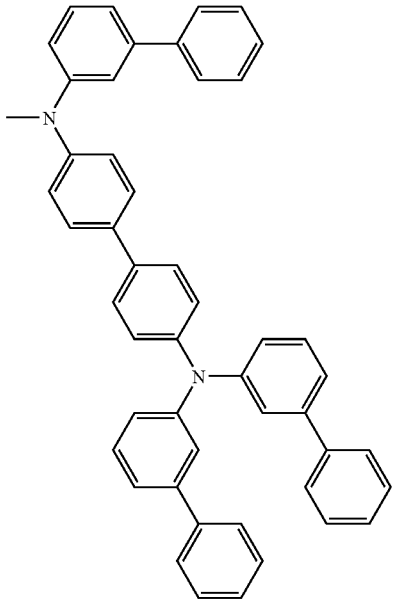
465
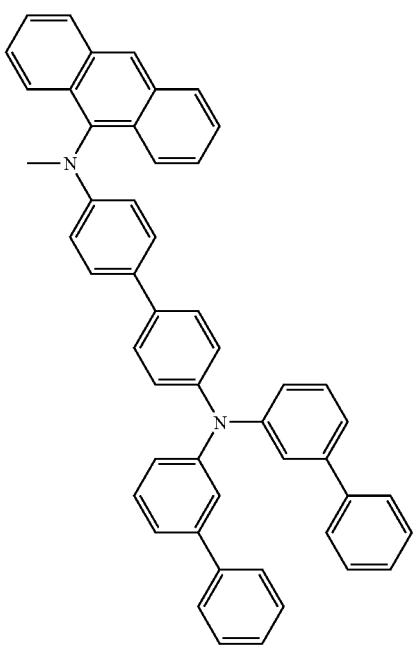
466
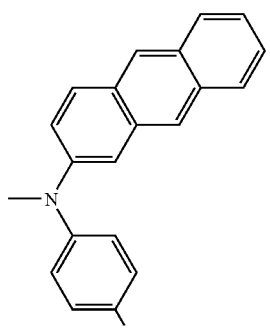

227
-continued
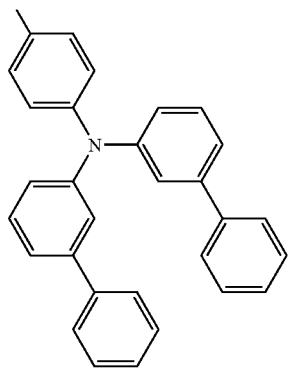
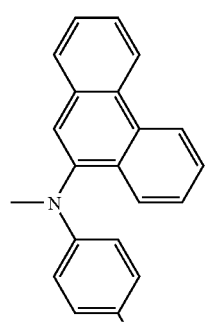
467
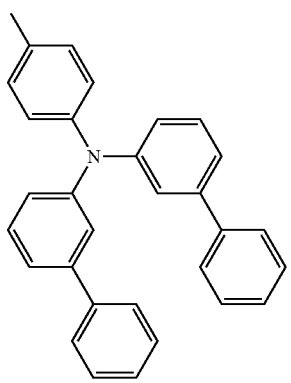
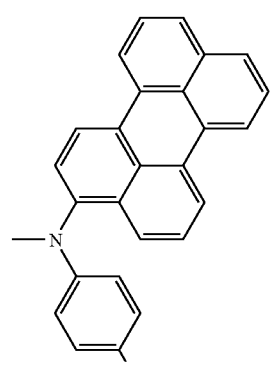
468
228
-continued
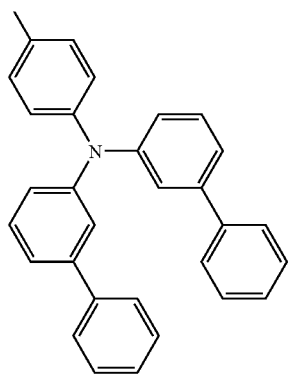
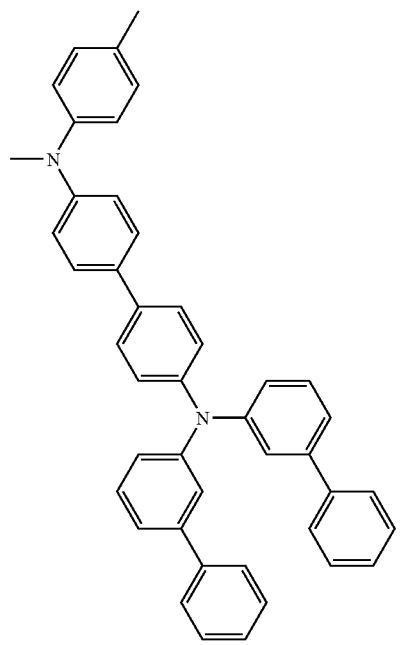
469
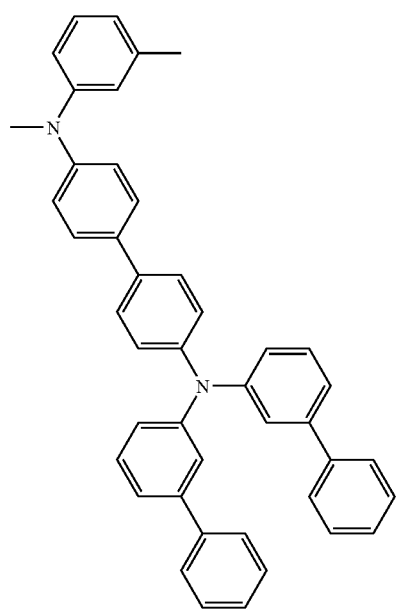
470

229
-continued
471
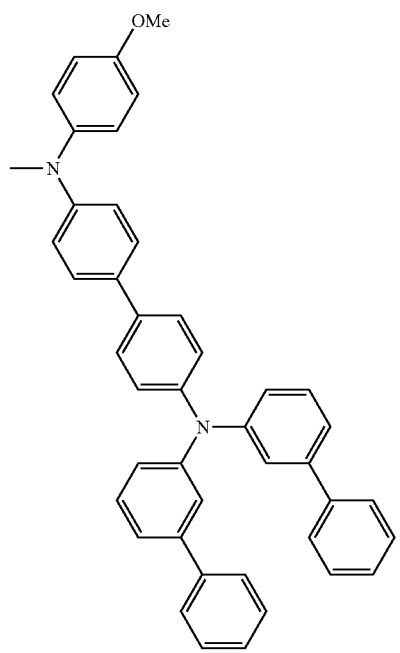
472
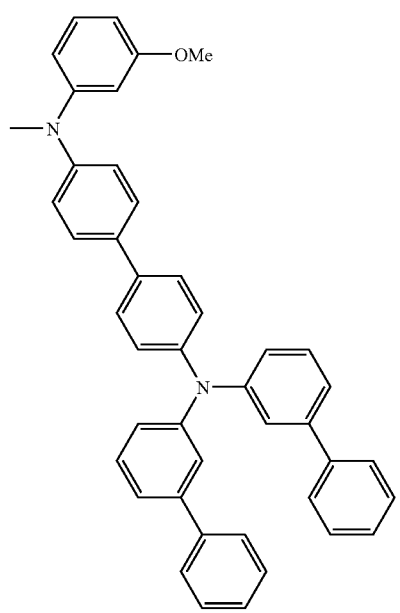
230
-continued
473
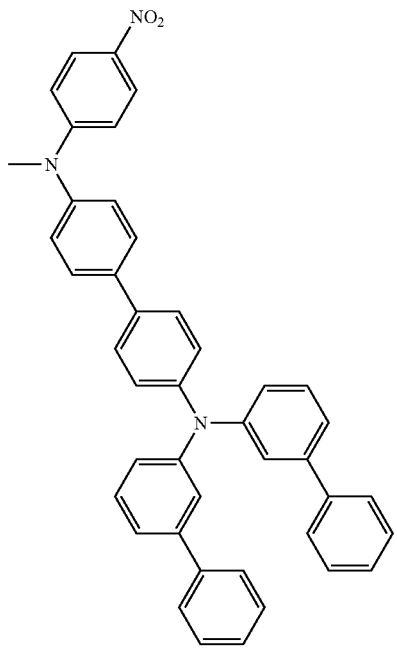
474
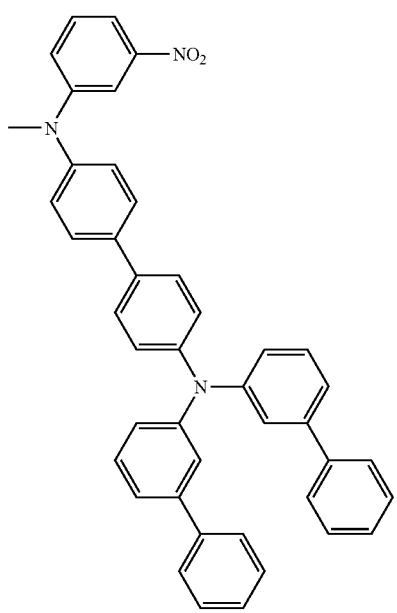

-continued

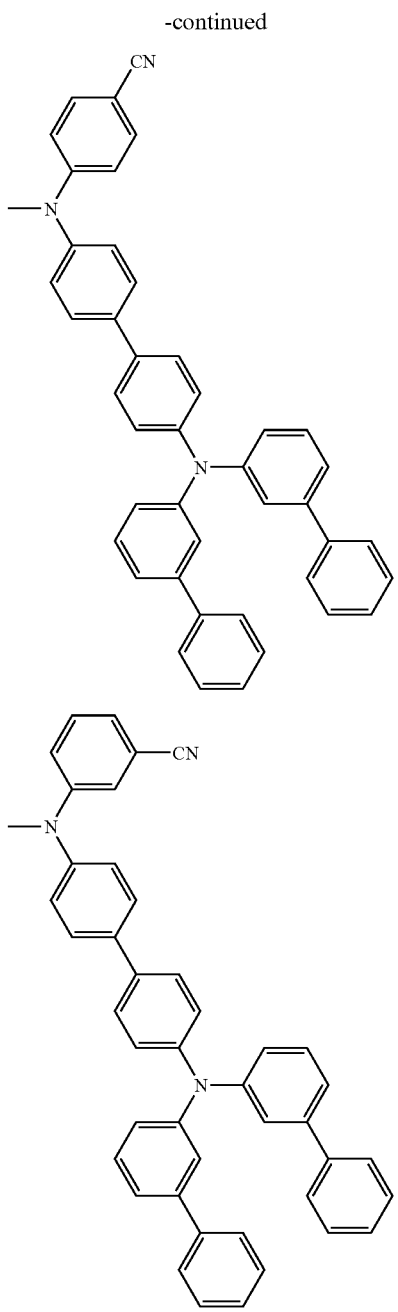

475

476

BRIEF DESCRIPTION OF THE DRAWINGS

FIG. 1 illustrates an organic light emitting device comprising a substrate 1, an anode 2, a light emitting layer 3, and a cathode 4; and FIG. 2 illustrates an organic light emitting device comprising a substrate 1, an anode 2, a hole injection layer 5, a hole transport layer 6, a light emitting layer 7, an electron transport layer 8, and a cathode 4.

BEST MODE FOR CARRYING OUT THE INVENTION

Hereinafter, a detailed description will be given of the present invention.

Various substituent groups are introduced into a core structure shown in Formula 1, in detail, the core structure in which a fluorene group is bonded to a combination of an acridine group and a carbazolyl group to form a spiro structure, thereby the compound of Formula 1 has characteristics suitable for application to an organic material layer used in an organic light emitting device. This will be described in detail, below.

The steric core structure of the compound of Formula 1 can be divided into two portions, A and B, for explanation as shown in the following Formula.

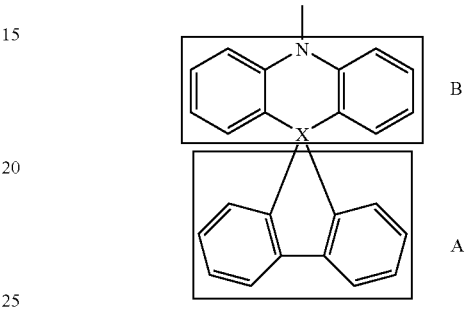

The compound of Formula 1 has the steric core structure in which a plane A meets with a plane B at right angles around X, and conjugation does not occur between the A and B portions around X. Furthermore, since one nitrogen atom is positioned among three aryl groups in the plane B, conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R9 positions and Z1 to Z8 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into R1 to R9 and Z1 to Z8 of the core structure.

Additionally, various substituent groups are introduced into the core structure to produce compounds having intrinsic characteristics of the substituent groups. For example, substituent groups, which are frequently applied to hole injection layer, hole transport layer, light emitting layer, and electron transport layer materials during the production of the organic light emitting device, are introduced into the core structure so as to produce substances capable of satisfying the requirements of each organic material layer. Particularly, since the core structure of the compound of Formula includes the arylamine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low actuating voltage and a high light efficiency.

Furthermore, various substituent groups are symmetrically introduced into the core structure (the A and B portions are located at both sides of the core structure) so as to precisely control the energy band gap, improve interfacial characteristics with organic materials, and apply the compound to various fields.

As well, if the numbers of nitrogen contained in the substituent groups A and B are each set to 2 or more (if Y1 to Y4 and Z1 to Z8 are hetero aromatic amine compounds, the number of nitrogen contained in them is not counted), it is possible to precisely control the HOMO and LUMO energy levels and the energy band gap, and on the other hand interfacial characteristics with the organic materials is improved and thereby make it possible to apply the compound to various fields.

Additionally, various substituent groups are introduced into the steric structure of the compound of Formula 1 using spiro bonding to control the three-dimensional structure of the organic material so as to minimize π-π interaction in the organic material, thereby formation of excimers is prevented.

Meanwhile, since the compound of Formula 1 has a high glass transition temperature (Tg), it has excellent thermal stability. For example, the glass transition temperature of the compound of Formula 3-1 is 159° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

For example, the compound of Formula 1 has excellent solubility to a polar solvent, such as xylene, dichloroethane, or NMP, which is used during the production of the device, and forms a thin film very well through the process using a solution, thus the solution coating process may be applied to produce the device.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

In the organic light emitting device of the present invention, a compound, in which a thermosetting or photo-crosslinkable functional group is introduced into the compound of Formula 1, may be used instead of the compound of Formula 1. The former compound has the basic physical properties of the compound of Formula 1, and may be used to form a thin film using a solution coating process and then be cured so as to form an organic material layer during the production of the device.

The method of forming the organic material layer, which comprises introducing the curable functional group into the organic material during the production of the organic light emitting device, forming the organic thin film using the solution coating process, and curing the resulting film, is disclosed in U.S. Pat. No. 2003-0044518 and EP Pat. No. 1146574A2.

The above documents state that, if the organic material layer is formed through the above-mentioned method using a material having a thermosetting or photo-crosslinkable vinyl or acryl group so as to produce an organic light emitting device, it is possible to produce an organic light emitting device having a low voltage and high brightness as well as an organic light emitting device having a multilayered structure using the solution coating process. This operation mechanism may be applied to the compound of the present invention.

In the present invention, the thermosetting or photo-crosslinkable functional group may be a vinyl or acryl group.

The organic light emitting device of the present invention can be produced using known materials through a known process, modified only in that at least one layer of organic material layer(s) include the compound of the present invention, that is, the compound of Formula 1.

The organic material layer(s) of the organic light emitting device according to the present invention may have a single layer structure, or alternatively, a multilayered structure in which two or more organic material layers are layered. For example, the organic light emitting device of the present invention may comprise a hole injection layer, a hole transport layer, a light emitting layer, an electron transport layer, or an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the production of the organic light emitting device using the same will be described in detail in the following preparation examples and examples. However, the following preparation examples and examples are set forth to illustrate, but are not to be construed to limit the present invention.

MODE FOR THE INVENTION

A better understanding of a method of producing an organic compound represented by Formula 1 and the production of an organic light emitting device using the same may be obtained in light of the following preparation examples and examples which are set forth to illustrate, but are not to be construed to limit the present invention.

In order to produce the compound represented by Formula 1, compounds of the following Formulae, a or b, may be used as a starting material.

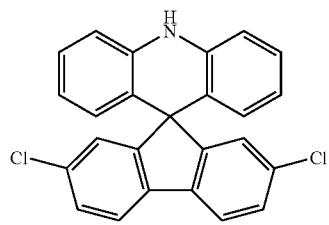

[Formula a]

-continued

[Formula b]

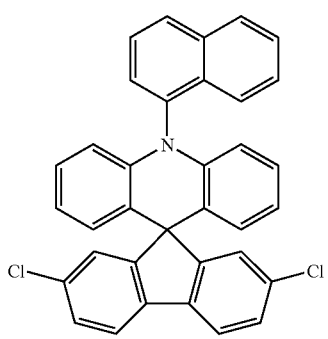

PREPARATION EXAMPLE 1

Production of a Starting Material Represented by Formula a

1) After 10 g of diphenylamine (59 mmol) and 8.04 ml of bromomethyl methyl ether (88.6 mmol) were dissolved in 100 ml of tetrahydrofuran, 12.4 ml of triethylamine (88.6 mmol) were added thereto. Stirring was conducted in a nitrogen atmosphere for 5 hours, and an organic layer was then extracted using distilled water. The extracted organic layer was subjected to a column separation process at a ratio of n-hexane/tetrahydrofuran of 15:1, and vacuum dried to produce 12 g of tertiary amine (yield 90%).

2) The amine compound produced in 1) (12.0 g, 56.3 mmol) was dissolved in 100 ml of purified THF and cooled to −78° C., and n-BuLi (2.5 M hexane solution, 22.5 ml, 56.3 mmol) was slowly dropped thereon. Stirring was conducted at the same temperature for 30 min, and a 2,7-dichloro-9-fluorenone compound (14.0 g, 56.3 mmol) was added thereto. After stirring at the same temperature for 40 min, the temperature was raised to normal temperature and stirring was carried out for an additional 3 hours. The reaction was completed in an ammonium chloride aqueous solution, and extraction was conducted with ethyl ether. Water was removed from an organic material layer using anhydrous magnesium sulfate, and an organic solvent was then removed therefrom. The produced solid was dispersed in ethanol, stirred for one day, filtered, and vacuum dried. After an intermediate material was dispersed in 100 ml of acetic acid, ten drops of concentrated sulfuric acid were added thereto and reflux was conducted for 4 hours. The resulting solid was filtered, washed with ethanol, and vacuum dried to produce 21.8 g of amine (96.8% yield). MS: [M+H]+=401.

PREPARATION EXAMPLE 2

Preparation of a Starting Material Represented by Formula b

A compound of Formula a (9.00 g, 22.5 mmol), 1-iodonaphthalene (11.4 g, 45.0 mmol), potassium carbonate (6.22 g, 45.0 mmol), copper iodide (214 mg, 1.13 mmol), and xylene (250 ml) were heated in a nitrogen atmosphere overnight. After cooling to normal temperature, a product was extracted with ethyl acetate, water was removed with anhydrous magnesium sulfate, and the solvent was removed at a reduced pressure. The resulting product was passed through a silica gel column using a hexane solvent to produce a compound, the solvent was removed at a reduced pressure, and vacuum drying was conducted to produce the compound of Formula b (5.0 g, 42% yield). MS: [M+H]+=527.

EXAMPLE 1

Preparation of the Compound Represented by Formula 3-1

1) Synthesis of arylamine (4-(N-phenyl-N-phenylamino)phenyl-1-phenylamine) to produce the compound represented by Formula 3-1:13.5 g of 4-bromophenyl-N-phenyl-N-phenylamine (41.6 mmol) and 3.98 ml of aniline (43.7 mmol) were dissolved in 120 ml of toluene, 10.00 g of sodium-tert-butoxide (104.1 mmol), 0.48 g of bis(dibenzylidene acetone)palladium(0) (0.83 mmol), and 0.58 ml of 50 wt % tri-tert-butylphosphine toluene solution (1.25 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (9.6 g, yield 69%). MS: [M+H]+=336.

2) 4.68 g of compound of Formula b (8.88 mmol) and 6.86 g of 4-(N-phenyl-N-phenylamino)phenyl-1-phenylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 3-1 (5.2 g, yield 52%). MS: [M+H]+=1127.

EXAMPLE 2

Preparation of the Compound Represented by Formula 3-2

1) Synthesis of arylamine (4-(N-phenyl-N-phenylamino)phenyl-1-naphthylamine) to produce the compound represented by Formula 3-2:15.0 g of 4-bromophenyl-N-phenyl-N-phenylamine (46.3 mmol) and 7.29 g of 1-naphthylamine (50.9 mmol) were dissolved in 200 ml of toluene, 13.34 g of sodium-tert-butoxide (138.8 mmol), 0.53 g of bis(dibenzylidene acetone)palladium(0) (0.93 mmol), and 0.56 ml of 50 wt % tri-tert-butylphosphine toluene solution (1.39 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (13 g, yield 73%). MS: [M+H]+=386.

2) 4.68 g of compound of Formula b (8.88 mmol) and 7.88 g of 4-(N-phenyl-N-phenylamino)phenyl-1-naphthylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol)

were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 3-2 (5.4 g, yield 50%). MS: $[M+H]^+=1227$.

EXAMPLE 3

Preparation of the Compound Represented by Formula 3-4

1) Synthesis of arylamine (4-(N-phenyl-N-phenylamino) phenyl-1-biphenylamine) to produce the compound represented by Formula 3-4:17.4 g of 4-bromophenyl-N-phenyl-N-phenylamine (53.7 mmol) and 9.99 g of 4-aminobiphenyl (59.0 mmol) were dissolved in 250 ml of toluene, 17.02 g of sodium-tert-butoxide (177.1 mmol), 0.68 g of bis(dibenzylidene acetone)palladium(0) (1.2 mmol), and 0.72 ml of 50 wt % tri-tert-butylphosphine toluene solution (1.8 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (16 g, yield 73%). MS: $[M+H]^+=412$.

2) 4.68 g of compound of Formula b (8.88 mmol) and 8.42 g of 4-(N,N-diphenylamino)phenyl-4-biphenylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 3-4 (5.2 g, yield 45.8%). MS: $[M+H]^+=1279$.

EXAMPLE 4

Preparation of the Compound Represented by Formula 3-21

1) Synthesis of arylamine (4-(N-phenyl-N-naphthylamino)phenyl-1-biphenylamine) to produce the compound represented by Formula 3-21:14.0 g of 4-bromophenyl-N-phenyl-N-naphthylamine (37.4 mmol) and 6.96 g of 4-aminobiphenyl (41.2 mmol) were dissolved in 200 ml of toluene, 0.47 g of bis(dibenzylidene acetone)palladium(0) (0.82 mmol), 0.50 ml of 50 wt % tri-tert-butylphosphine toluene solution (1.2 mmol), and 11.86 g of sodium-tert-butoxide (123.4 mmol) were added thereto. After reflux was conducted in a nitrogen atmosphere for 2 hours, distilled water was added to the reaction solution to complete the reaction. The organic layer was extracted, and a column separation process was conducted using a developing solvent of n-hexane and tetrahydrofuran at a ratio of 10:1, stirring was conducted using petroleum ether, and vacuum drying was conducted to produce an arylamine connection group (7.5 g, yield 43%). MS: $[M+H]^+=462$.

2) 4.68 g of compound of Formula b (8.88 mmol) and 9.44 g of 4-(N-phenyl-1-naphthylamino)phenyl-4-biphenylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 3-21 (5.5 g, yield 45%). MS: $[M+H]^+=1379$.

EXAMPLE 5

Production of an Organic Light Emitting Device

A glass substrate (corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. The substrate was dry washed using oxygen plasma for 5 min, and then transported to a vacuum evaporator.

Hexanitrile hexaazatriphenylene (hereinafter, referred to as "HAT") of the following Formula was vacuum deposited to a thickness of 80 Å by heating on a transparent ITO electrode, which was prepared through the above procedure, so as to form an anode including an ITO conductive layer and an N-type organic material.

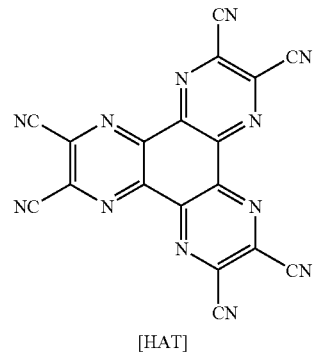

[HAT]

Interfacial characteristics between the substrate and a hole injection layer can be improved using the thin film. Subsequently, the compound of Formula 3-1 was deposited to a thickness of 800 Å on the thin film to form the hole injection layer. NPB was deposited thereon to a thickness of 300 Å so as to form a hole transport layer, and Alq3 was deposited thereon to a thickness of 300 Å to form the light emitting layer. An electron transport layer material of the following Formula was deposited to a thickness of 200 Å on the light emitting layer to form an electron transport layer.

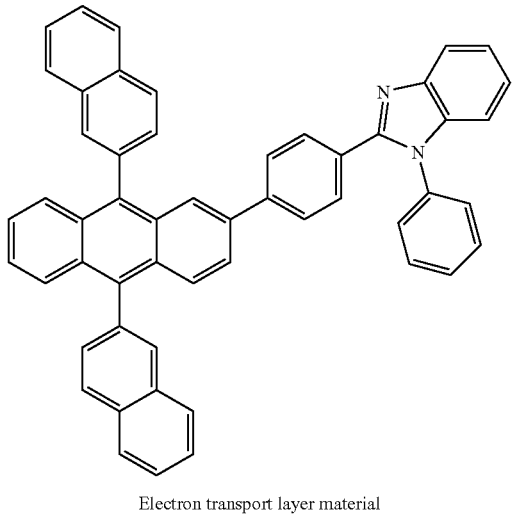

Electron transport layer material

Lithium fluoride (LiF) having a thickness of 12 Å and aluminum having a thickness of 2000 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3\times 10^{-7}$.

The resulting device had an electric field of 4.76 V at a forward current density of 100 mA/cm$^2$, and a spectrum having a light efficiency of 1.93 lm/W. The operation and light emission of the device at the above-mentioned actuating voltage mean that the compound of Formula 3-1, which formed the layer between the thin film on the substrate and the hole transport layer, functions to inject holes.

EXAMPLE 6

Production of an Organic Light Emitting Device

The procedure of example 5 was repeated to produce a device except that the compound of Formula 3-1 used as a hole injection layer was substituted with the compound of Formula 3-2.

The resulting device had an electric field of 4.72 V at a forward current density of 100 mA/cm$^2$, and a spectrum having a light efficiency of 1.94 lm/W. The operation and light emission of the device at the above-mentioned actuating voltage mean that the compound of Formula 3-2, which formed a layer between a thin film on a substrate and a hole transport layer, functions to inject holes.

EXAMPLE 7

Production of an Organic Light Emitting Device

The procedure of example 5 was repeated to produce a device except that the compound of Formula 3-1 used as a hole injection layer was substituted with the compound of Formula 3-4.

The resulting device had an electric field of 4.65 V at a forward current density of 100 mA/cm$^2$, and a spectrum having a light efficiency of 1.92 lm/W. The operation and light emission of the device at the above-mentioned actuating voltage mean that the compound of Formula 3-4, which formed a layer between a thin film on a substrate and a hole transport layer, functions to inject holes.

EXAMPLE 8

Production of an Organic Light Emitting Device

The procedure of example 5 was repeated to produce a device except that the compound of Formula 3-1 used as a hole injection layer was substituted with the compound of Formula 3-21.

The resulting device had an electric field of 4.60 V at a forward current density of 100 mA/cm$^2$, and a spectrum having a light efficiency of 1.97 lm/W. The operation and light emission of the device at the above-mentioned actuating voltage mean that the compound of Formula 3-21, which formed a layer between a thin film on a substrate and a hole transport layer, functions to inject holes.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

The invention claimed is:
1. An organic light emitting device, comprising:
a first electrode;
organic material layer(s) comprising a light emitting layer, wherein at least one layer of the organic material layer(s) includes the compound of Formula 1; and
a second electrode;
wherein the first electrode, the organic material layer(s), and the second electrode form a layered structure,

[Formula 1]

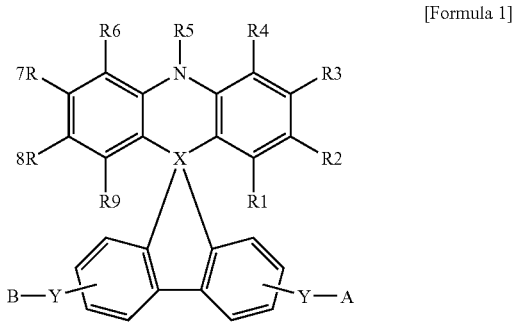

wherein X is C or Si;

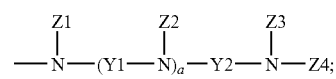

A is

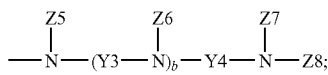

B is a and b are zero or positive integer;

Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;

Y1 to Y4 are each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;

Z1 to Z8 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophene group which is substituted with hydrocarbons having a carbon number of 1-20 or aromatic hydrocarbons having a carbon number of 6-20; or a boron group which is substituted with aromatic hydrocarbons;

R1 to R4, and R6 to R9 are each independently selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, and an ester group, and R1 to R4 and R6 to R9 may form aliphatic or hetero condensation rings along with adjacent groups;

R5 is selected from the group consisting of hydrogen, a substituted or unsubstituted alkyl group, a substituted or unsubstituted cycloalkyl group, a substituted or unsubstituted alkenyl group, a substituted or unsubstituted aryl group, and a substituted or unsubstituted heterocyclic group; and with a proviso that when R5 is the aryl group or the heterocyclic group, carbon at an ortho-position of the aryl or heterocyclic group and R4 or R6 may form a condensation ring along with a group selected from the group consisting of O, S, NR, PR, C=O, CRR', and SiRR', wherein R and R' each independently are selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, and an ester group, and may form a condensation ring to form a spiro compound.

2. The organic light emitting device as set forth in claim 1, wherein R5 of Formula 1 is an aryl or a heterocyclic group.

3. The organic light emitting device as set forth in claim 2, wherein R5 of Formula 1 is an aryl or a heterocyclic group, and carbon at the ortho-position of the aryl or heterocyclic group and R4 or R6 form the condensation ring along with a group selected from the group consisting of O, S, NR, PR, C=O, CRR', and SiRR'.

4. The organic light emitting device as set forth in claim 1, wherein the compound of Formula 1 is any one of compounds of Formulae 2 to 119:

[Formulae 2 to 119]

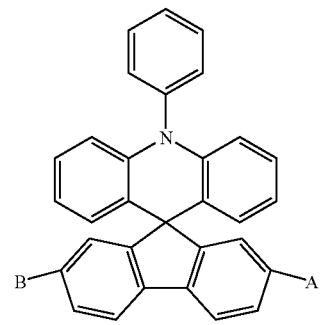

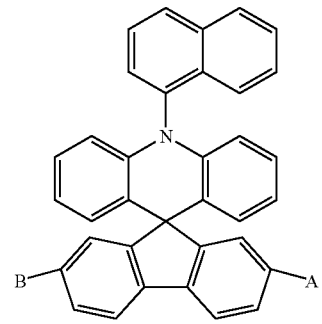

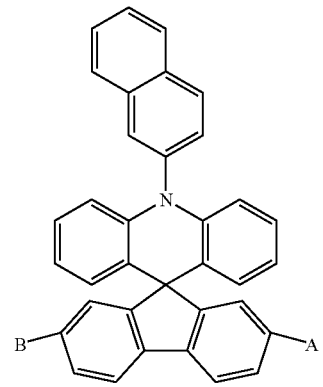

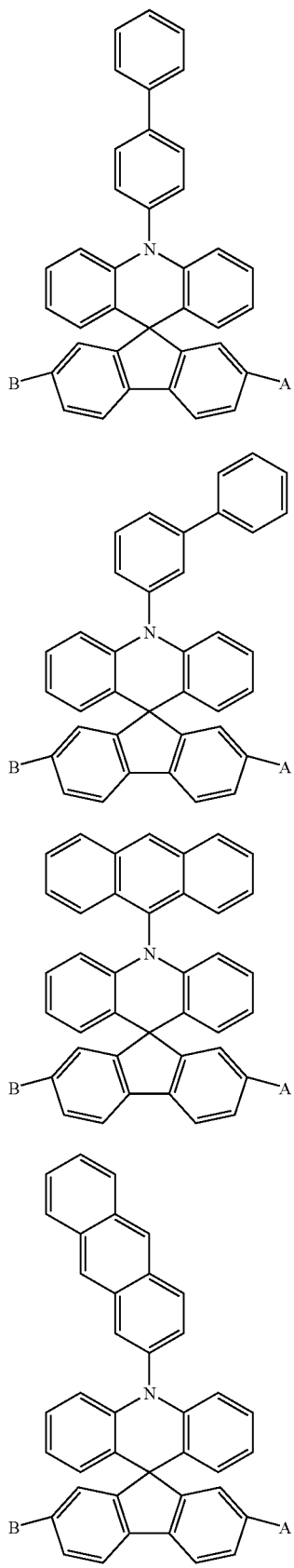
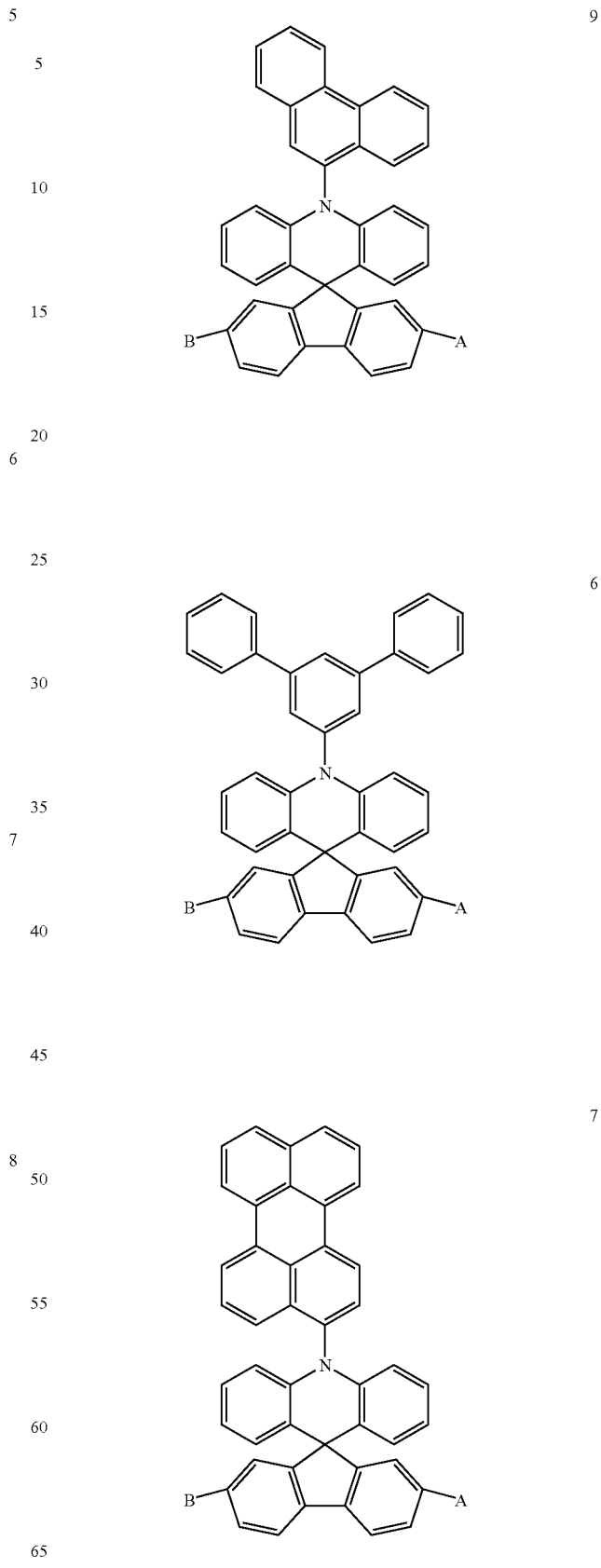

-continued
8
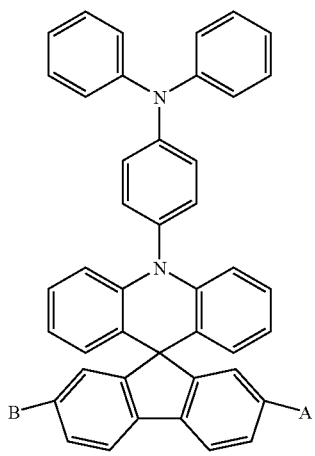
9
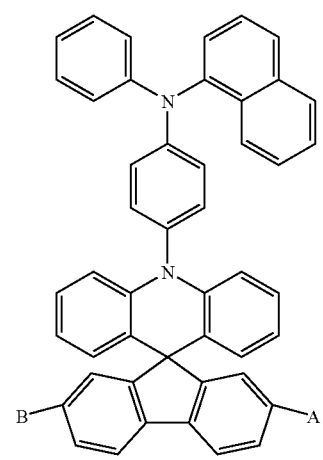
10
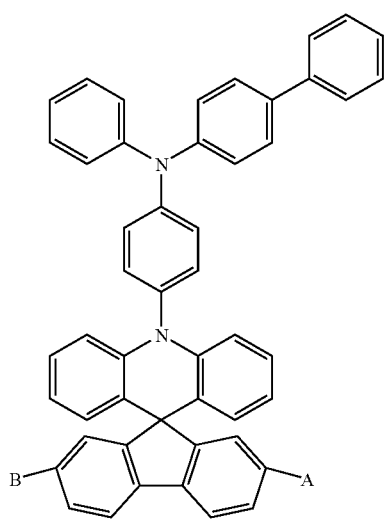
-continued
11
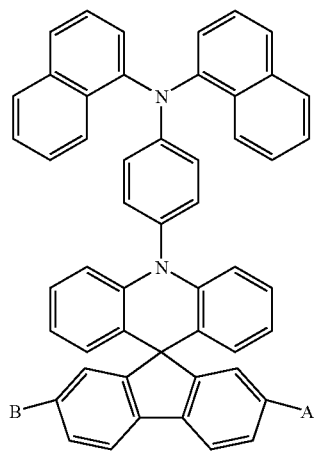
12
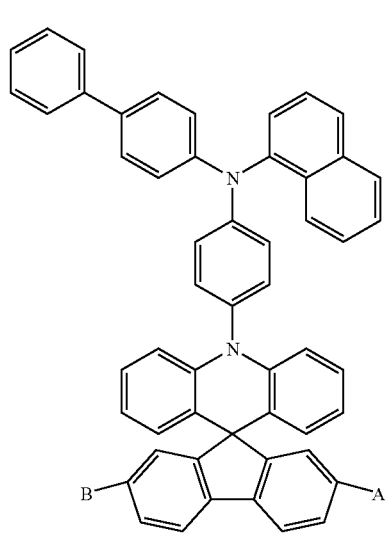
13
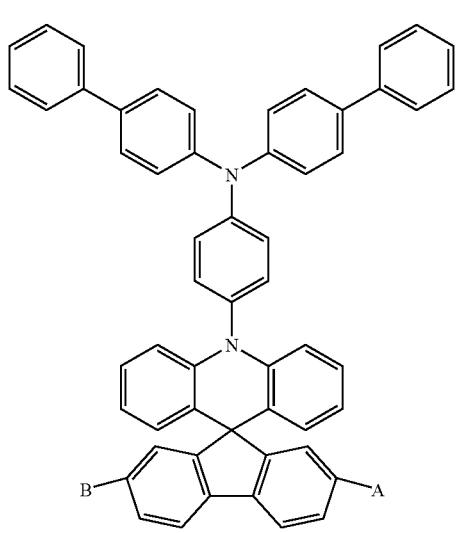

-continued
14
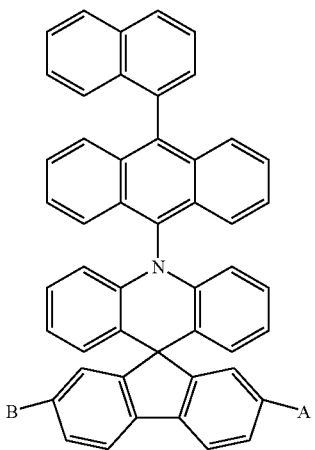
15
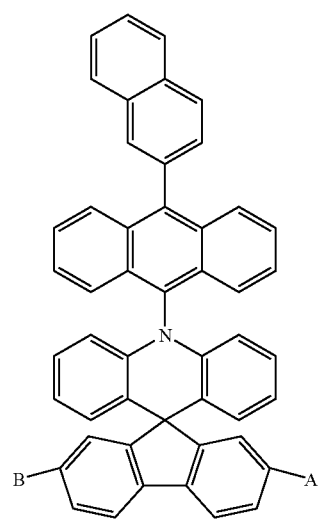
16
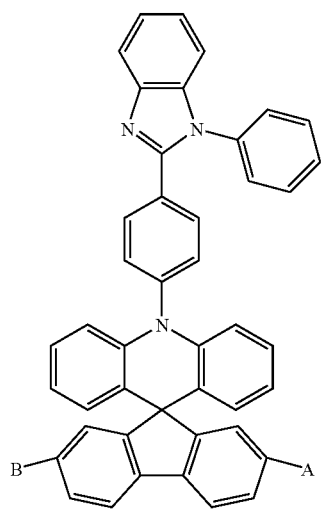
-continued
17
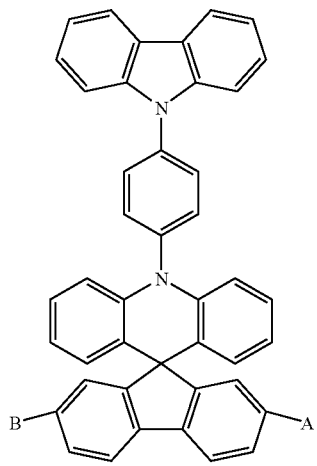
18
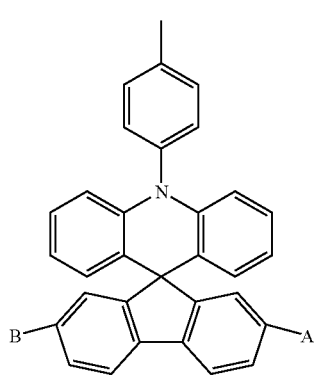
19
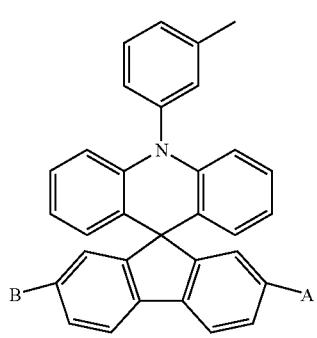
20
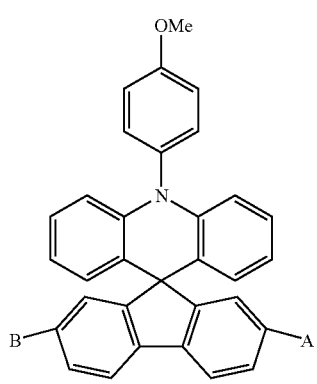

-continued
21
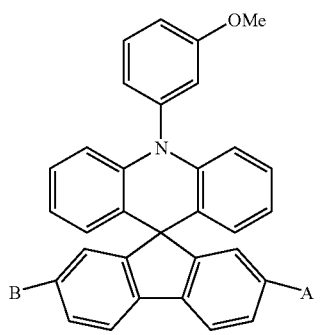
22
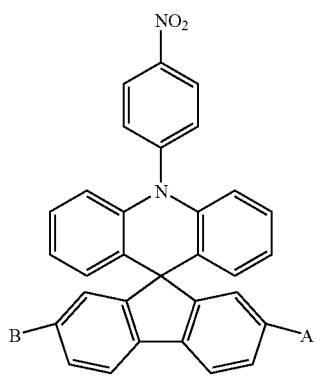
23
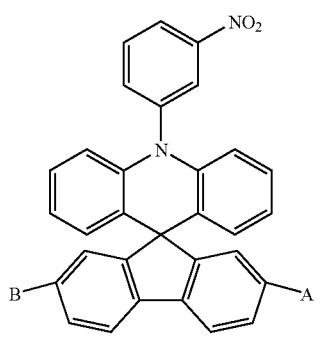
24
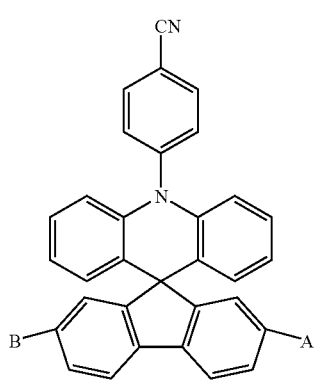
-continued
25
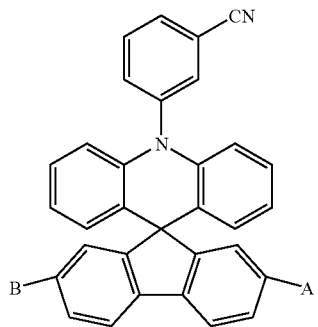
26
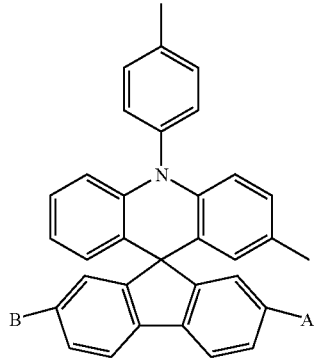
27
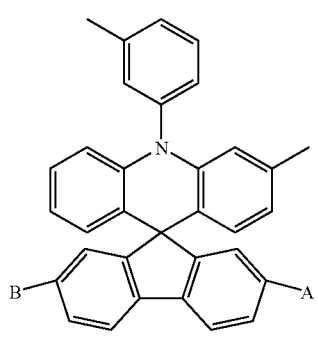
28
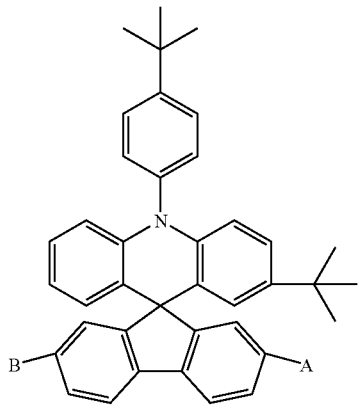

-continued
29
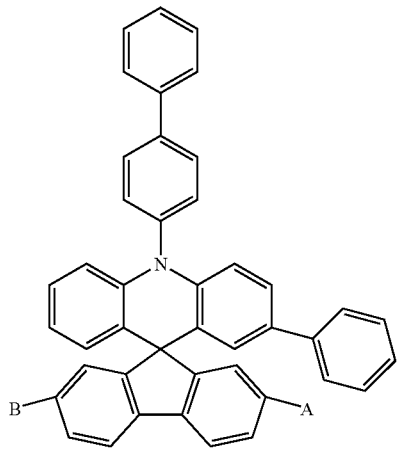
30
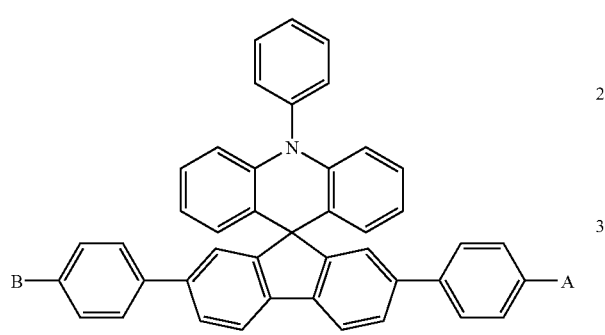
31
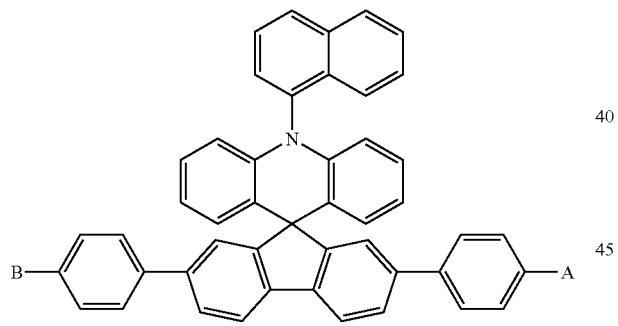
32
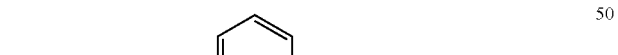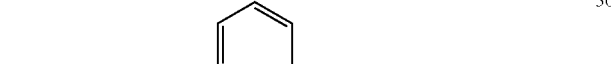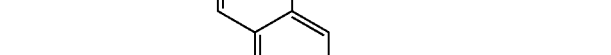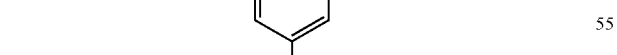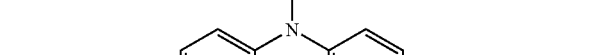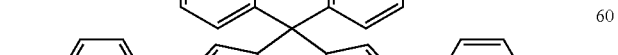
-continued
33
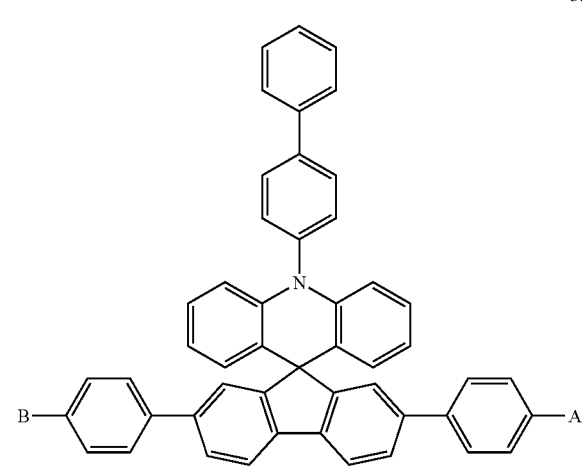
34
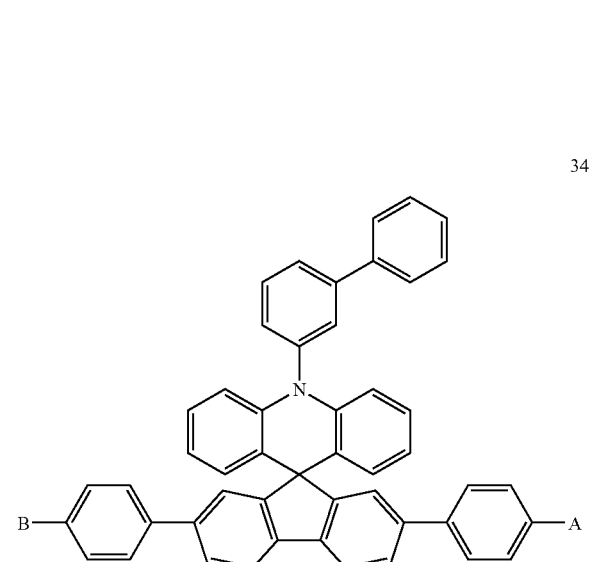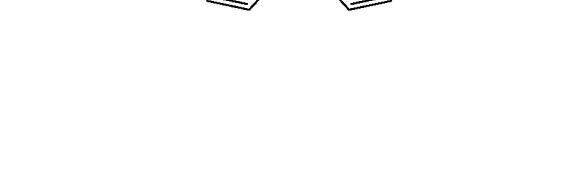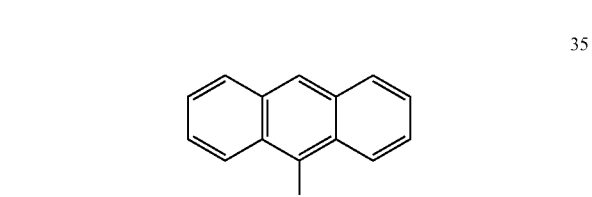
35
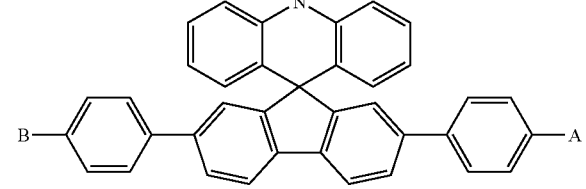

-continued

36

37

38

-continued

39

40

41

42
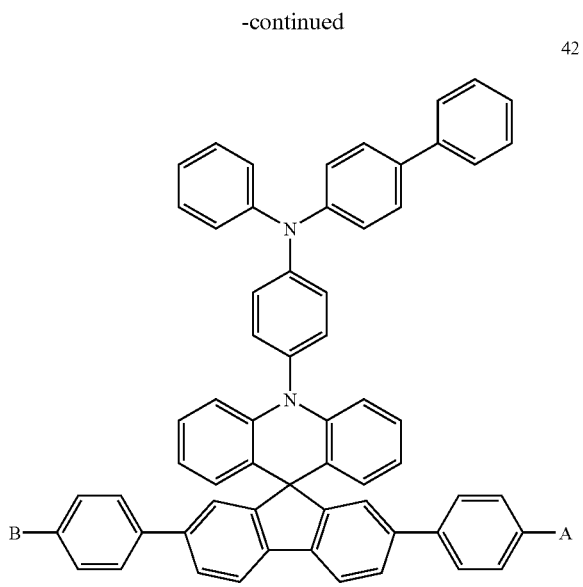
43
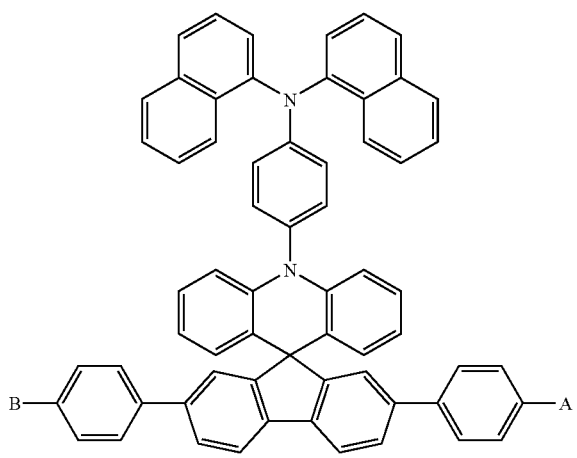
44
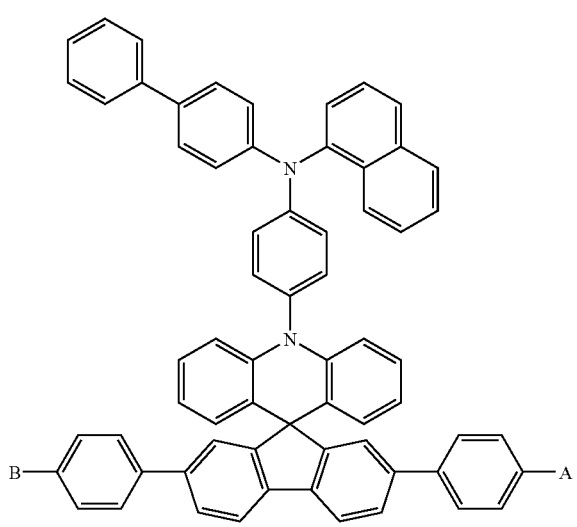
45
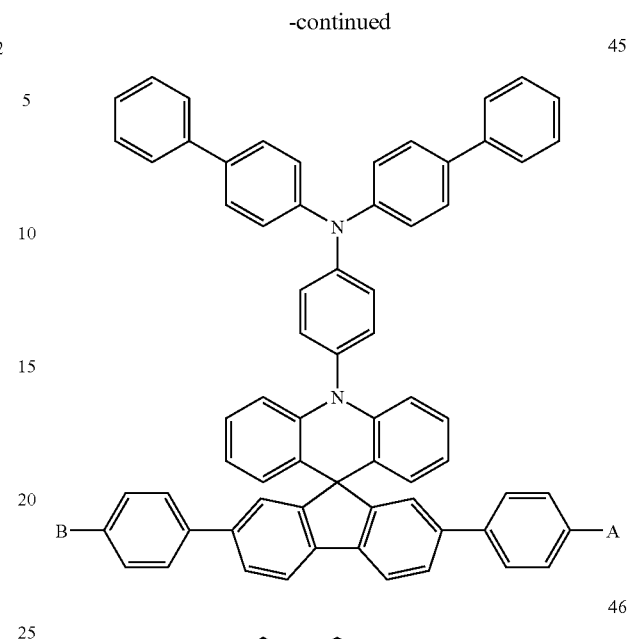
46
47
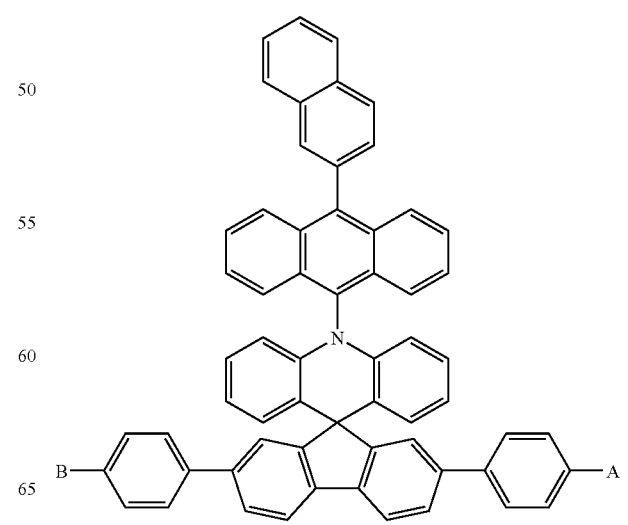

48
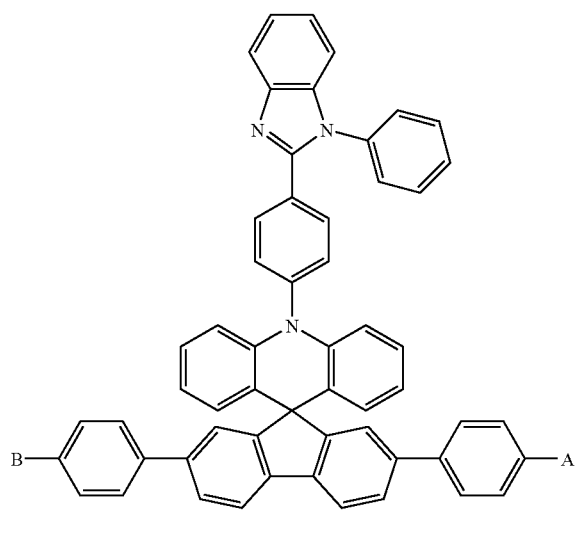
49
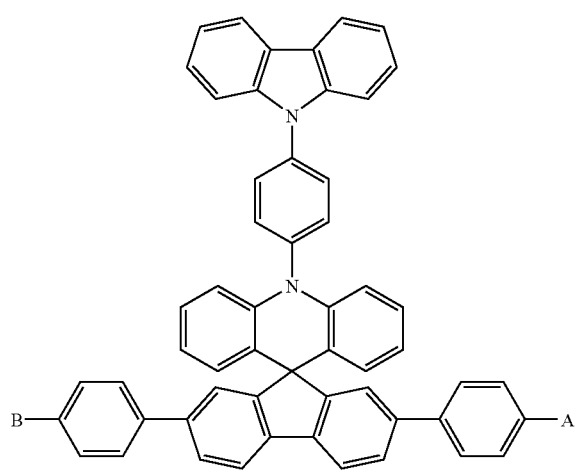
50
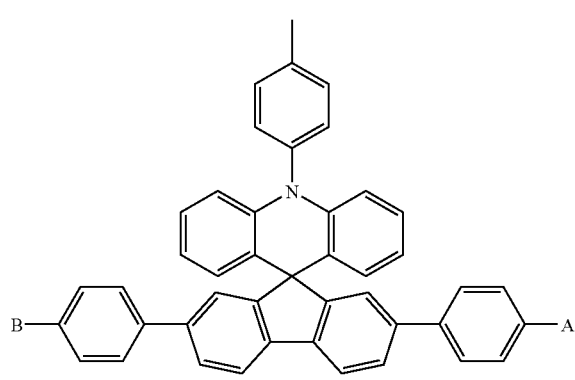
51
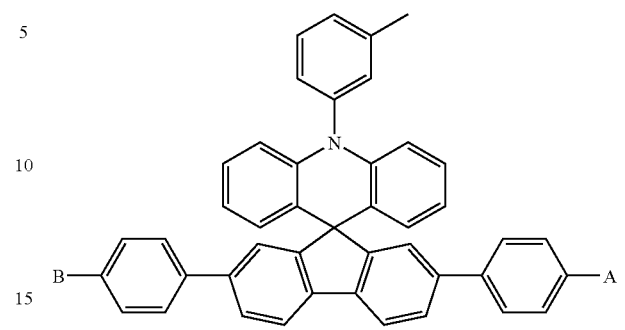
52
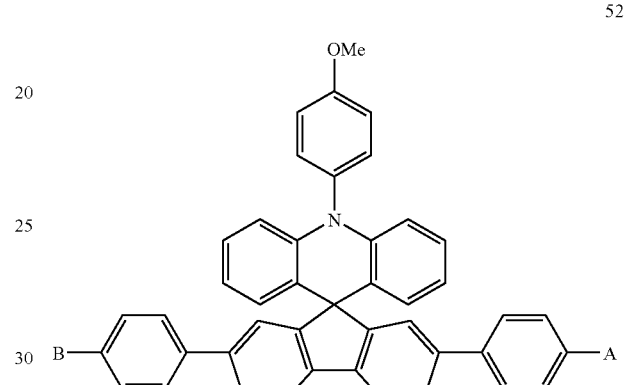
53
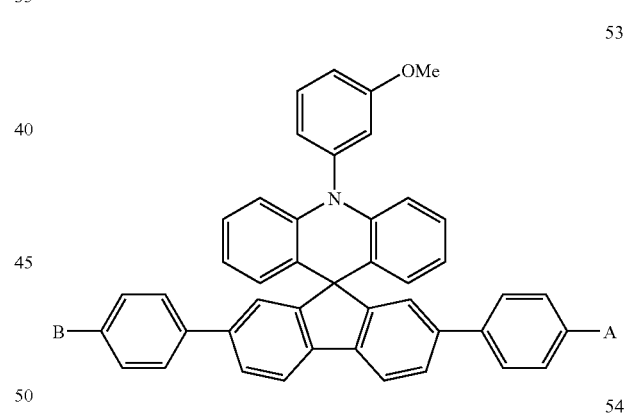
54
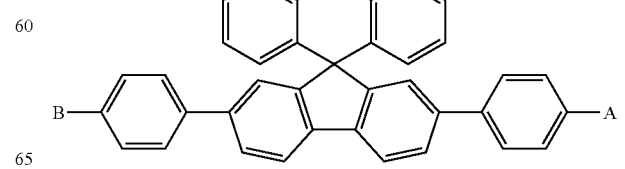

-continued
55
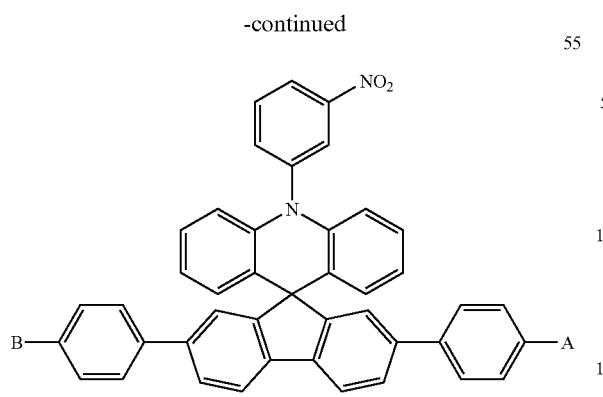
56
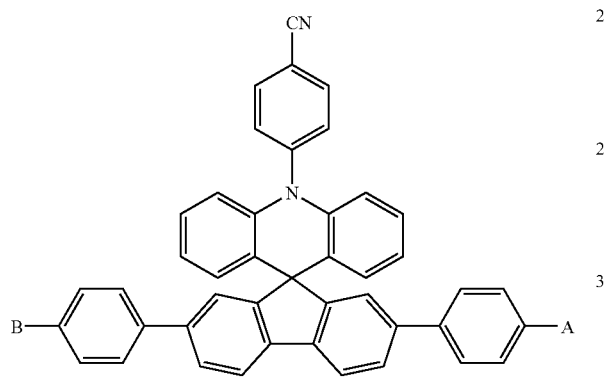
57
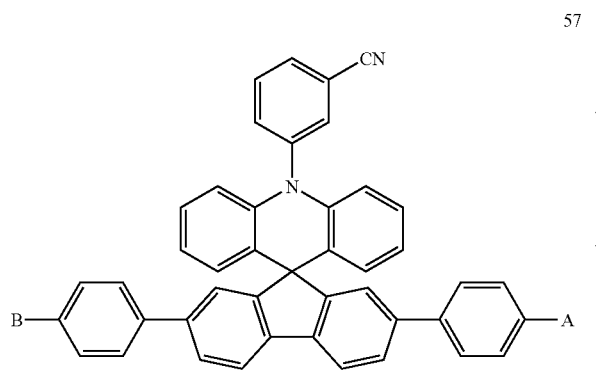
58
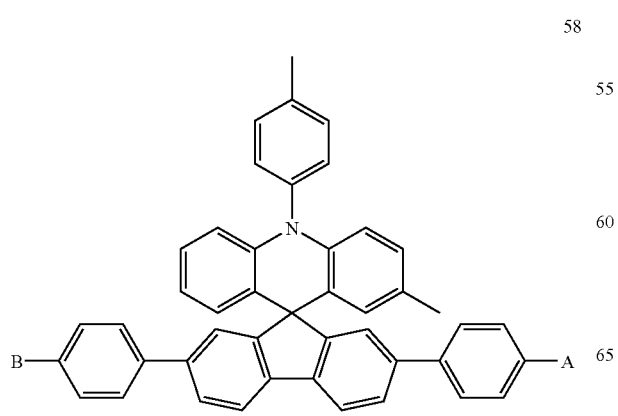
-continued
59
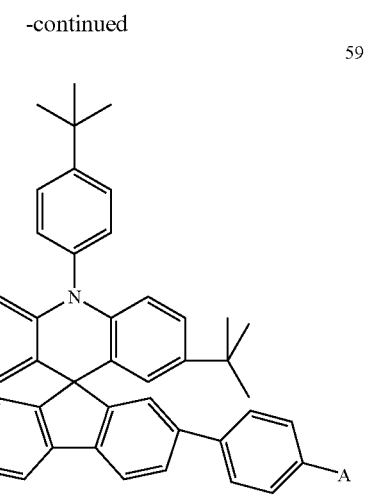
60
61
62

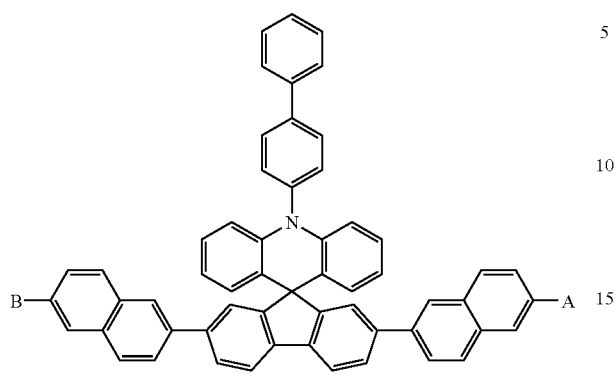
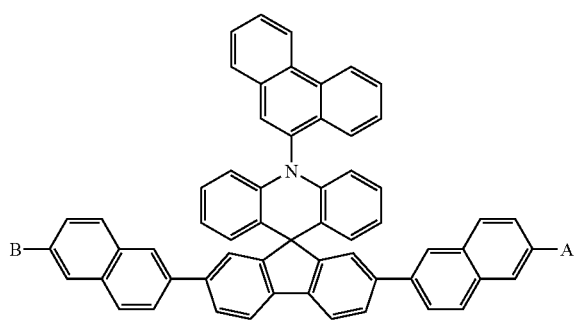

263
-continued
71
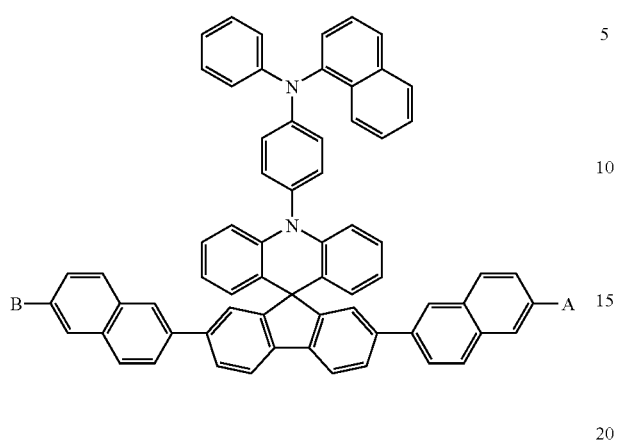
72
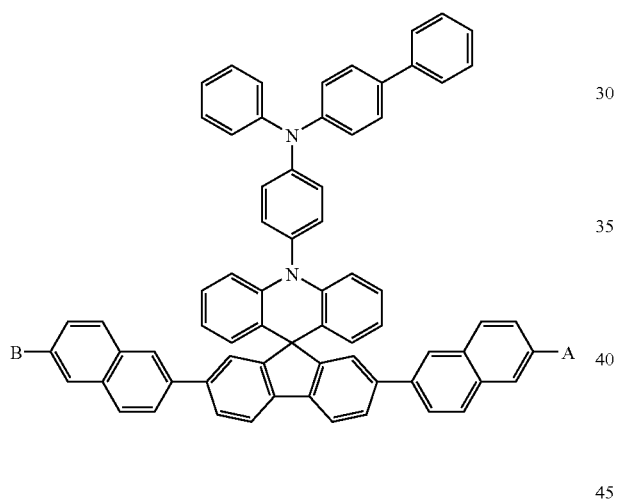
73
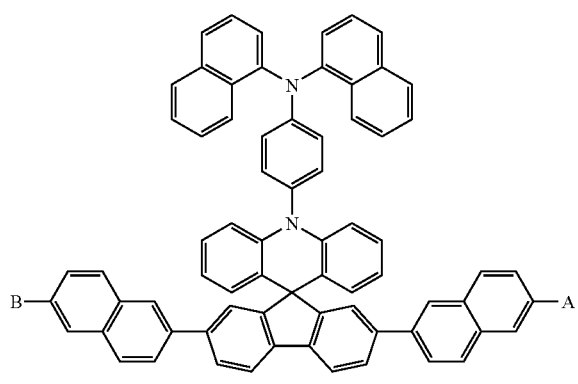
264
-continued
74
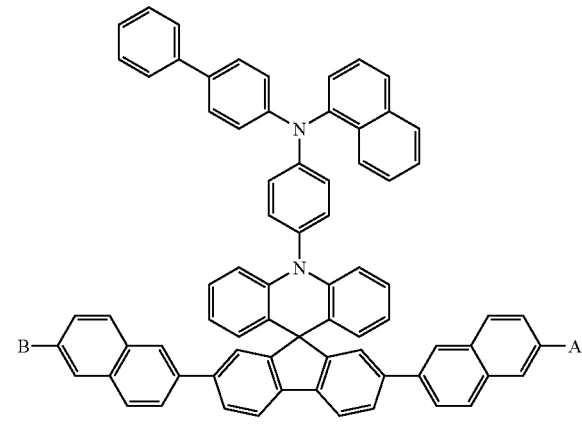
75
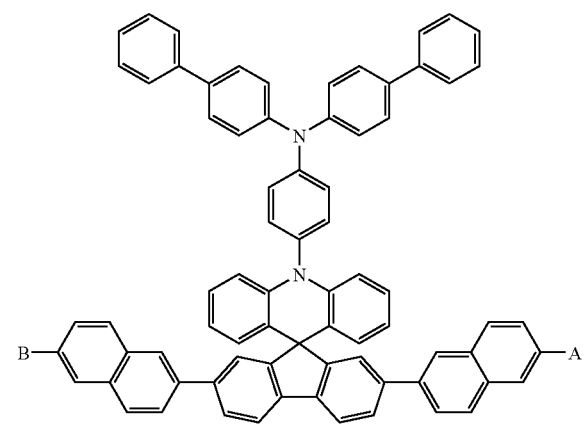
76
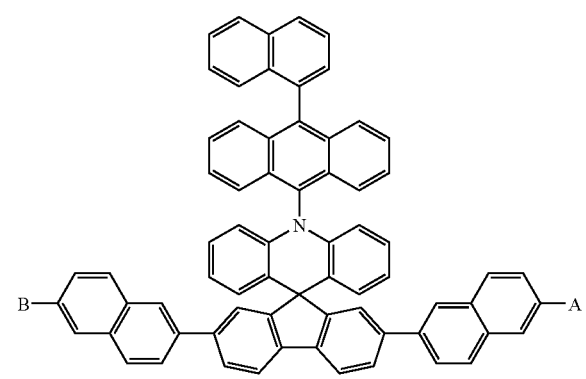

-continued
77
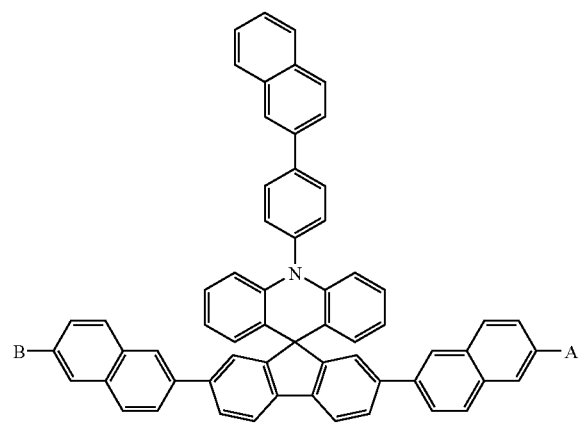
78
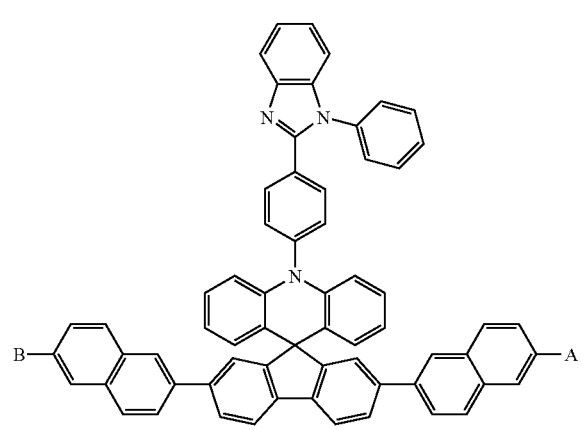
79
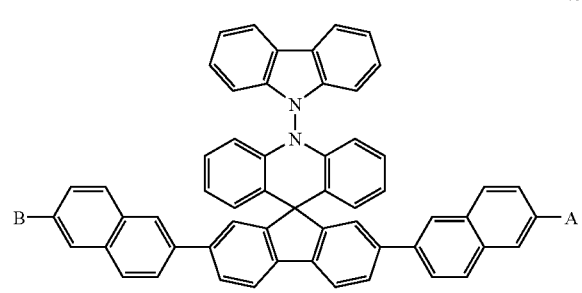
80
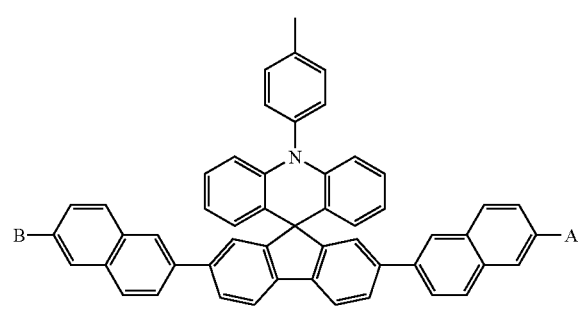
-continued
81
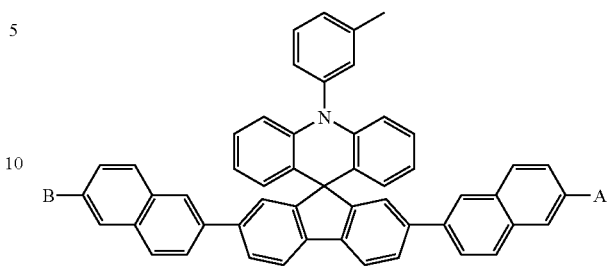
82
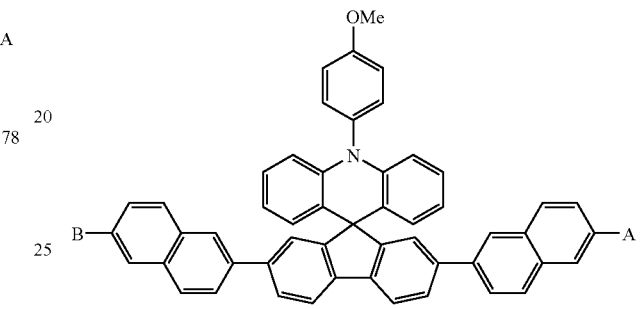
83
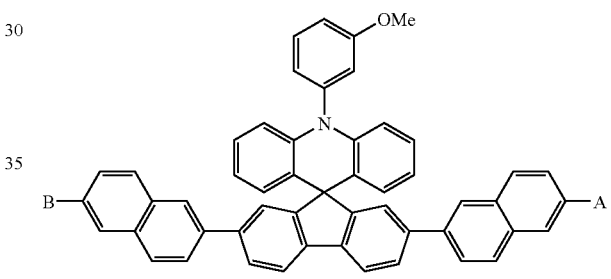
84
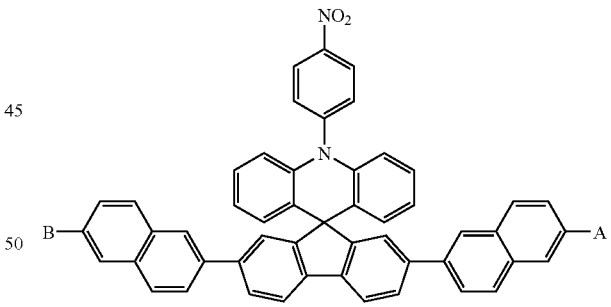
85
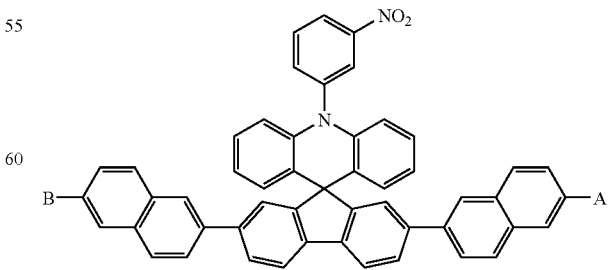

86
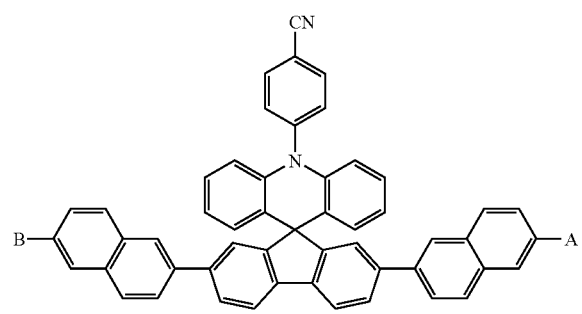
87
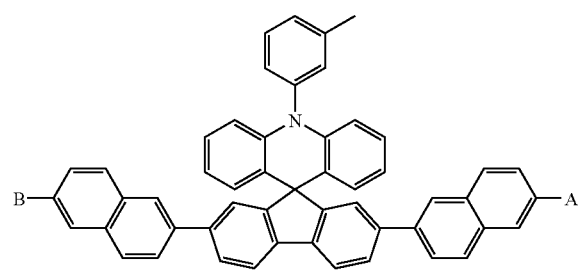
88
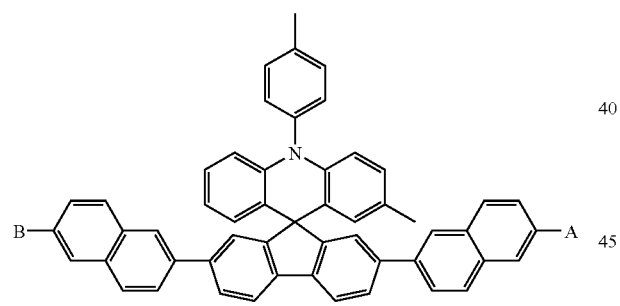
89
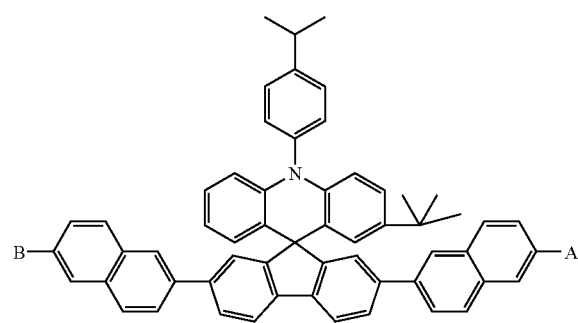
90
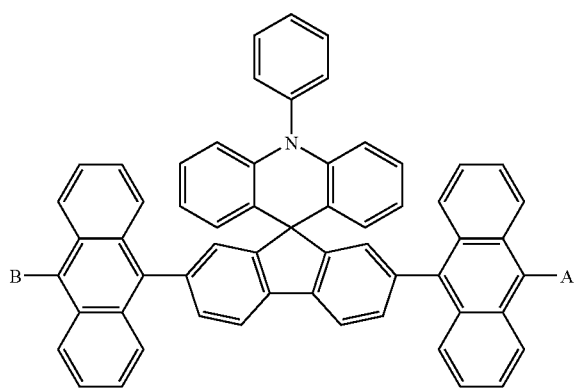
91
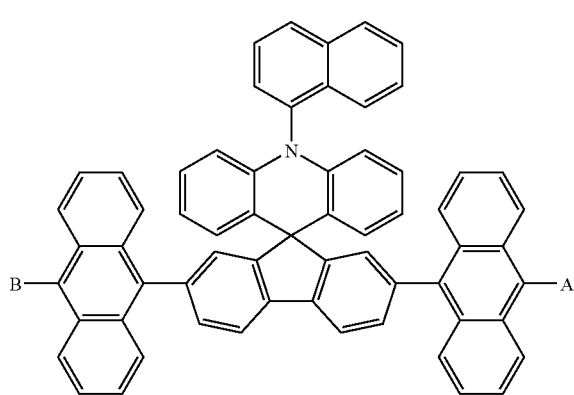
92
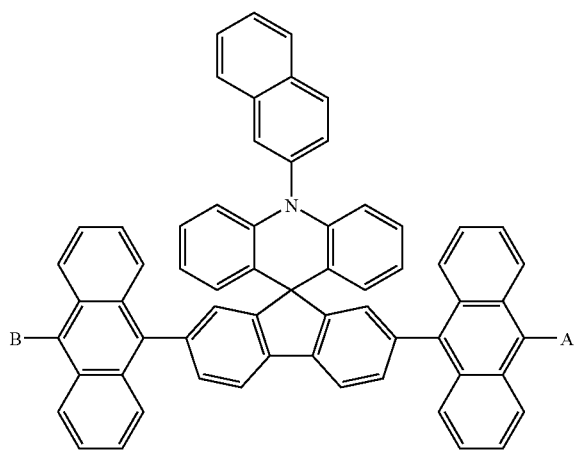

269
-continued
93
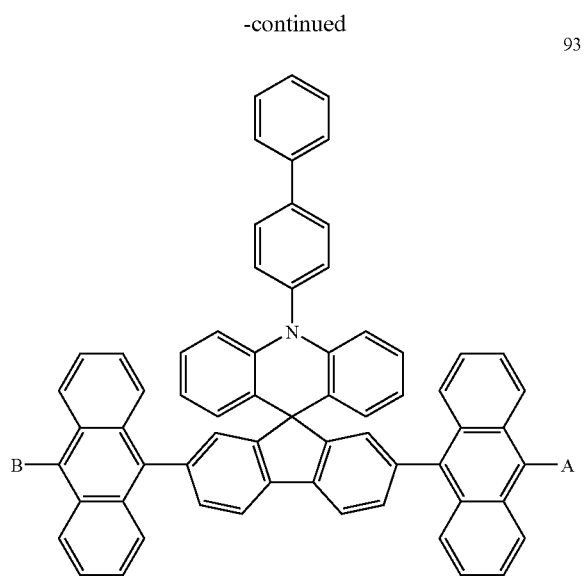
94
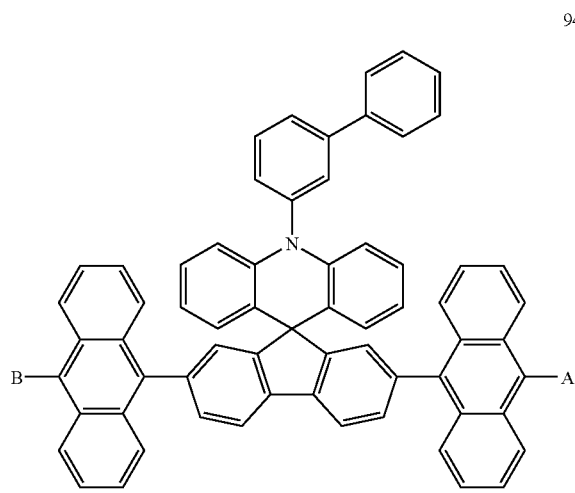
95
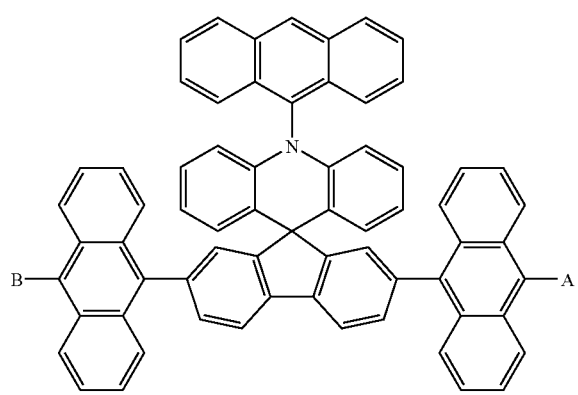
270
-continued
96
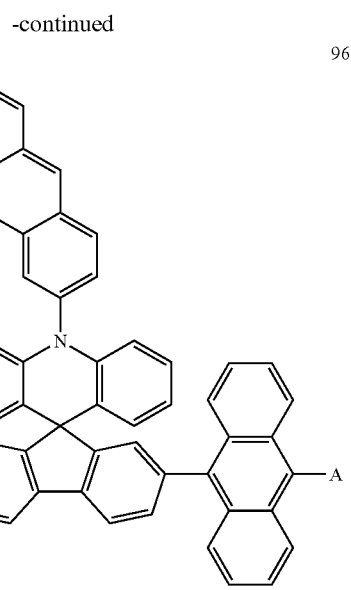
97
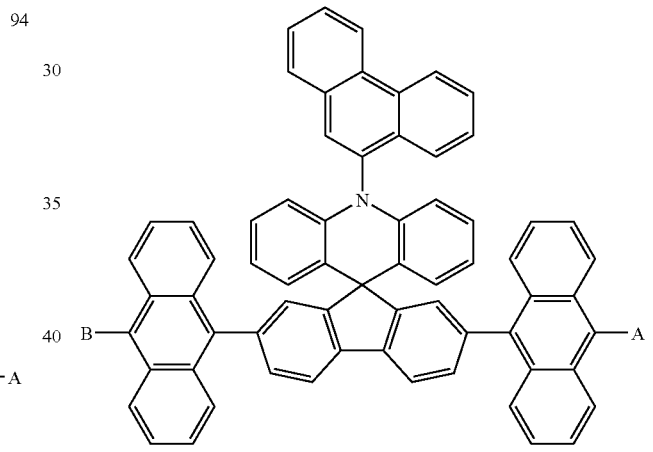
98
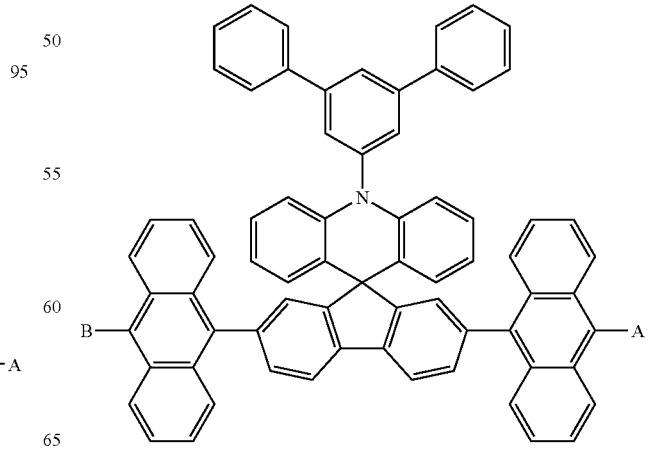

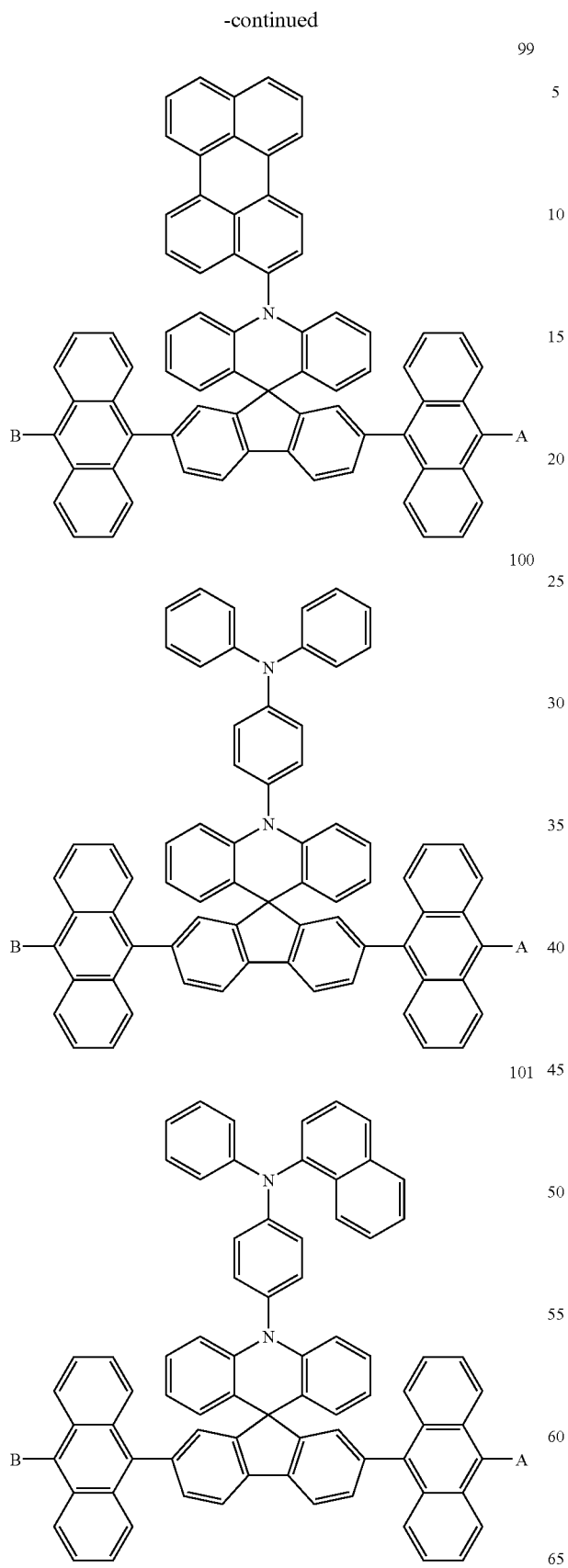

-continued
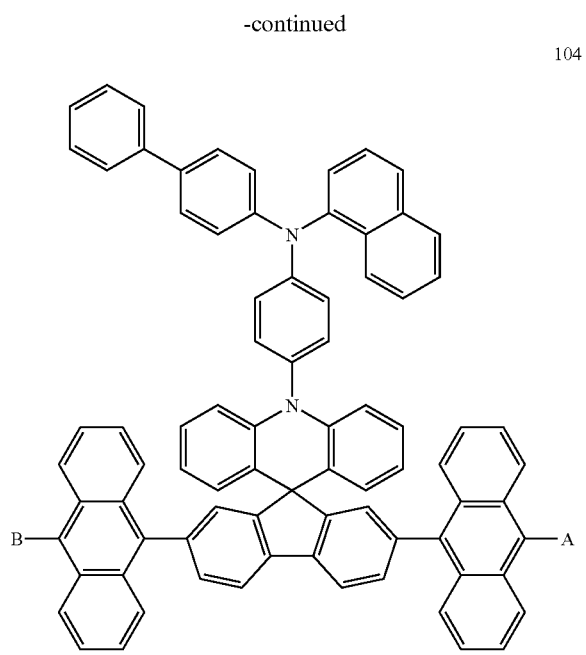
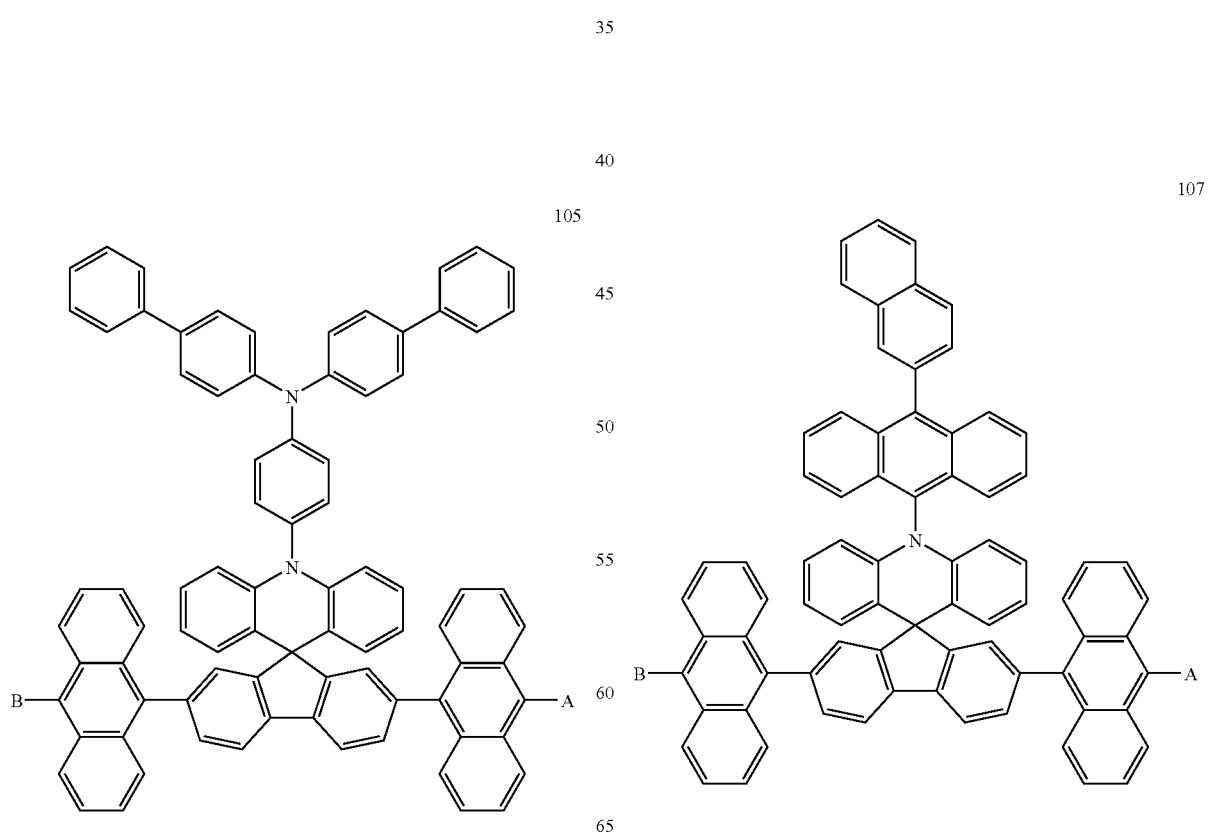

108
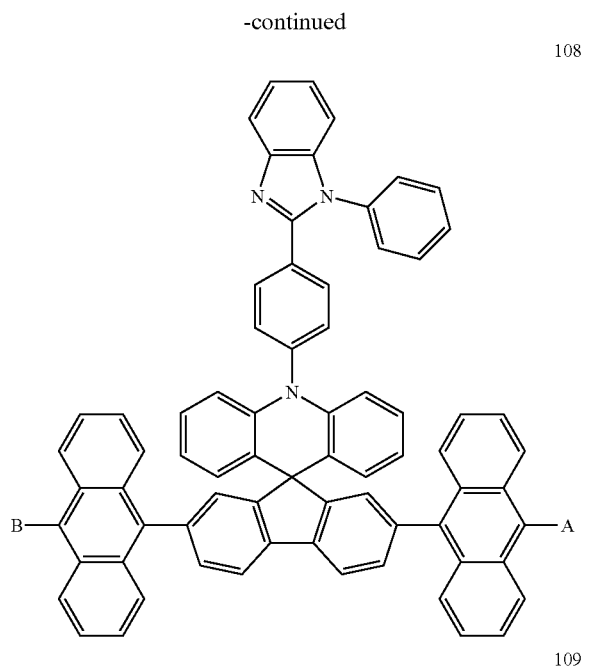
109
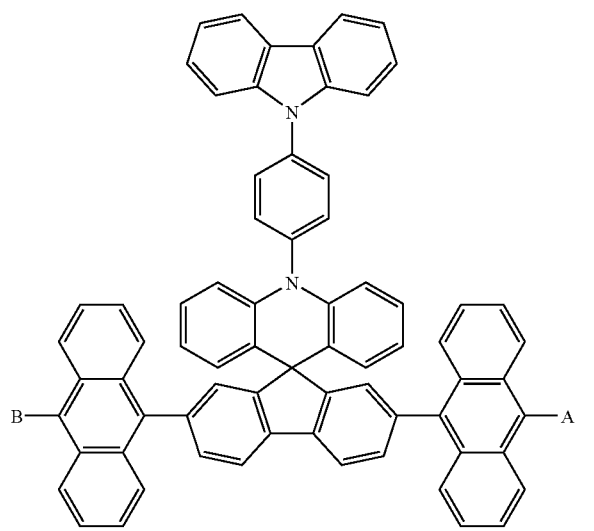
110
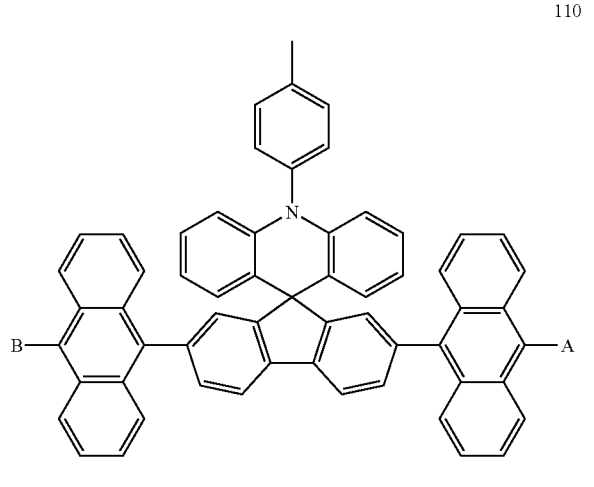
111
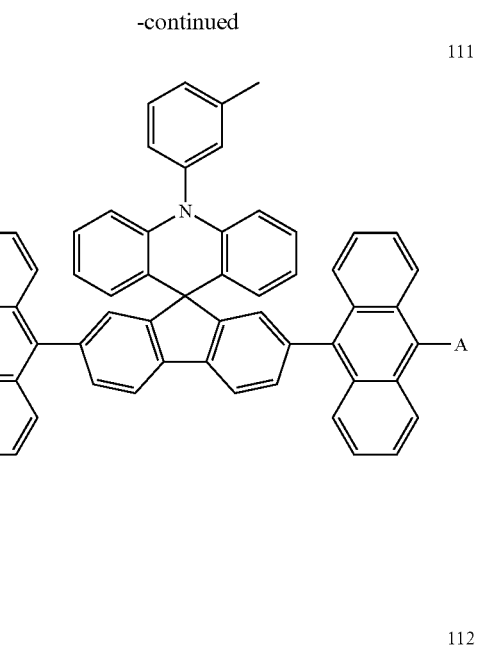
112
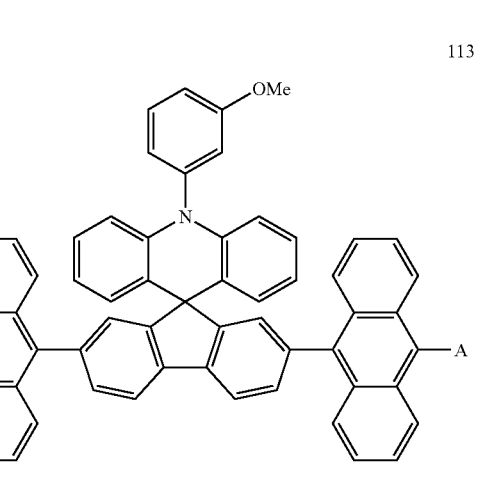
113

114
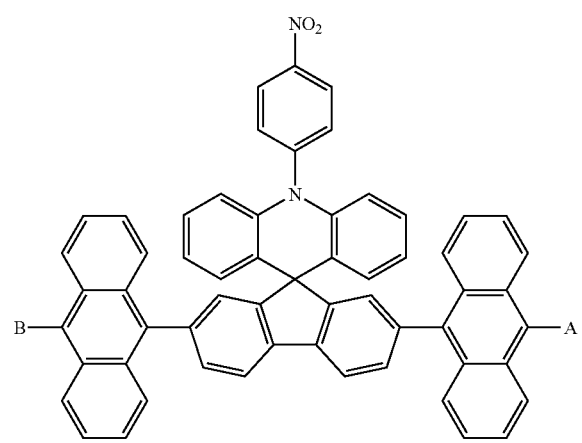
115
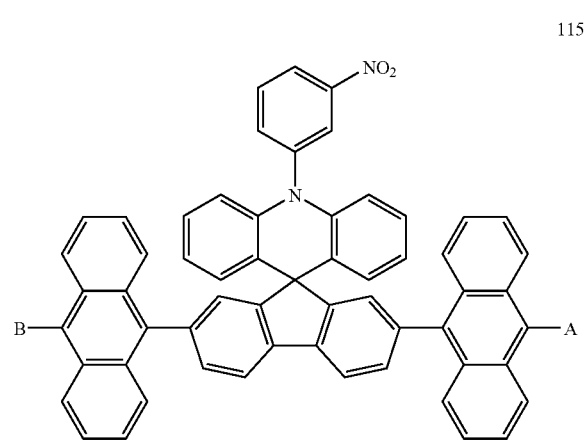
116
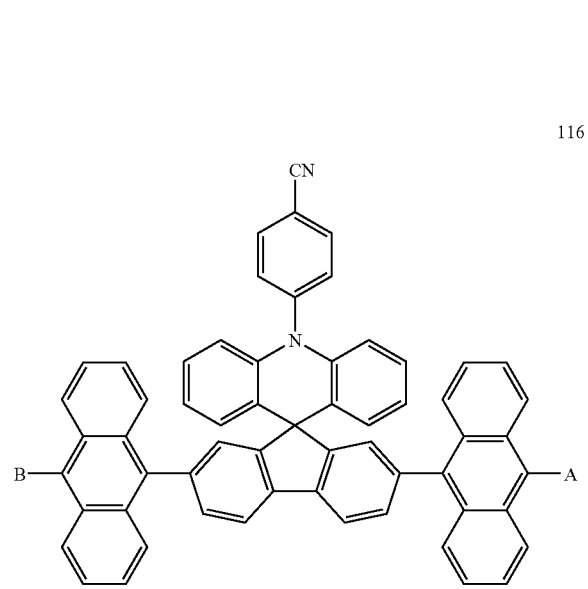
117
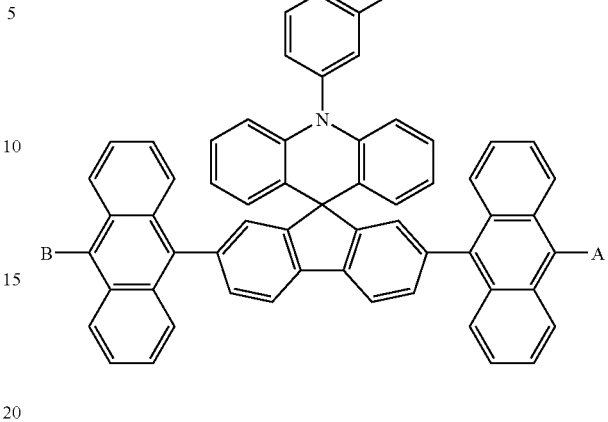
118
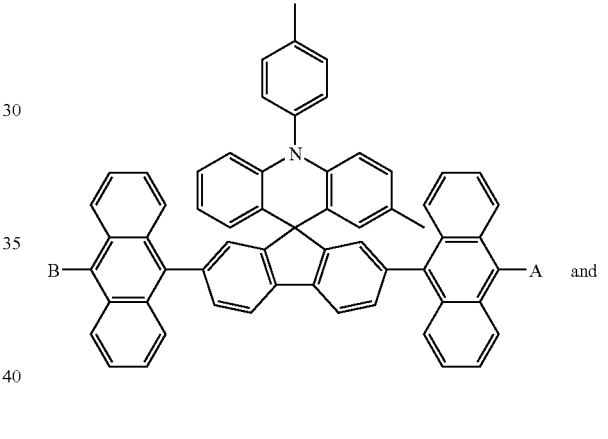
and
119
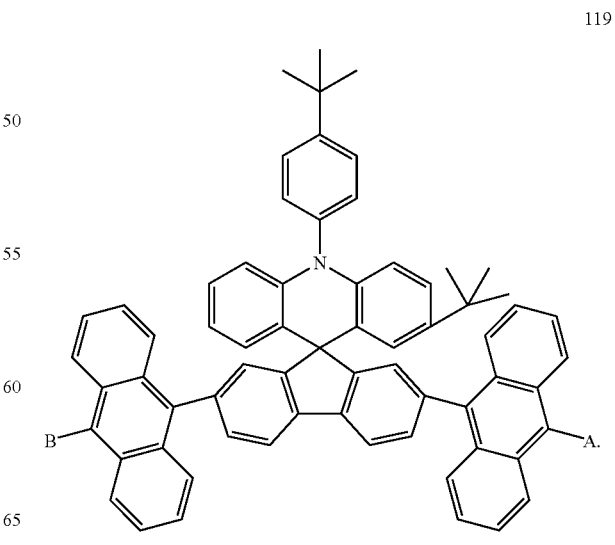

5. The organic light emitting device as set forth in claim 4, wherein A and B are each independently any one of following groups:
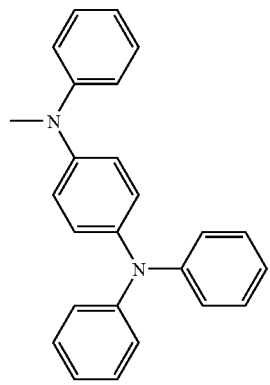
1
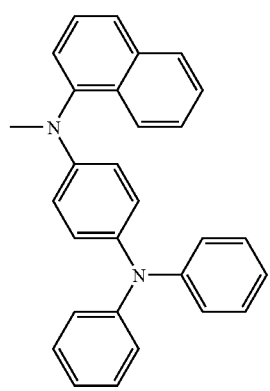
2
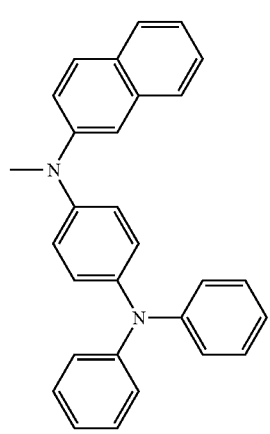
3
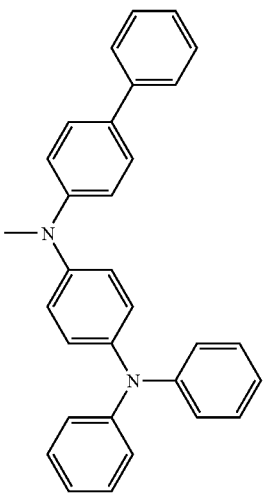
4
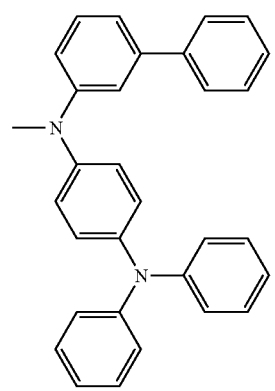
5
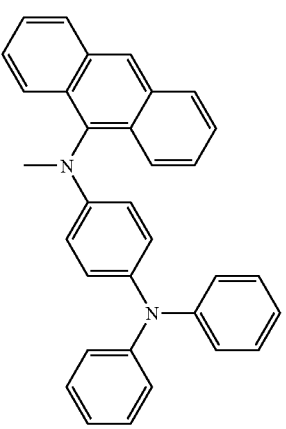
6

-continued
7
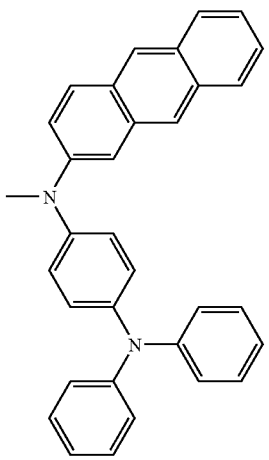
8
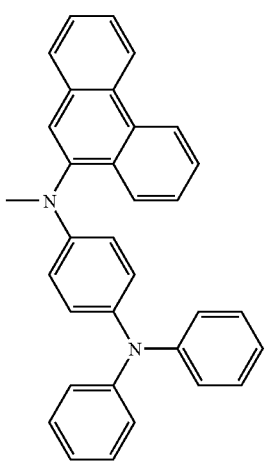
9
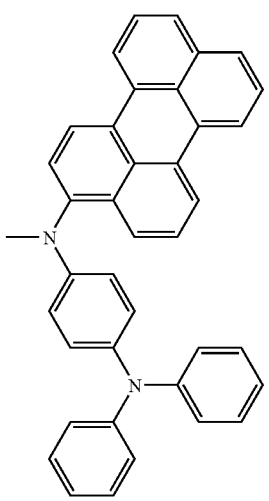
-continued
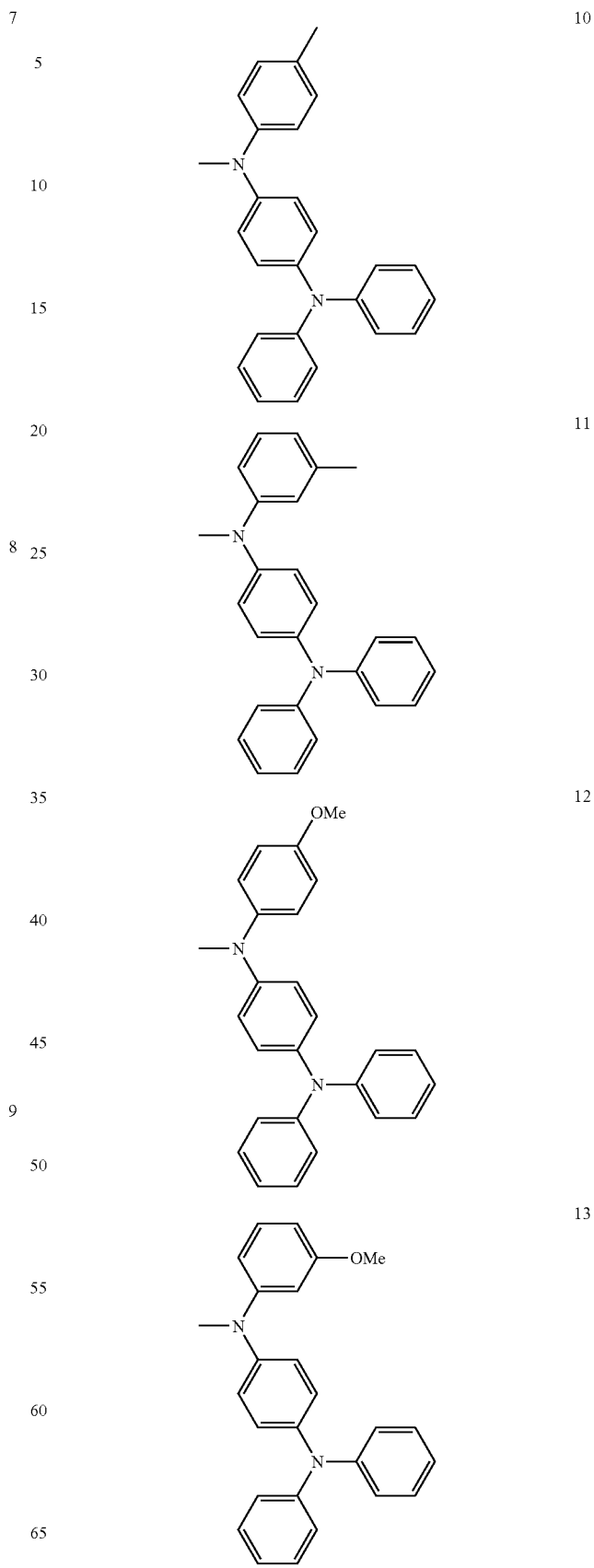

-continued
14
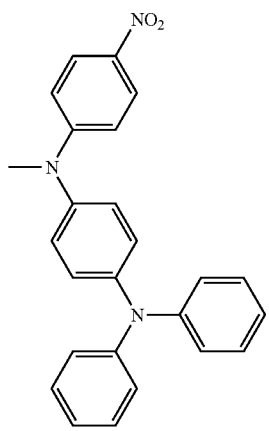
15
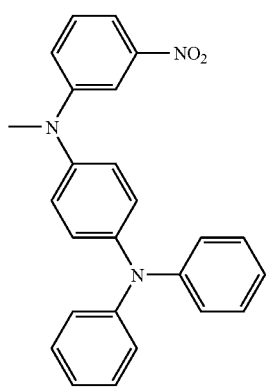
16
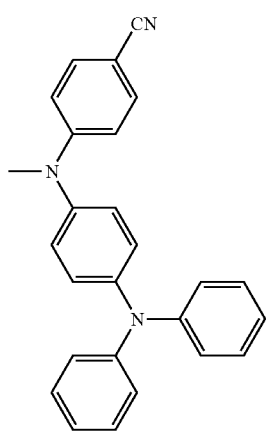
17
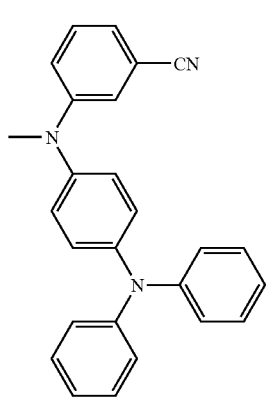
-continued
18
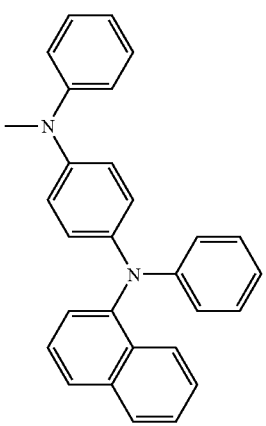
19
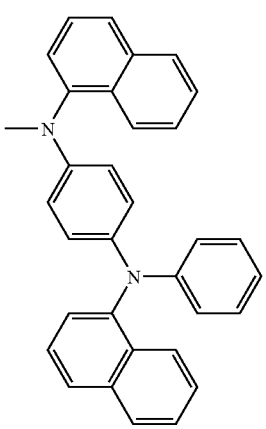
20
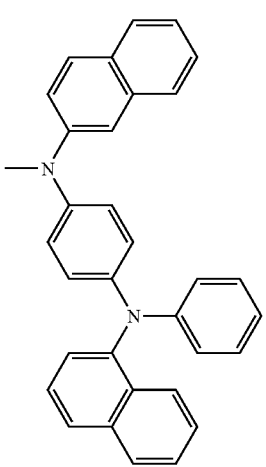

21
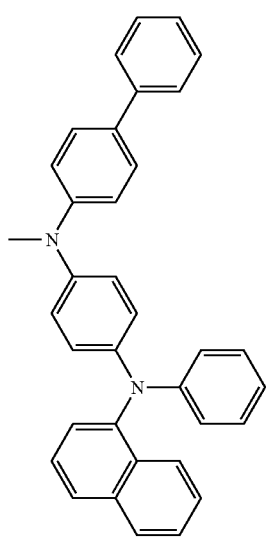
22
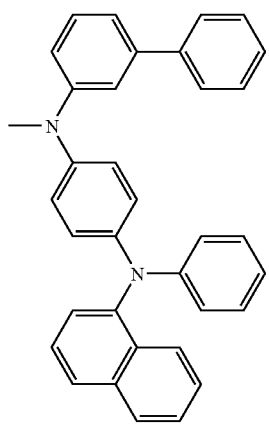
23
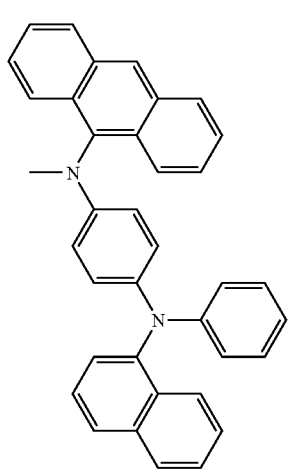
24
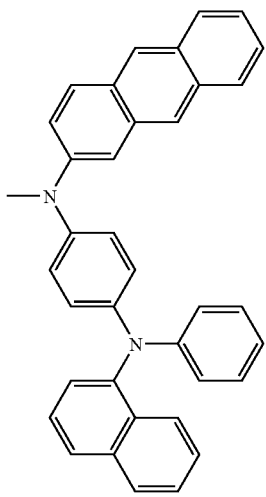
25
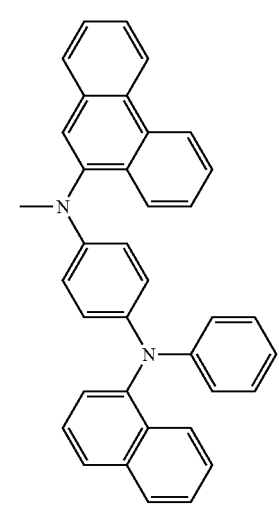
26
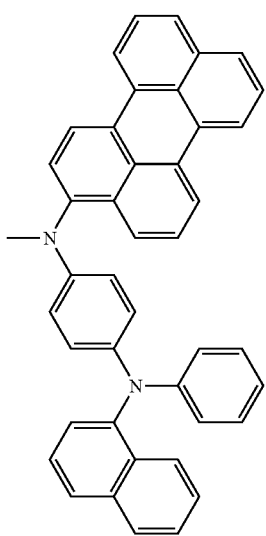

27
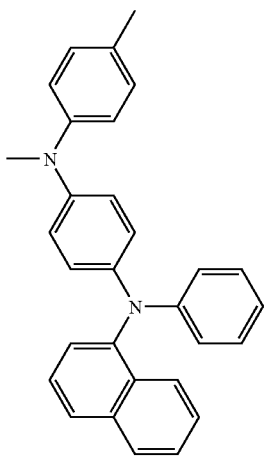
28
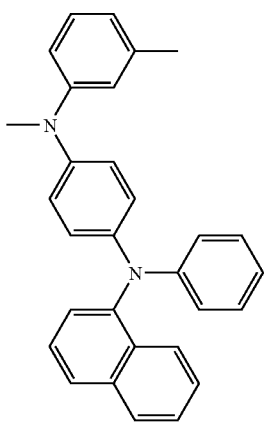
29
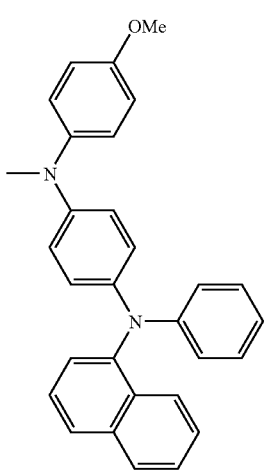
30
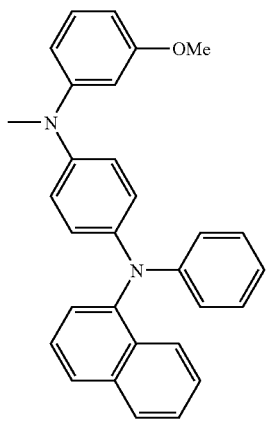
31
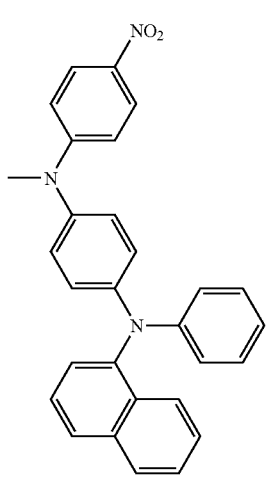
32
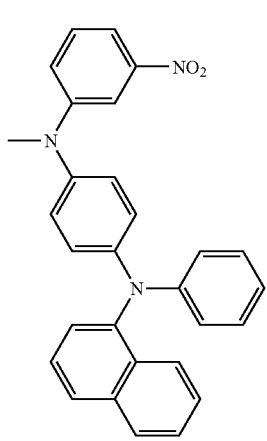

33
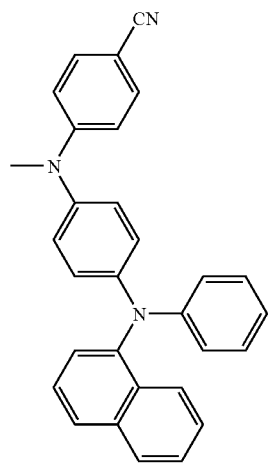
34
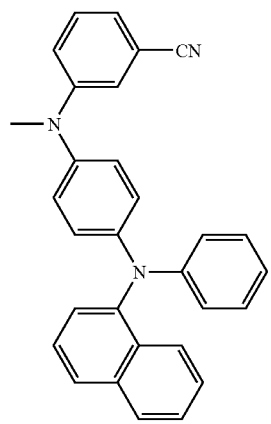
35
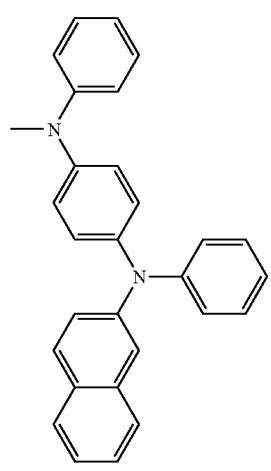
36
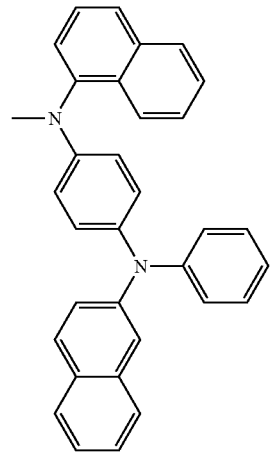
37
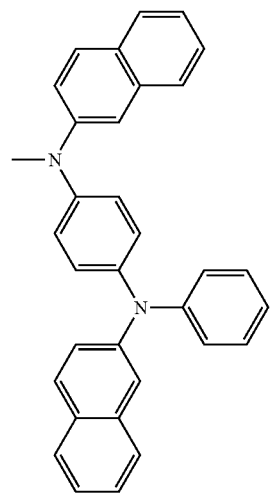
38

-continued
39
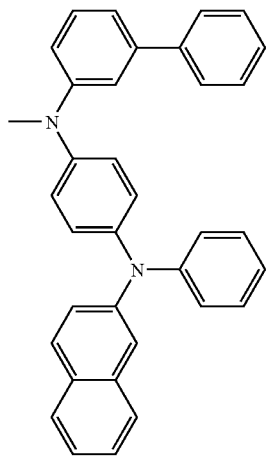
40
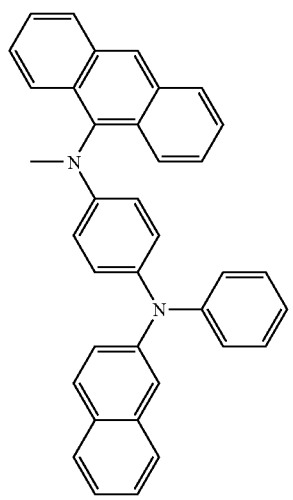
41
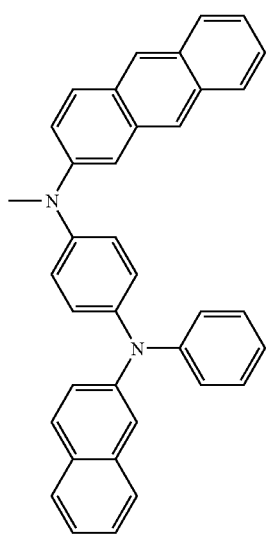
-continued
42
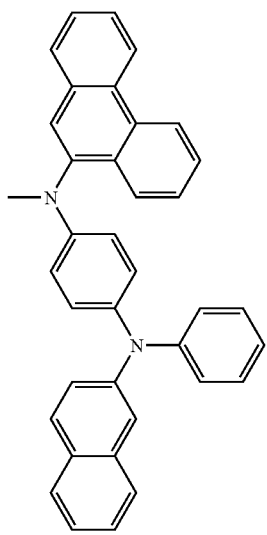
43
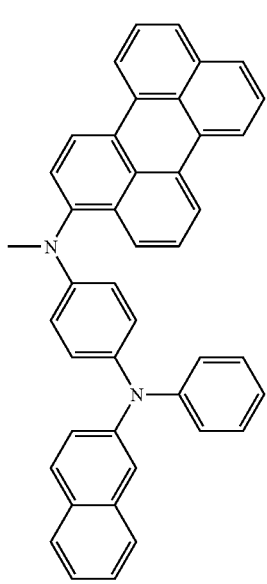
44
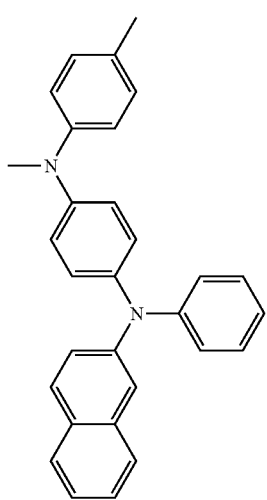

45
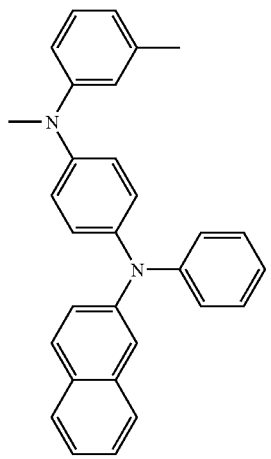
46
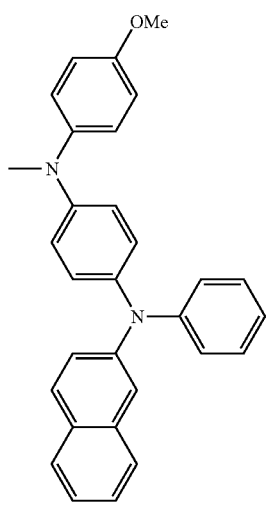
47
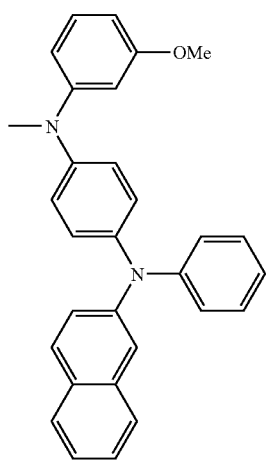
48
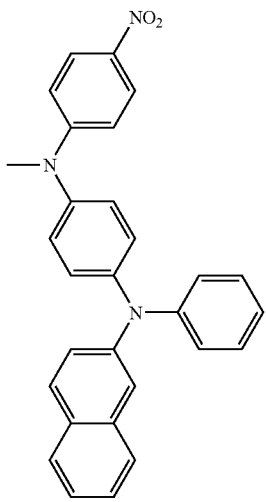
49
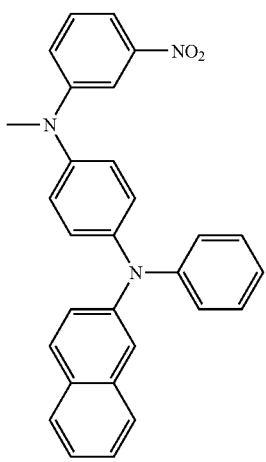
50
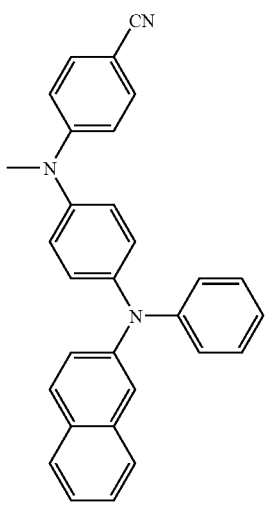

-continued
51
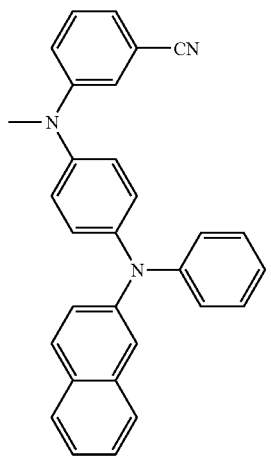
52
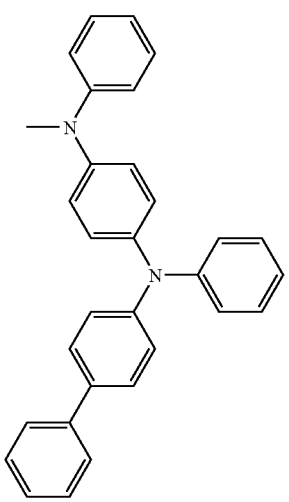
53
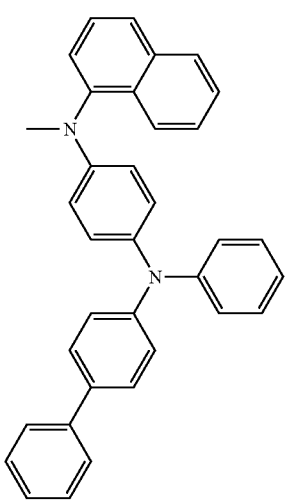
-continued
54
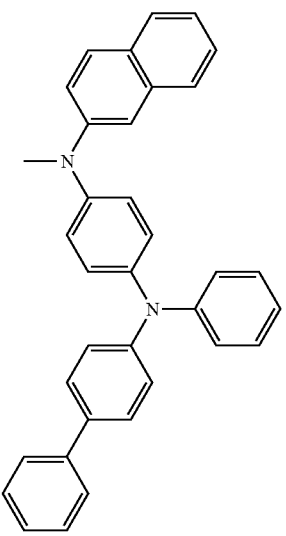
55
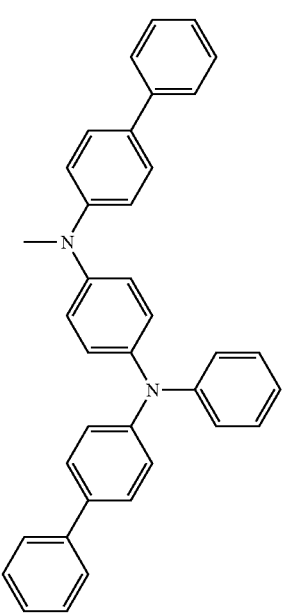
56
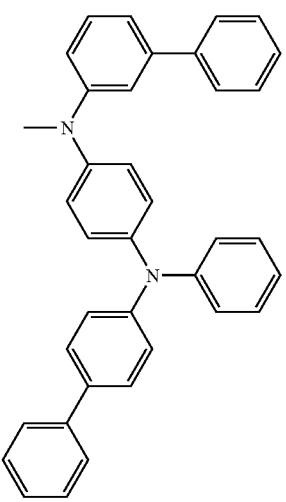

-continued
297
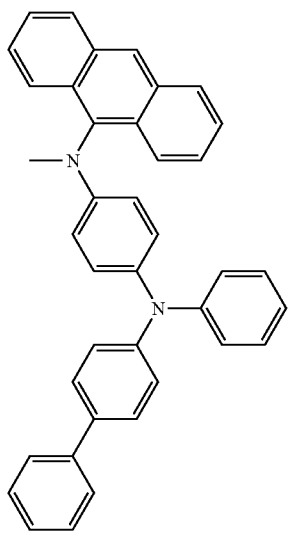
298
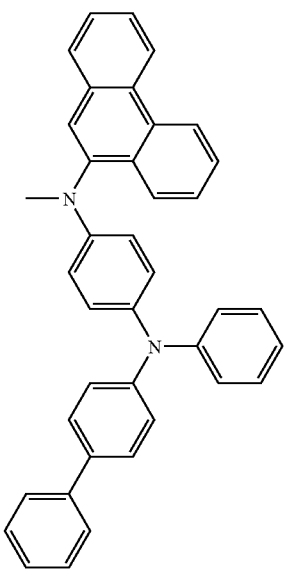

-continued
61
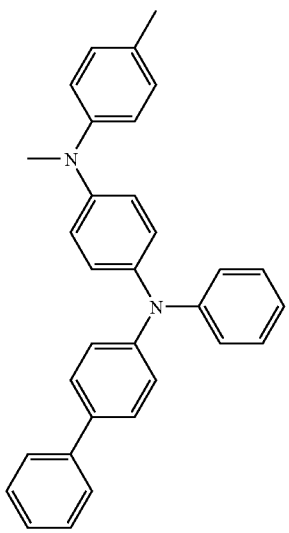
62
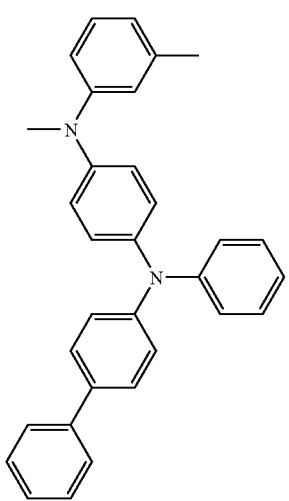
63
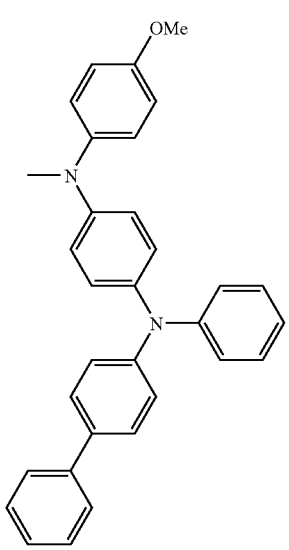
-continued
64
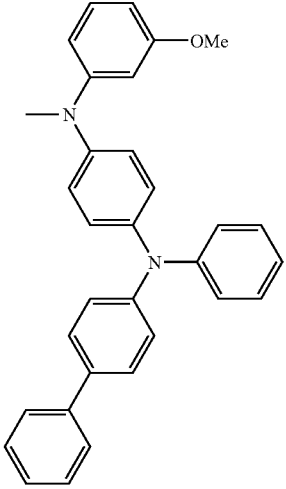
65
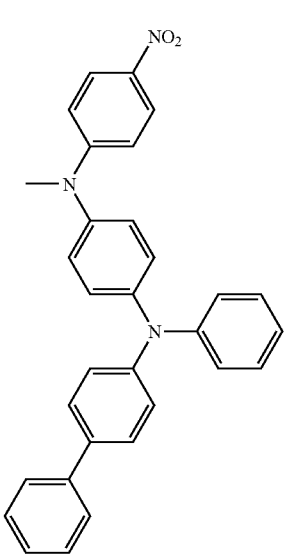
66
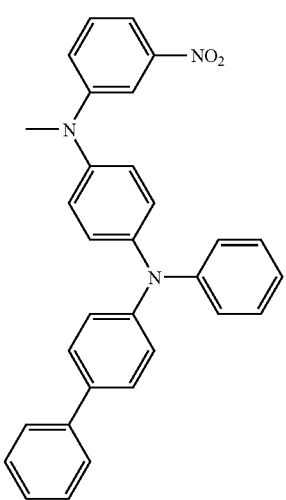

-continued
67
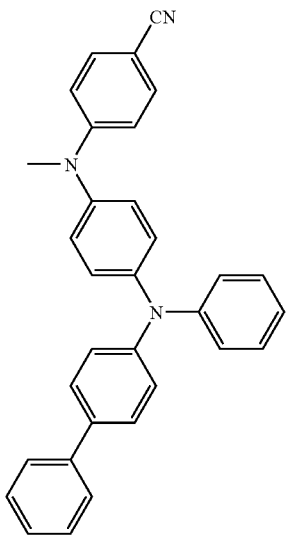
68
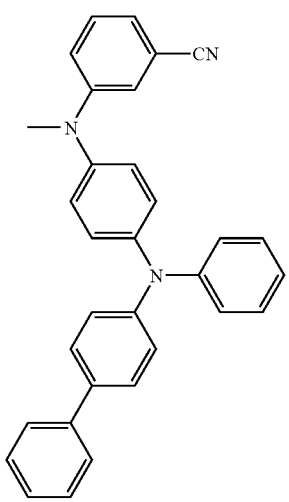
69
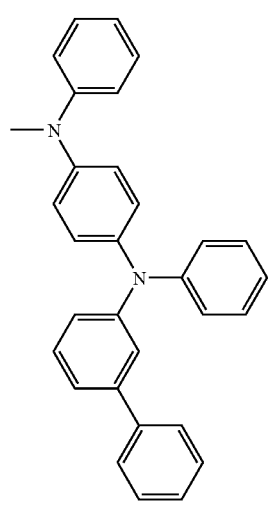
-continued
70
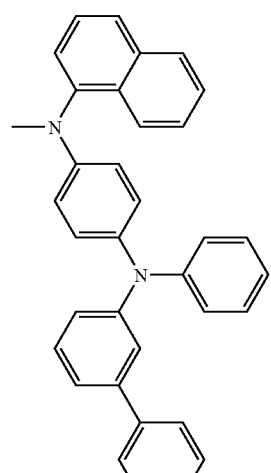
71
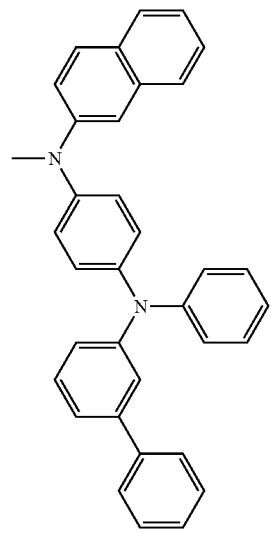
72
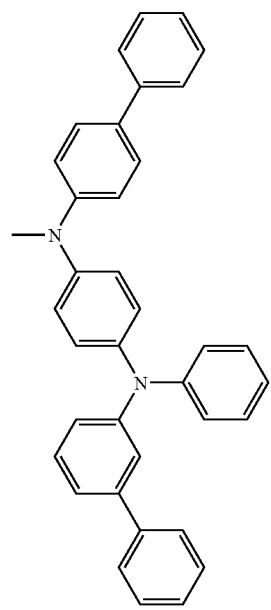

303
-continued
73
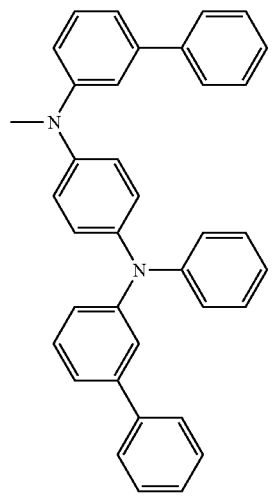
74
75
304
-continued
76
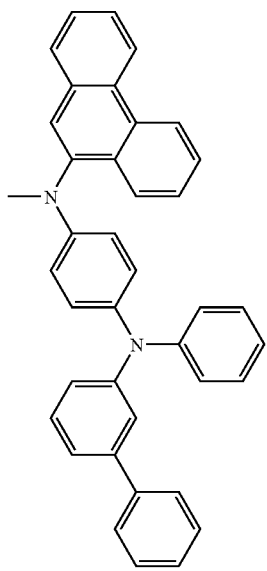
77
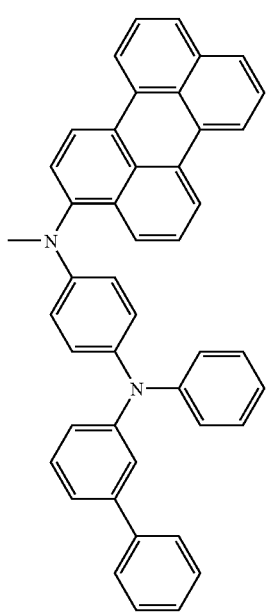

305 306
-continued
-continued
78
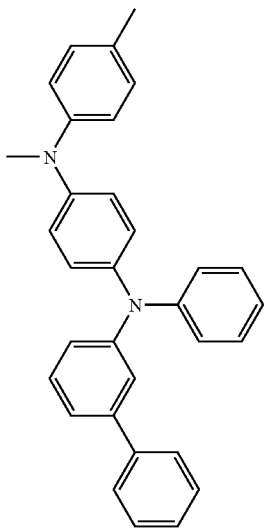
81
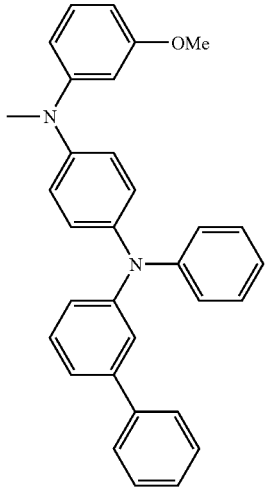
79
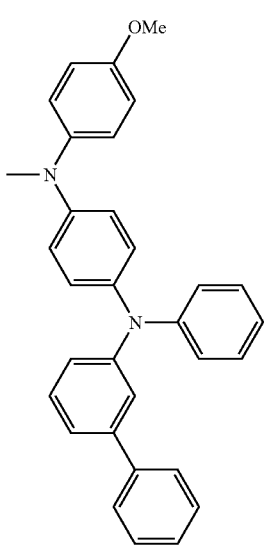
82
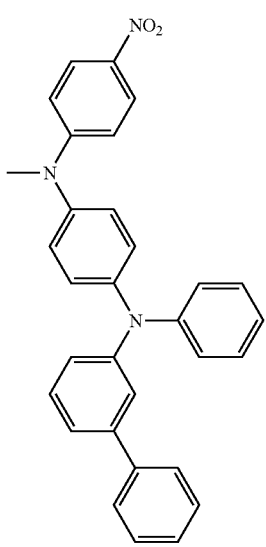
80
83
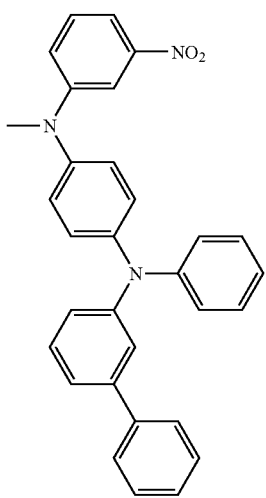

84
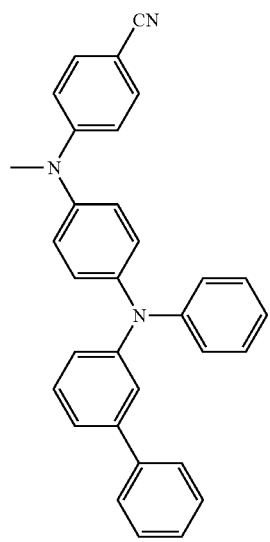
85
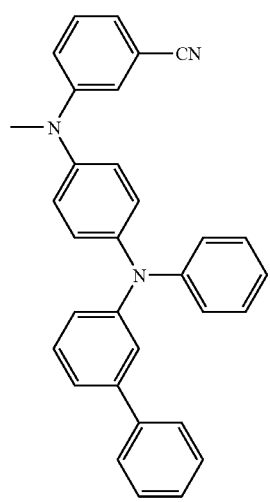
86
87
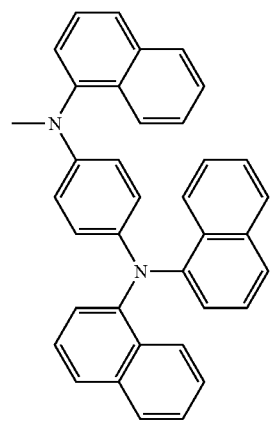
88
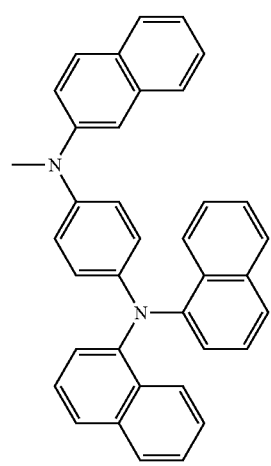
89
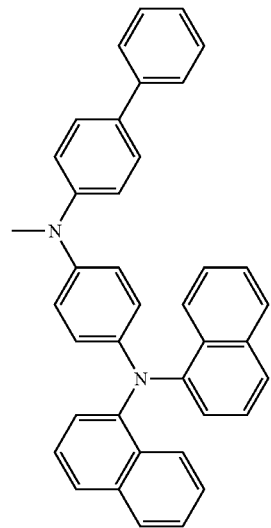

-continued
90
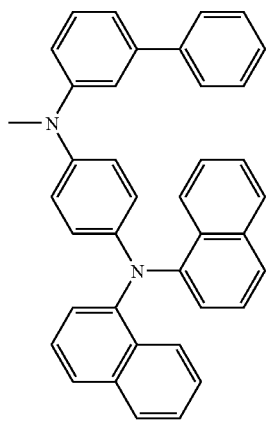
91
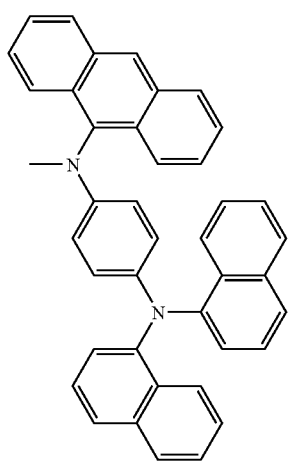
92
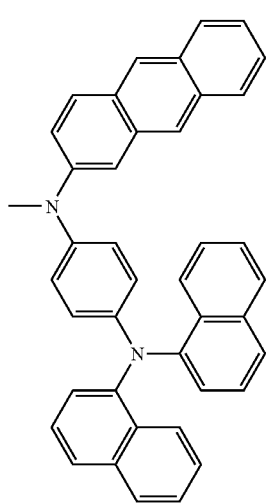
-continued
93
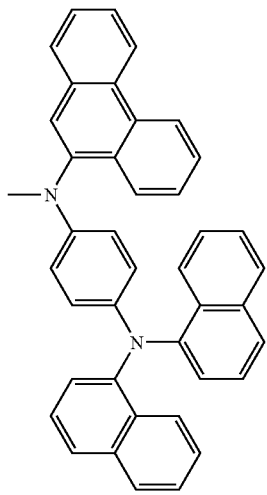
94
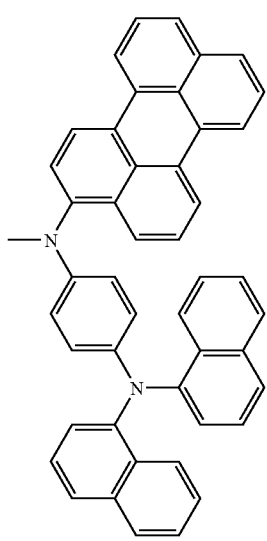
95
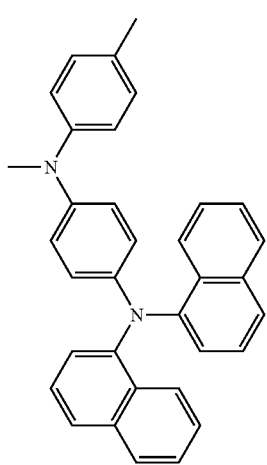

96
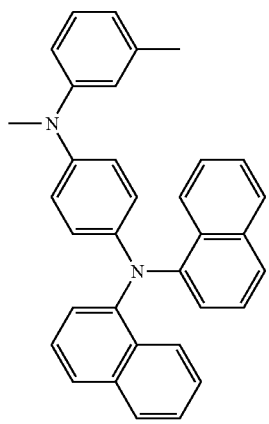
97
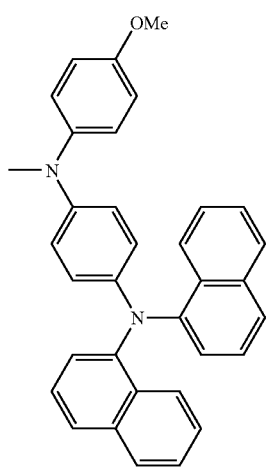
98
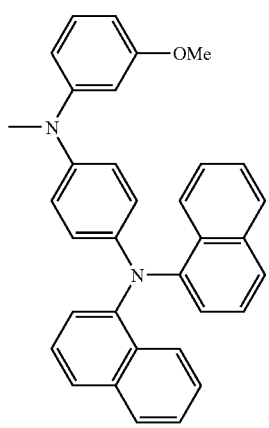
99
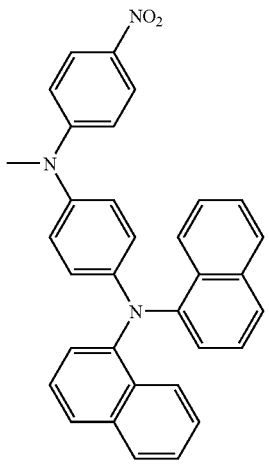
100
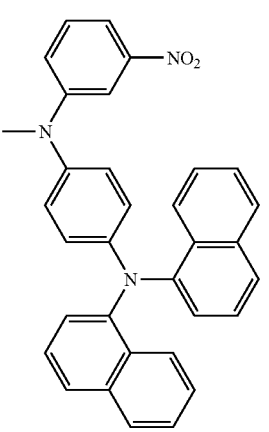
101
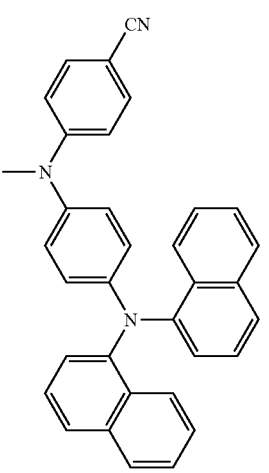

-continued
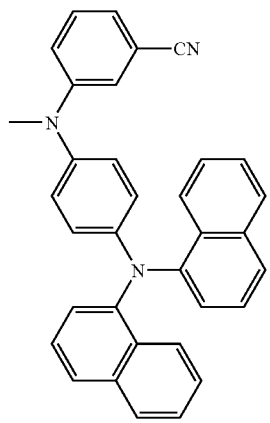
102
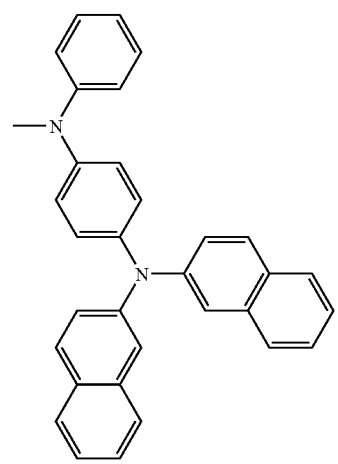
103
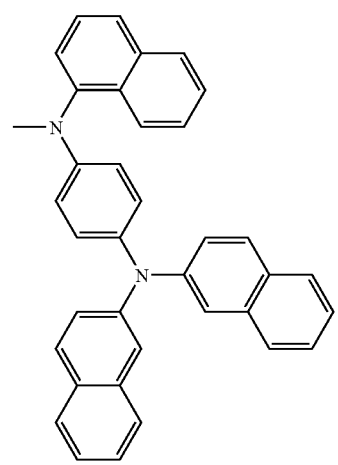
104
-continued
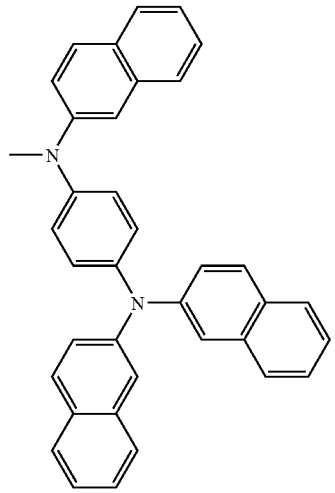
105
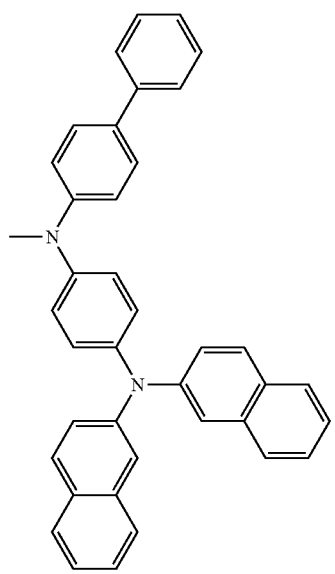
106
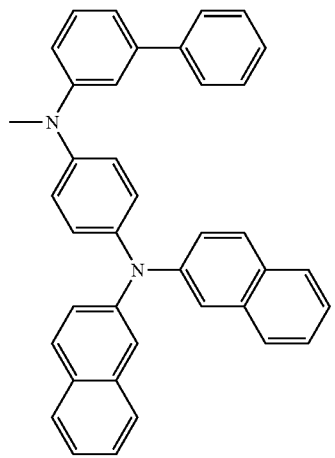
107

108
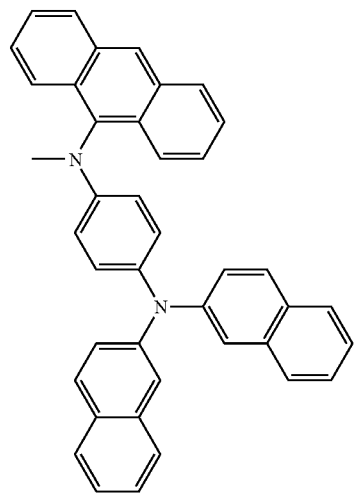
109
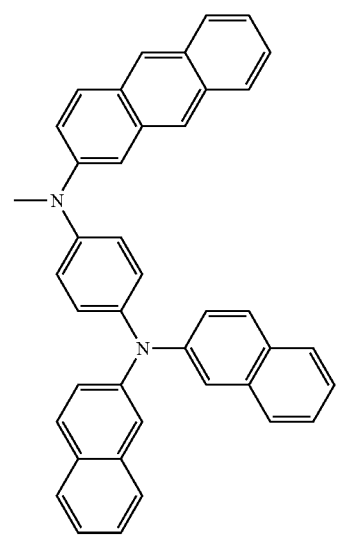
110
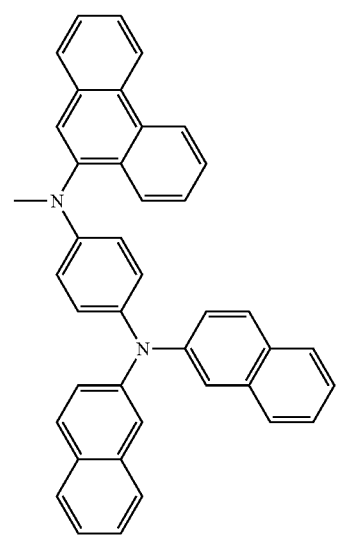
111
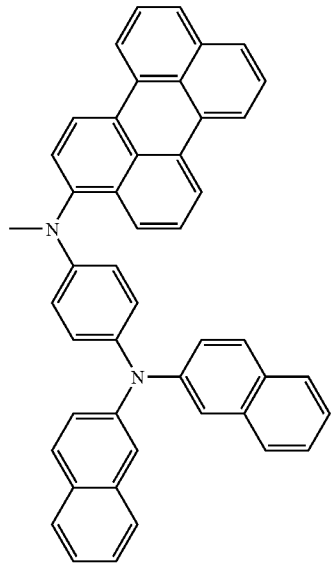
112
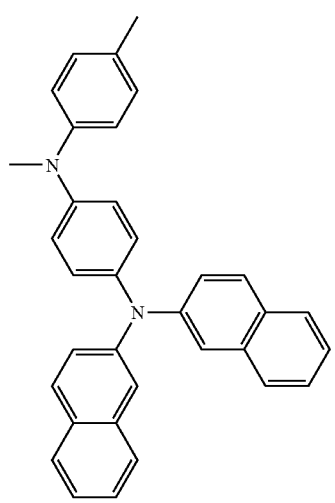
113
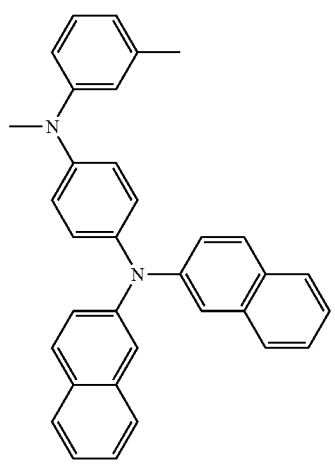

-continued
114
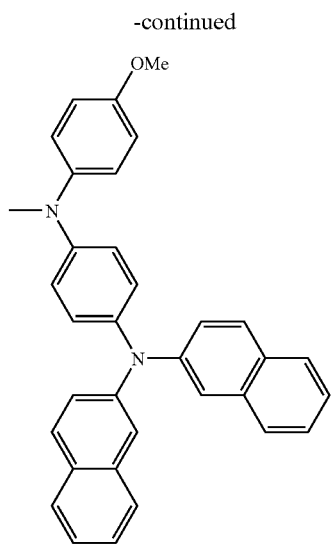
115
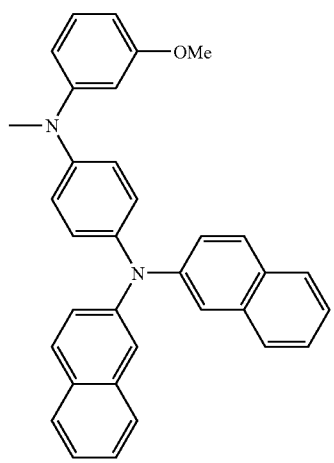
116
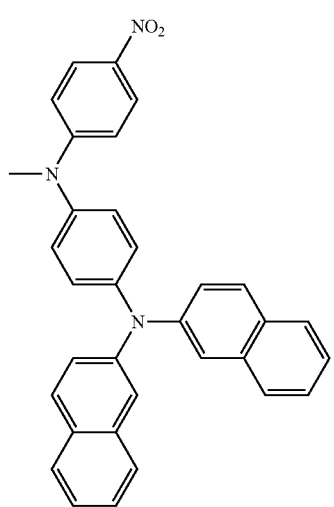
-continued
117
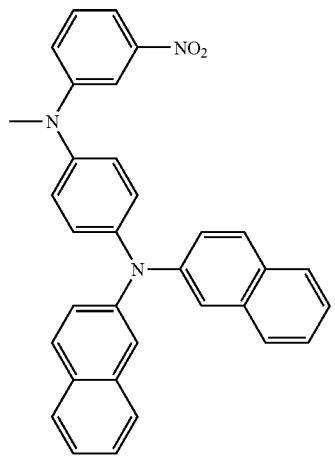
118
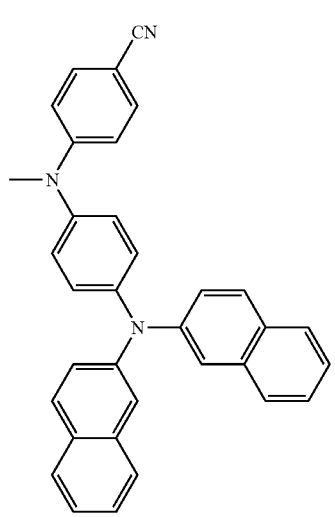
119
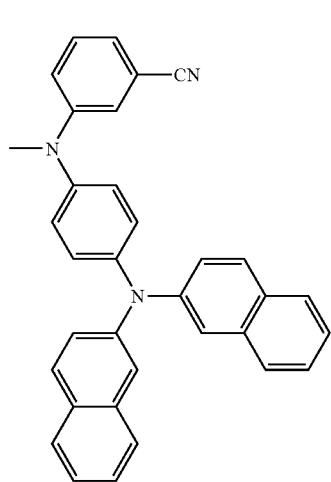

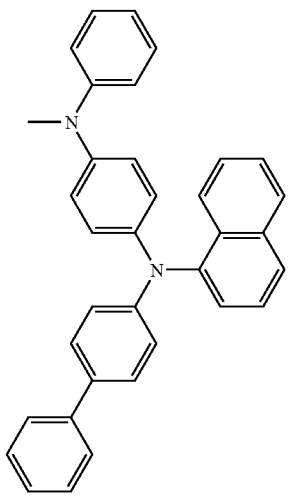
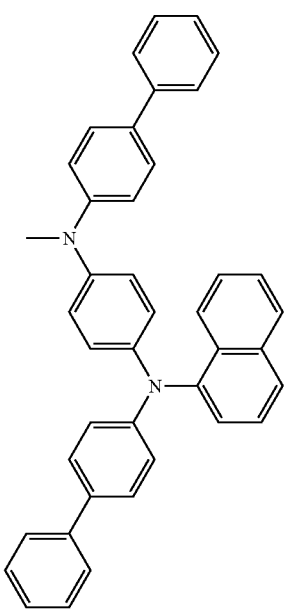

321
-continued
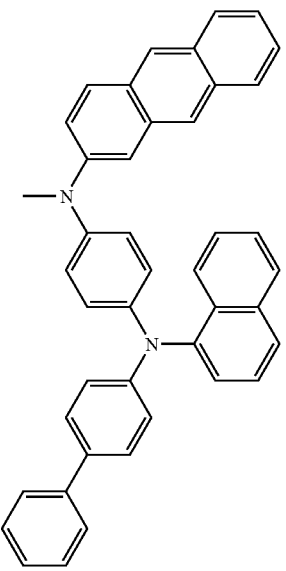
322
-continued
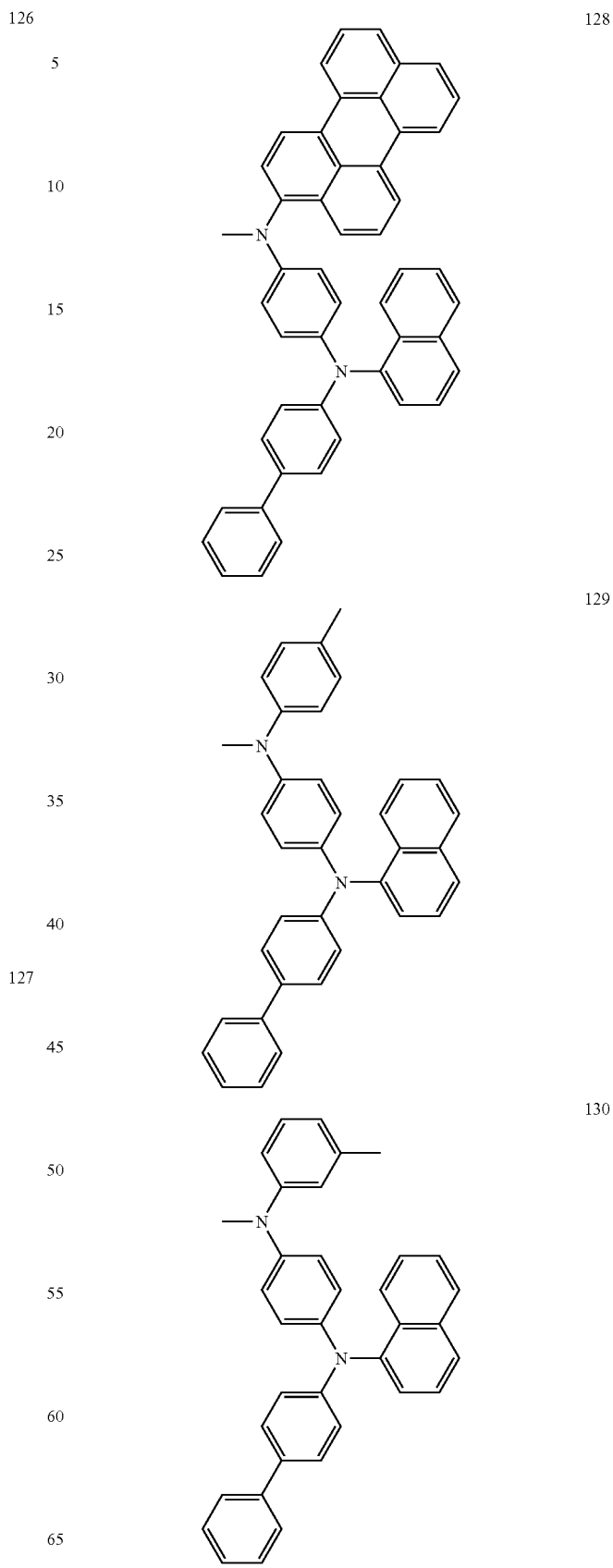

-continued
131
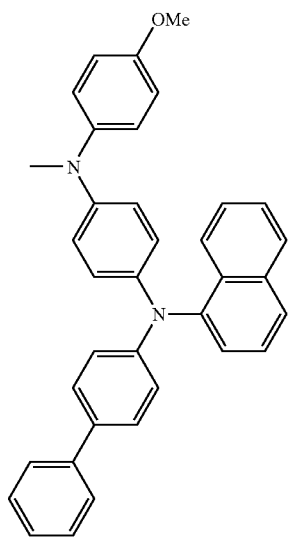
132
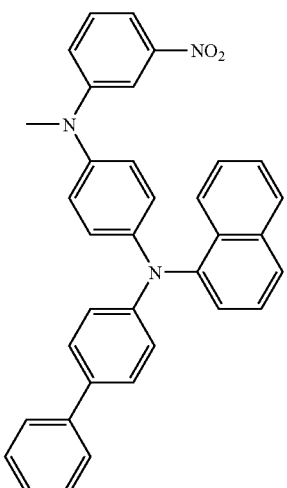
133
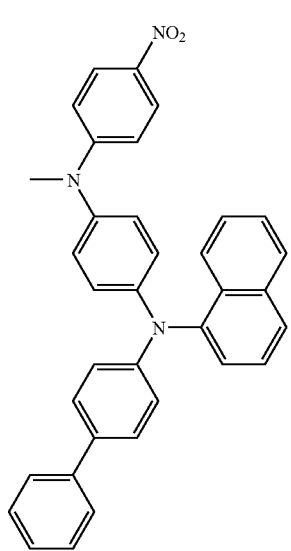
-continued
134
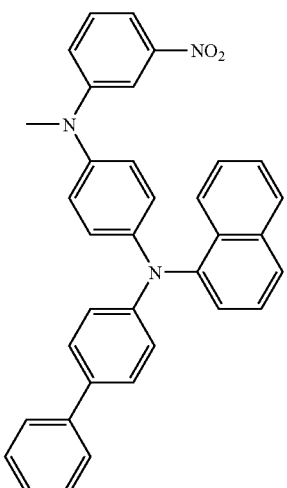
135
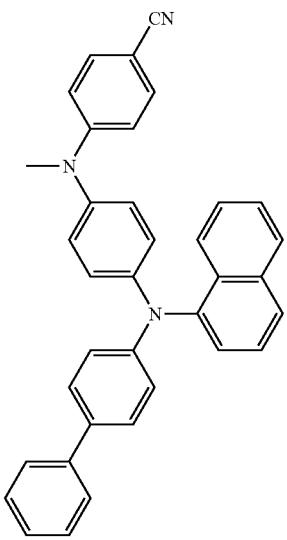
136
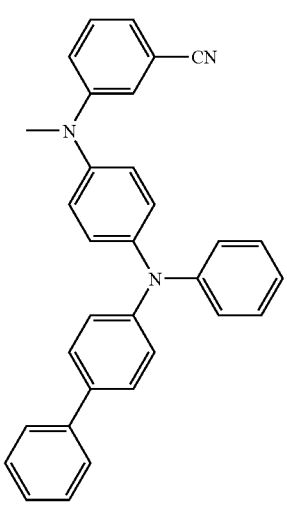

-continued
137
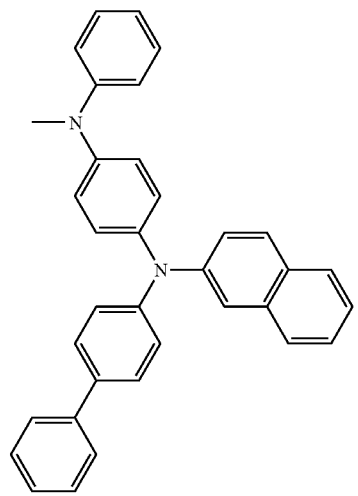
138
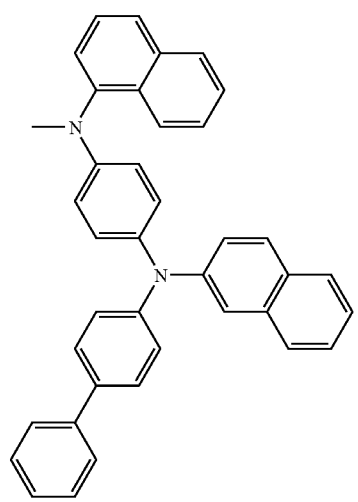
139
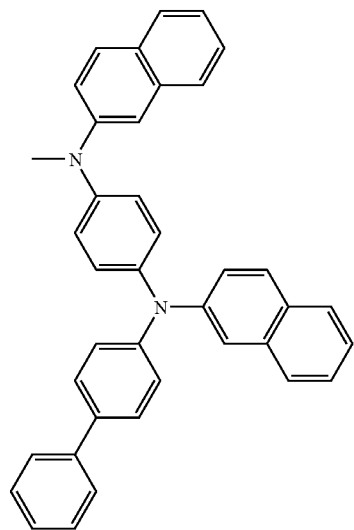
-continued
140
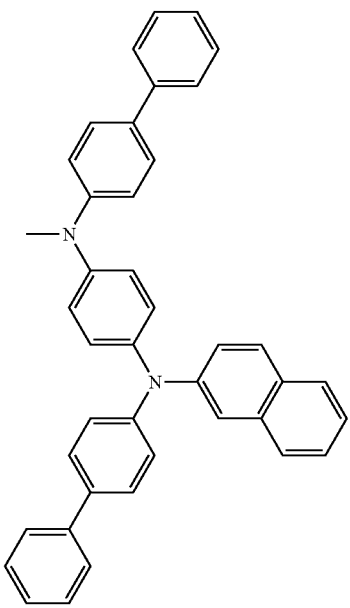
141
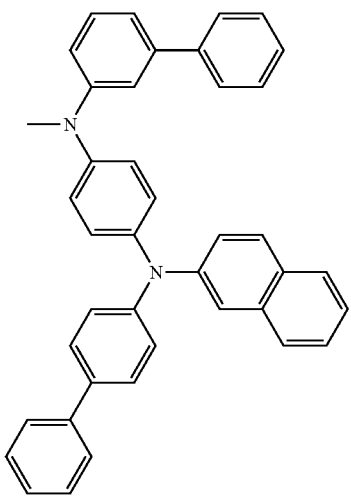
142
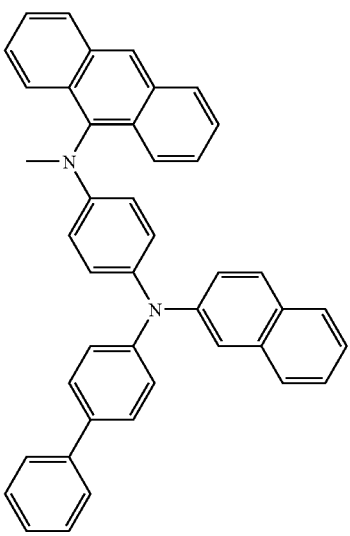

143
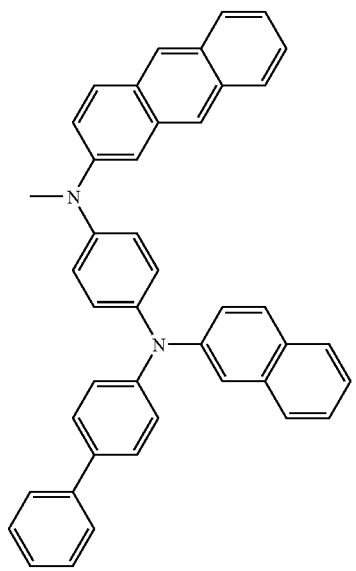
144
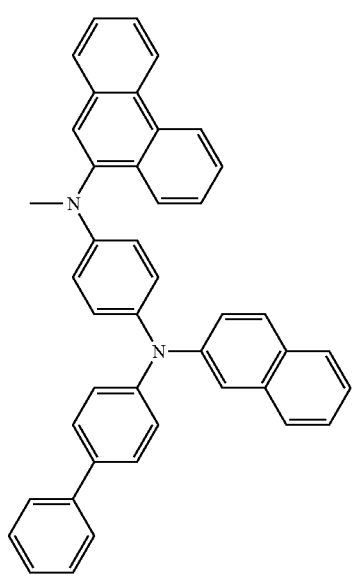
145
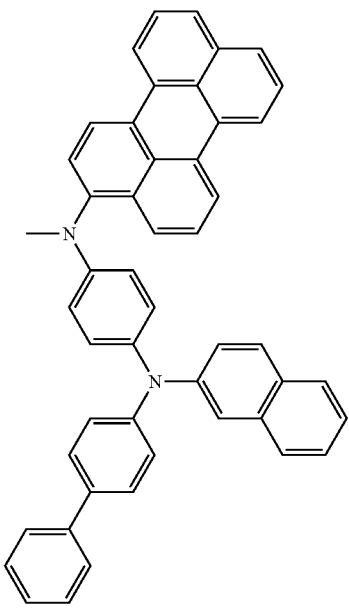
146
147
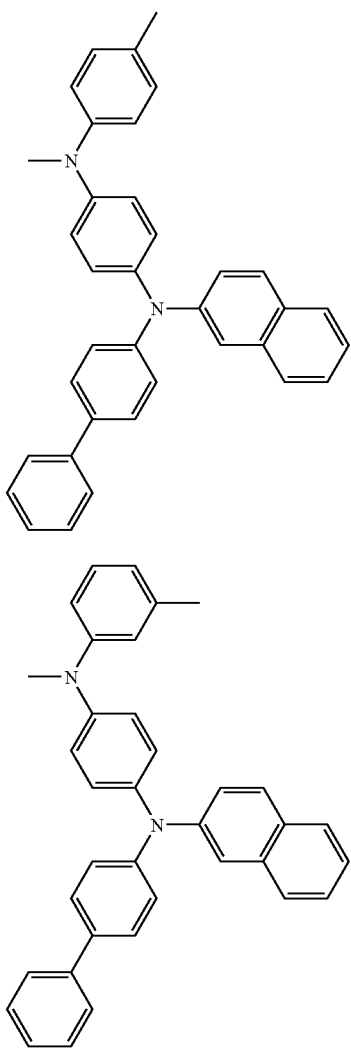

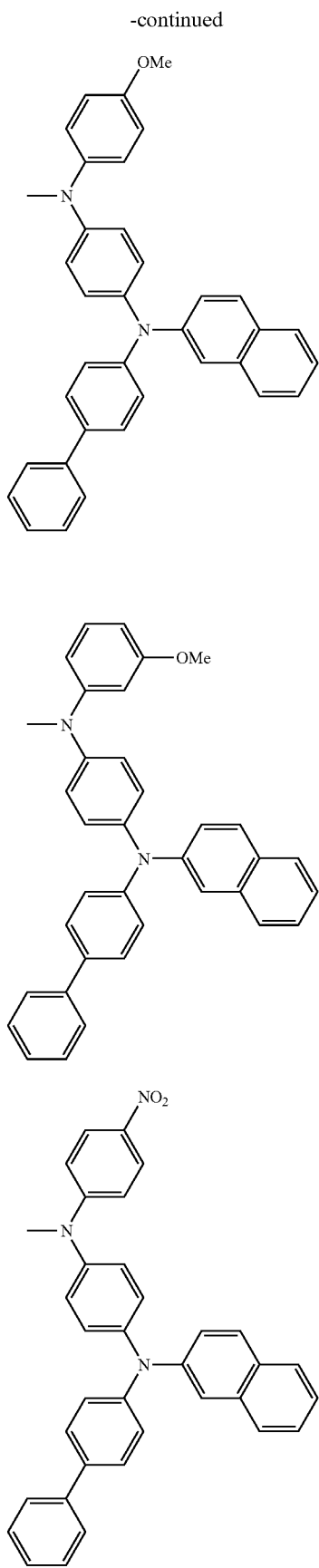
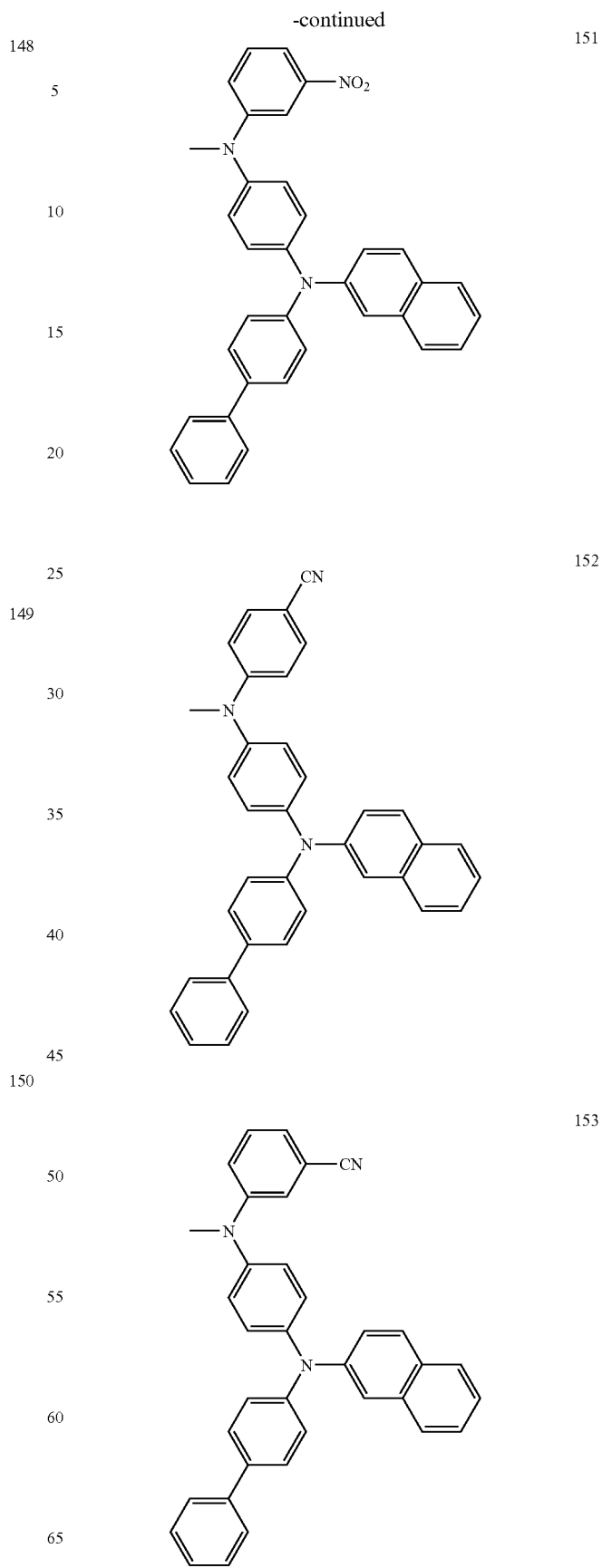

-continued
154
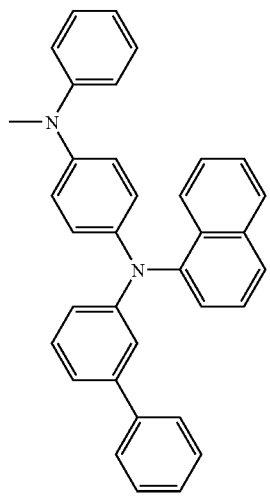
155
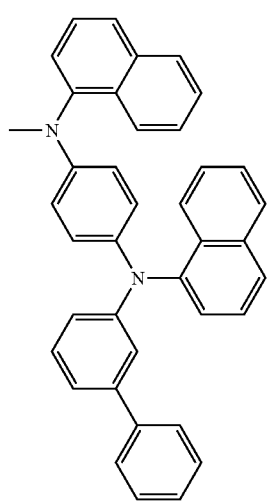
156
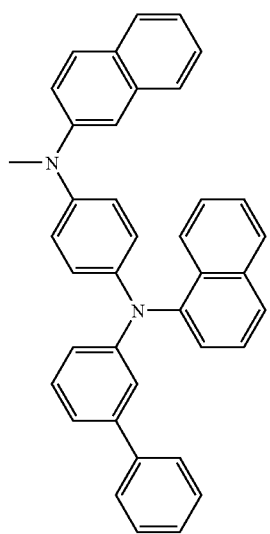
-continued
157
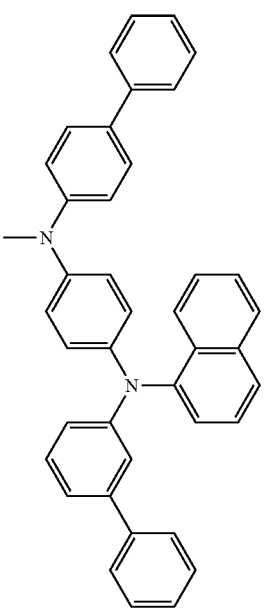
158
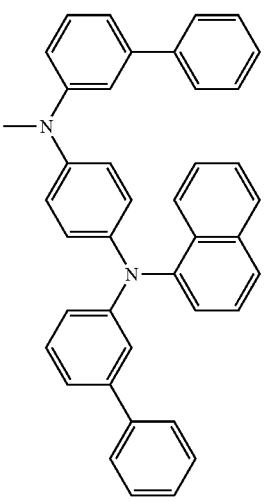
159
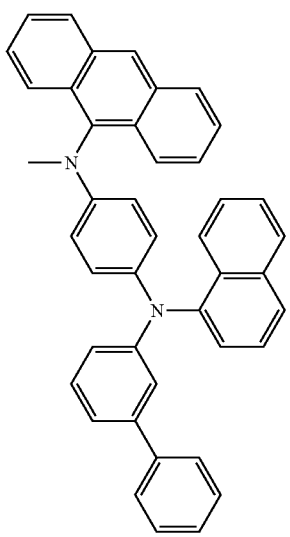

160
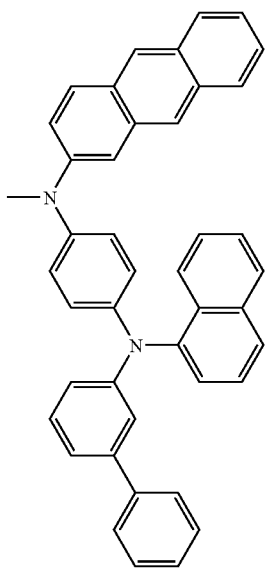
161
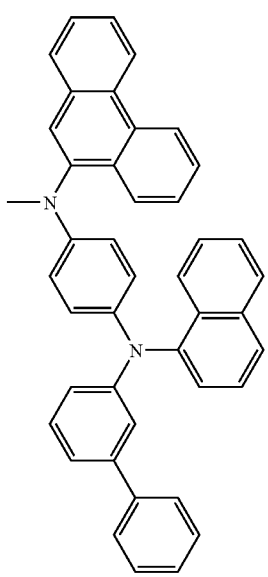
162
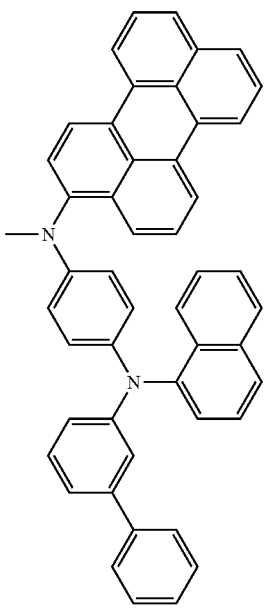
163
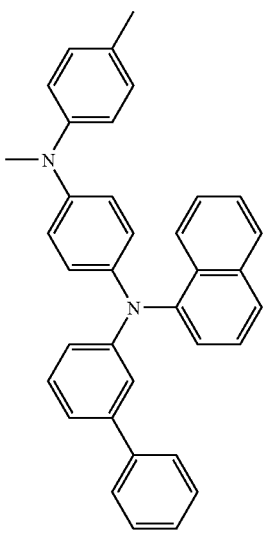
164
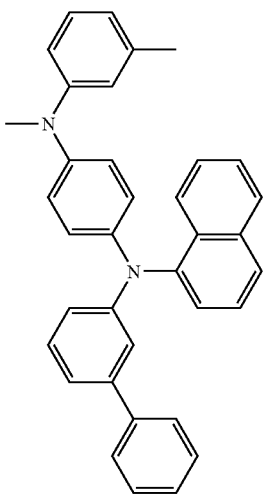

335
-continued
165
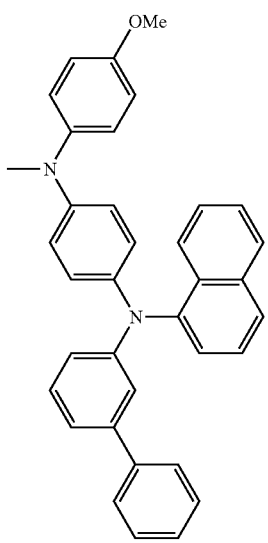
166
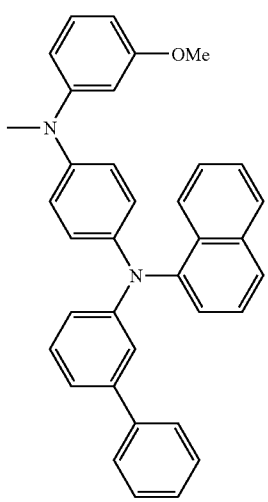
167
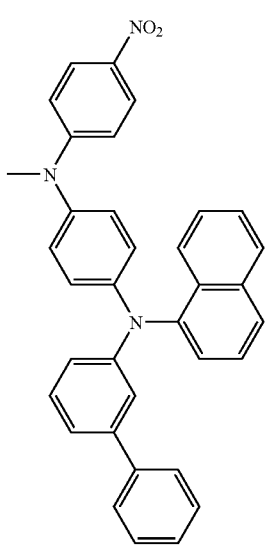
336
-continued
168
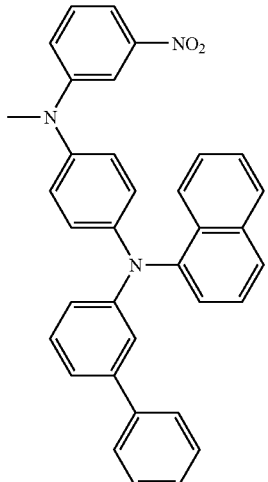
169
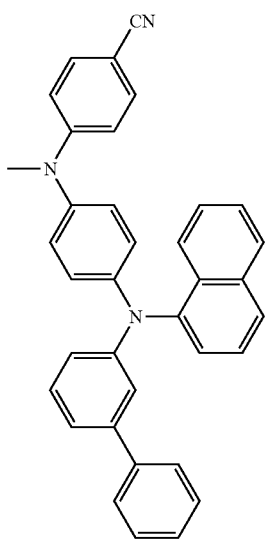
170
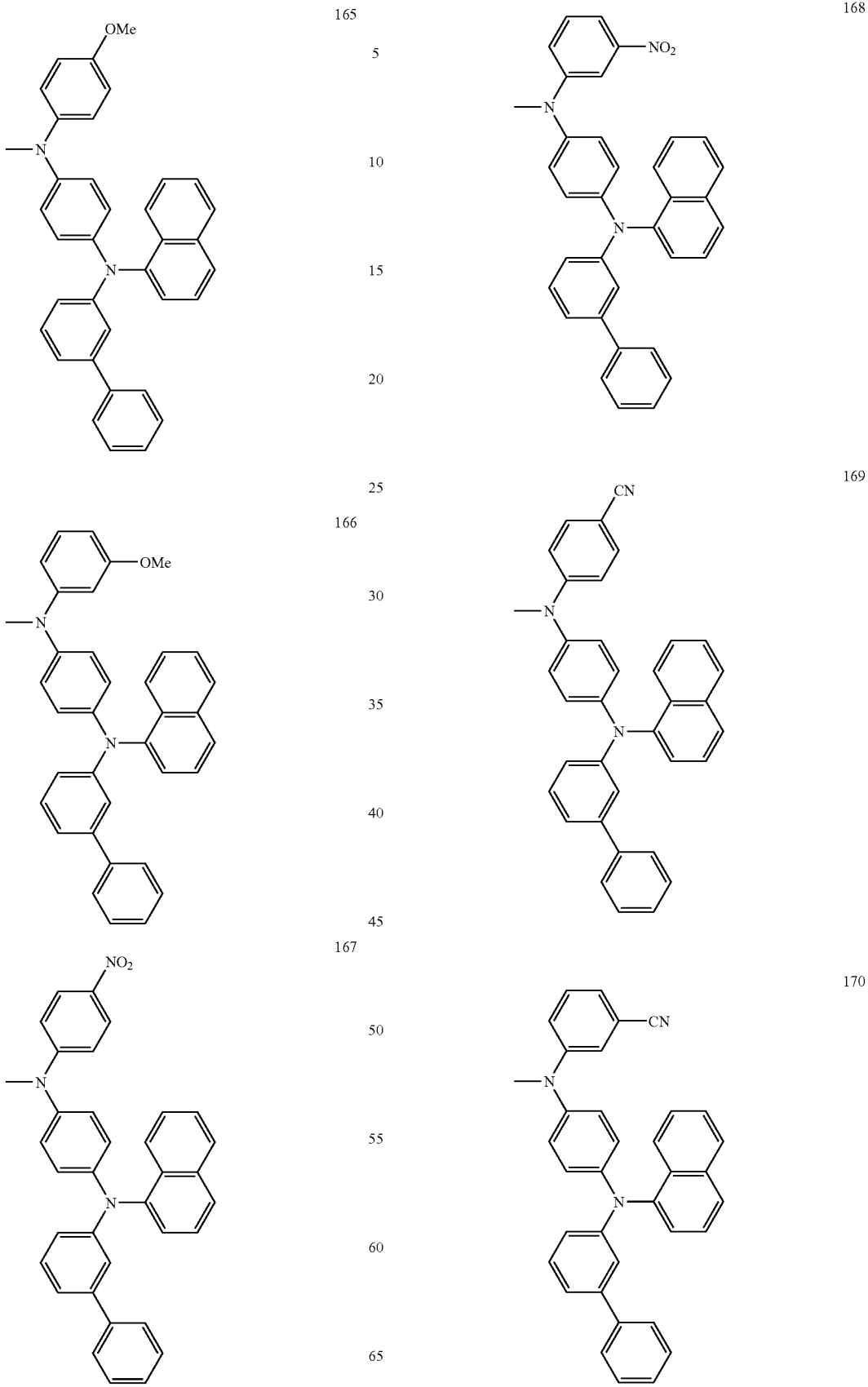

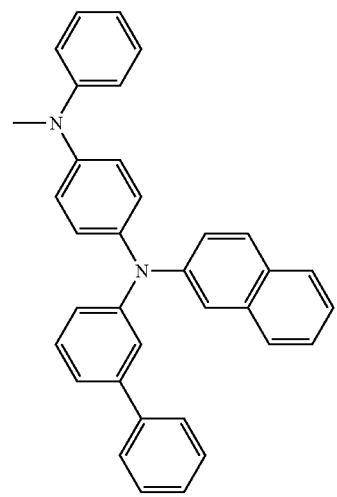
171
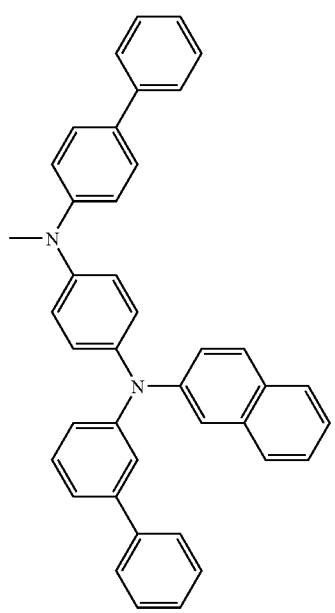
174
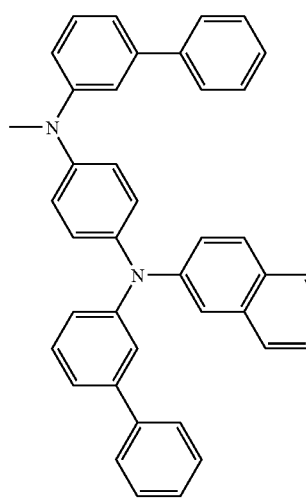
175
172
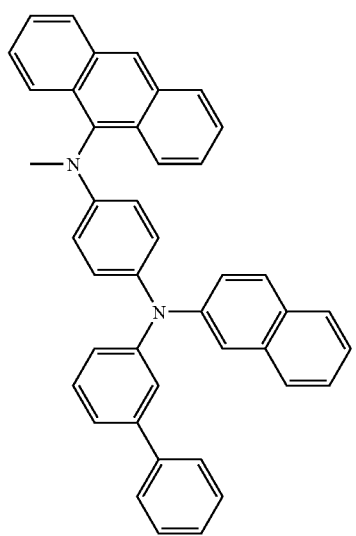
176
173

339
-continued
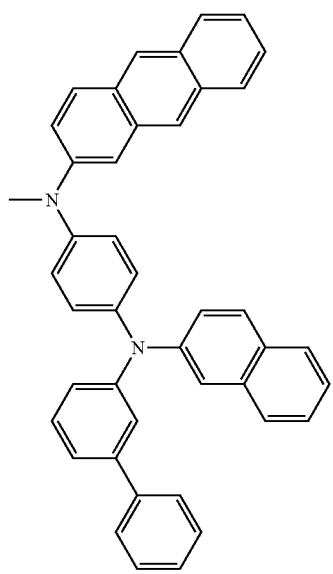
177
178
340
-continued
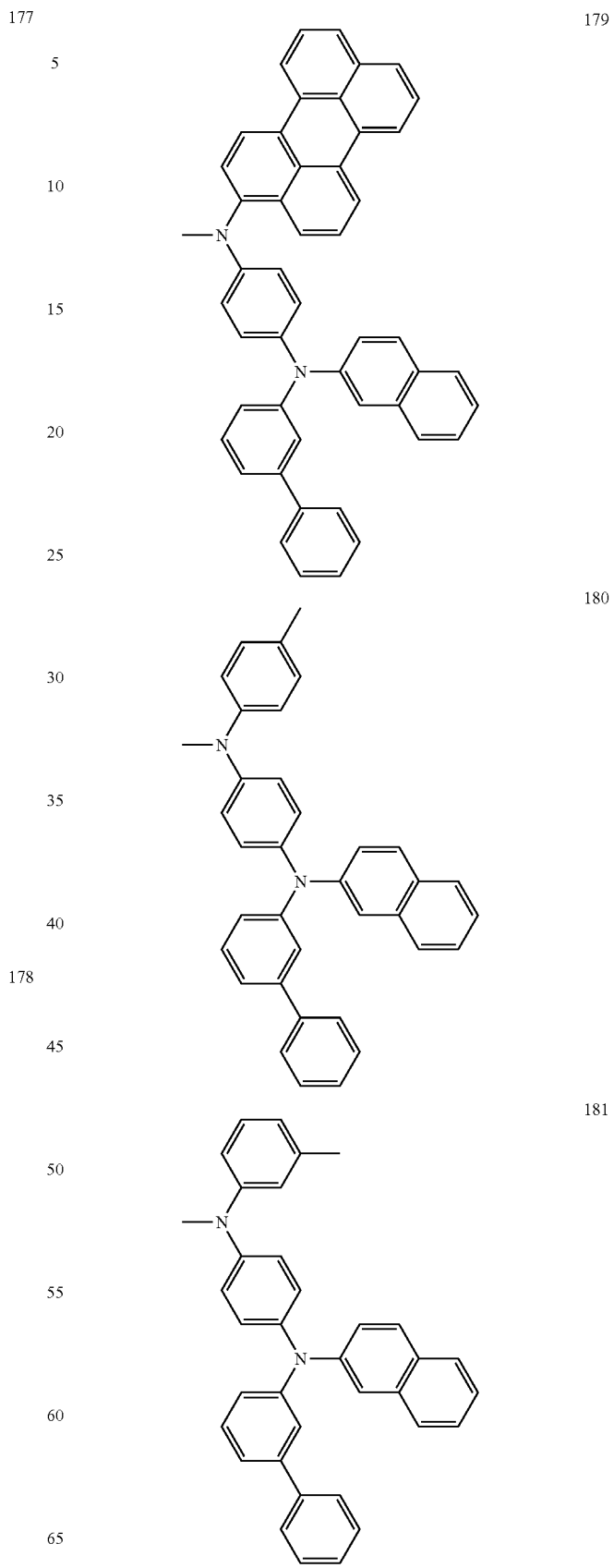
179
180
181

-continued
182
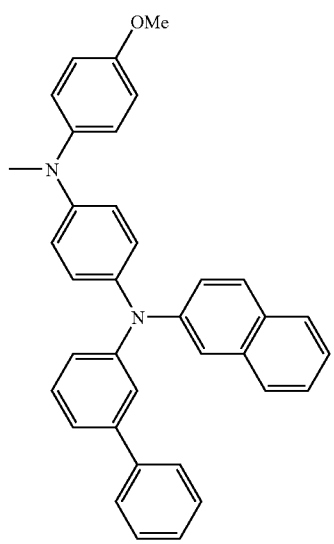
183
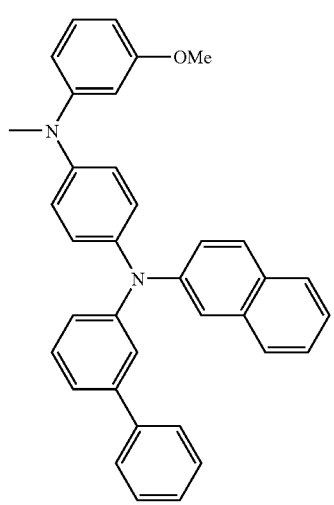
184
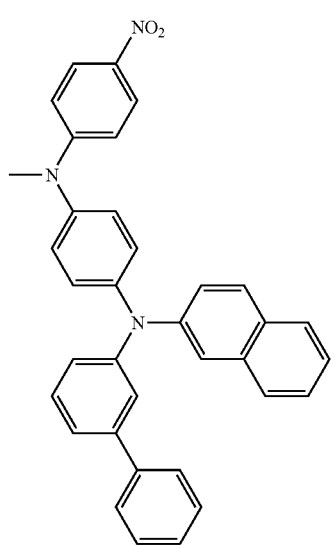
-continued
185
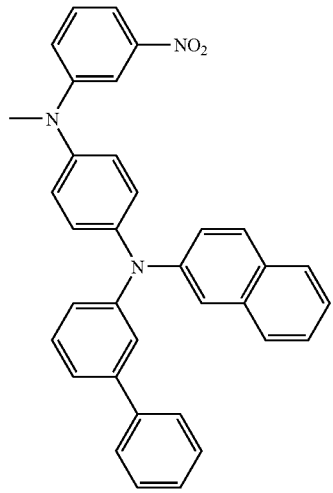
186
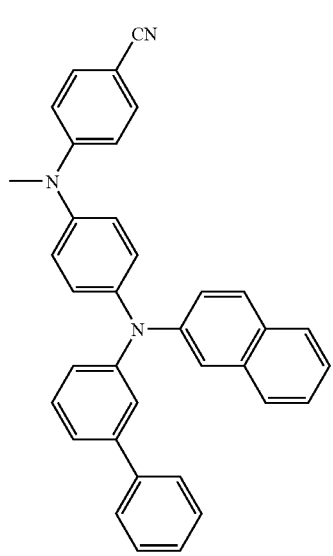
187
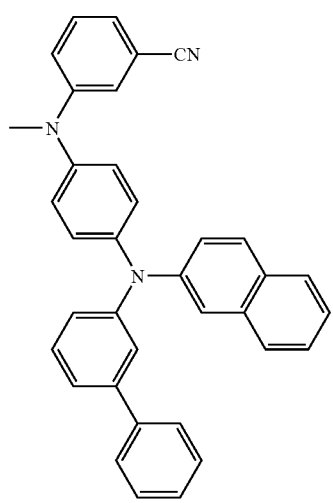

-continued
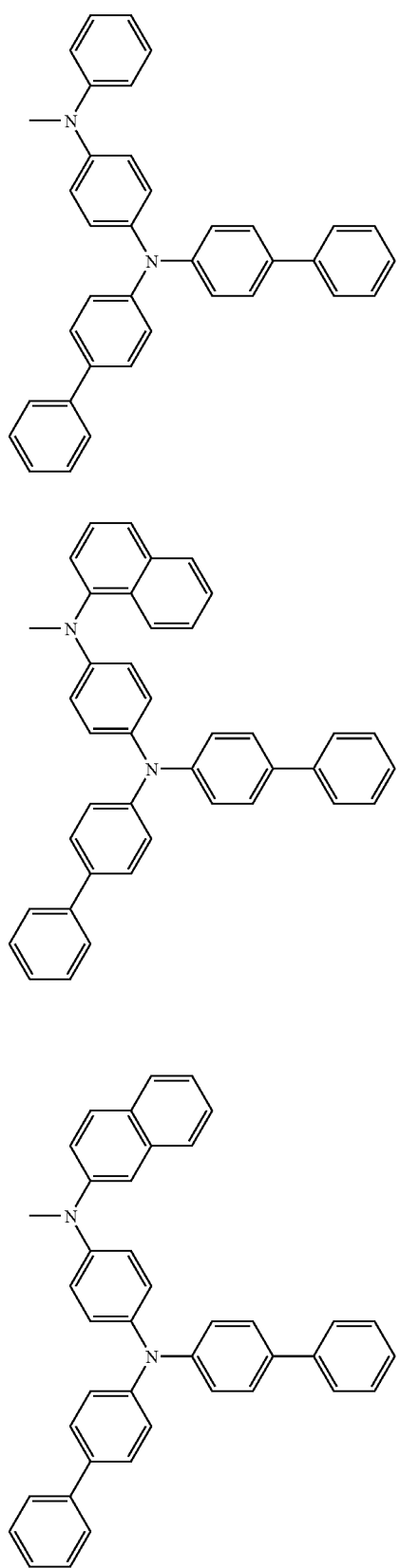
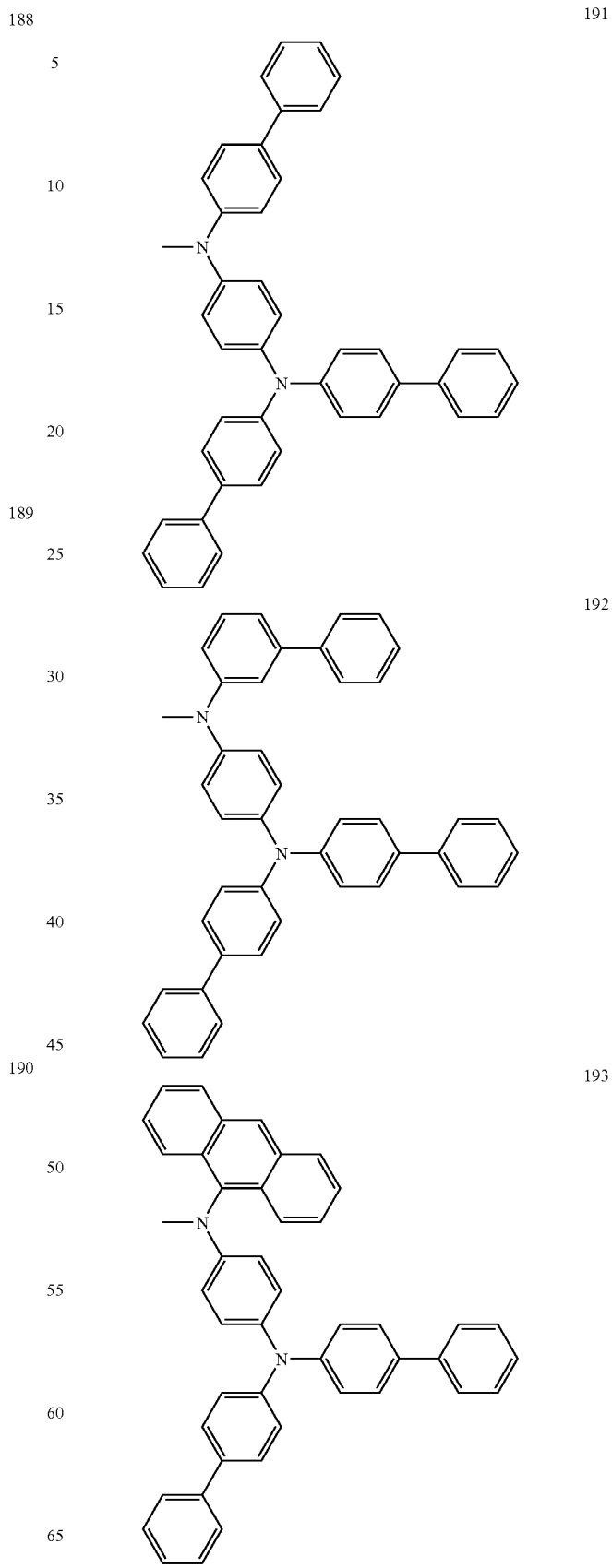

-continued
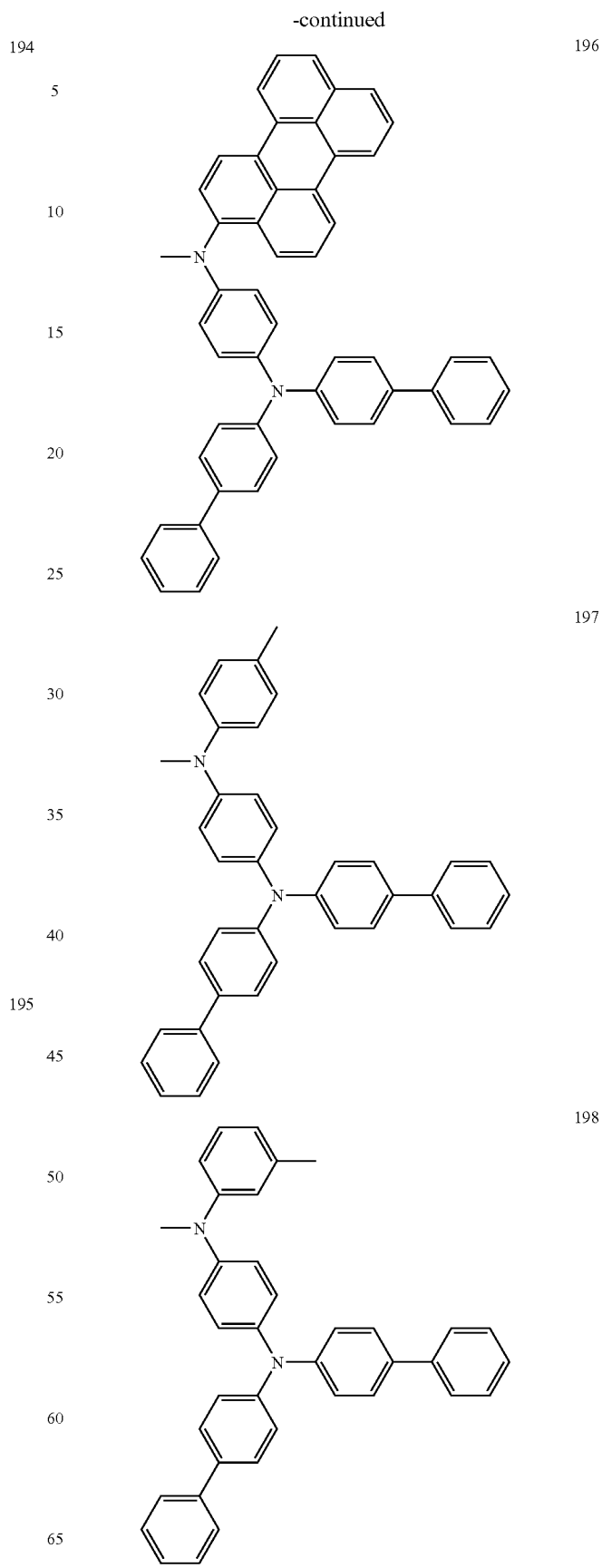

199
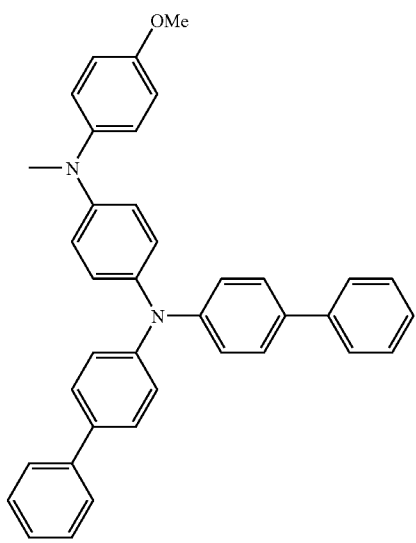
200
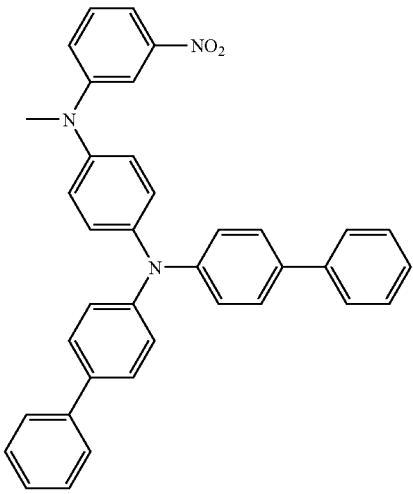
201
202
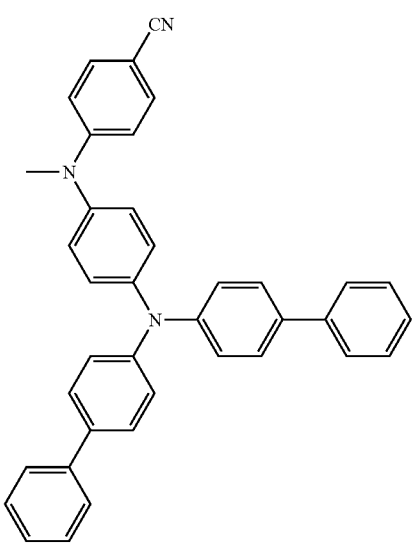
203
204
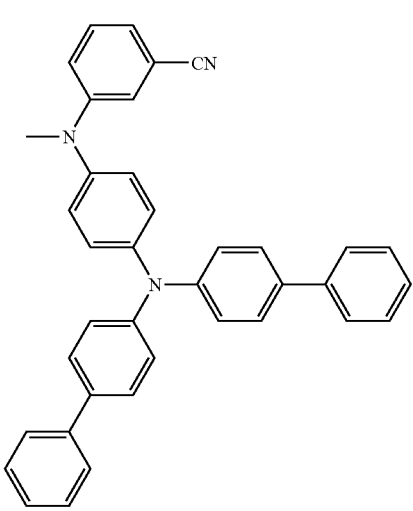

-continued
205
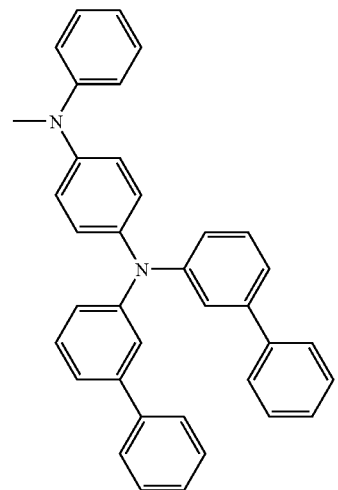
206
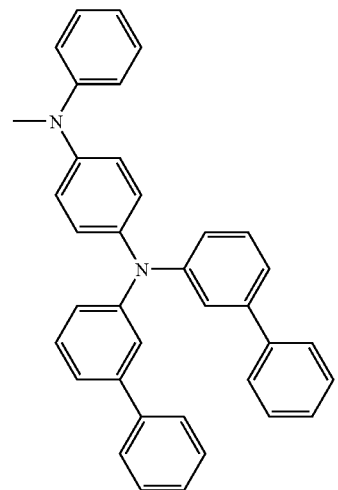
207
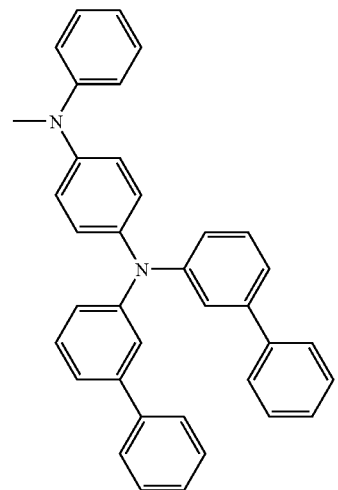
-continued
208
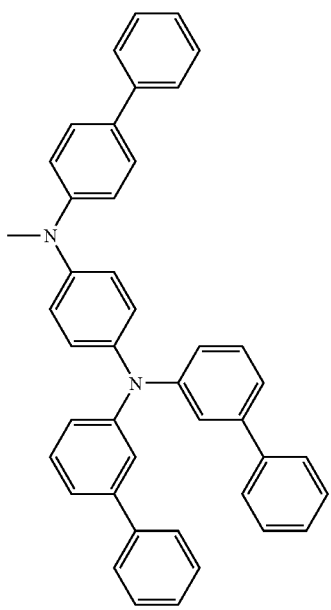
209
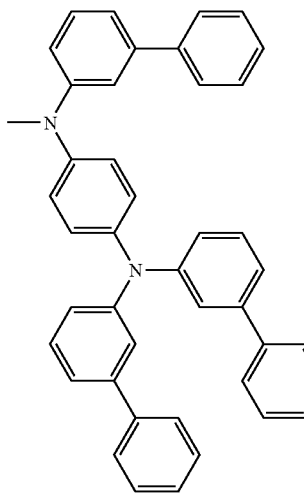
210
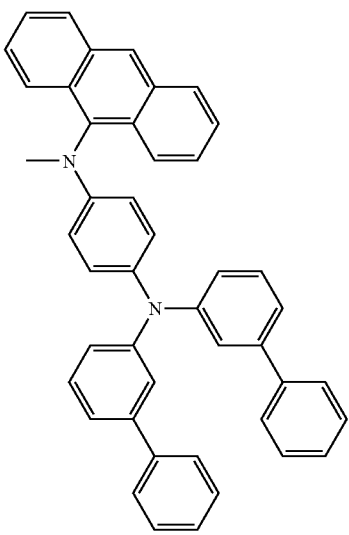

-continued
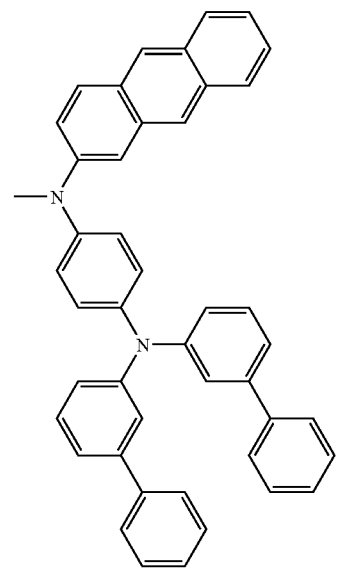
211
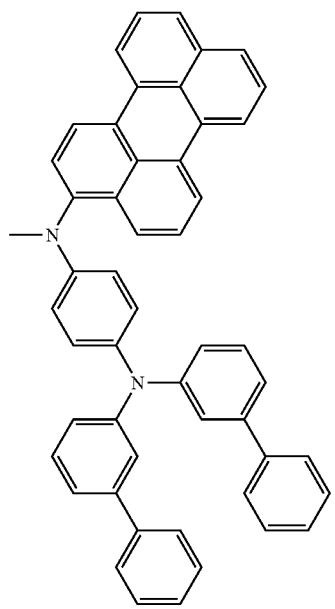
213
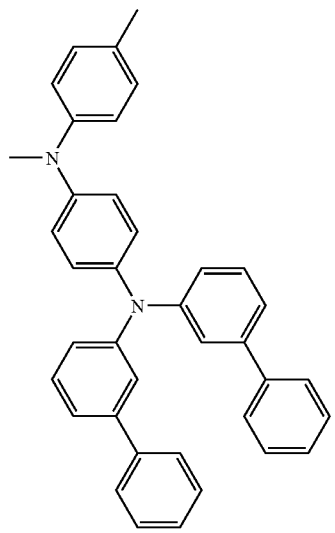
212
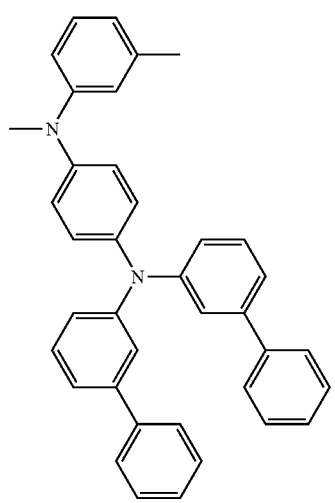
214
215

-continued
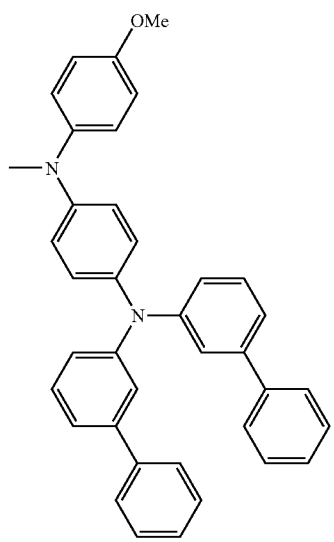
216
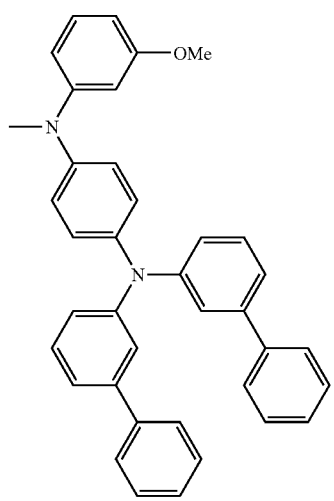
217
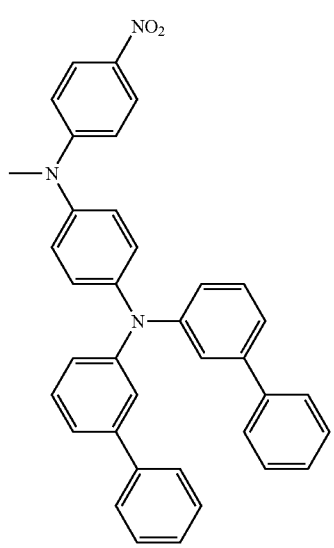
218
-continued
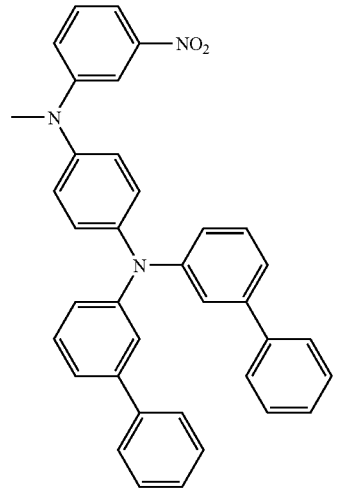
219
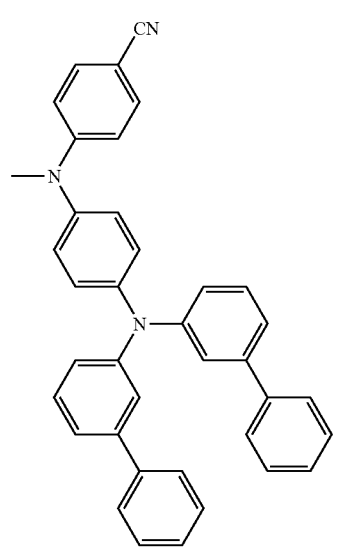
220
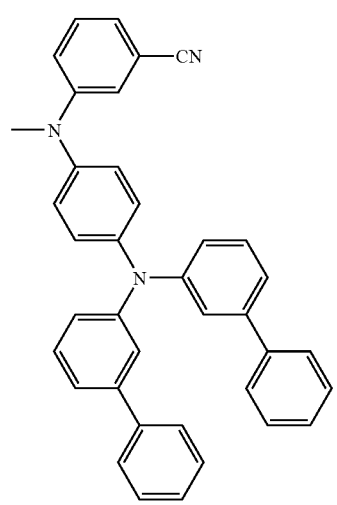
221

-continued
222
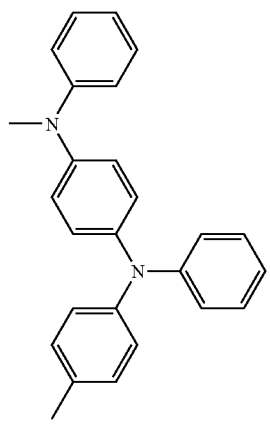
223
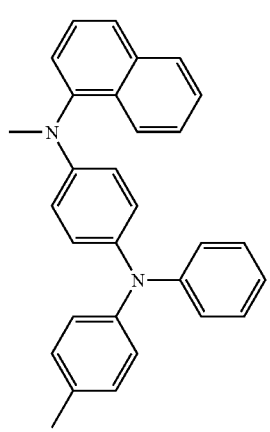
224
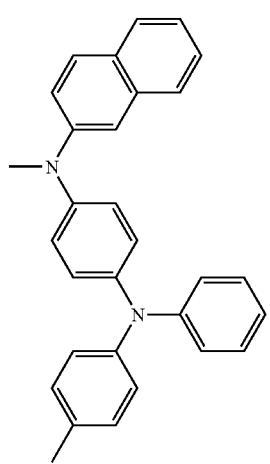
-continued
225
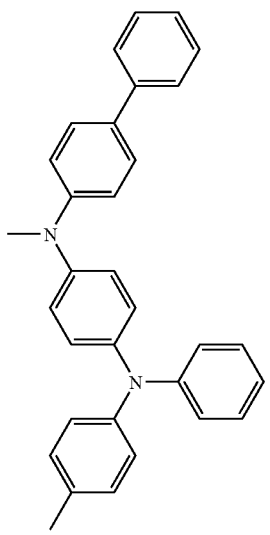
226
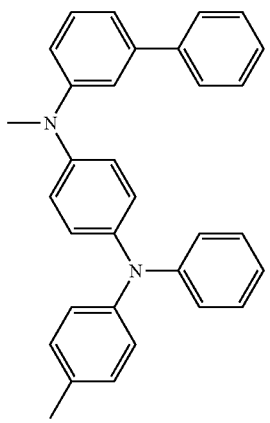
227
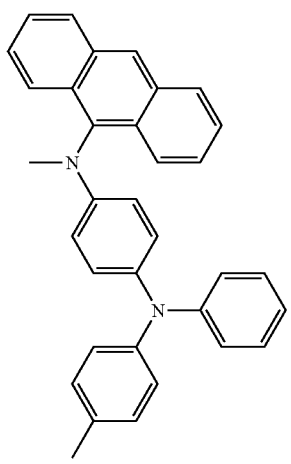

-continued

228

229

230

-continued

231

232

233

-continued
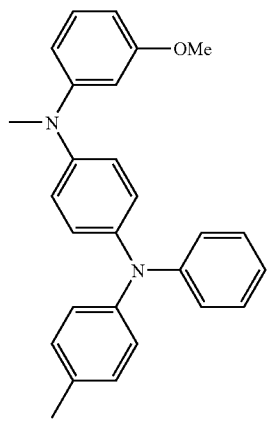
234
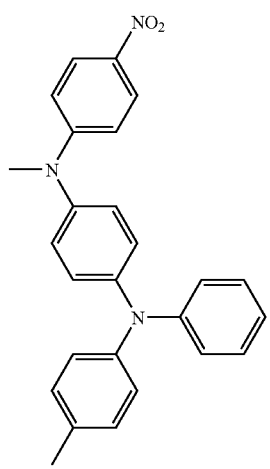
235
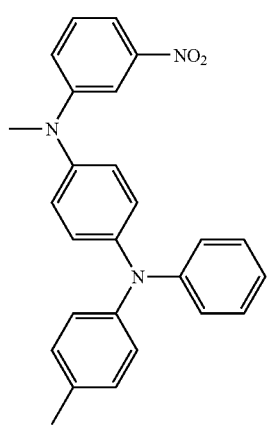
236
-continued
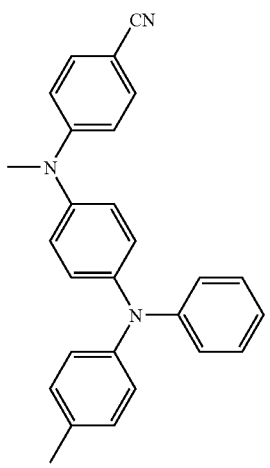
237
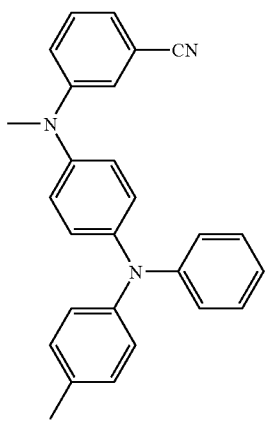
238
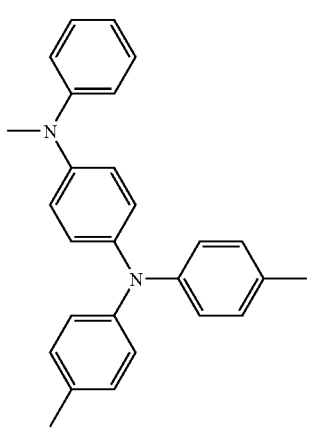
239

-continued
240
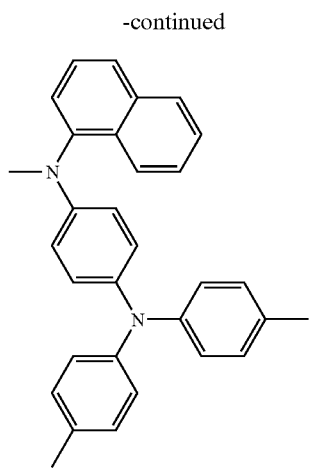
241
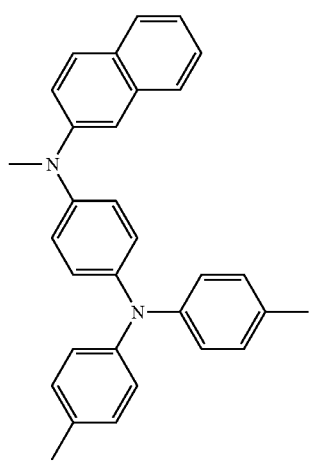
242
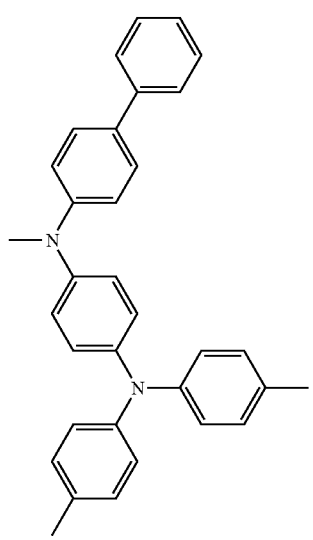
-continued
243
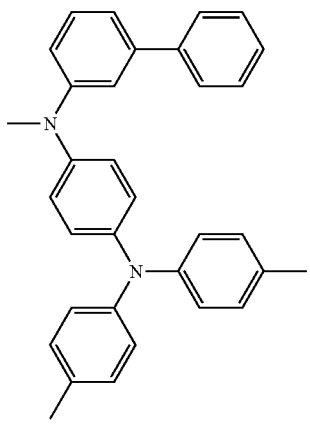
244
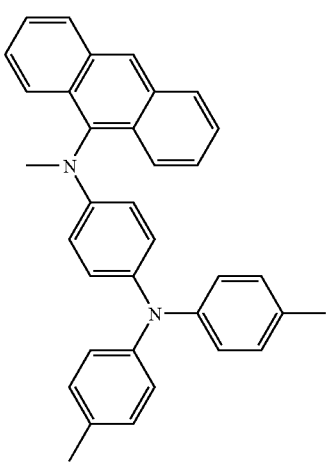
245
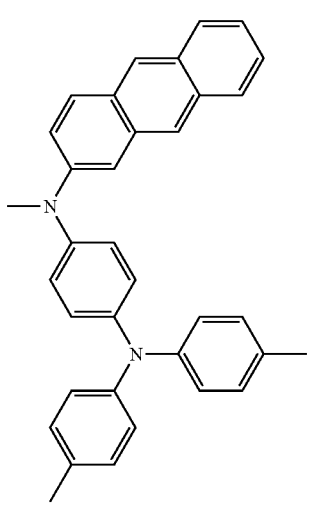

-continued
246
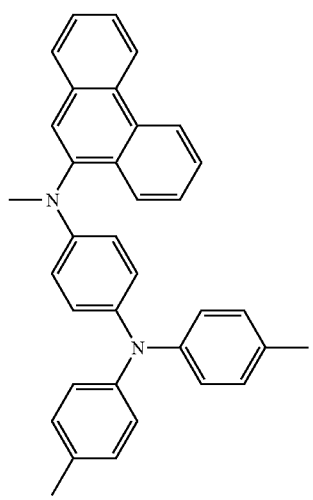
247
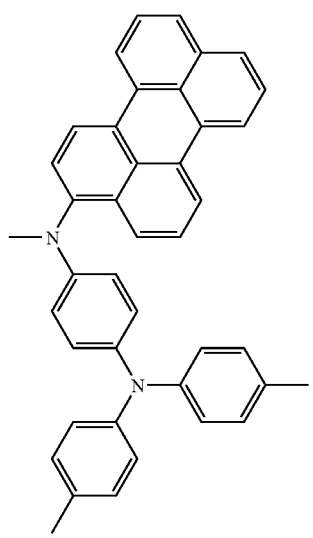
248
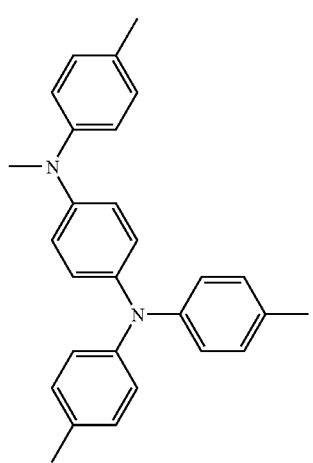
-continued
249
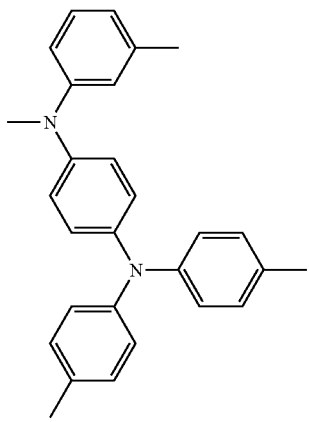
250
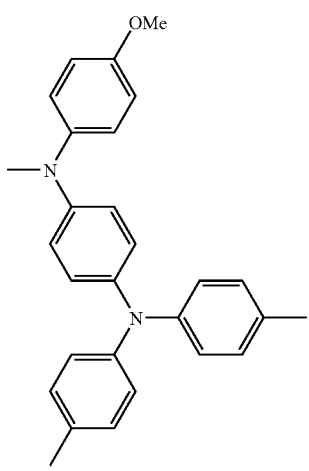
251
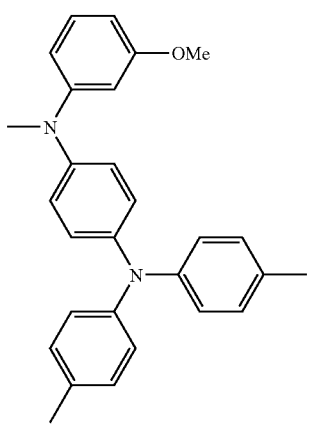

-continued
252
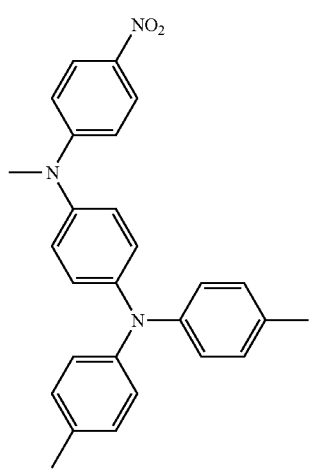
253
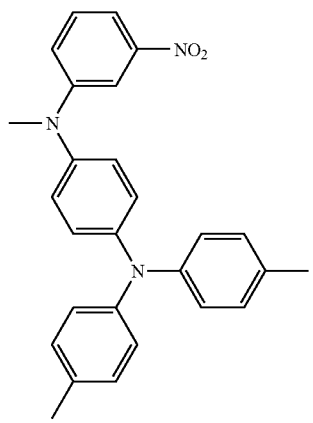
254
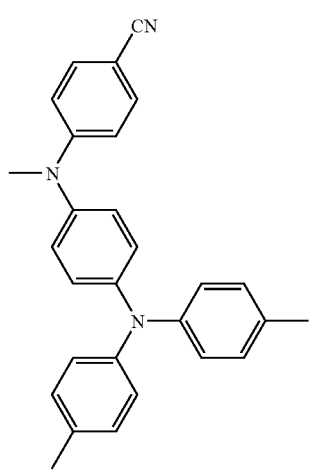
-continued
255
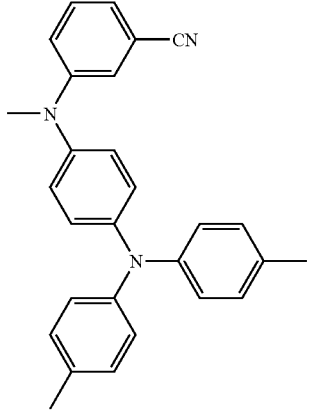
256
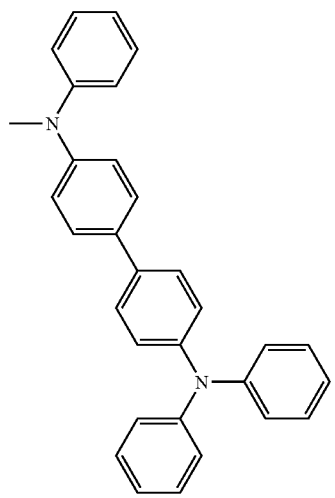
257
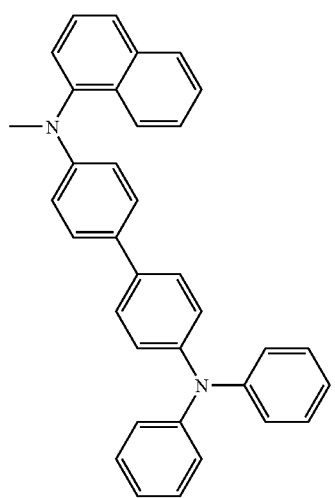

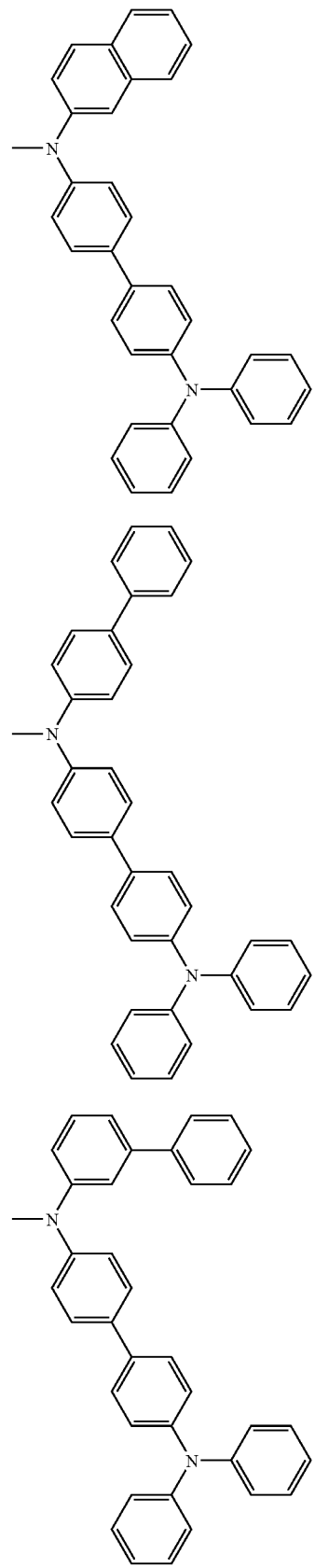
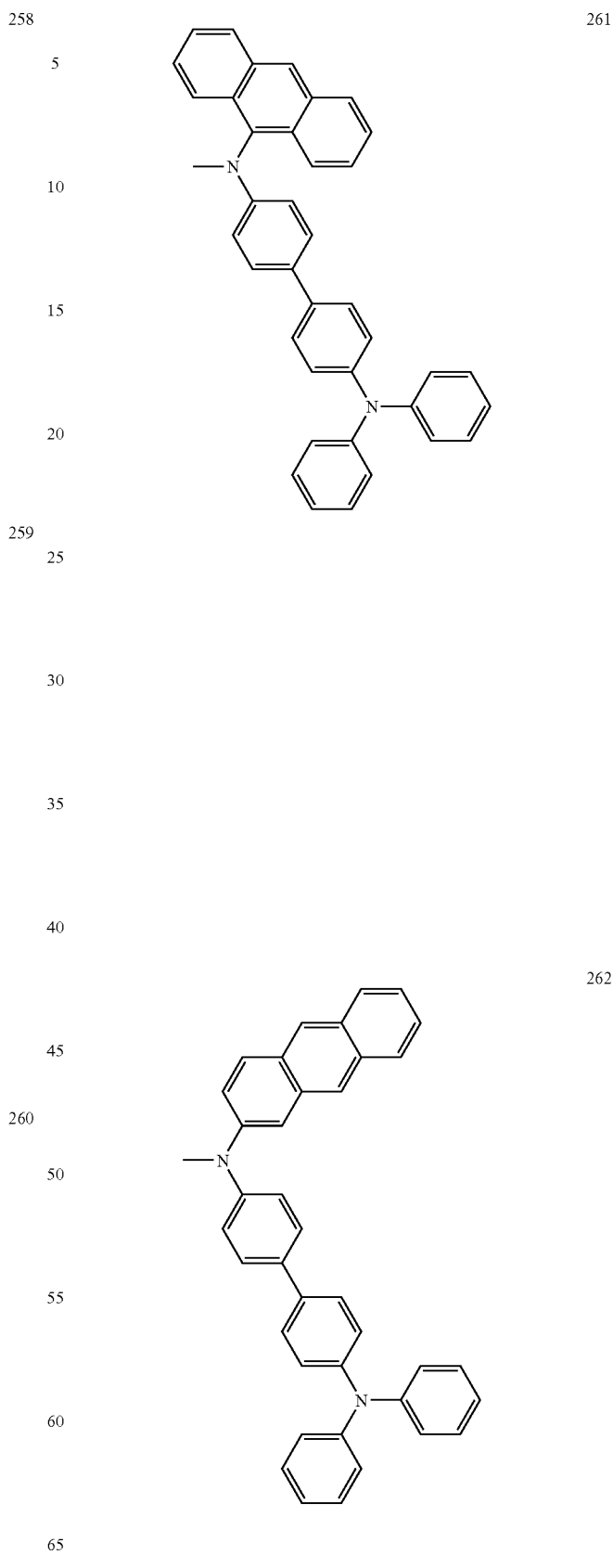

-continued
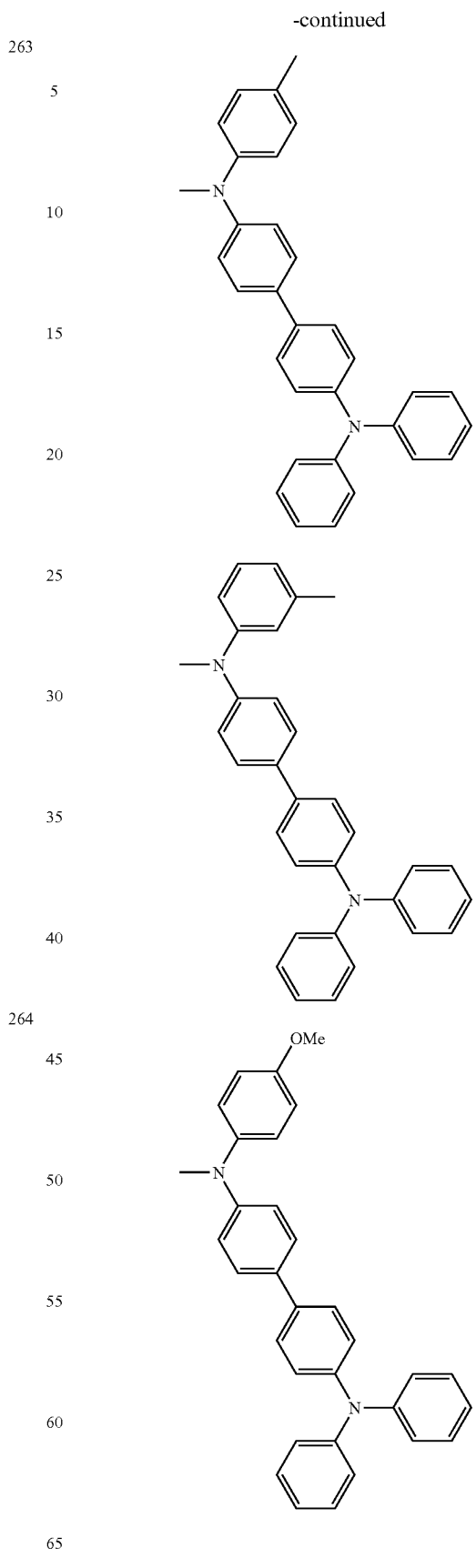

371  372
-continued  -continued
268
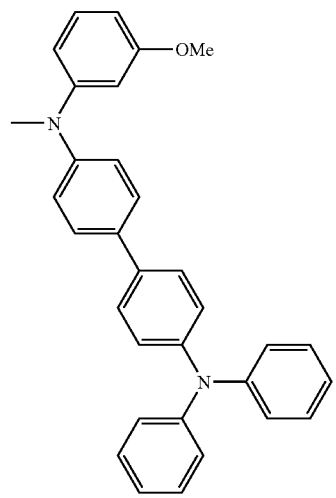
271
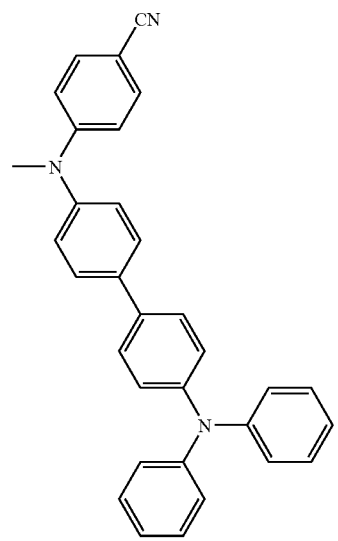
269
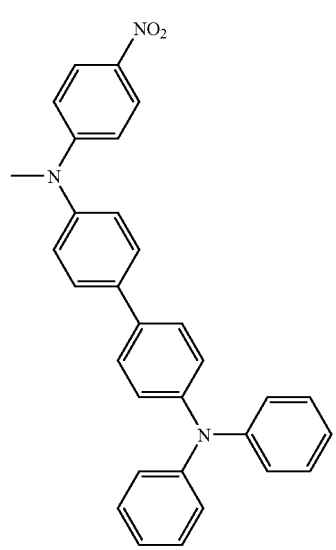
272
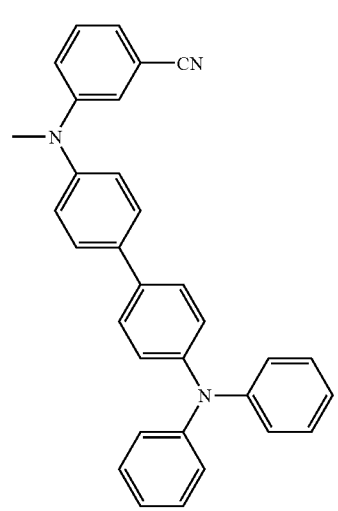
270
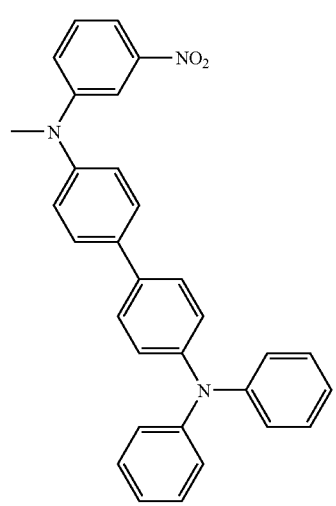
273
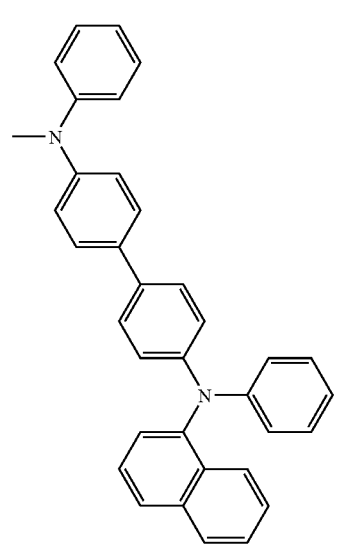

-continued
274
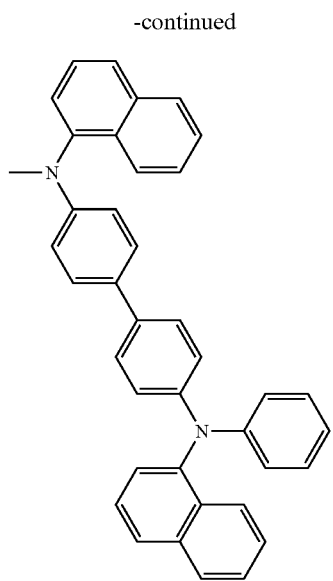
275
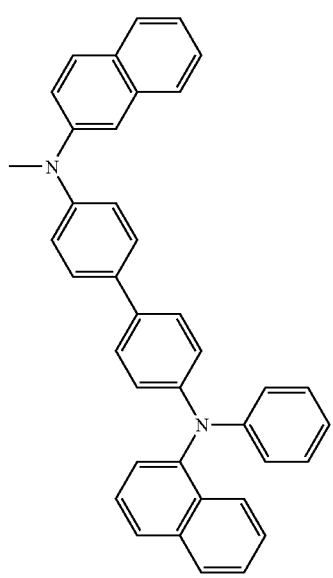
-continued
276
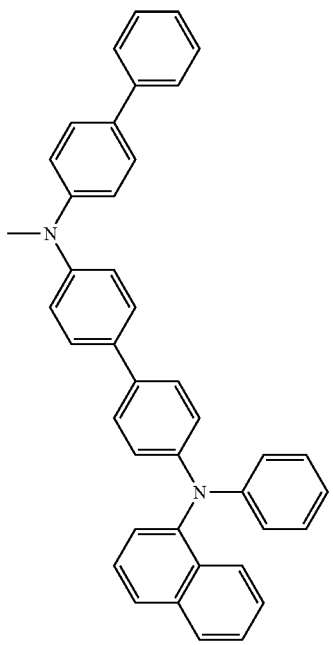
277
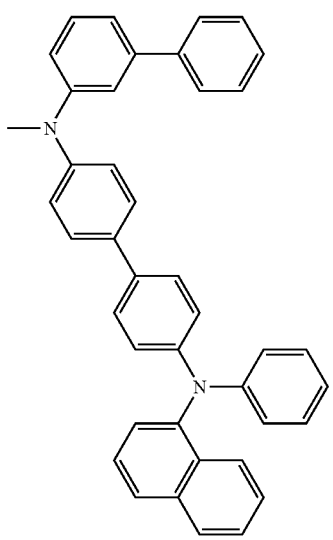

-continued
278
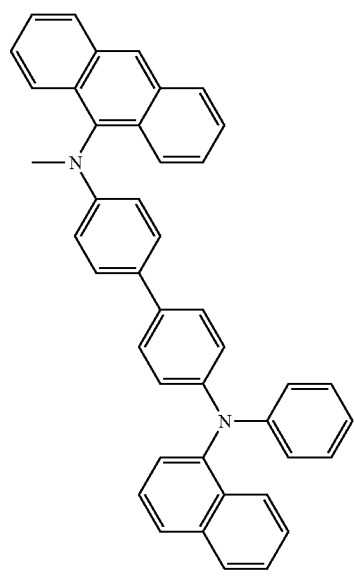
279
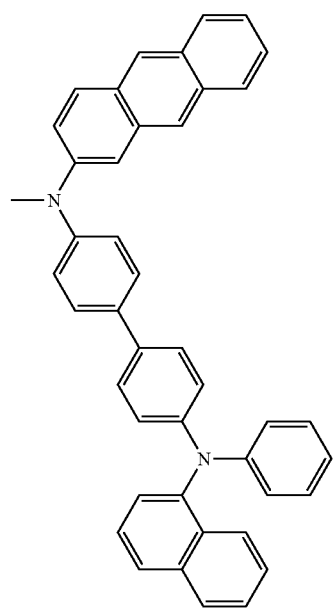
-continued
280
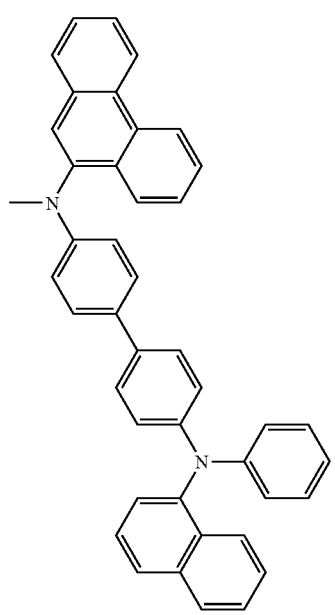
281
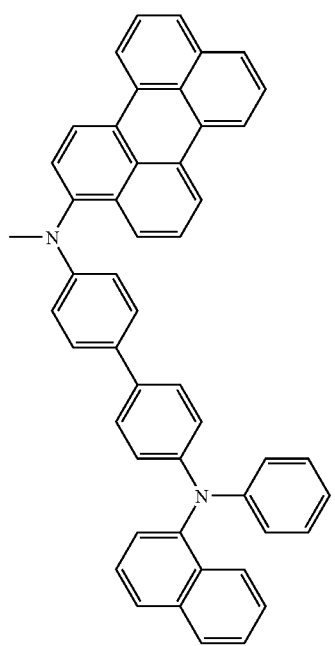

-continued
282
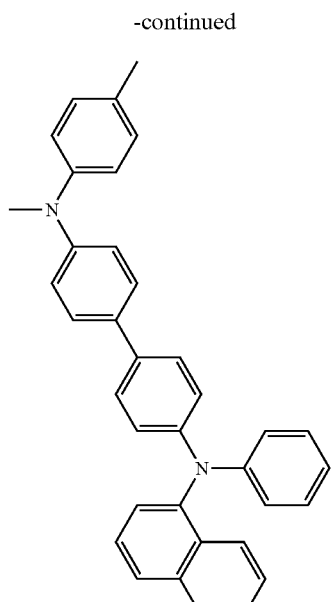
283
284
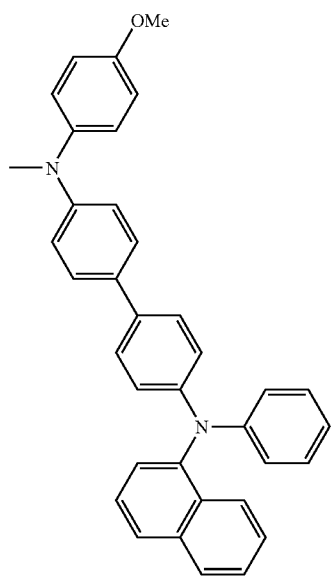
285
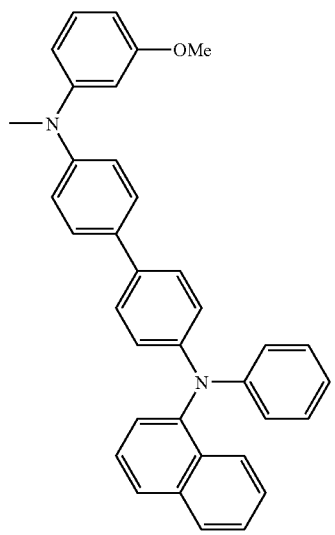

286
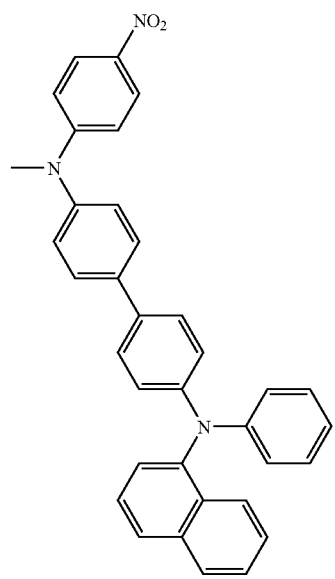
287
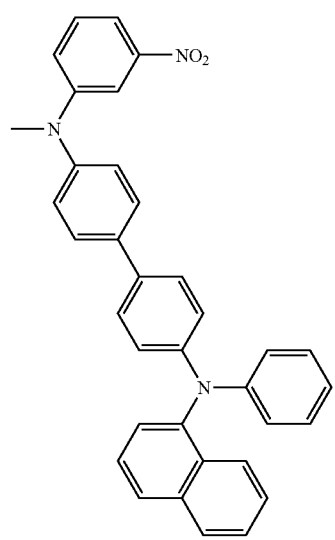
288
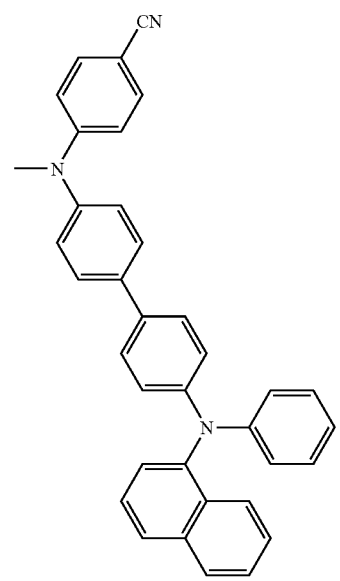
289
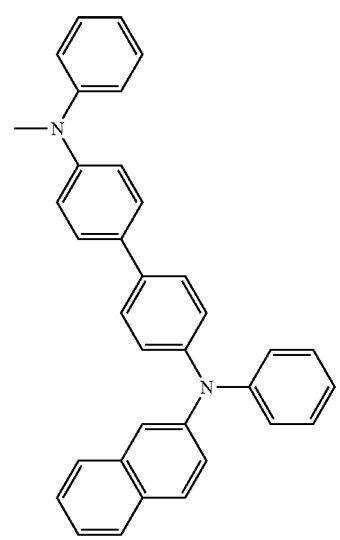
290

-continued
291
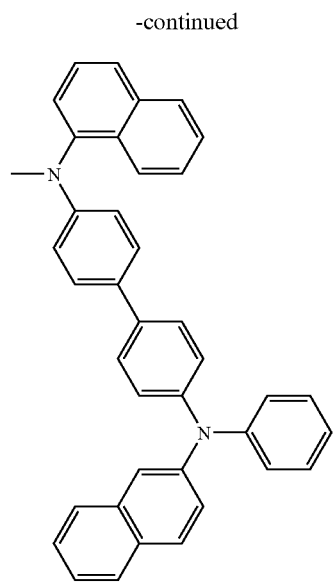
292
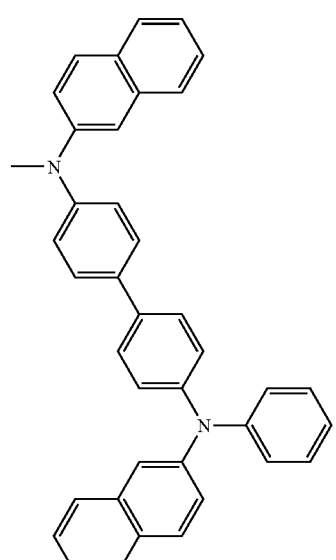
-continued
293
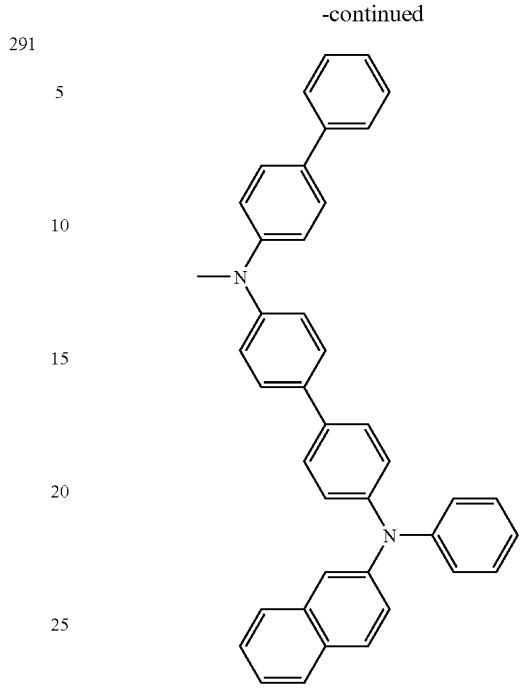
294
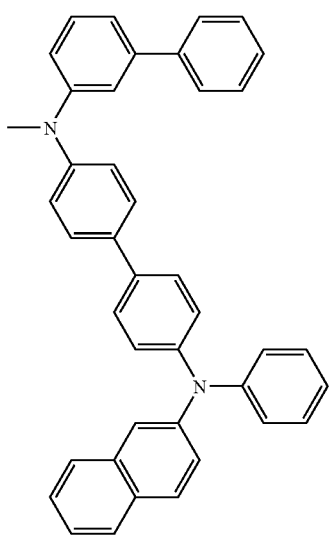

295
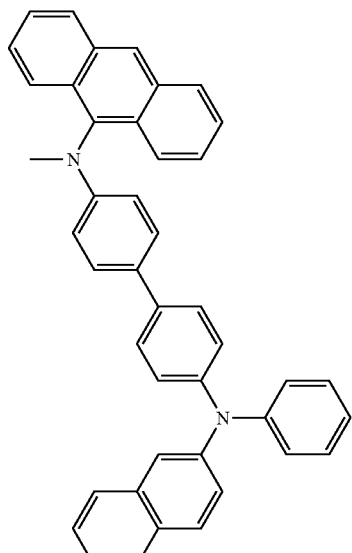
296
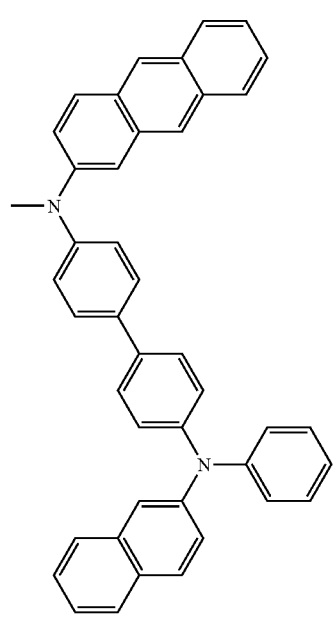
297
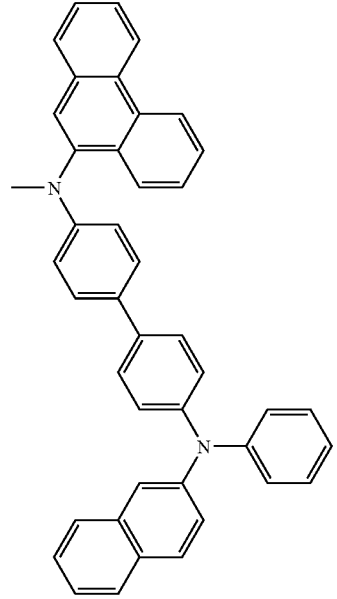
298
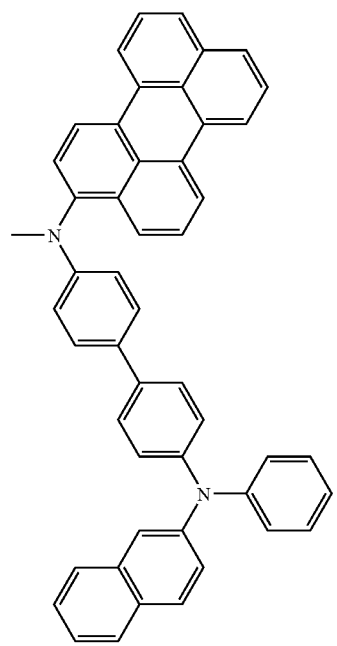

299
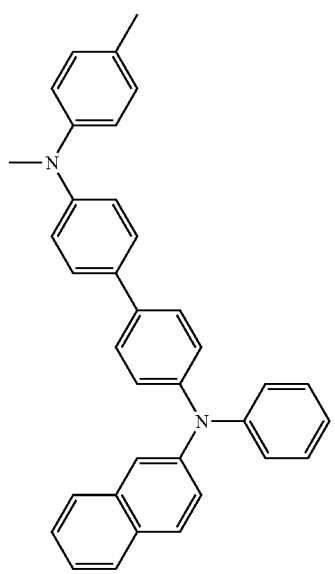
301
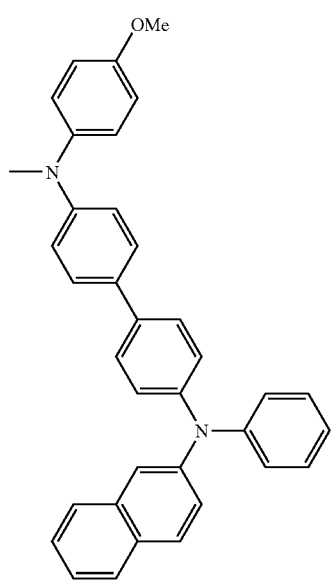
300
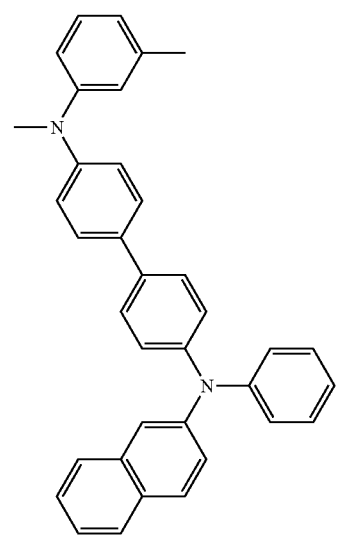
302
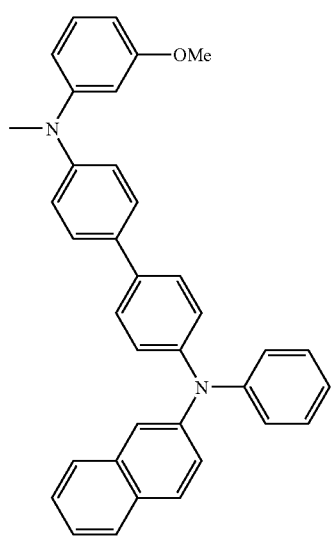

-continued
303
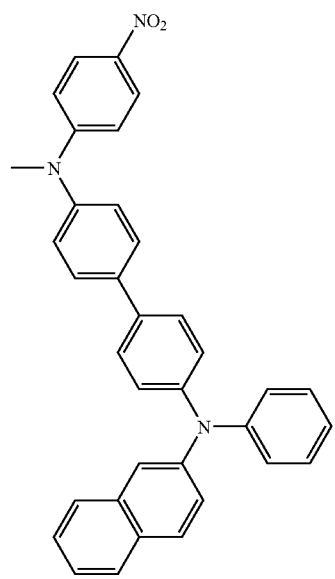
304
305
-continued
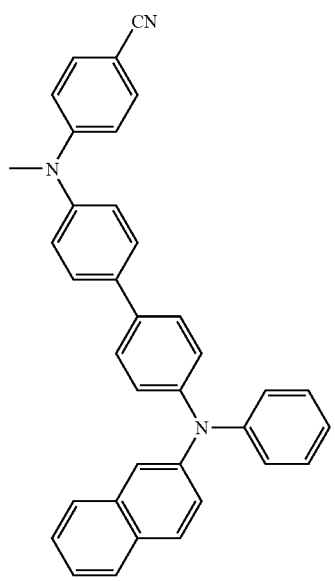
306

389
-continued
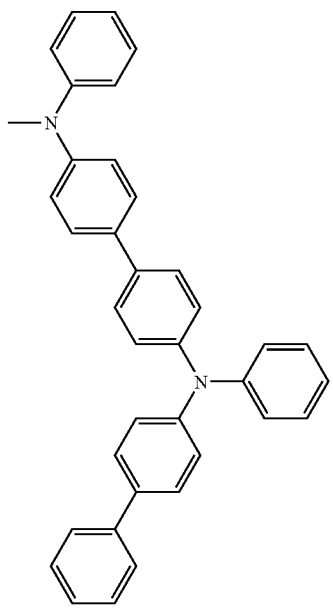
307
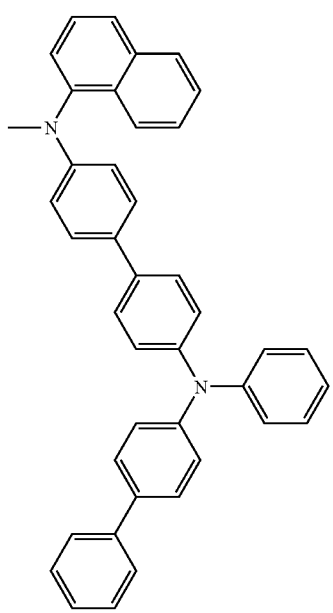
308
390
-continued
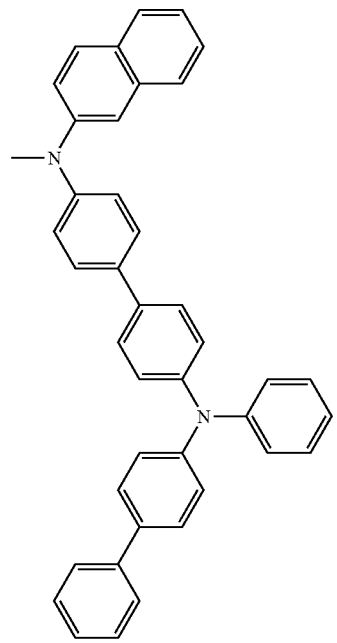
309
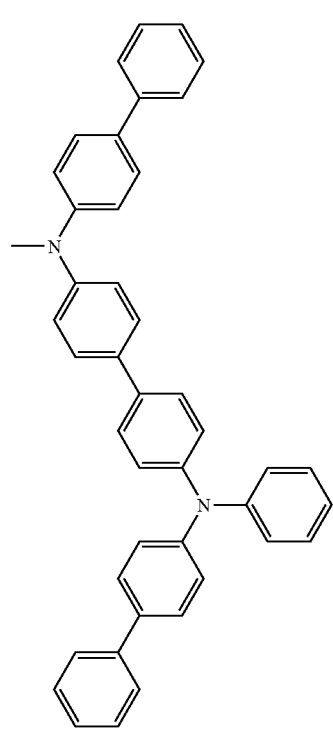
310

-continued
391
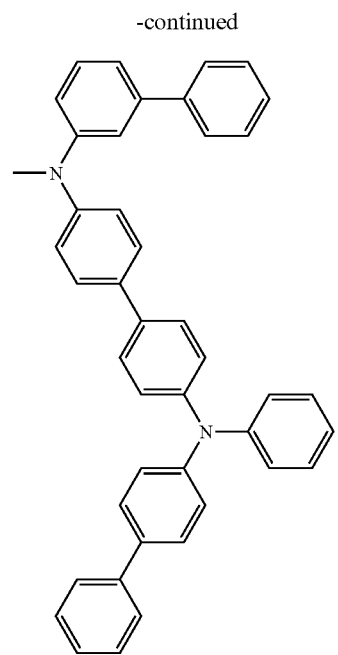
311
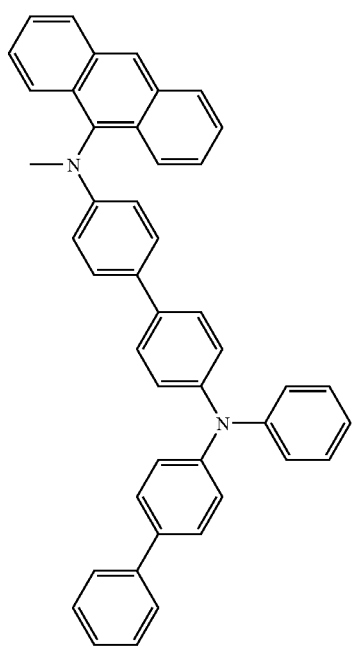
312
392
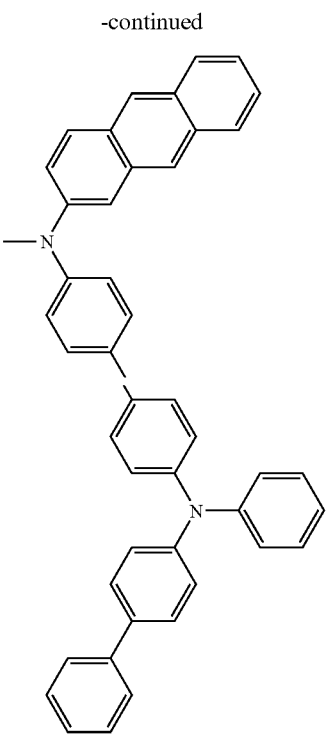
313
314

393 394
-continued
315
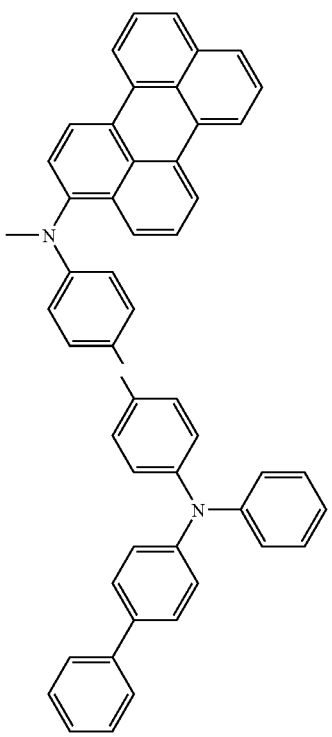
317
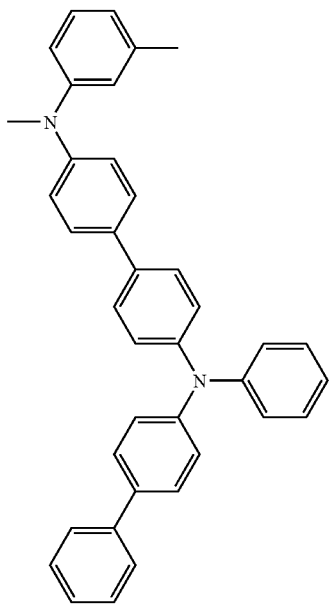
316
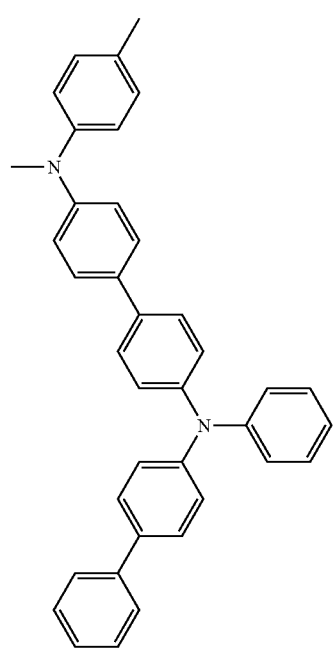
318
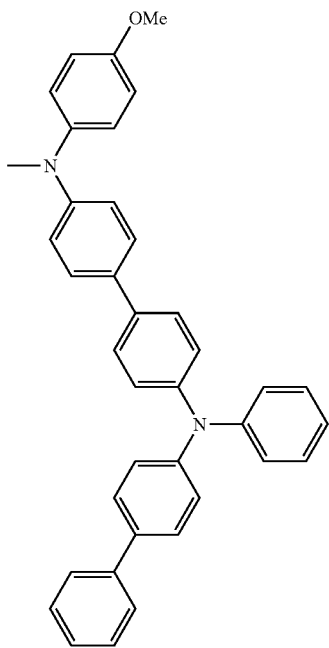

-continued
319
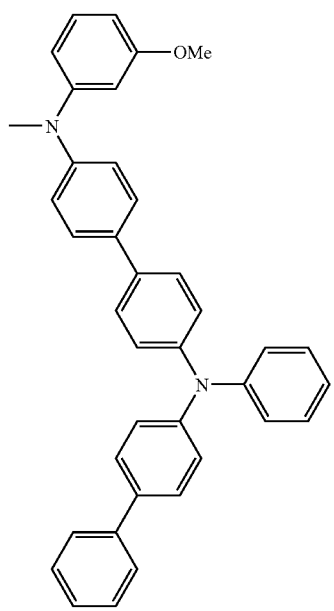
320
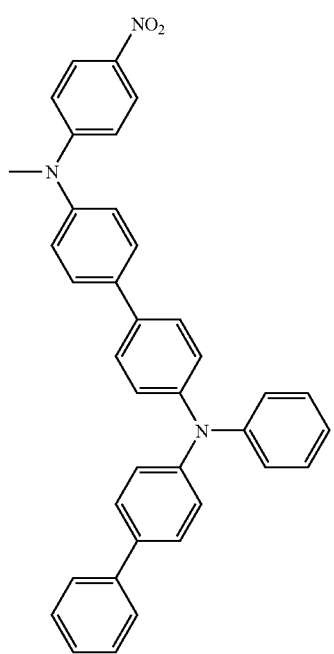
-continued
321
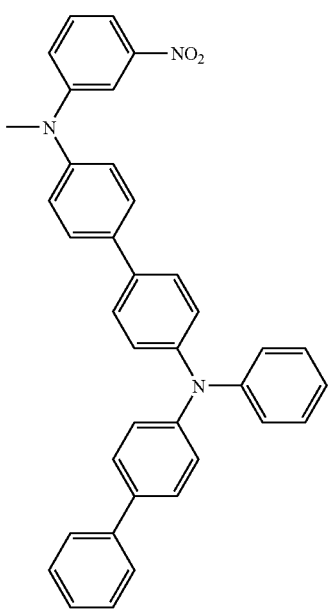
322
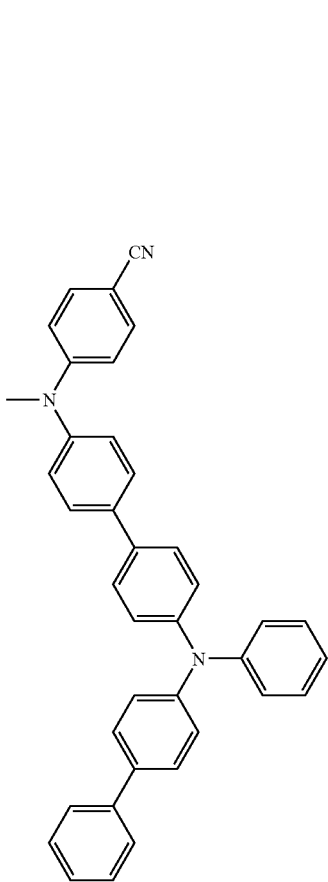

-continued
323
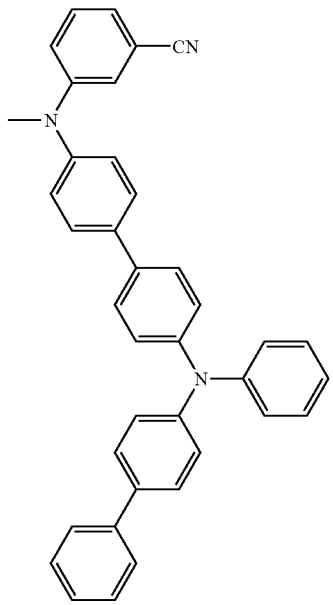
324
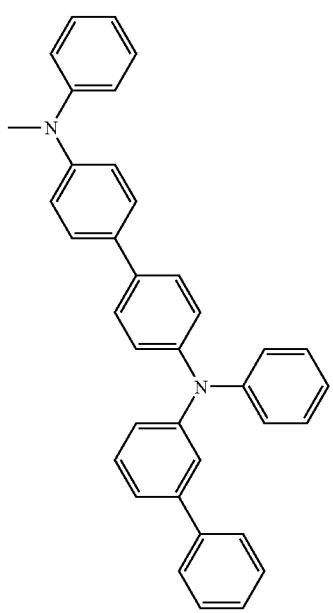
-continued
325
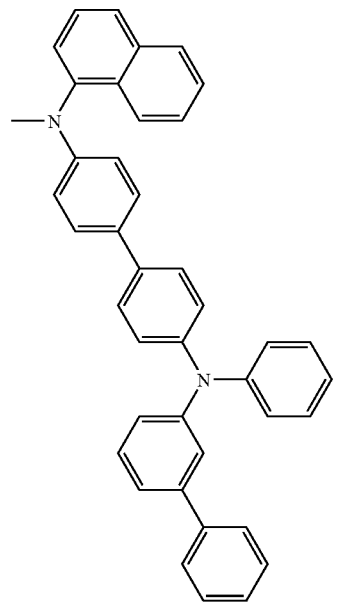
326
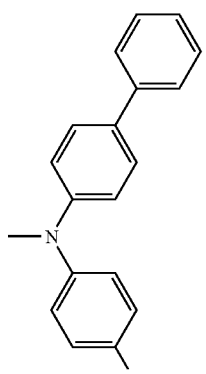
327

399
-continued
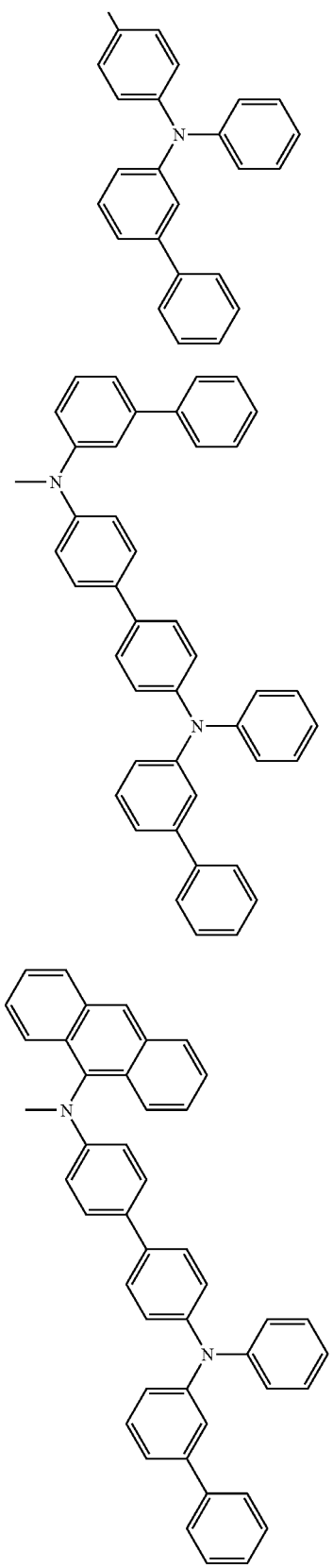
328
329
400
-continued
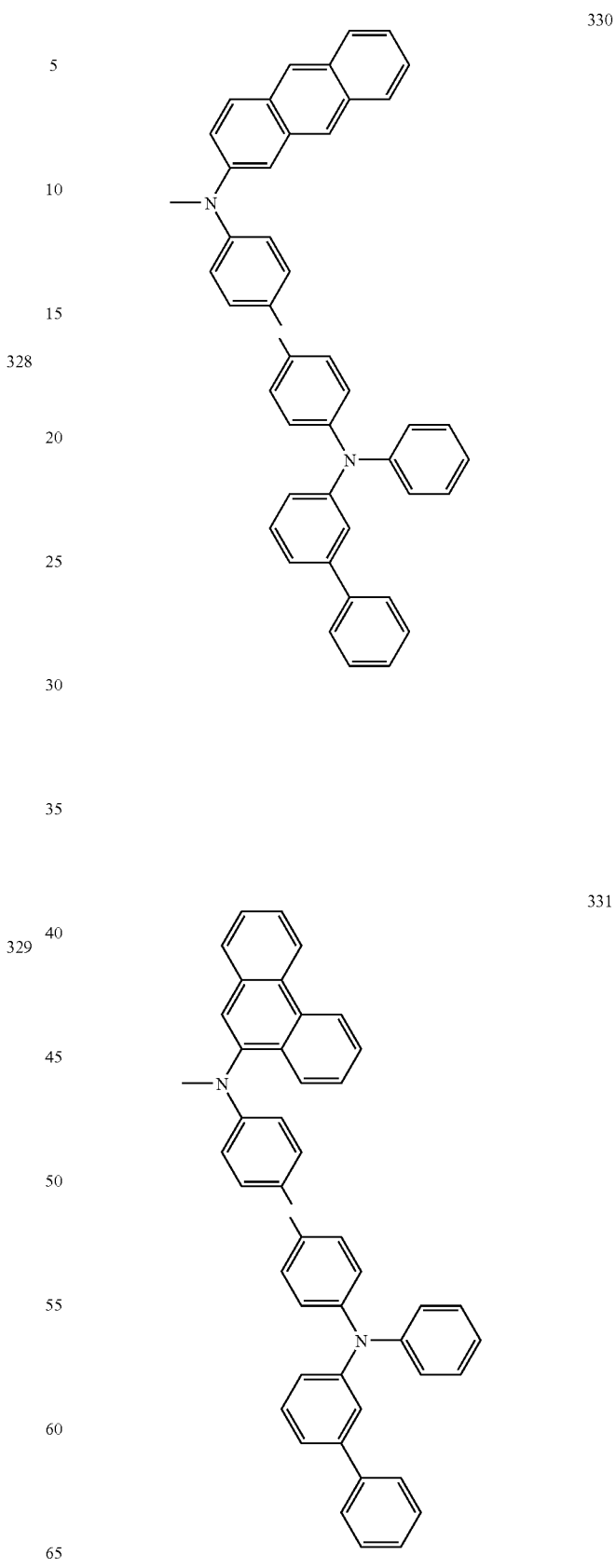
330
331

-continued
332
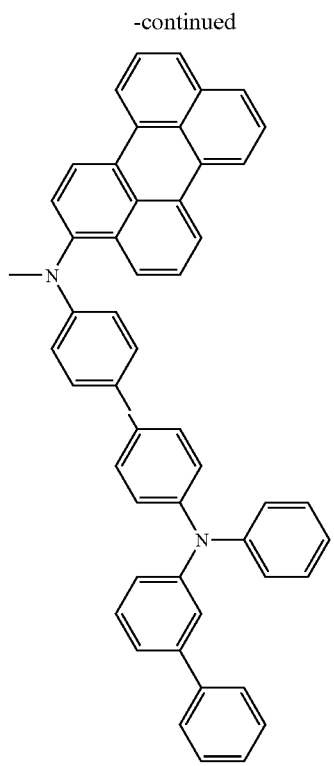
333
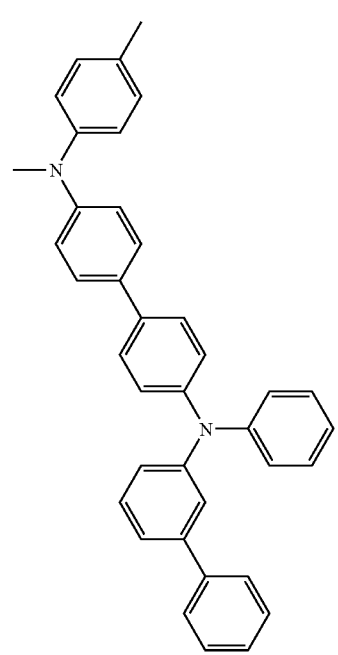
-continued
334
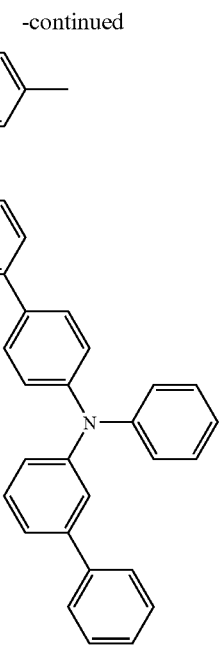
335
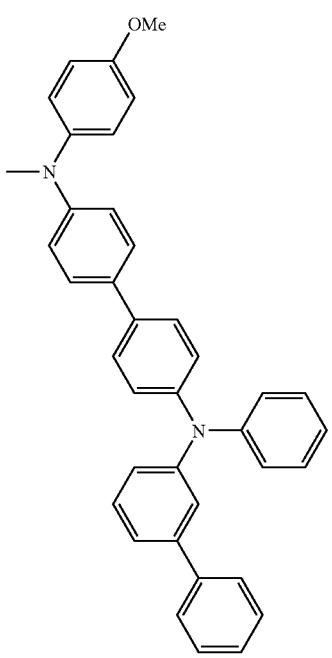

-continued
336
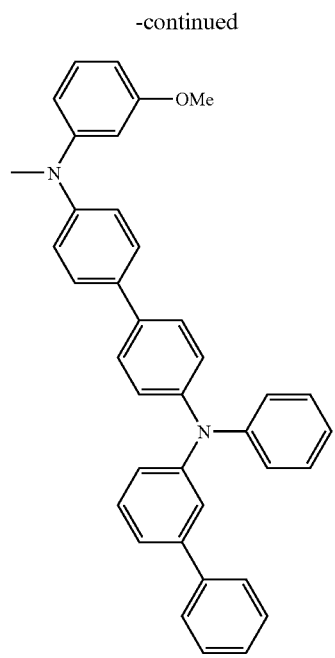
337
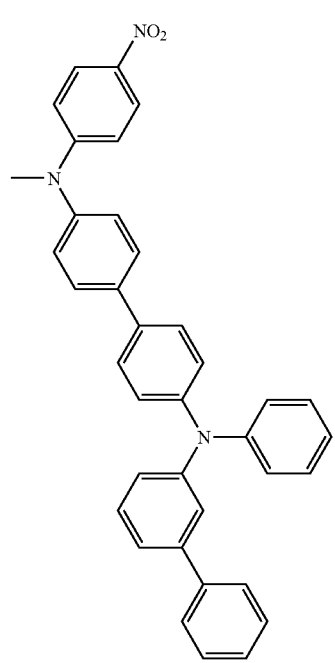
-continued
338
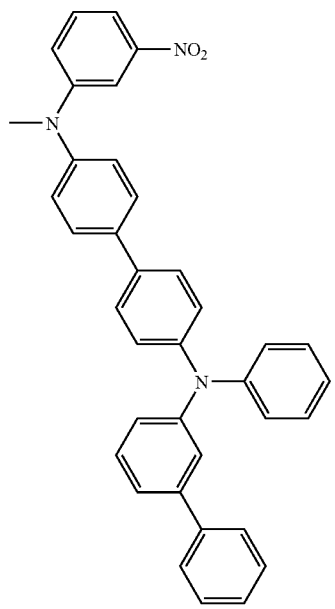
339
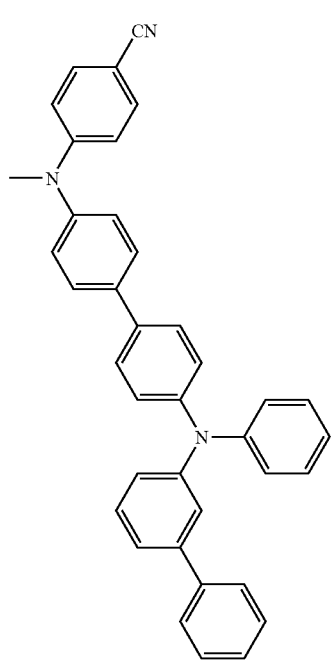

405
-continued
340
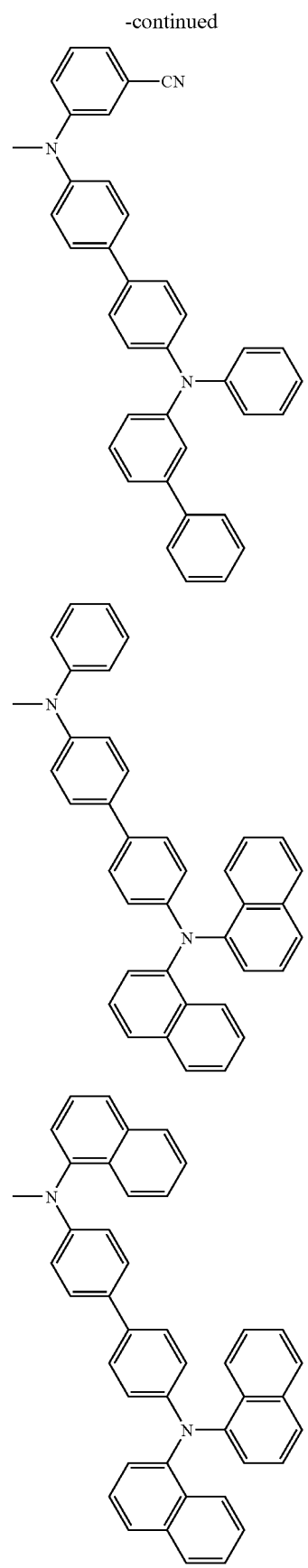
341
342
406
-continued
343
344

407
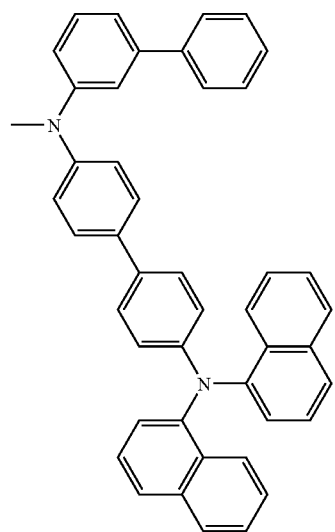
345
408
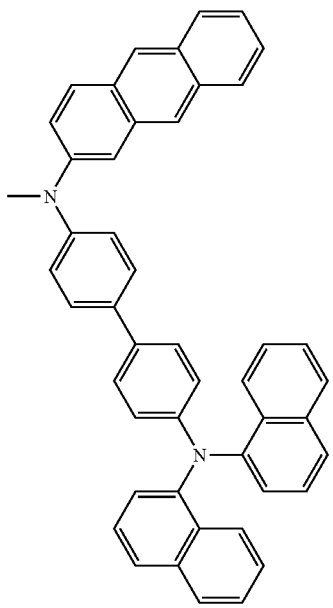
347
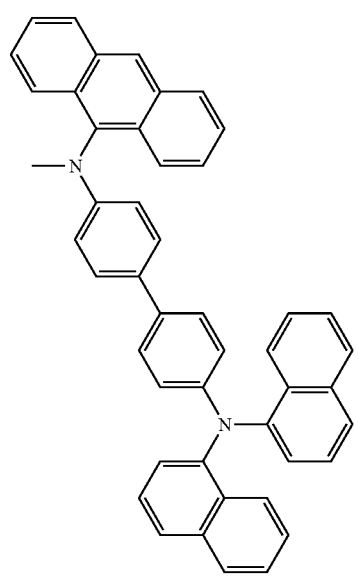
346
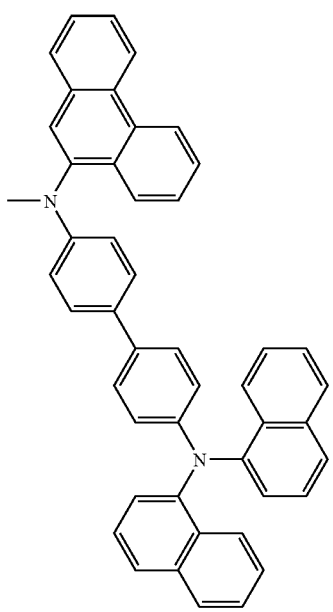
348

349
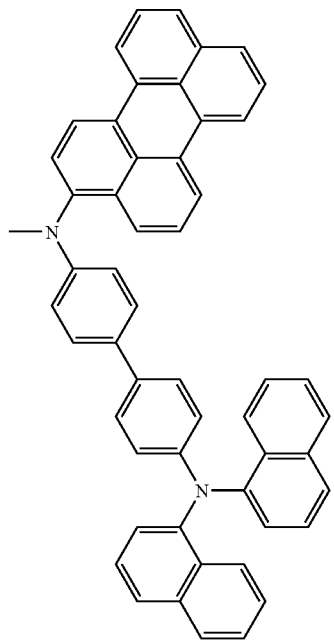
350
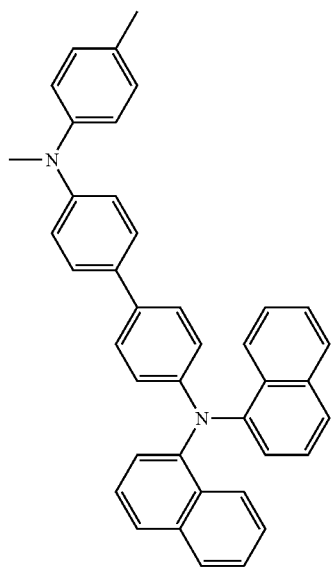
351
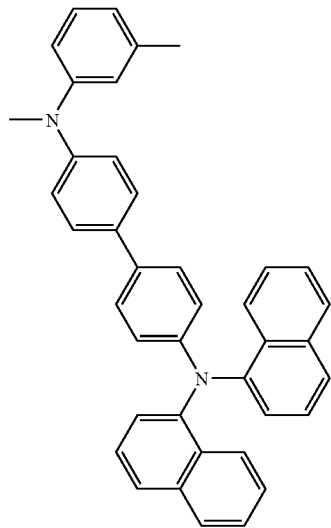
352
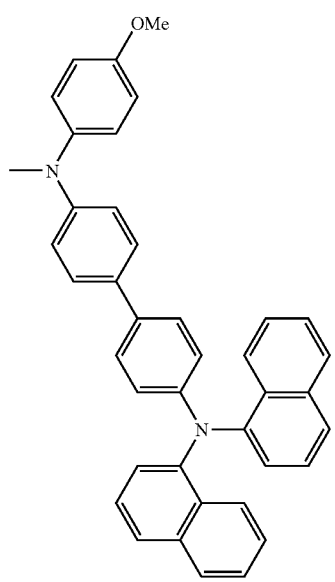
353
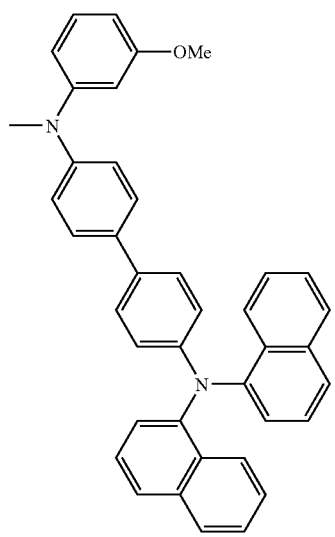

-continued
354
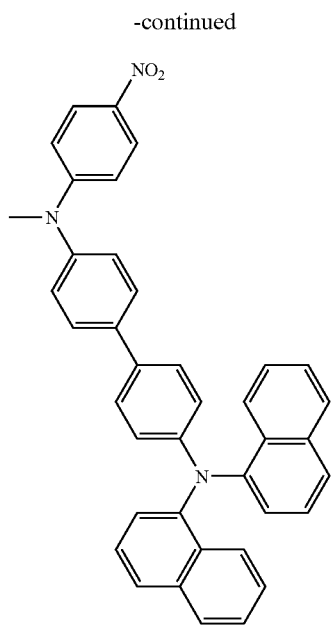
355
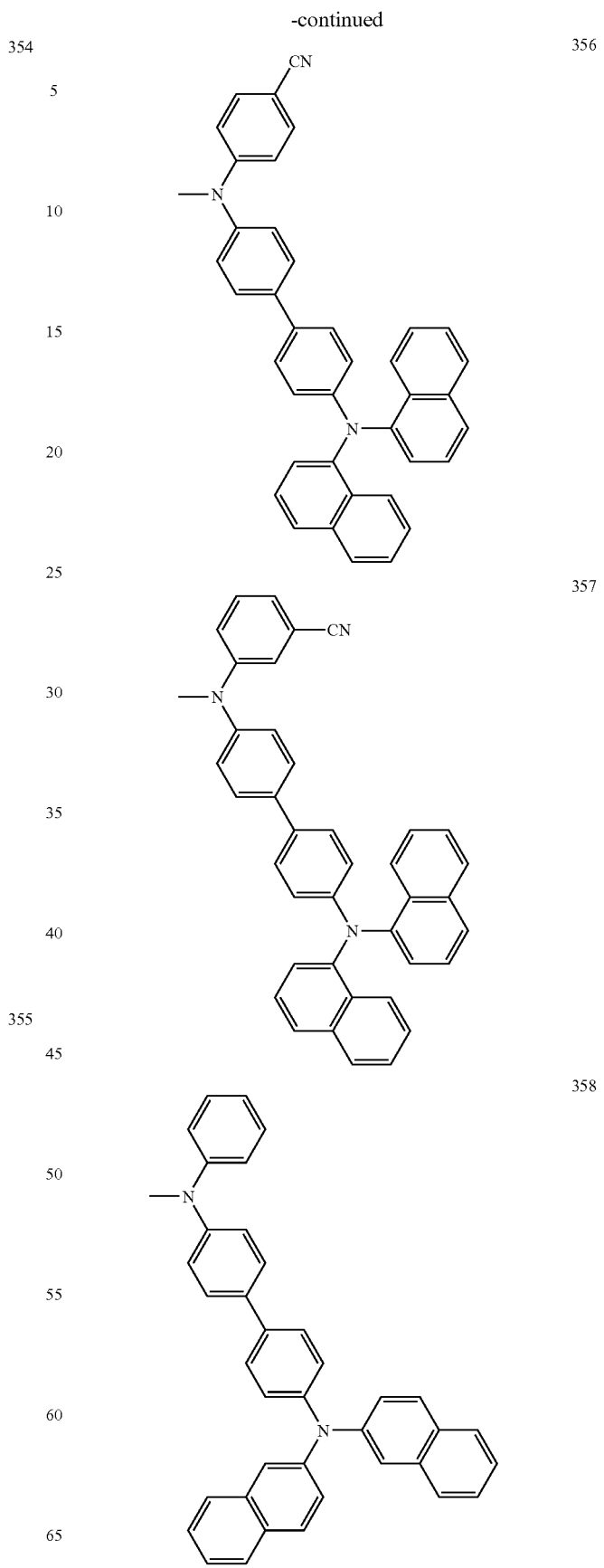

-continued
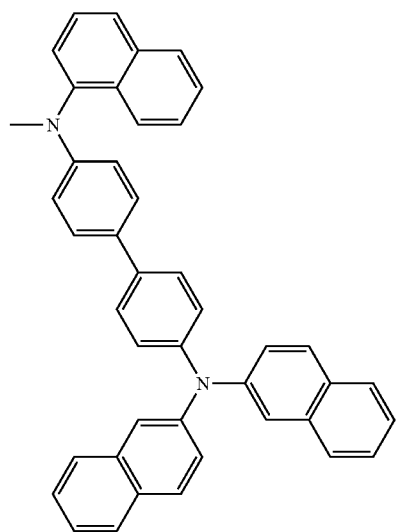
359
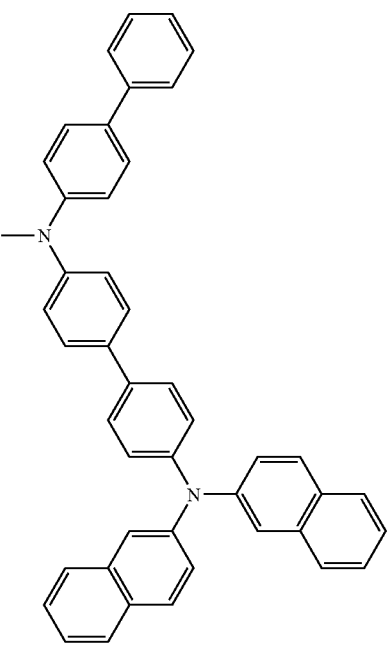
361
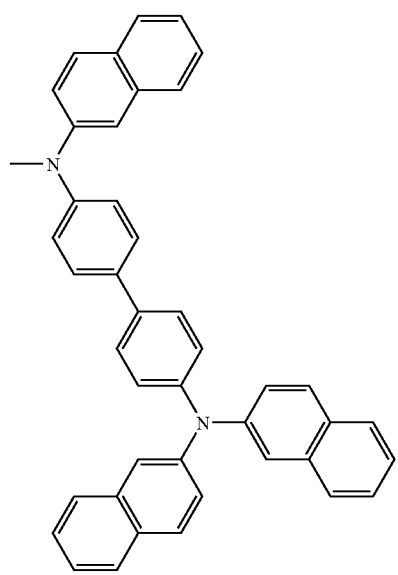
360
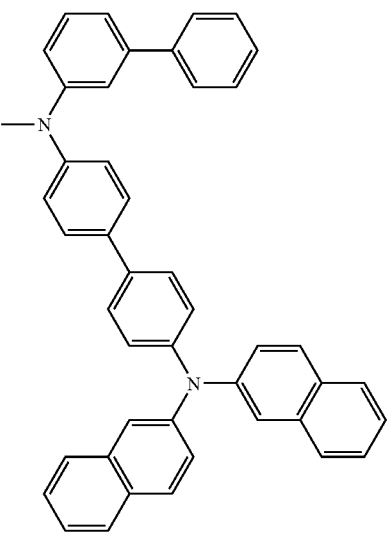
362

415
-continued
363
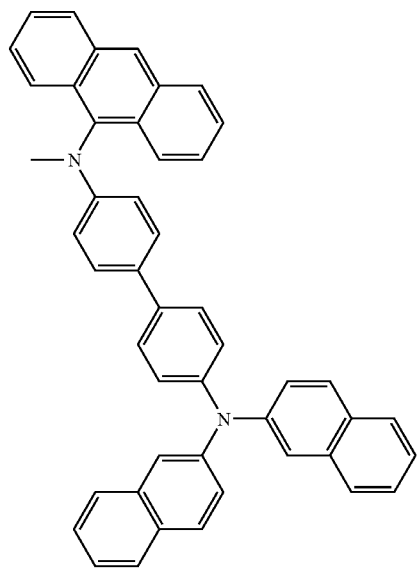
364
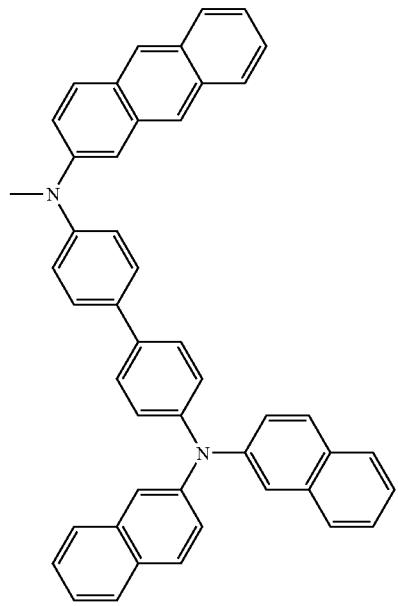
416
-continued
365
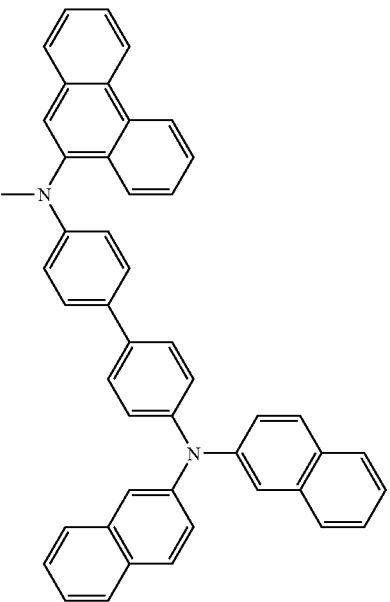
366
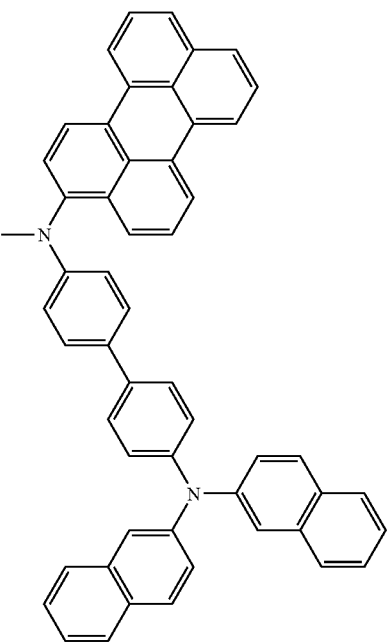

417 418
367
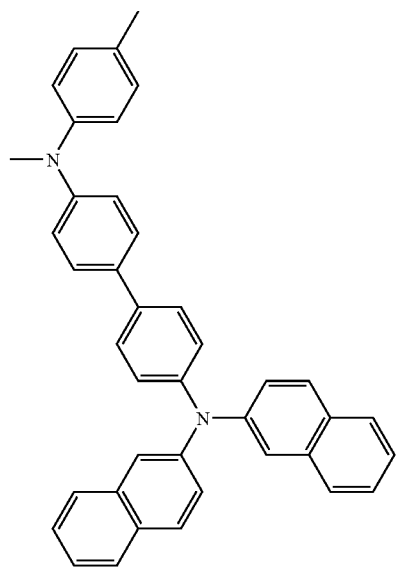
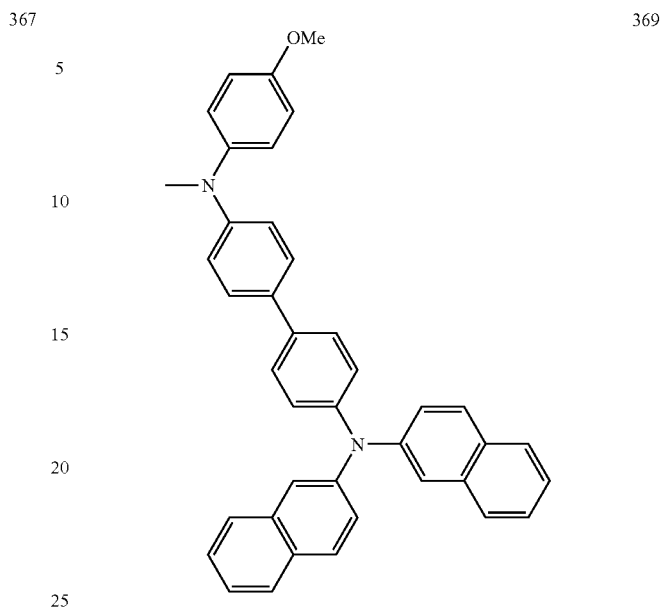
368
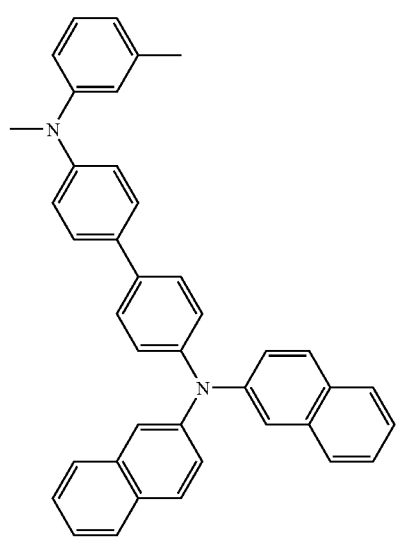

-continued
371
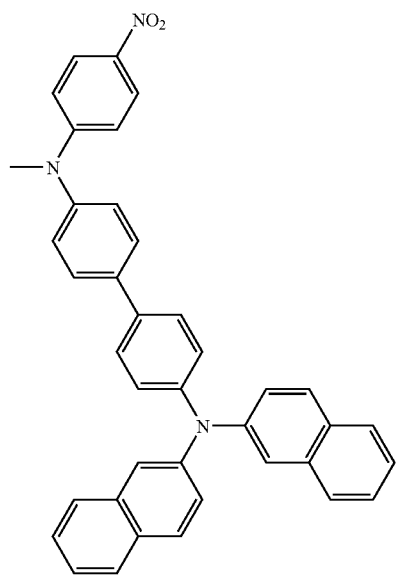
372
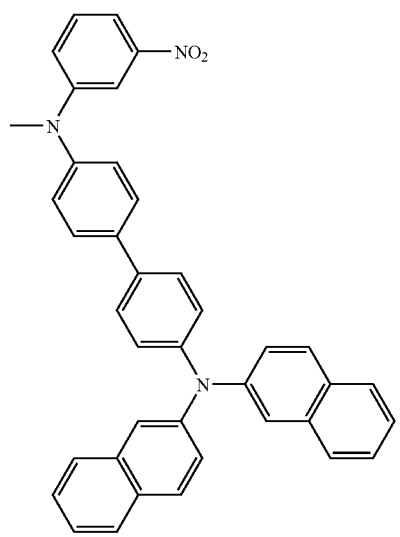
-continued
373
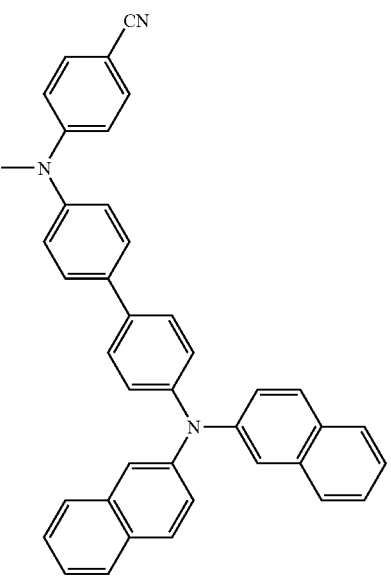
374
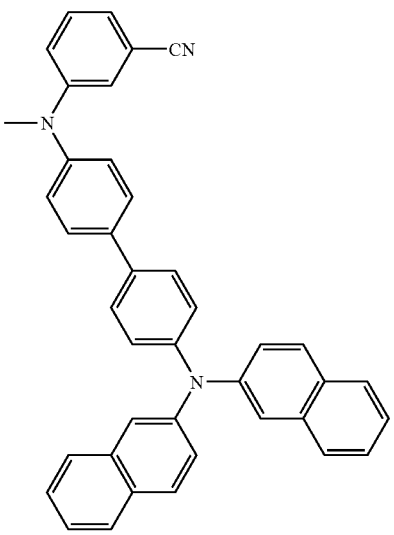

421
-continued
375
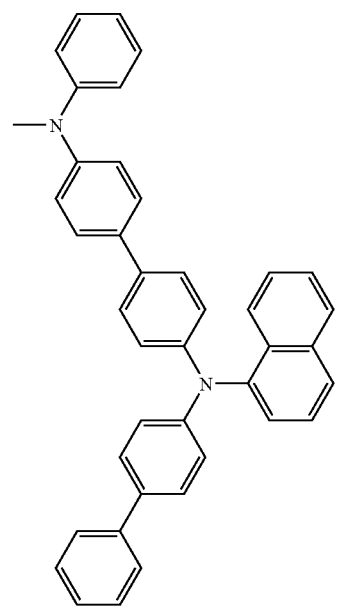
422
-continued
377
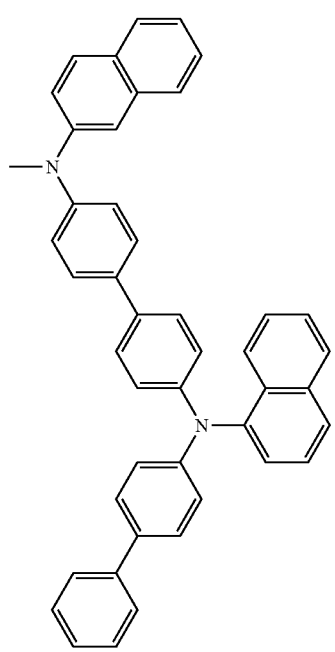
376
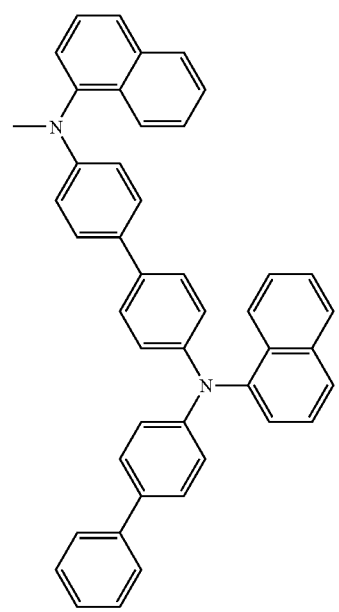
378
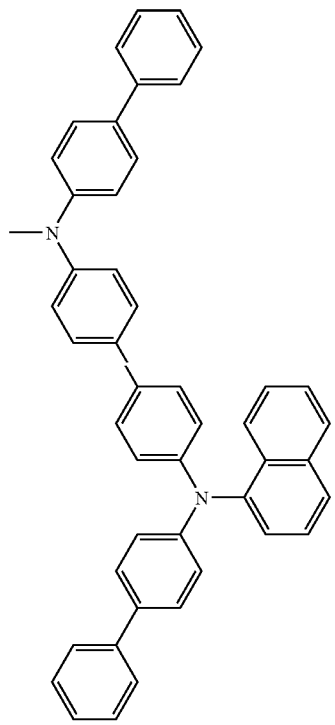

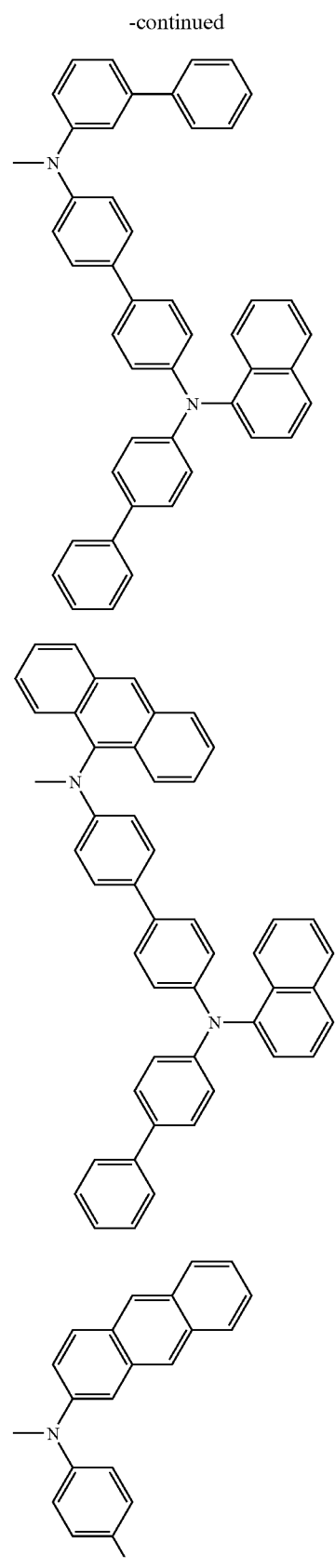
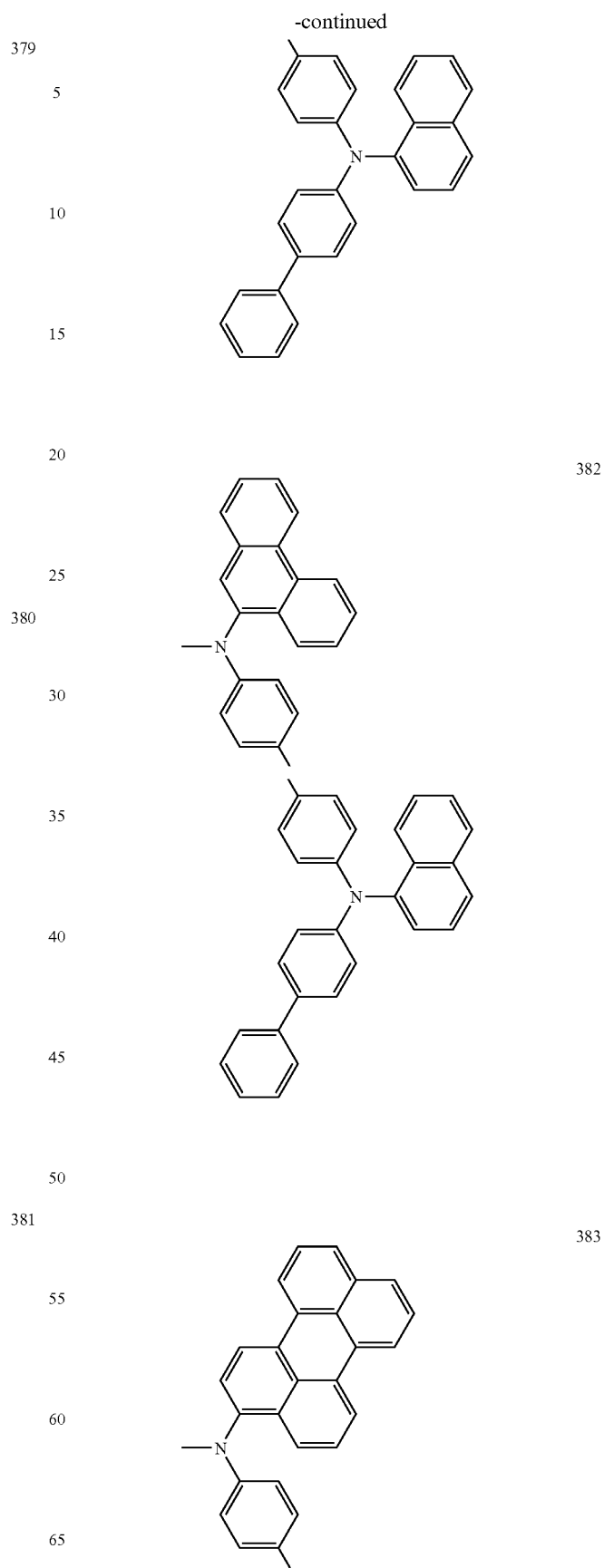

-continued
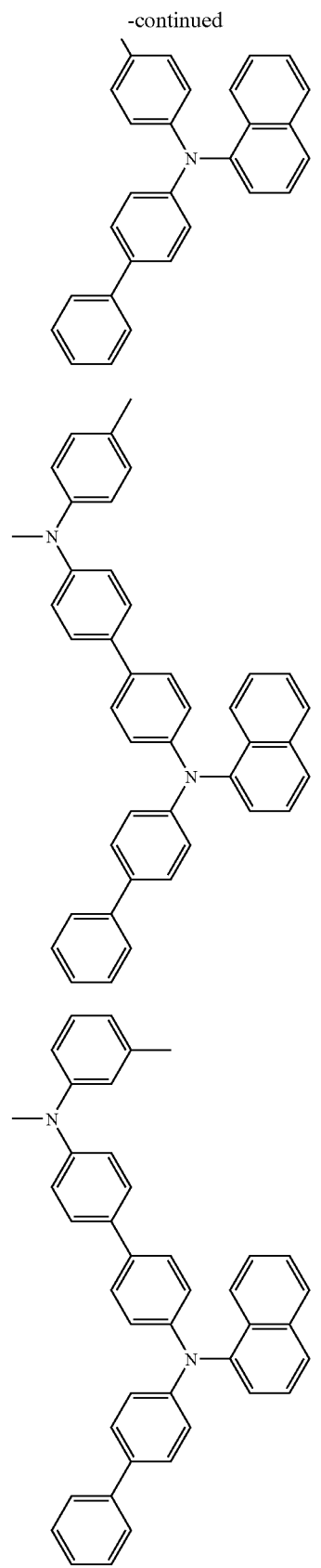
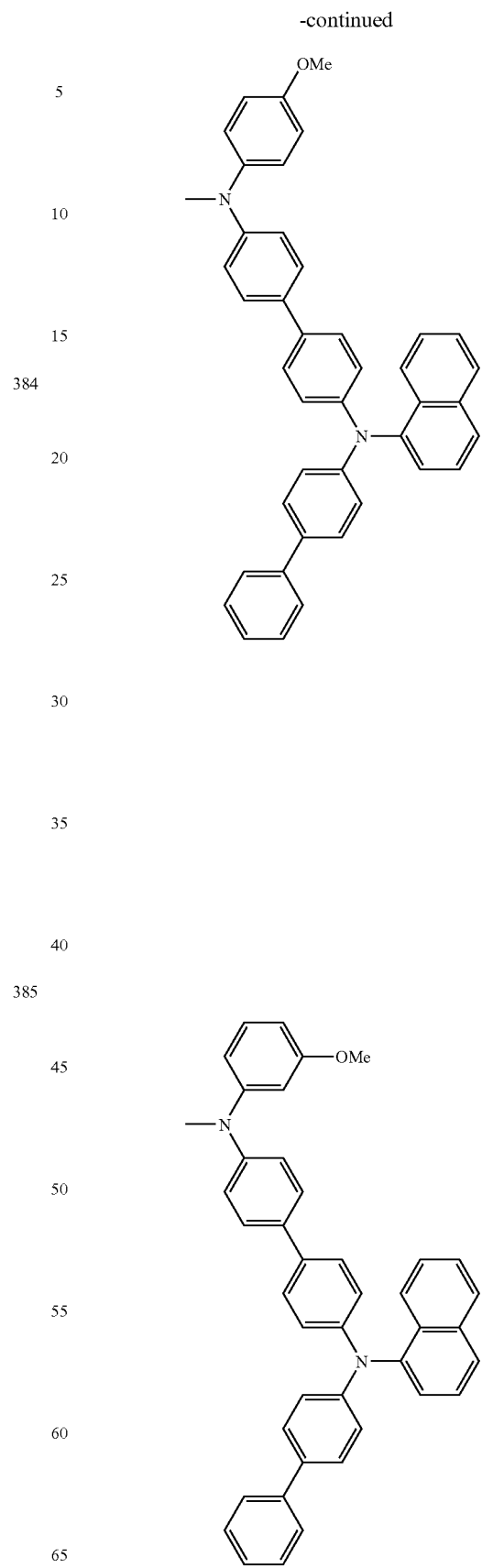

427
-continued
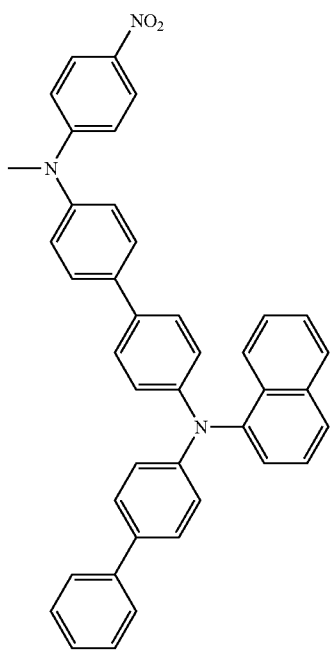
388
389
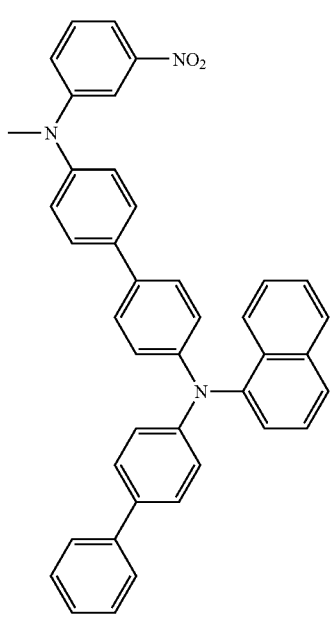
428
-continued
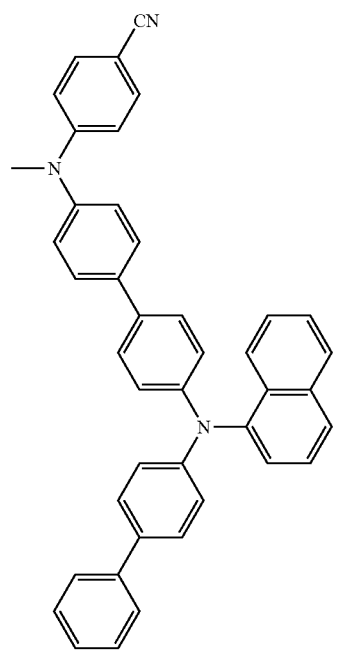
390
391
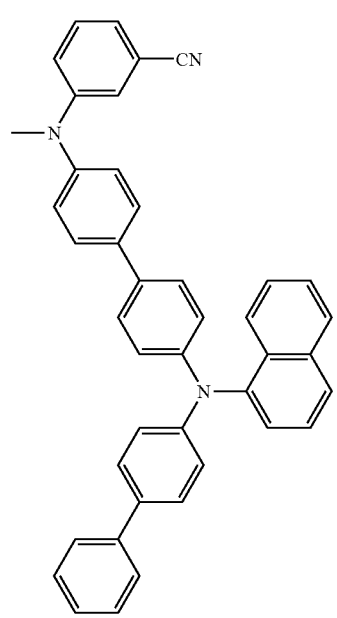

392
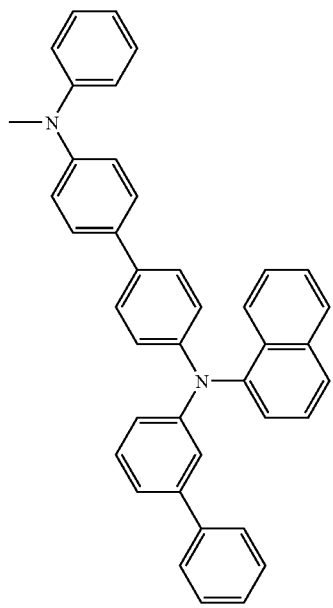
393
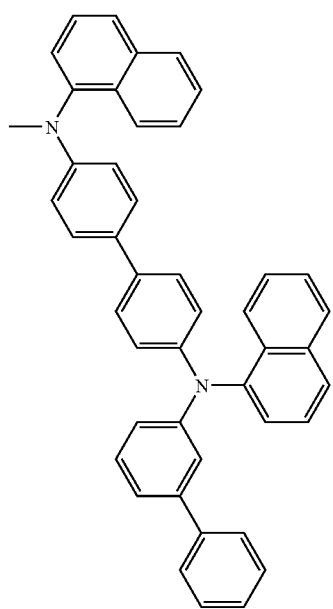
394
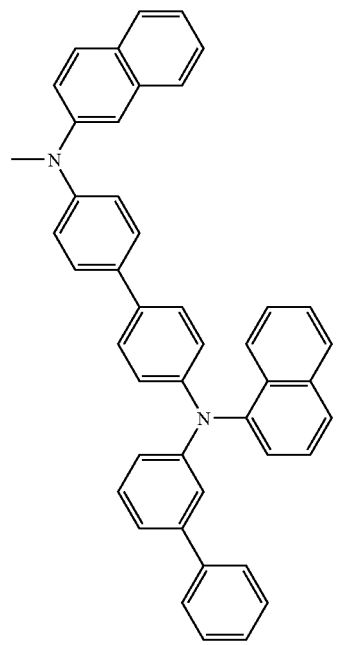
395
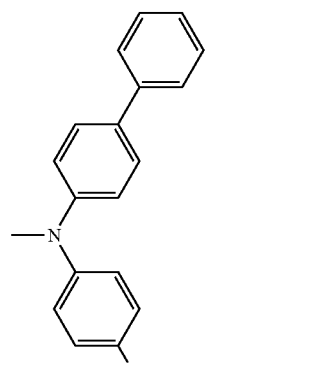
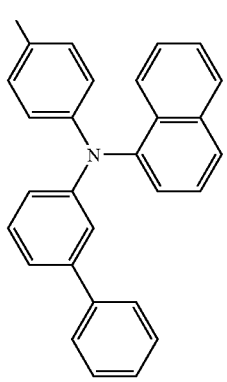

431
-continued
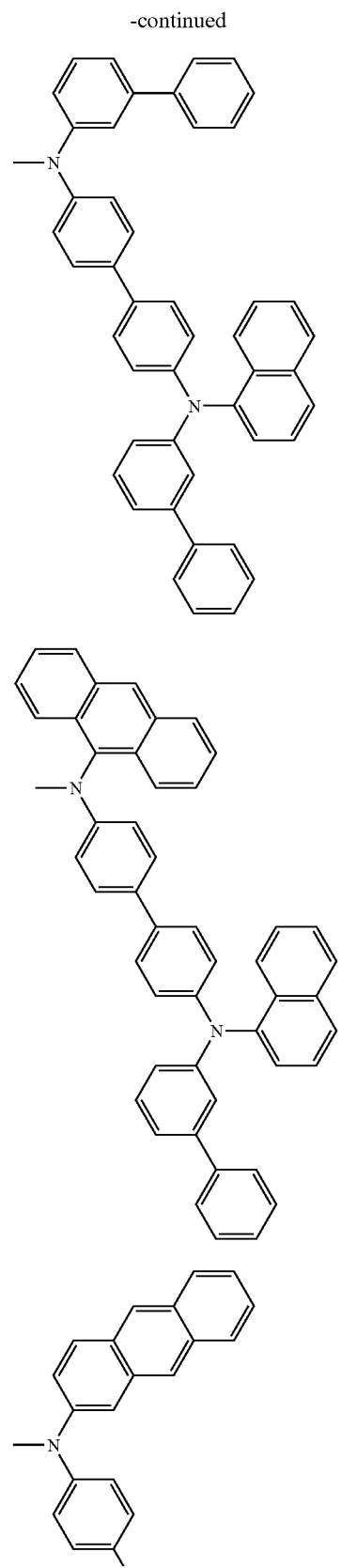
432
-continued
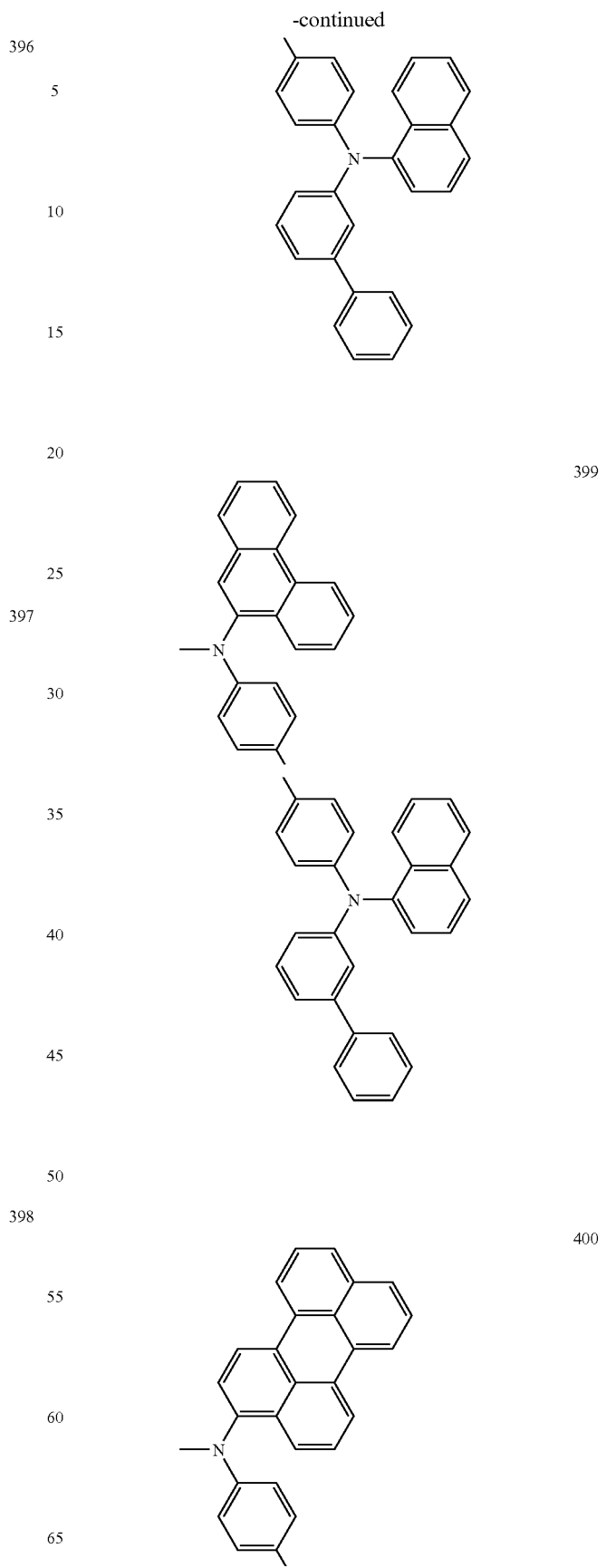

-continued
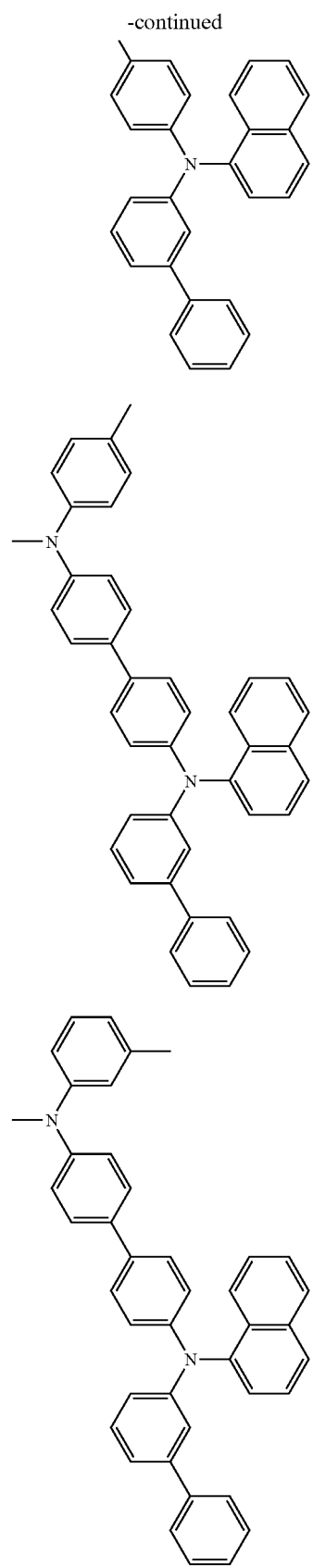
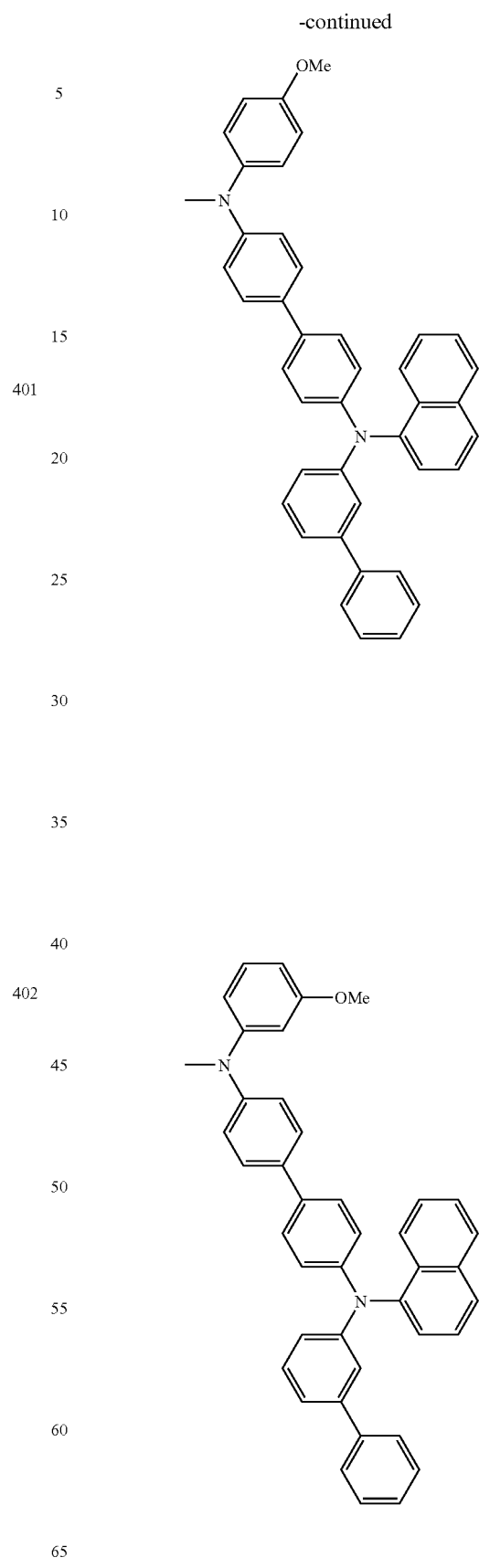

-continued
405
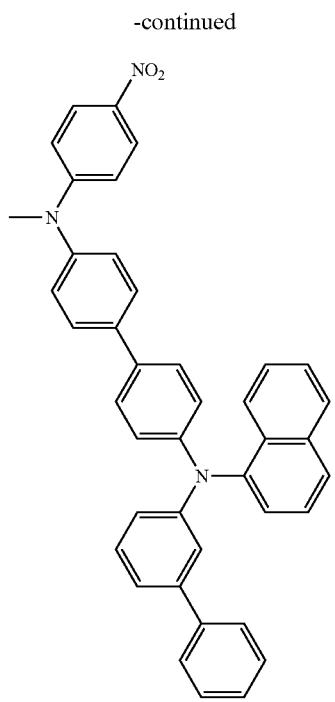
406
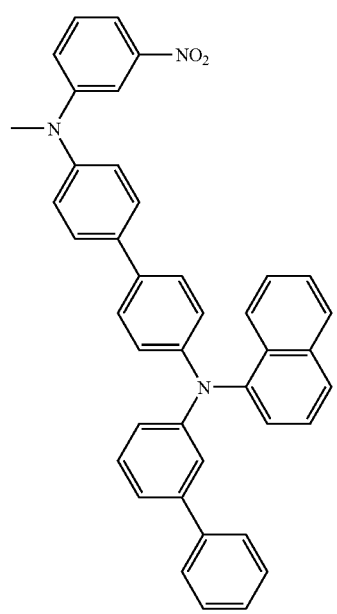
-continued
407
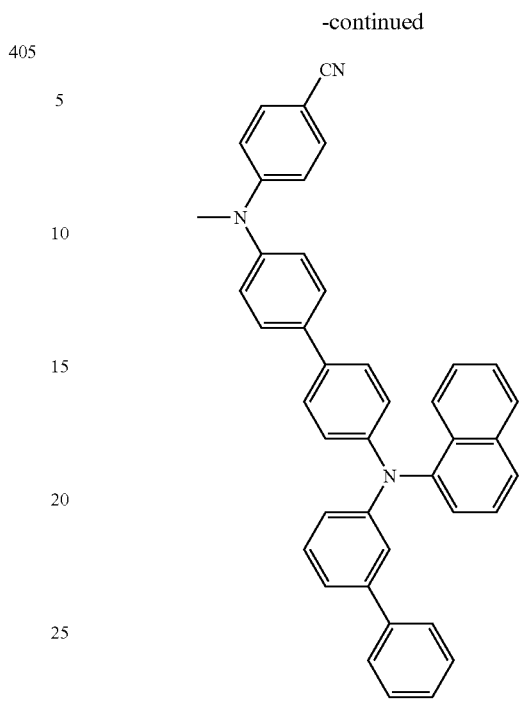
408
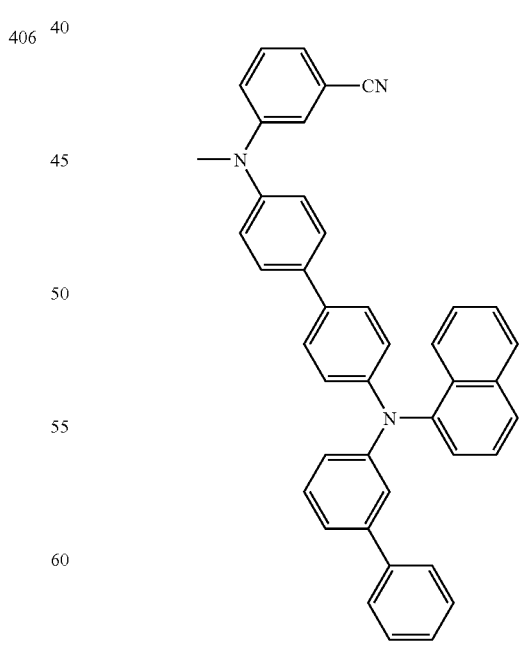

437
-continued
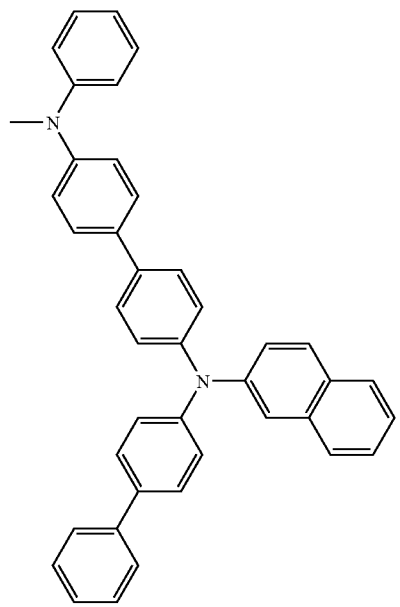
409
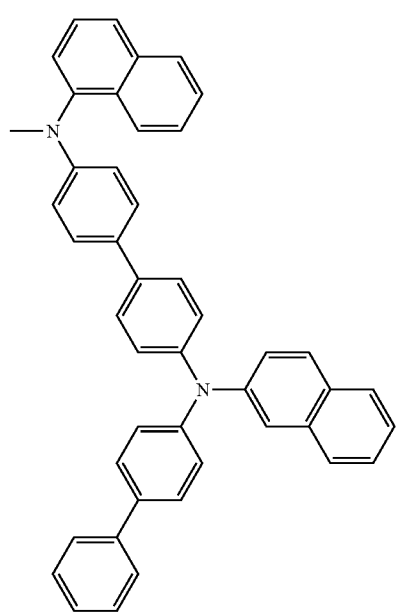
410
438
-continued
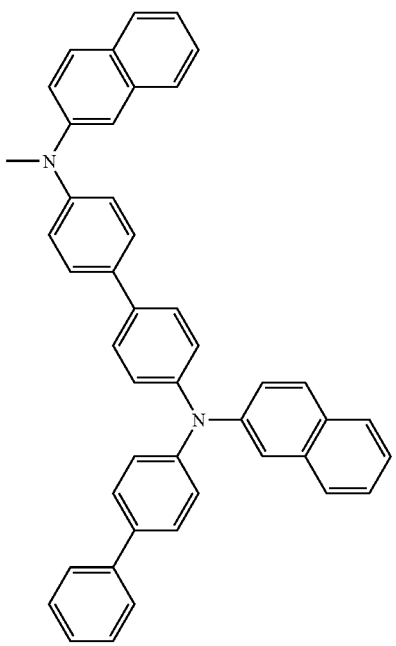
411
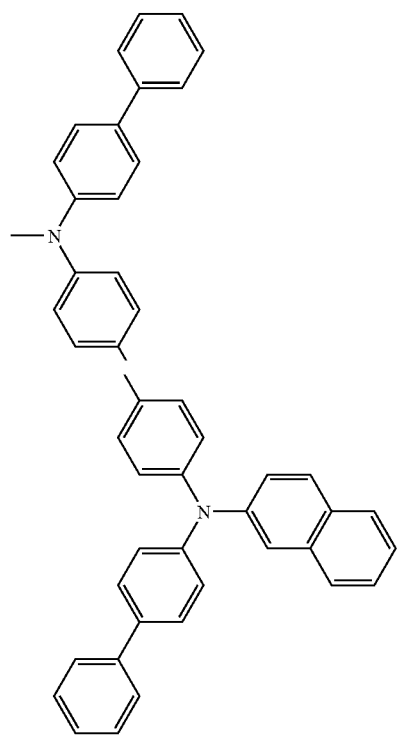
412

-continued
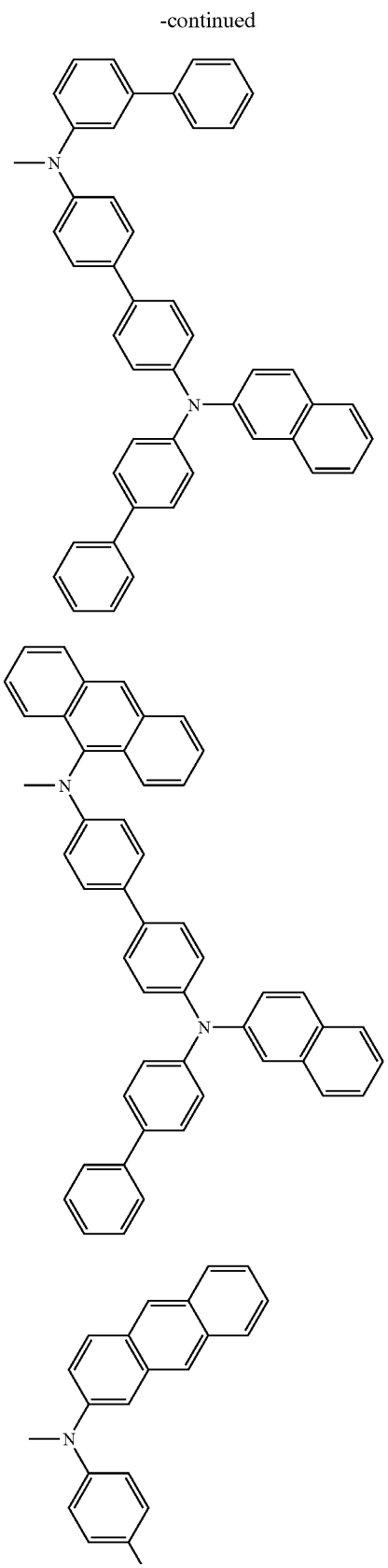
-continued
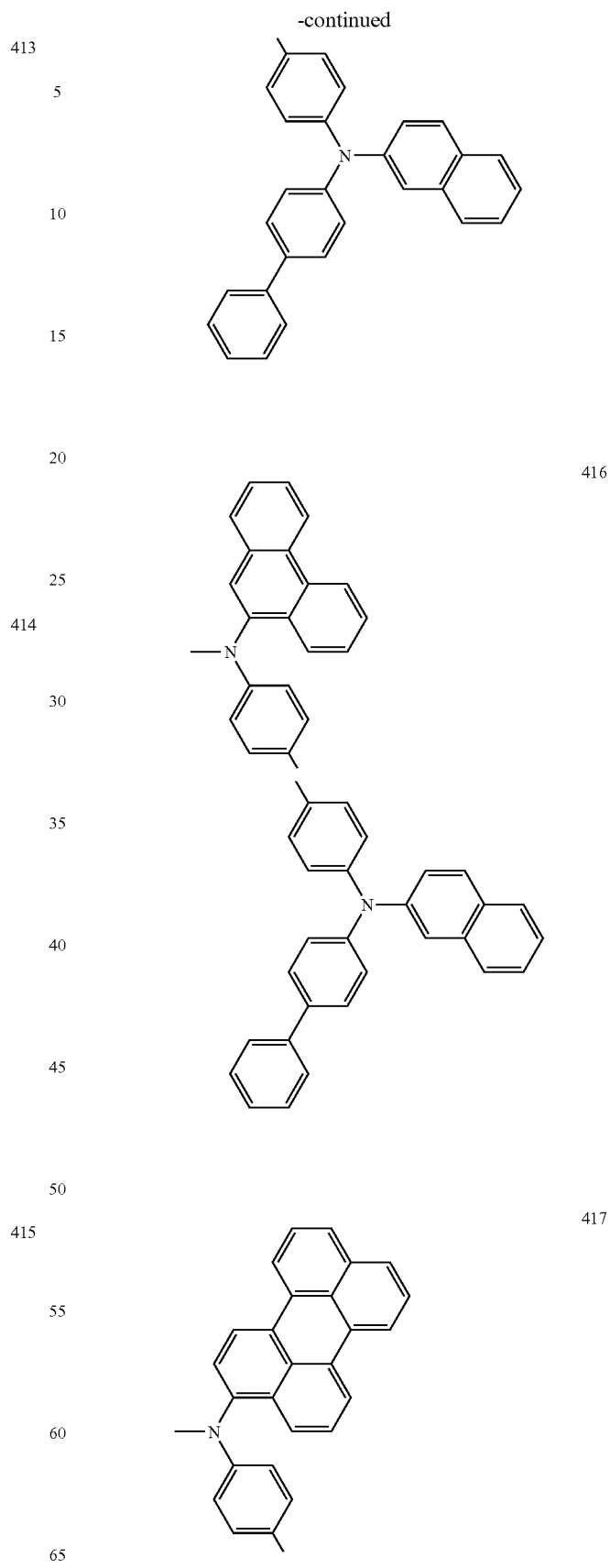

441
-continued
442
-continued
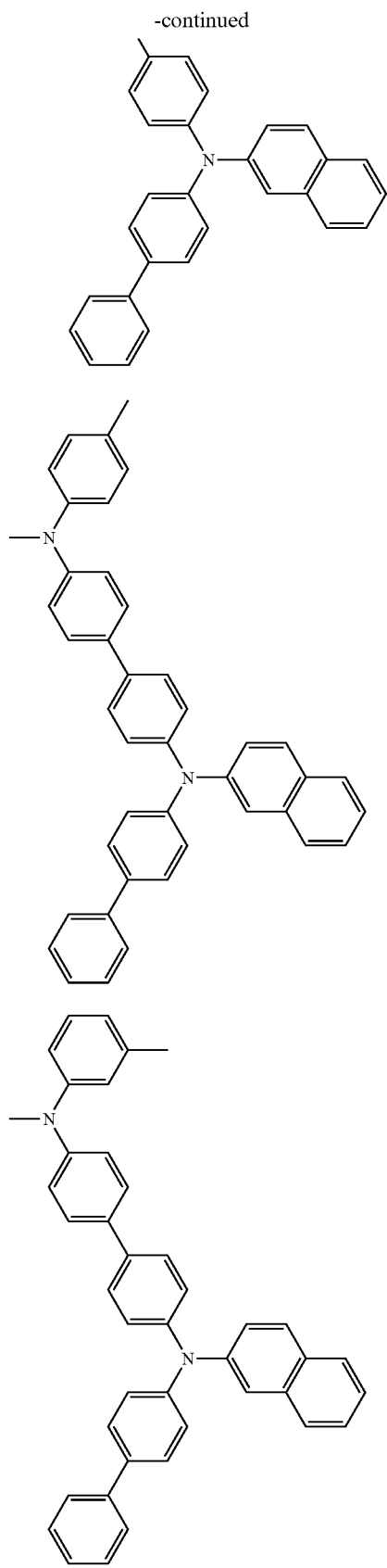
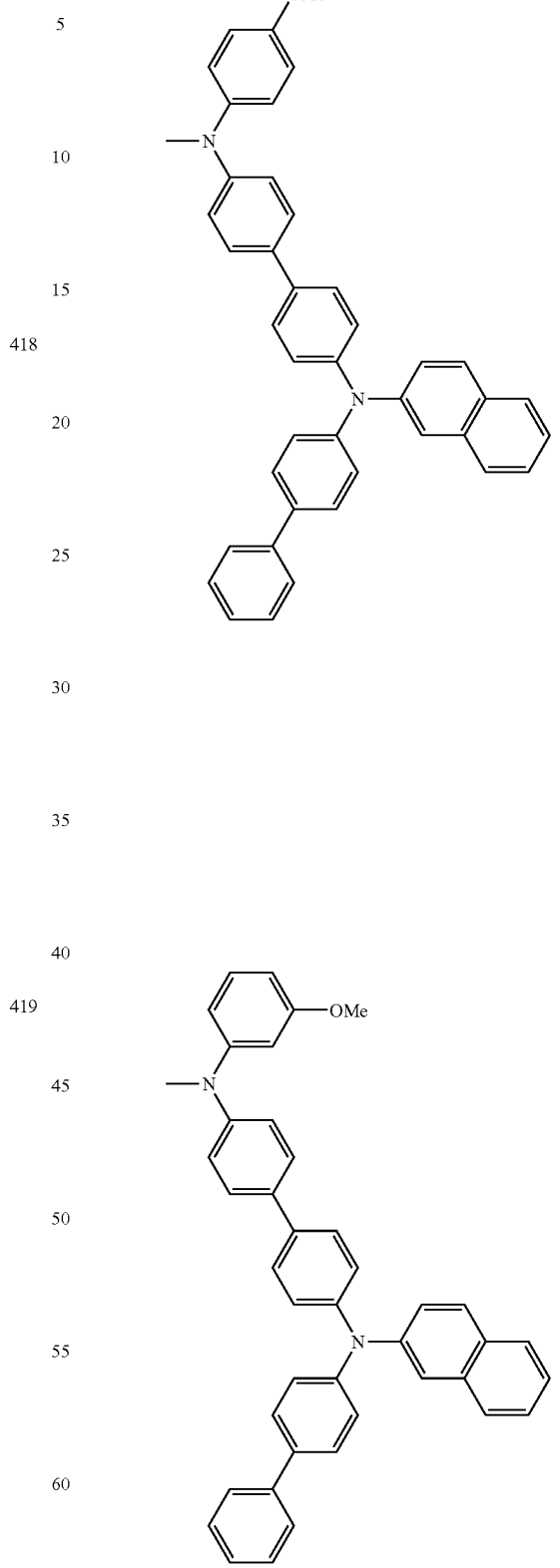

443
-continued
422
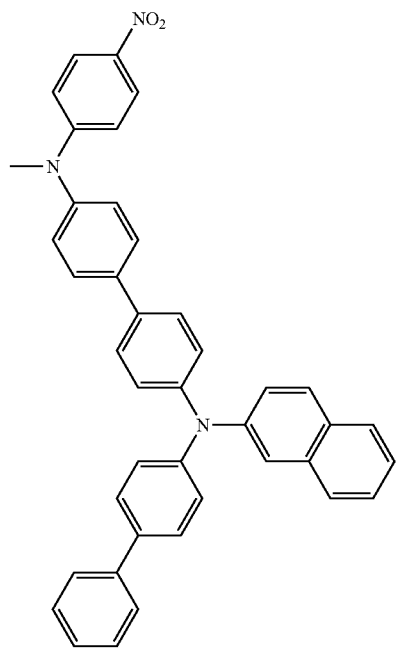
423
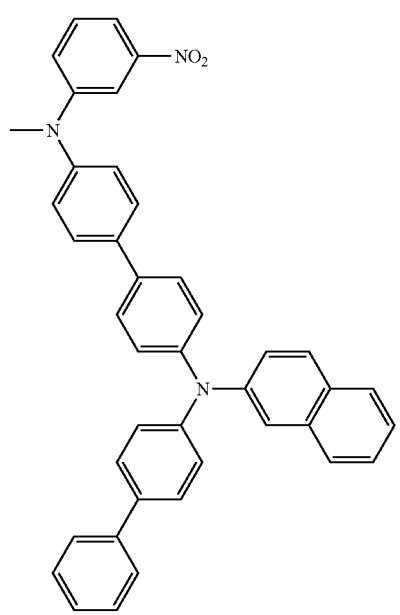
444
-continued
424
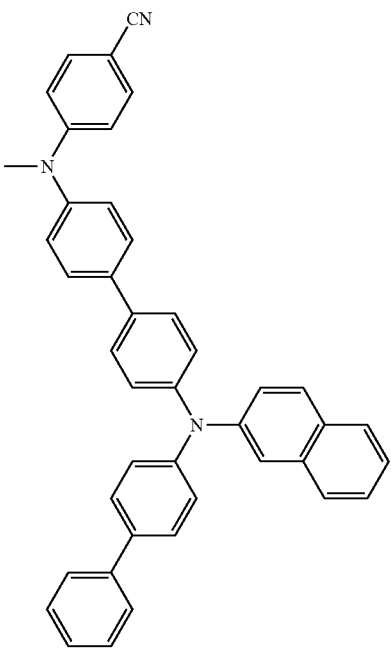
425
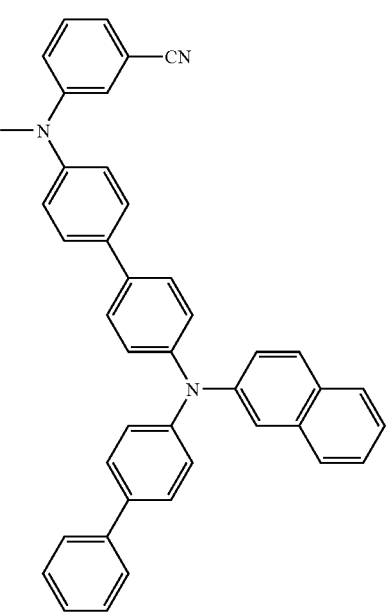

-continued
426
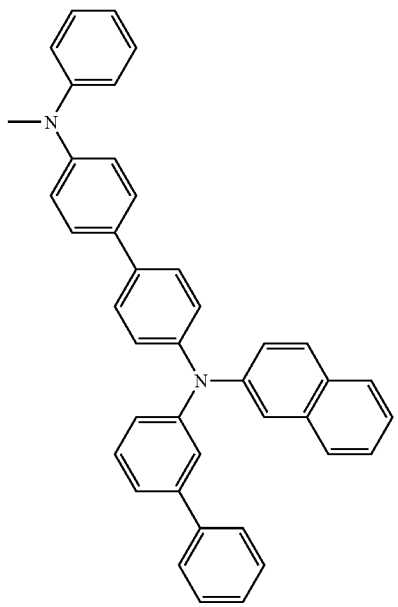
427
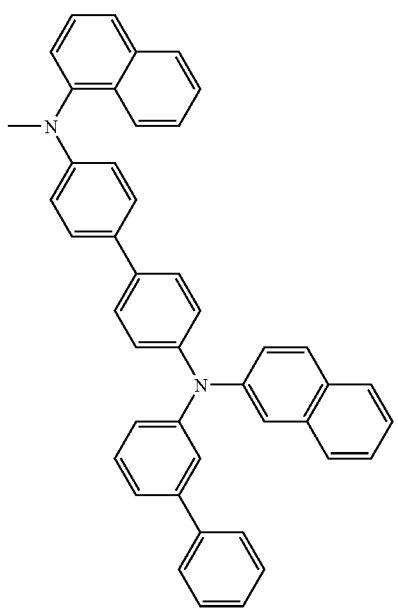
428
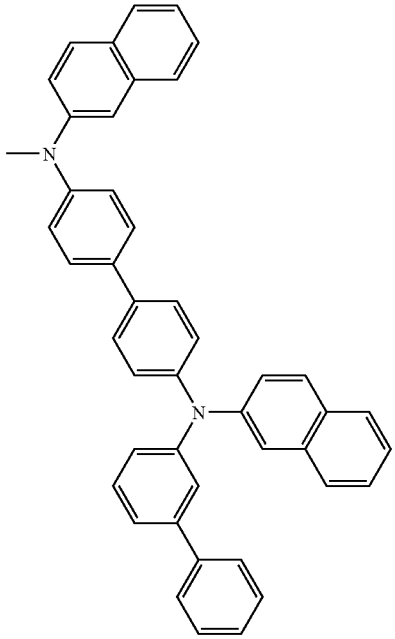
429
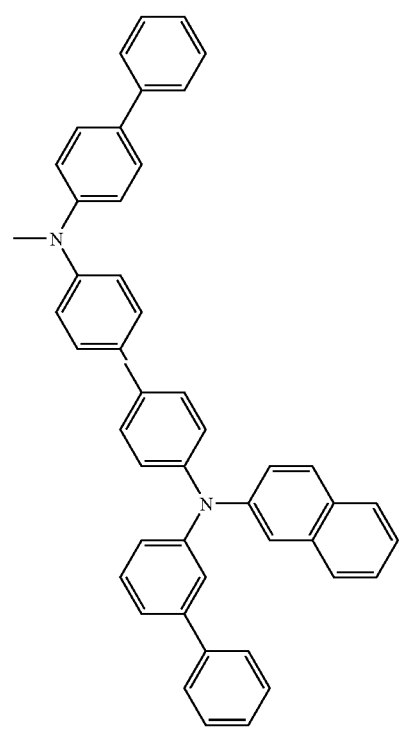

-continued
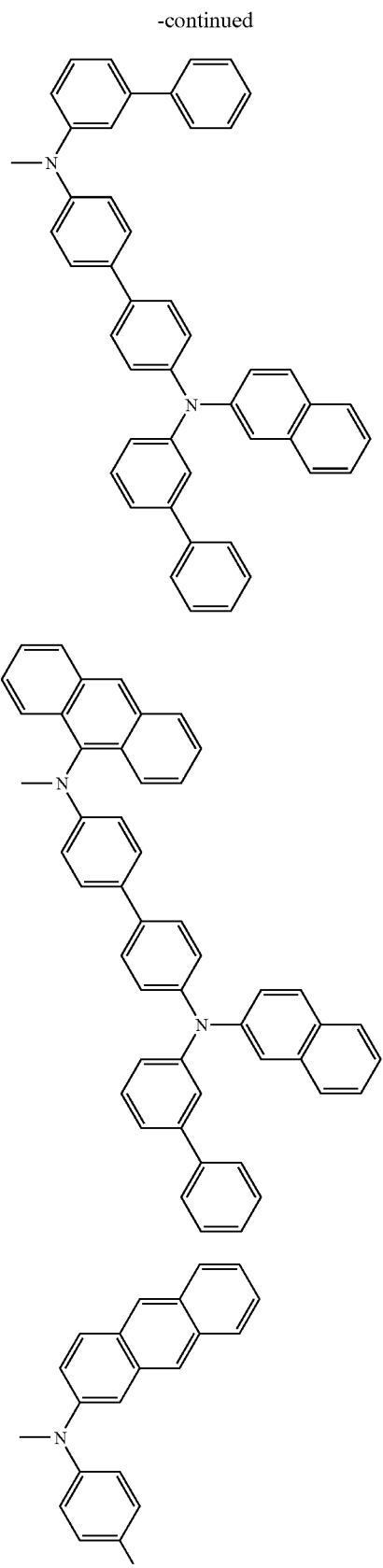
430
431
432
-continued
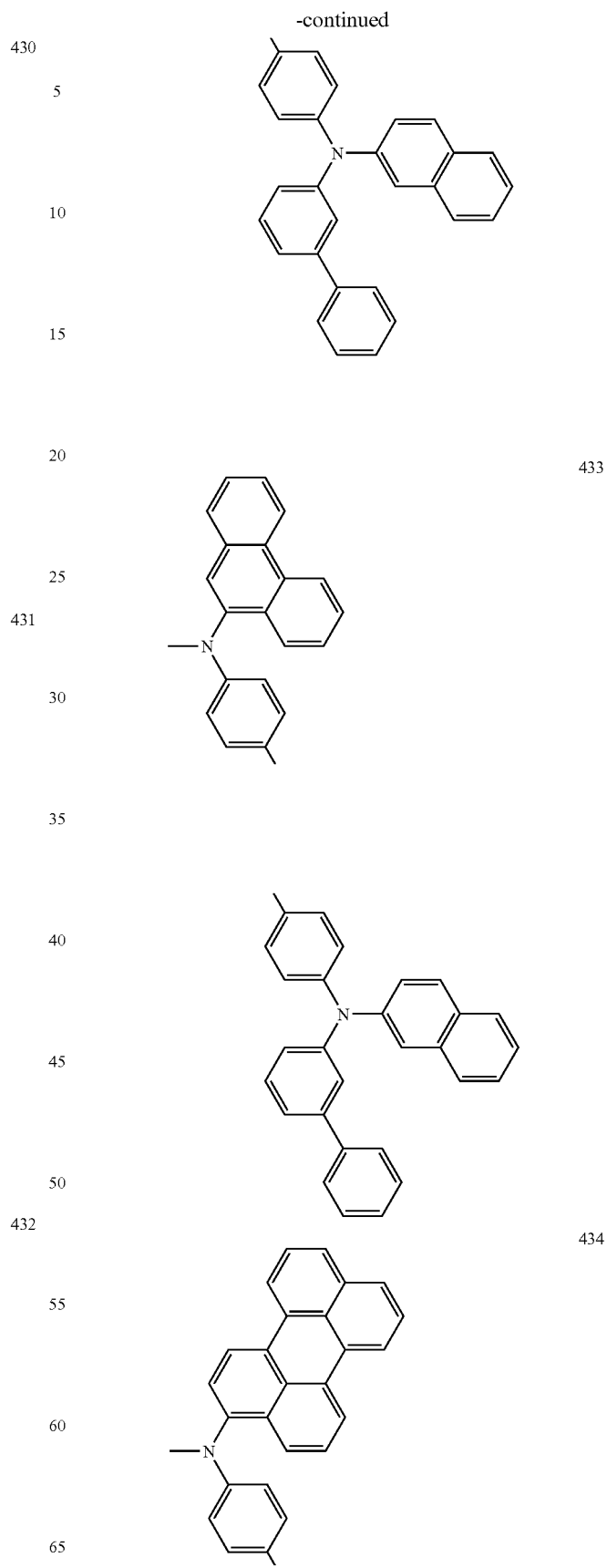
433
434

-continued
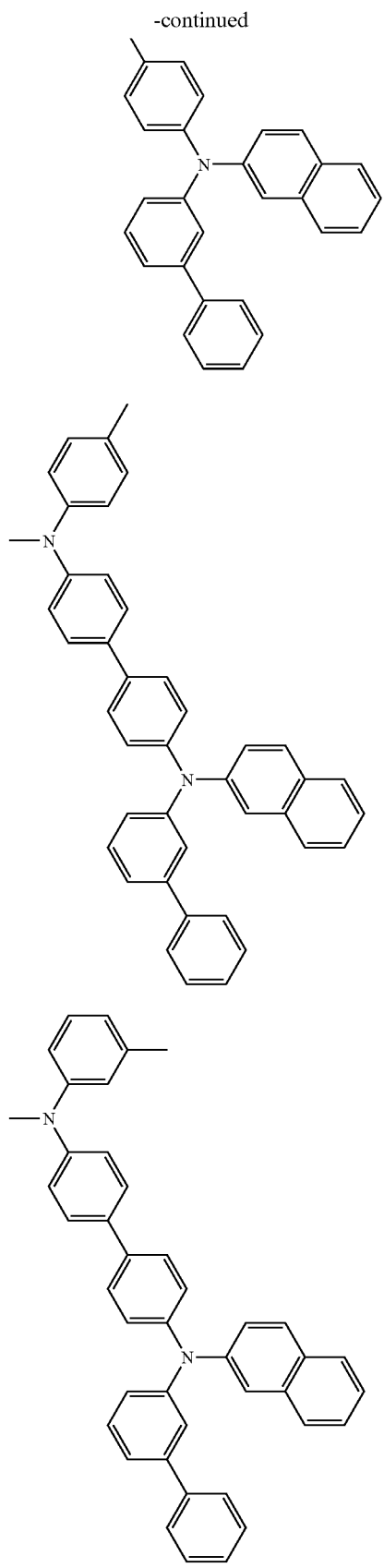
435
436
-continued
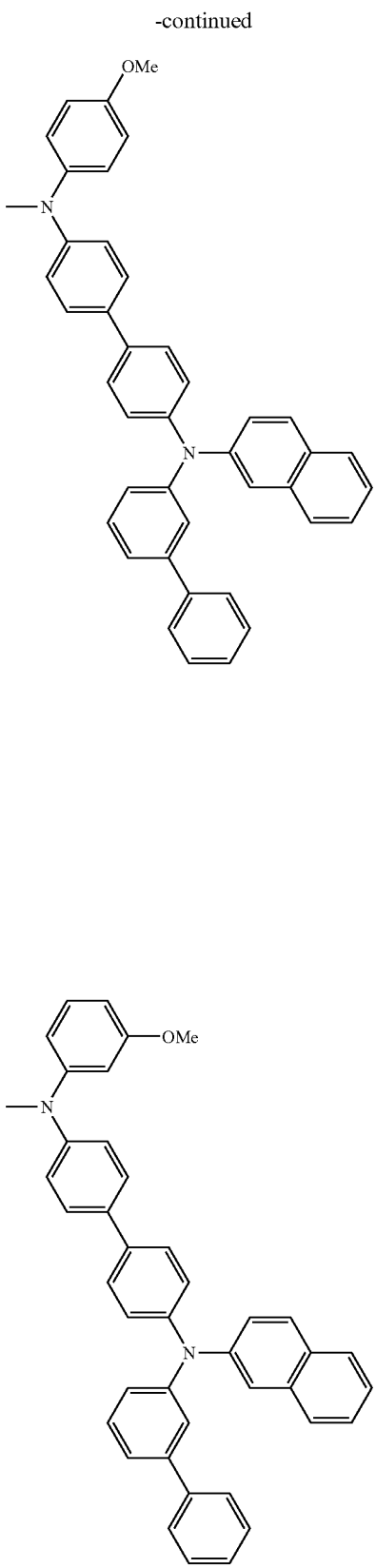
437
438

439
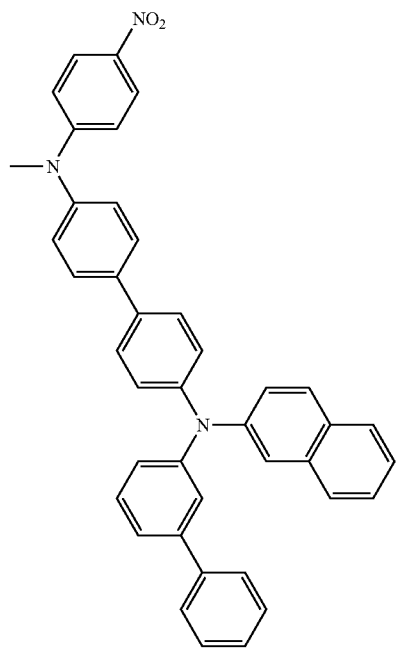
440
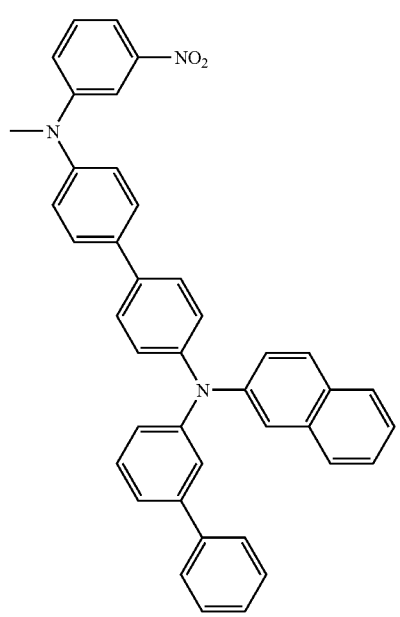
441
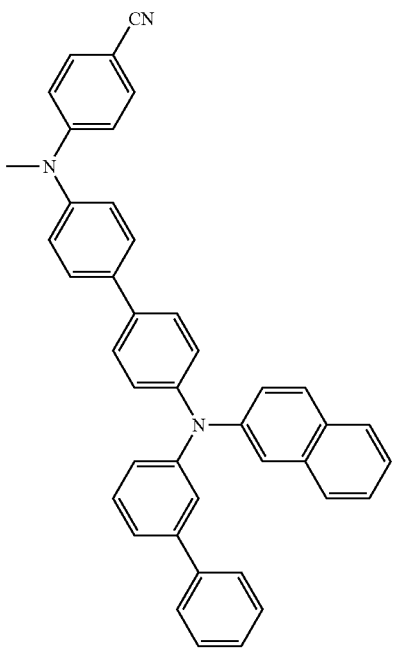
442
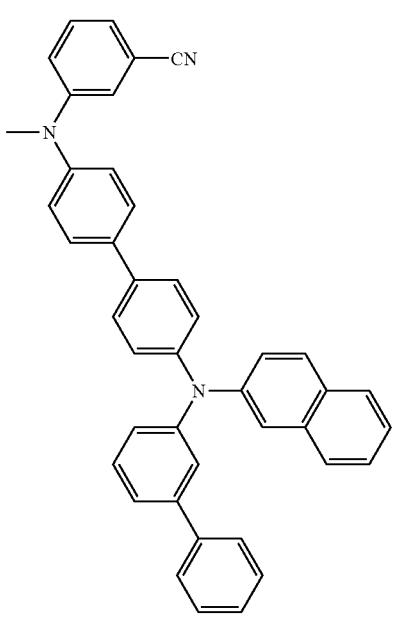

-continued
443
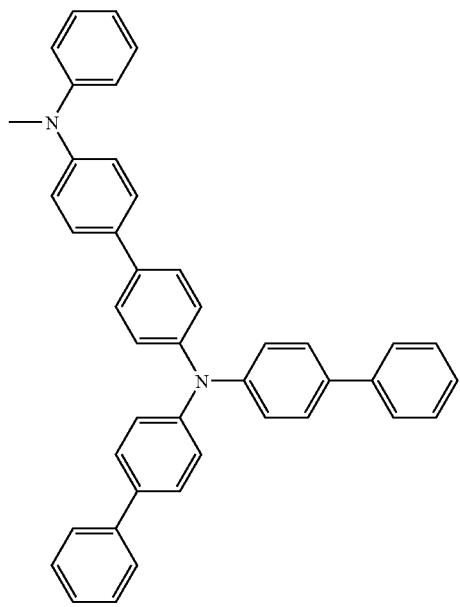
444
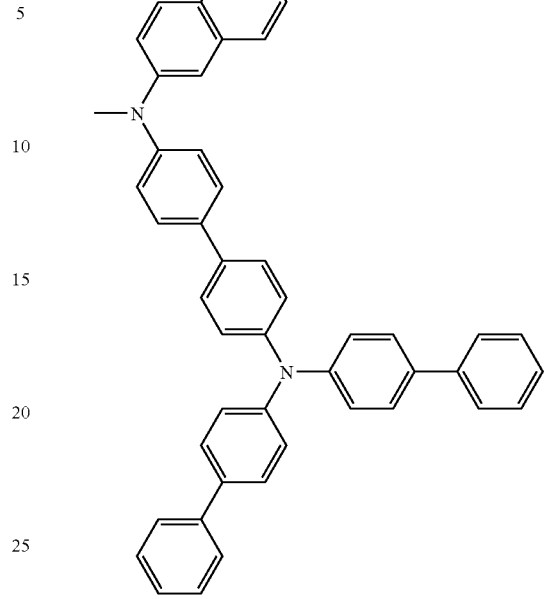
445
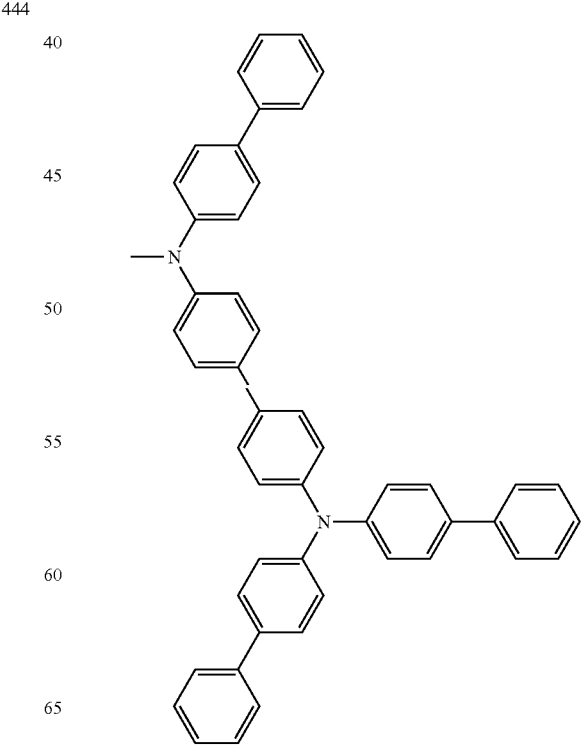
446

455
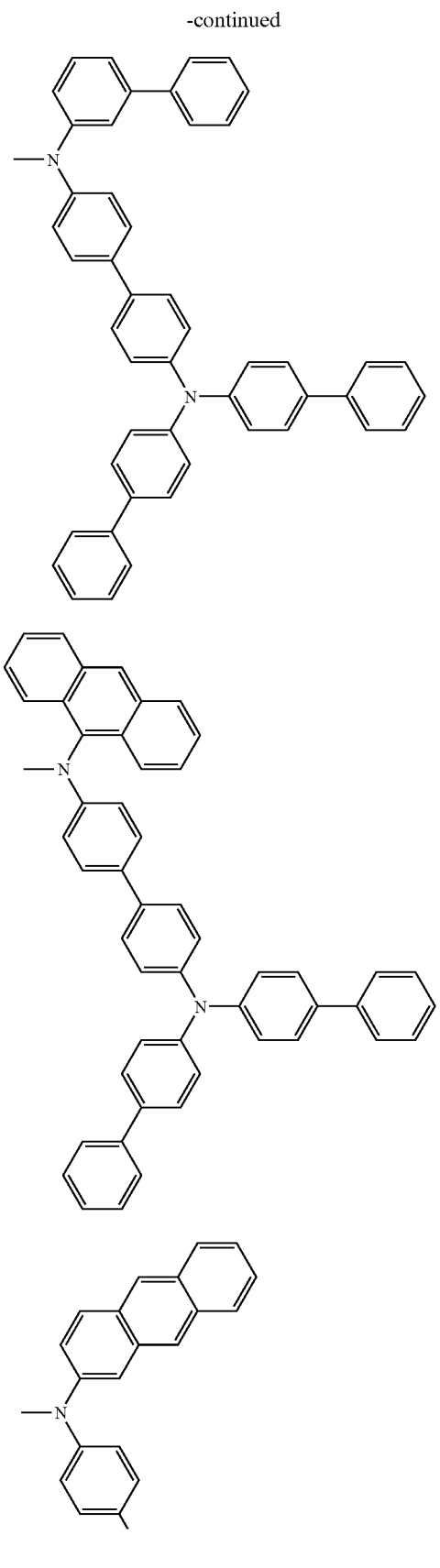
456
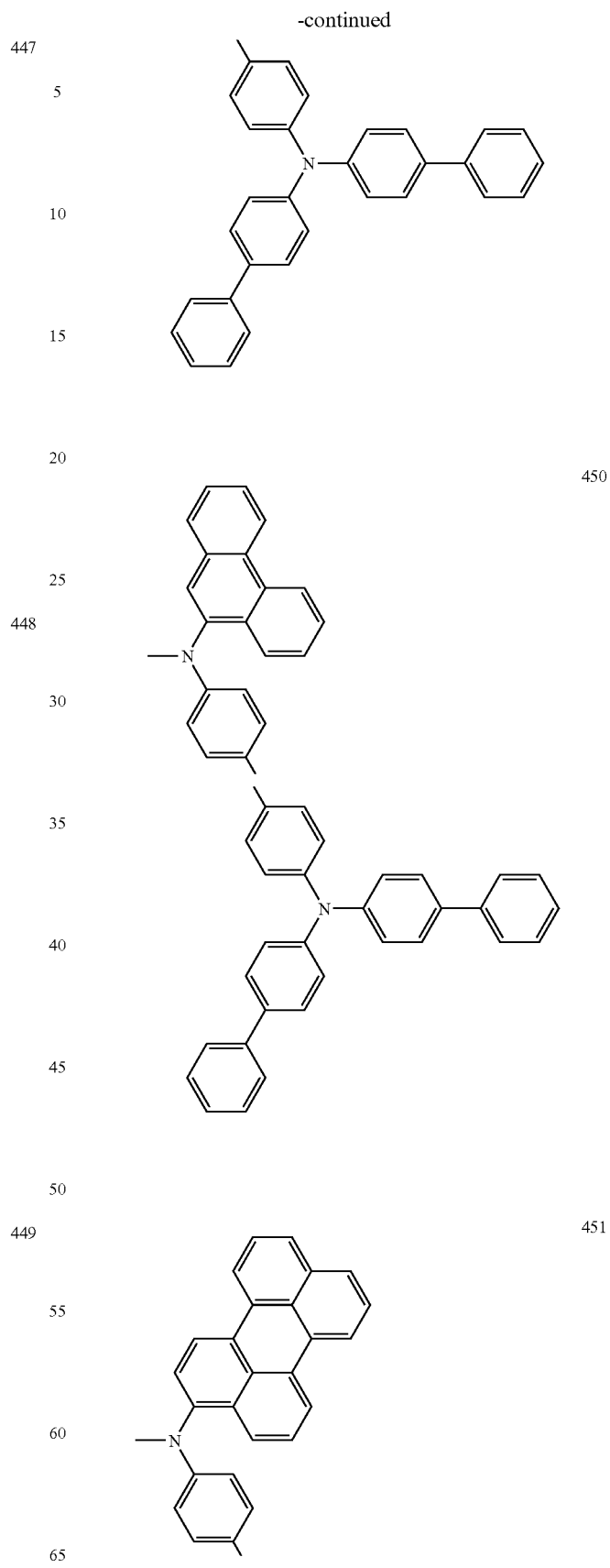

457
458
-continued
-continued
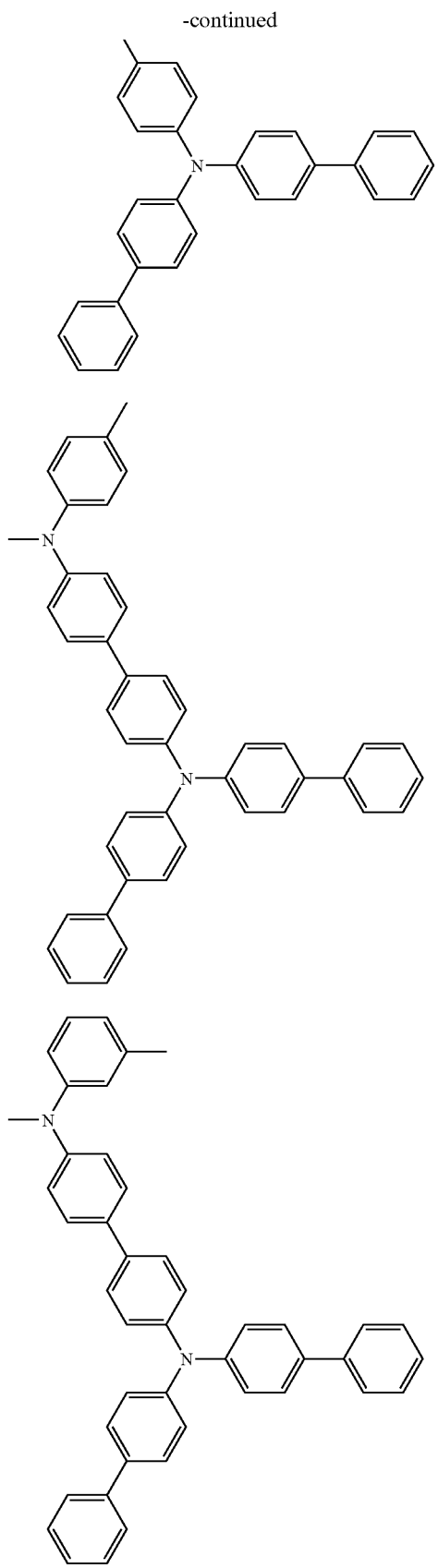
452
453
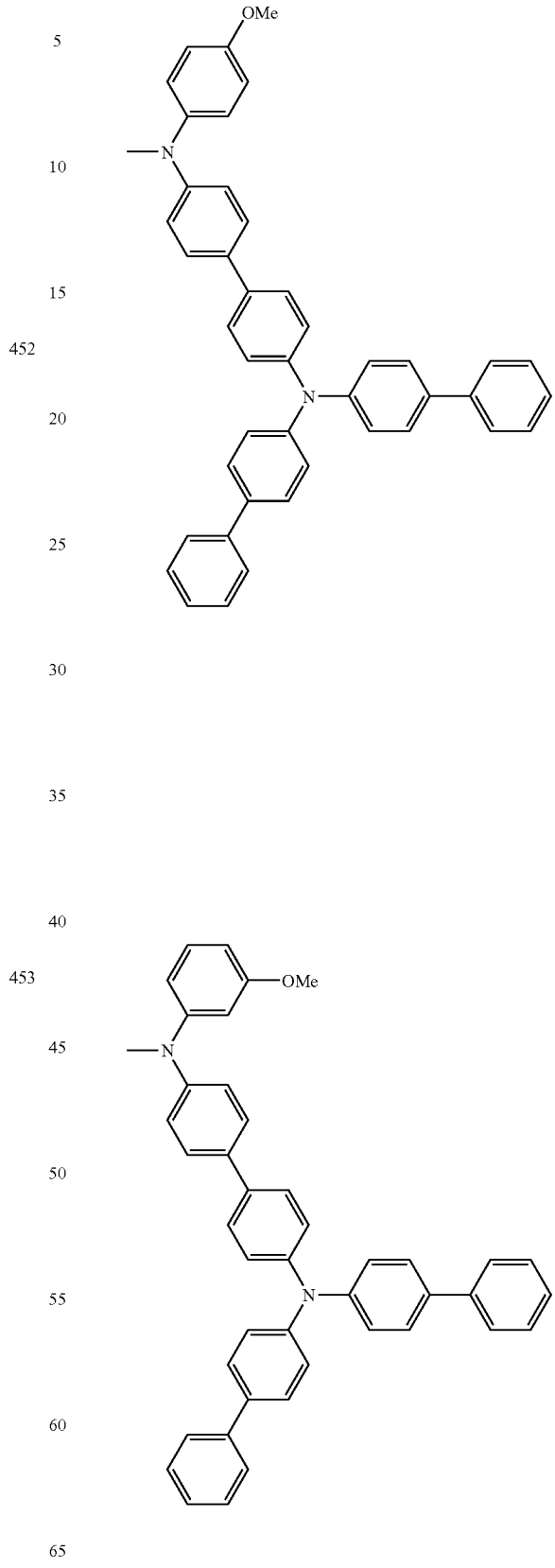
454
455

-continued
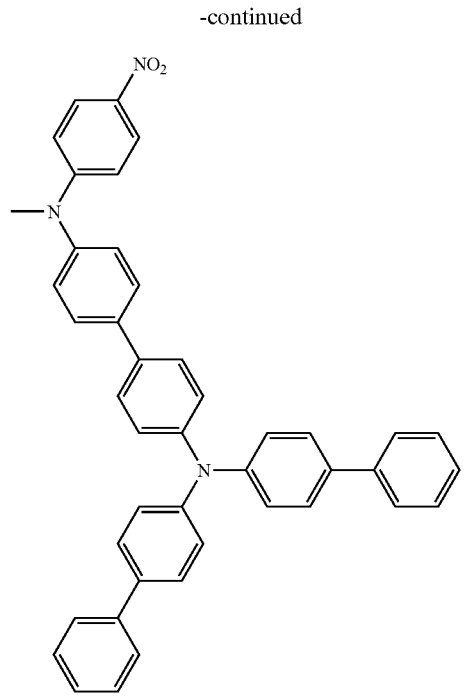
456
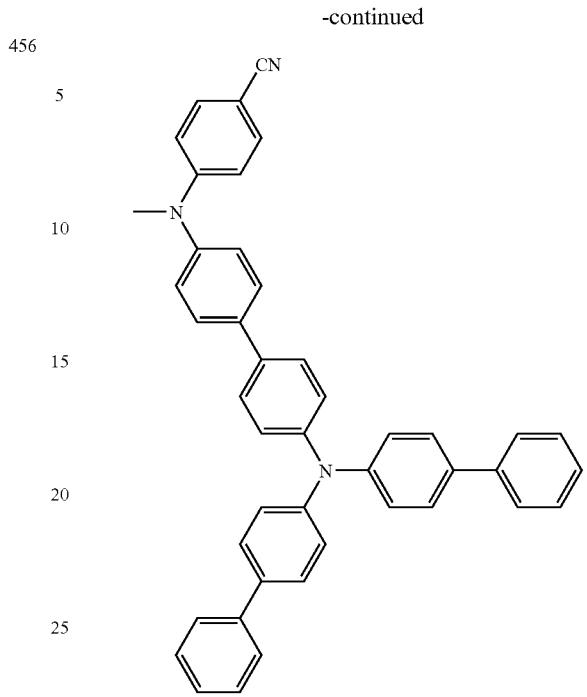
458
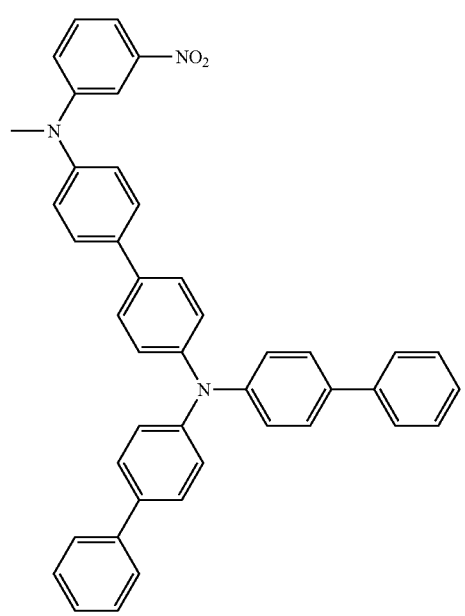
457
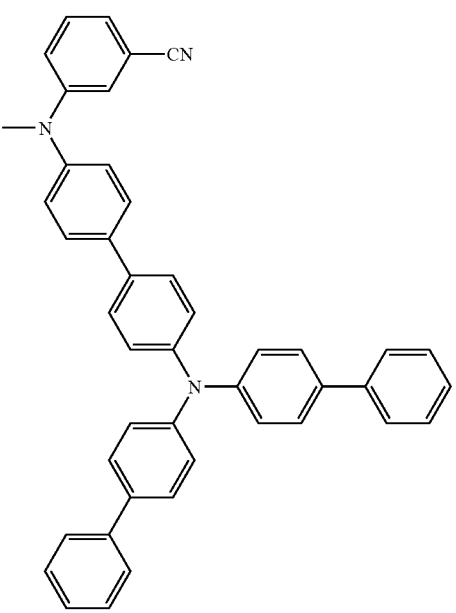
459

461
-continued
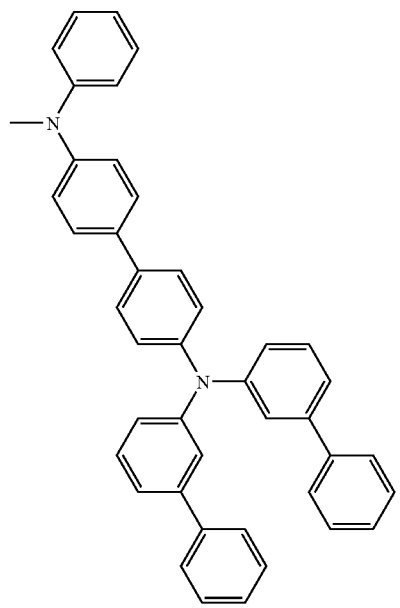
460
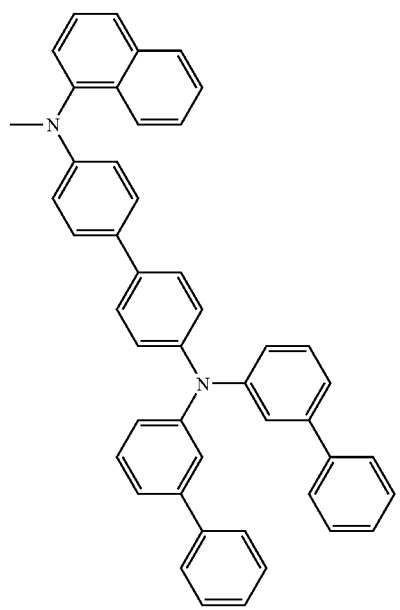
461
462
-continued
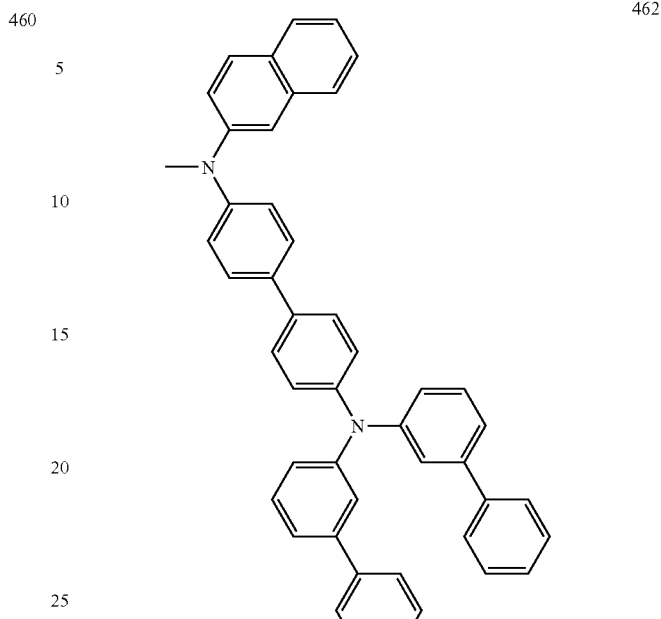
462
463
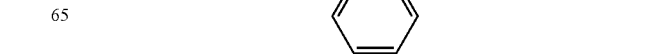

-continued
463
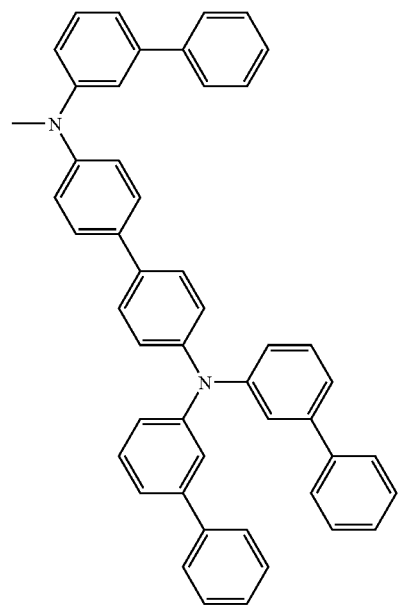
465
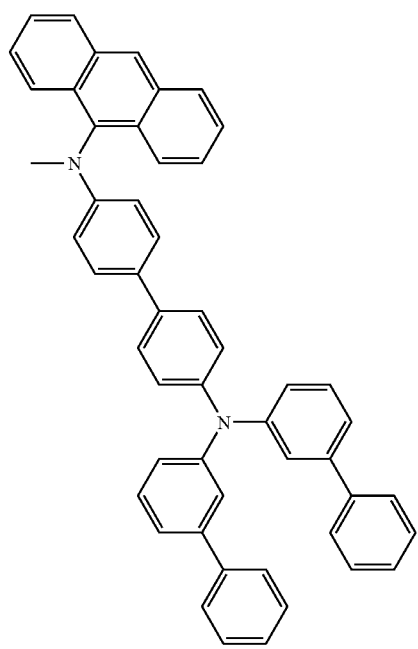
466
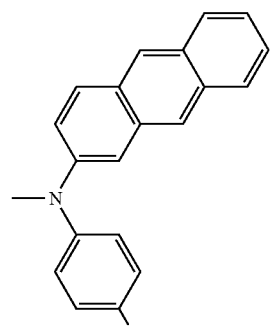
-continued
464
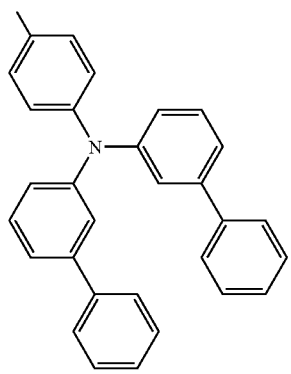
467
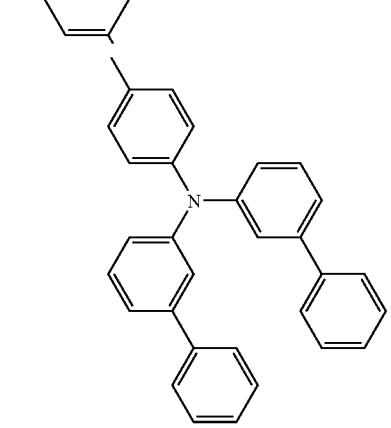
468
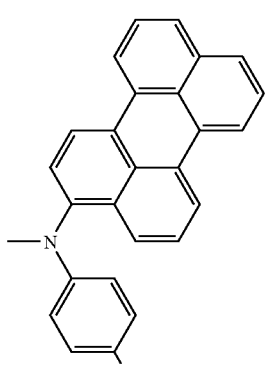

-continued
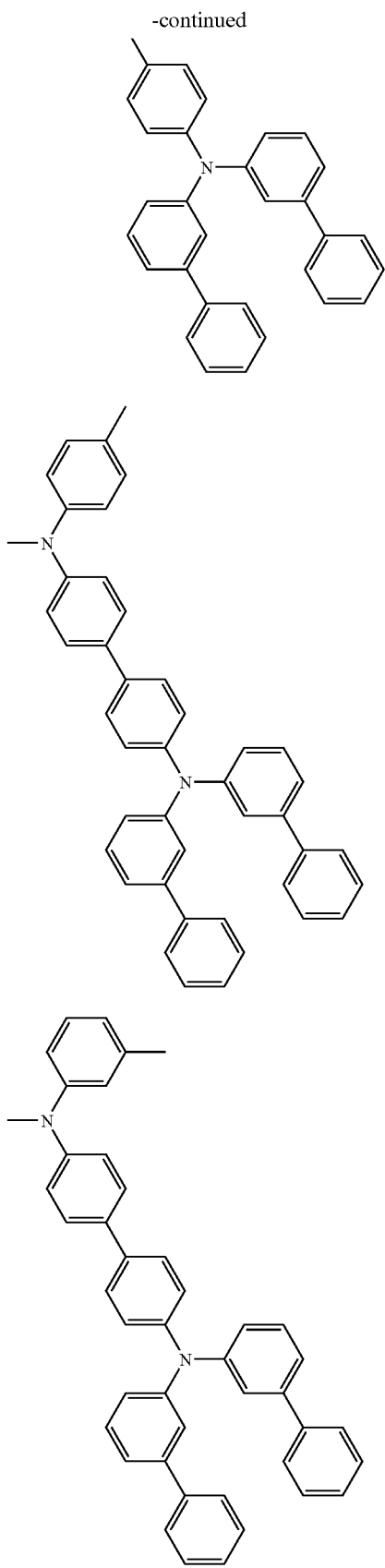
-continued
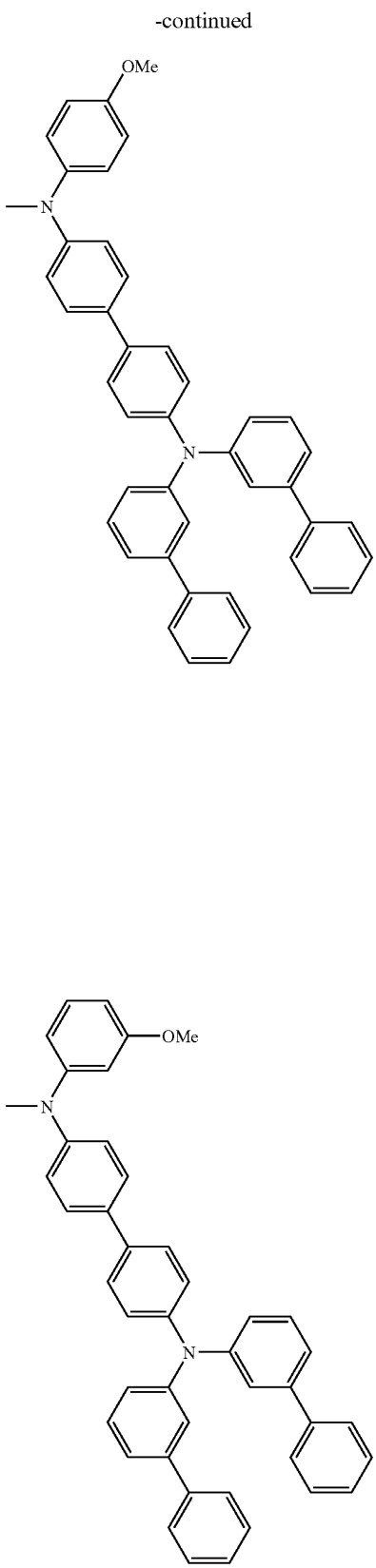

467          468

473

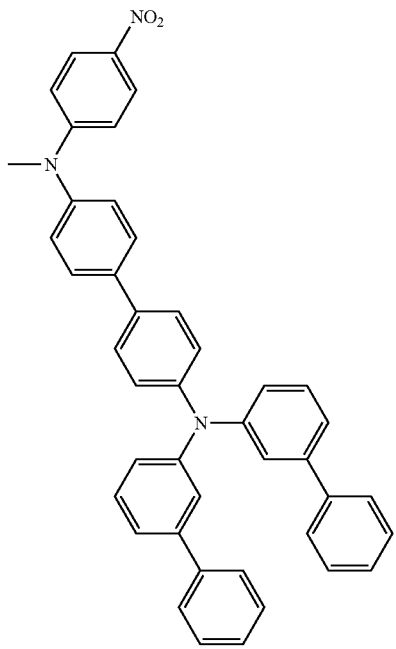

475

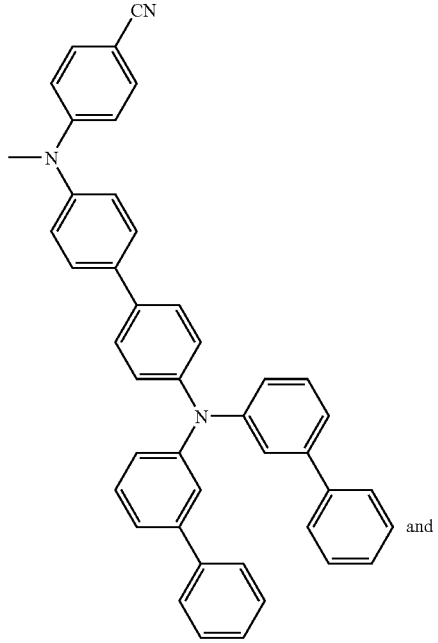

and

474

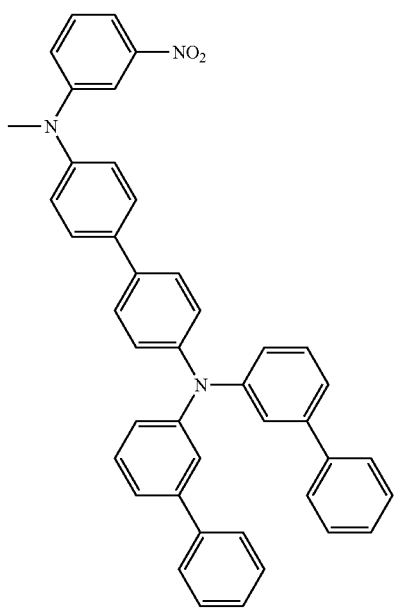

6. The organic light emitting device as set forth in claim 1, wherein the organic material layer(s) comprise a hole transport layer, and the hole transport layer includes the compound of Formula 1.

7. The organic light emitting device as set forth in claim 1, wherein the organic material layer(s) comprise a hole injection layer, and the hole injection layer includes the compound of Formula 1.

8. The organic light emitting device as set forth in claim 1, wherein the organic material layer(s) comprise a layer which both injects and transports holes and which includes the compound of Formula 1.

* * * * *